(12) United States Patent
Ness et al.

(10) Patent No.: US 6,902,922 B2
(45) Date of Patent: Jun. 7, 2005

(54) SUBTILISIN VARIANTS

(75) Inventors: Jon E. Ness, Sunnyvale, CA (US);
Mark Welch, Fremont, CA (US);
Lorraine J. Giver, Santa Clara, CA (US);
Joel R. Cherry, Davis, CA (US);
Torben V. Borchert, Birkeroed (DK);
Willem P. C. Stemmer, Los Gatos, CA (US); Jeremy Minshull, Menlo Park, CA (US)

(73) Assignees: Novozymes A/S, Bagsvaerd (DK); Maxygen, Inc., Redwood City, CA (US)

( * ) Notice: Subject to any disclaimer, the term of this patent is extended or adjusted under 35 U.S.C. 154(b) by 0 days.

(21) Appl. No.: 09/824,893

(22) Filed: Apr. 2, 2001

(65) Prior Publication Data

US 2003/0049827 A1 Mar. 13, 2003

Related U.S. Application Data

(60) Provisional application No. 60/194,143, filed on Apr. 3, 2000.
(51) Int. Cl.[7] ............................. C12N 9/50; C12N 9/54; C12N 15/57; C12N 15/74; C11D 3/386
(52) U.S. Cl. ................. 435/219; 435/69.1; 435/220; 435/221; 435/222; 435/320.1; 435/471; 510/350; 536/23.2
(58) Field of Search ................ 435/39.1, 471, 435/252.31, 220, 221, 320.1; 536/23.2; 510/350

(56) References Cited

U.S. PATENT DOCUMENTS

| | | | |
|---|---|---|---|
| 5,316,935 A | | 5/1994 | Arnold et al. .............. 435/222 |
| 5,340,735 A | * | 8/1994 | Christianson et al. ....... 435/221 |
| 6,482,628 B1 | * | 11/2002 | Poulouse et al. ........... 435/221 |
| 2003/0049827 A1 | * | 3/2003 | Ness et al. .................. 435/226 |

FOREIGN PATENT DOCUMENTS

| | | |
|---|---|---|
| WO | WO 94/02618 | 2/1994 |
| WO | WO 95/10591 | 4/1995 |
| WO | WO 2001/75087 A2 * | 10/2001 |

OTHER PUBLICATIONS

Zhao et al., Proc. Natl. Acad. Sci. USA, vol. 94, pp. 7997–8000, Jul. 1997.
Ness et al., Nature Biotechnology, vol. 17, Sep. 1999, 893–896.

* cited by examiner

Primary Examiner—Ponnathapu Achutamurthy
Assistant Examiner—William W. Moore
(74) Attorney, Agent, or Firm—Elias J. Lambiris

(57) ABSTRACT

New subtilisin homologues (both nucleic acids and proteins) are provided. Compositions which include these new proteins, recombinant cells, shuffling methods involving the new homologues, antibodies to the new homologues, and methods of using the homologues are also provided.

27 Claims, 10 Drawing Sheets

Figure 2D:
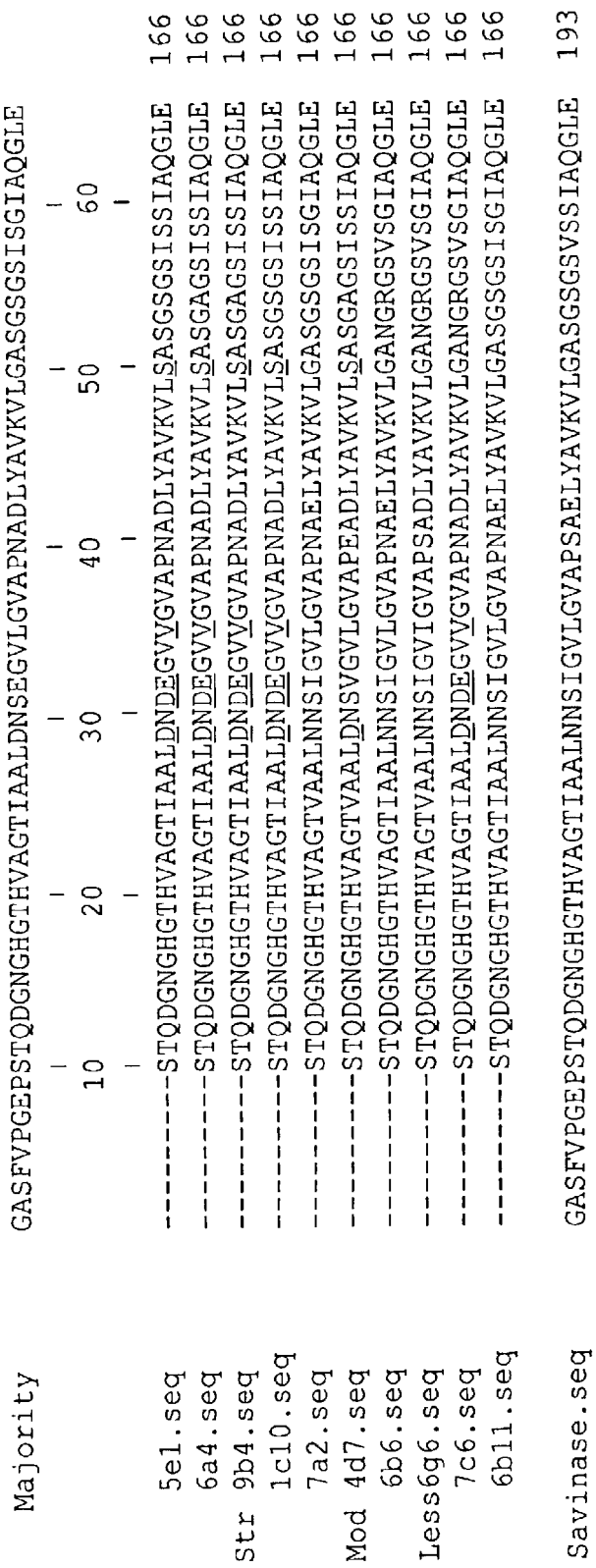

DNA and Amino Acid Sequences of the Diversified
Region of Subtilisin.

Amino acid sequence of pre-pro peptide shown in small letters. Amino acid sequence of
the mature peptide are shown in capital letters. Amino acid sequence of the diversified
region are shown in capital, bold letters.

```
-100   tallisvafs    ssiasaaeea    kekyligfne    qeavsefveq    m             kkplgkivas
 -50   seeeeveiel    lhefetipvl    svelspedvd    aleldpaisy    veandevail
   1   AQSVPWGISR    VQAPAAHNRG    LTGSGVKVAV    LDTGISTHPD    ieedaevttm
  51   PGEPSTQDGN    GHGTHVAGTI    AALNNSIGVL    GVAPSAELYA    LNIRGGASFV
 101   SVSSIAQGLE    WAGNNGTHVA    NLSLGSPSPS    ATLEQAVNSA    VKVLGASGSG
 151   SGNSGAGSIS    YPARYANAMA    VGATDQNNNR    ASFSQYGAGL    TSRGVLVVAA
 201   STYPGSTYAS    LNGTSMATPH    VAGVAALVKQ    KNPSWSNVQI    DIVAPGVNVQ
 251   LGSTNLYGSG    LVNAEAATR                                 RNHLKNTATS
```

FIG. 1

Subtilisin Structure-Function Correlation
Thermostability Motifs

```
Majority      STQDGNGHGHGTHVAGTVAALNNSIGVIGVAPSADLYAVKVLGANGRGSVSGIAQGLE
                       10        20        30        40        50        60

3a3.seq       --------STQDGNGHGHGTHVAGTVAALNNSIGVIGVAPSADLYAVKVLGANGRGSVSGIAQGLE  166
6g6.seq       --------STQDGNGHGHGTHVAGTVAALNNSIGVIGVAPSADLYAVKVLGANGRGSVSGIAQGLE  166
4c6.seq       --------STQDGNGHGHGTHVAGTVAALNNSIGVIGVAPSADLYAVKVLGANGRGSVSGIAQGLE  166
3b3.seq       --------STQDGNGHGHGTHVAGTIAALDNSIGVIGVAPSADLYAVKVLGANGRGSVSGIAQGLE  166
3e2.seq       --------STQDGNGHGHGTHVAGTVAALNNSIGVIGVAPSADLYAVKVLGANGRGSVSGIAQGLE  166
5h9.seq       --------STQDGNGHGHGTHVAGTIAALDNSIGVIGVAPSADLYAVKVLGANGSGSVSGIARGLE  166
3a7.seq       --------STQDGNGHGHGTHVAGTVAALXNSIGVIGVAPSADLYAVKVLGANGRGSVSGIAQGLE  166
5b11.seq      --------STQDGNGHGHGTHVAGTIAALNNSIGVIGVAPSADLYAVKVLGANGRGSVSGIAQGLE  166
4d10.seq      --------STQDGNGHGHGTHVAGTIAALNNSIGVLGVAPNAELYAVKVLGANGRGSVSGIAQGLE  166
1f6.seq       --------STQDGNGHGHGTHVAGTIAALNNSIGVIGVAPSADLYAVKVLGANGRGSVSGIAQGLE  166
4c2.seq       --------STQDGNGHGHGTHVAGTVAALNNSIGVIGVAPSADLYAVKVLGANGRGSVSGIAQGLE  166

Savinase.seq  GASFVPGEPSTQDGNGHGHGTHVAGTIAALNNSIGVLGVAPSAELYAVKVLGASGSGSVSSIAQGLE 193
```

FIG. 2A

```
Majority        WAAANNMHIANMSLGSDAPSTTLERAVNYATSQGVLVIAATGNNGSSVGYPARYANAMAVGATD

|         |         |         |         |         |
                         70        80        90        100       110       120       130

3a3.seq         WAAANNMHIANMSLGSDAPSTTLERAVNYATSQGVLVIAATGNNGSSVGYPARYANAMAVGATD    361
6g6.seq         WAAANNMHIANMSLGSDAPSTTLERAVNYATSQGVLVIAATGNNGSSVGYPARYANAMAVGATD    361
4c6.seq         WAAANNMHIANMSLGSDAPSTTLERAVNYATSQGVLVIAATGNNGSSVGYPARYANAMAVGATD    361
3b3.seq         WAAANNMHIANMSLGSDAPSTTLERAVNYATSQGVLVIAATGNNGSSVGYPARYANAMAVGATD    361
3e2.seq         WAAANNMHIANMSLGSDAPSTTLERAVNYATSQGVLVIAATGNNGSSVGYPARYANAMAVGATD    361
5h9.seq         WAATNNMHIANMSLGSDAPSTTLERAVNYATSQGVLVIAATGNNGSSVGYPARYANAMAVGATD    361
3a7.seq         WAAANNMHIANMSLGSDAPSTTLERAVNYATSQGVLVIAATGNNGSSVGYPARYANAMAVGATD    361
5b11.seq        WAAANNMHIANMSLGSDAPSTTLERAVNYATSQGVLVIAATGNNGSSVGYPARYANAMAVGATD    361
4d10.seq        WAAANNMHIANMSLGSDAPSTTLERAVNYATSQGVLVIAATGNNGSSVGYPARYANAMAVGATD    361
1f6.seq         WAAANNMHIANMSLGSDAPSTTLERAVNYATSRDVLVIAATGNNGSSVGYPARYANAMAVGATD    361
4c2.seq         WAAANNMHIANMSLGSDAPSTTLERAVNYATSQGVLVIAATGNNGSSVGYPARYANAMAVGATD    361

Savinase.seq    WAGNNGMHVANLSLGSPSPSATLEQAVNSATSRGVLVVAASGNSGAGSISYPARYANAMAVGATD    388
```

FIG. 2B

```
Majority        QNNRRANFSQYGTGIDIVAPGVNVQSTYPGNRYASLNGTSMATPHVAGAAALVK
                         |         |         |         |         |
                        140       150       160       170       180       190

3a3.seq         QNNRRANFSQYGTGIDIVAPGVNVQSTYPGNRYVSMSGTSMATPHVAGAAALVK-------523
6g6.seq         QNNRRANFSQYGTGIDIVAPGVNVQSTYPGGQYAELSGTSMASPHVAGAGAALVK-------523
4c6.seq         QNNRRANFSQYGTGIDIVAPGVNVQSTYPGNRYASLSGTSMATPHVAGAAALVK-------523
3b3.seq         QNNRRANFSQYGTGIDIVAPGVNVQSTYPGNRYASLNGTSMATPHVAGAAALVK-------523
3e2.seq         QNNRRANFSQYGTGIDIVAPGVNVQSTYPGNRYASLSGTSMATPHVAGVAALVK-------523
5h9.seq         QNNRRANFSQYGTGIDIVAPGVNVQSTYPGNRYASLNGTSMATPHVAGAAALVK-------523
3a7.seq         QNNRRANFSQYGTGIDIVAPGVNVQSTYPGNRYVSMNGTSMATPHVAGAAALVK-------523
5b11.seq        QNNRRANFSQYGTGIDIVAPGVNVQSTYPGNRYVSMNGTSMATPHVAGAAALVK-------523
4d10.seq        QNNRRANFSQYGTGIDIVAPGVNVQSTYPGNRYVSMNGTSMATPHVAGVAALVK-------523
1f6.seq         QNNRRANFSQYGTGIDIVAPGVNVQSTYPGNRYVSMNGTSMATPHVAGVAALVK-------523
4c2.seq         QNNRRANFSQYGTGIDIVAPGVNVQSTYPGNRYASLSGTSMATPHVAGVAALVK-------523

Savinase.seq    QNNNRASFSQYGAGLDIVAPGVNVQSTYPGSTYASLNGTSMATPHVAGAAALVKQKNPSWSNVX580
```

FIG. 2C

```
Majority      WAGENGMHIANLSLGSSAPSATLEQAVNYATSQGVLVIAASGNSGAGSVGYPARYANAMAVGATD
                      -         -         -         -         -         -         -
                     70        80        90       100       110       120       130

5e1.seq       WSGENGMDIANLSLGSSAPSATLEQAVNAATSRGVLVIAASGNSGAGSVGYPARYANAMAVGATD   361
6a4.seq       WSGENGMDIANLSLGSSAPSATLEQAVNAATSRGVLVIAASGNSGAGSVGYPARYANAMAVGATD   361
9b4.seq       WSGENGMDIANLSLGSSAPSATLEQAVNAATSRGVLVIAASGNSGAGSVGYPARYANAMAVGATD   361
1c10.seq      WSGENGMDIANLSLGSSAPSATLEQAVNAATSRGVLVIAASGNSGAGSVGYPARYANAMAVGATD   361
7a2.seq       WAAANNMHIANMSLGSDAPSTTLERAVNYATSQGVLVIAATGNNGSSGSVGYPARYANAMAVGATD   361
4d7.seq       WSAANNMHIANMSLGSDAPSTTLERAVNYATSQGVLVIAATGNNGSSGSVGYPARYANAMAVGATD   361
6b6.seq       WAAANNMHIANMSLGSDAPSTTLERAVNYATSQGVLVIAATGNNGSSGSVGYPARYANAMAVGATD   361
6g6.seq       WAAANNMHIANMSLGSDAPSTTLERAVNYATSQGVLVIAATGNNGSSGSVGYPARYANAMAVGATD   361
7c6.seq       WAAANNMHIANMSLGSDAPSTTLERAVNYATSQGVLVIAATGNNGSSGSVGYPARYANAMAVGATD   361
6b11.seq      WAAANNMHIANMSLGSDAPSTTLERAVNYATSQGVLVIAATGNNGSSGSVGYPARYANAMAVGATD   361

Savinase.seq  WAGNNGMHVANLSLGSPSPSATLEQAVNSATSRGVLVVAASGNSGAGSISYPARYANAMAVGATD    388
```

FIG. 2E

```
Majority      QNNNRASFSQYGAGLDIVAPGVGVQSTYPGNRYASLNGTSMATPHVAGVAALVKQKNPSWSNVX
                        |         |         |         |         |         |
                       140       150       160       170       180       190

5e1.seq       QNNNRASFSQYGAGLDIVAPGVGVQSTYPGNRYASLNGTSMATPHVAGAAALVK-----------523
6a4.seq       QNNNRASFSQYGAGLDIVAPGVGVQSTYPGNRYASLNGTSMATPHVAGVAALVK-----------523
9b4.seq       QNNNRASFSQYGAGLDIVAPGVGVQSTYPGSTYASLNGTSMATPHVAGVAALVK-----------523
1c10.seq      QNNNRASSSQYGAGLDIVAPGVGVQSTYPGNRYASLNGTSMATPHVAGVAALVK-----------523
7a2.seq       QNNRRANFSQYGTGIDIVAPGVEIESTYPGSSYDSLRGTSMATPHVAGAAALVK-----------523
4d7.seq       QNNRRANFSQYGTGIDIVAPGVNVQSTYPGNRYASLNGTSMATPHVAGVAALVK-----------523
6b6.seq       QNNNRASFSQYGAGLDIVAPGVNVQSTYPGSTYDSLSGTSMATPHVAGVAALVK-----------523
6g6.seq       QNNRRANFSQYGTGIDIVAPGVNVQSTYPGGQYAELSGTSMASPHVAGAAALVK-----------523
7c6.seq       QNNRRANFSQYGTGIDIVAPGVNVQSTYPGNRYASLNGTSMATPHVAGVAALVK-----------523
6b11.seq      QNNRRANFSQYGTGIDIVAPGVNVQSTYPGNRYASLNGTSMATPHVAGVAALVK-----------523

Savinase.seq  QNNNRASFSQYGAGLDIVAPGVNVQSTYPGSTYASLNGTSMATPHVAGAAALVKQKNPSWSNVX  580
```

FIG. 2F

Subtilisin Structure-Function Correlation
Activity in DMF Motifs

```
Majority    GASFVPGEPSTQDGNGHGTHVAGTIAALNNSIGVLGVAPNADLYAVKVLGANGSGSVSGIAQGLE
                    10        20        30        40        50        60

3d11.seq    ---------STQDGNGHGTHVAGTVAALNNSIGVIGVAPSADLYAVKVLGANGSGSVSGIARGLE  166
2b8.seq     ---------STQDGNGHGTHVAGTVAALNNSIGVIGVAPSADLYAVKVLGANGRGSVSGIARGLE  166
2b4.seq     ---------STQDGNGHGTHVAGTVAALNNSIGVIGVAPSADLYAVKVLGANGRGSVSGIAQGLE  166
2g6.seq     ---------STQDGNGHGTHVAGTIAALNNNVGVLGVAPNVELYGVKVLGASGSGSISGIAQGLQ  166
3g9.seq     ---------STQDGNGHGTHVAGTVAALNNSIGVIGVAPSADLYAVKVLGANGSGSVSGIAQGLE  166
5f4.seq     ---------STQDGNGHGTHVAGTIAALNNSIGVLGVAPNADLYAVKVLGANGSGSVSGIARGLE  166
9e3.seq     ---------STQDGNGHGTHVAGTIAALNNNVGVLGVAPNVELYGVKVLGASGSGSIAQGLQ  166
1c4.seq     ---------STQDGNGHGTHVAGTVAALNNSIGVIGVAPSADLYAVKVLGANGRGSVSGIAQGLE  166
8c2.seq     ---------STQDGNGHGTHVAGTIAALNNSIGVLGVAPNAELYAVKVLGANGRGSVSGIAQGLE  166
8h2.seq     ---------STQDGNGHGTHVAGTIAALNNSIGVLGVAPNADLYAVKVLGANGSGSVSGIARGLE  166

Savinase.seq GASFVPGEPSTQDGNGHGTHVAGTIAALNNSIGVLGVAPSAELYAVKVLGASGSGSVSSIAQGLE  193
```

FIG. 2G

```
Majority      WAAANNMHIANMSLGSDAPSATLEQAVNYATSRGVLVIAATGNNGSSVGYPARYANAMAVGATD
                     |         |         |         |         |         |
                    70        80        90        100       110       120       130

3d11.seq      WAATNNMHIANMSLGSDEPSSTLERAVNYATSRDVLVIAATGNNGSGSVGYPARYANAMAVGATD    361
2b8.seq       WAAANNMHIANMSLGSDAPSTTLERAVNYATSQGVLVIAATGNNGSGSVGYPARYANAMAVGATD    361
2b4.seq       WAAANNMHIANMSLGSDAPSTTLGRAVNYATSQGVLVIAATGNNGSGSVGYPARYANAMAVGATD    361
2g6.seq       WAGNNGMHIANMSLGTSAPSATLEQAVNAATSRGVLVIAASGNSGAGSVGYPARYANAMAVGATD    361
3g9.seq       WAAANNMHIANMSLGSDEPSSTLERAVNYATSRDVLVIAATGNNGSGSVGYPARYANAMAVGATD    361
5f4.seq       WAATNNMHIANMSLGSDAPSTTLERAVNYATSQGVLVIAATGNNGSGSVGYPARYANAMAVGATD    361
9e3.seq       WAGNNGMHIANMSLGTSAPSATLEQAVNAATSRGVLVIAASGNSGAGSVGYPARYANAMAVGATD    361
1c4.seq       WAAANNMHIANMSLGSDEPSSTLERAVNAATSRGVLVIAATGNNGSGSVGYPARYANAMAVGATD    361
8c2.seq       WAAANNMHIANMSLGSDAPSTTLKRAVNYATSQGVLVIAATGNNGSGSVGYPARYANAMAVGATD    361
8h2.seq       WAATNNMHIANMSLGSDEPSSTLERAVNYATSQGVLVIAATGNNGSGSVGYPARYANAMAVGATD    361

Savinase.seq  WAGNNGMHVANLSLGSPSPSATLEQAVNSATSRGVLVVAASGNSGAGSISYPARYANAMAVGATD    388
```

FIG. 2H

```
Majority       QNNRRANFSQYGTGIDIVAPGVNVQSTYPGNRYASLNGTSMATPHVAGVAALVKQKNPSWSNVX
                       140       150       160       170       180       190

3d11.seq       QNNRRANFSQYGTGIDIVAPGVNVQSTYPGNRYASLNGTSMATPHVAGAAALVK--------523
2b8.seq        QNNRRANFSQYGTGIDIVAPGVNVQSTYPGNRYASLNGTSMATPHVAGVAALVK--------523
2b4.seq        QNNRRANFSQYGTGIDIVAPGVNVQSTYPGNRYASLNGTSMATPHVAGVAALVK--------523
2g6.seq        QNNRRANFSQYGTGIDIVAPGVNVQSTYPGNRYVSMNGTSMATPHVAGVAALVK--------523
3g9.seq        QNNRRANFSQYGTGIDIVAPGVNVQSTYPGNRYASLNGTSMATPHVAGVAALVK--------523
5f4.seq        QNNRRANFSQYGTGIDIVAPGVNVQSTYPGNRYARLNGTSMATPHVAGVAALVK--------523
9e3.seq        QNNRRANFSQYGTGIDIVAPGVNVQSTYPGNRYVSMNGTSMATPHVAGVAALVK--------523
1c4.seq        QNNRRANFSQYGTGIDIVAPGVNVQSTYPGNRYASLNGTSMATPHVAGAAALVK--------523
8c2.seq        QNNRRANFSQYGTGIDIVAPGVNVQSTYPGNRYASLNGTSMATPHVAGVAALVK--------523
8h2.seq        QNNRRANFSQYGTGIDIVAPGVNVQSTYPGNRYASLNGTSMATPHVAGVAALVK--------523

Savinase.seq   QNNRRASFSQYGAGLDIVAPGVNVQSTYPGSTYASLNGTSMATPHVAGAAALVKQKNPSWSNVX 580
```

FIG. 21

SEQUENCE LISTING

<160> NUMBER OF SEQ ID NOS: 270

<210> SEQ ID NO 1
<211> LENGTH: 522
<212> TYPE: DNA
<213> ORGANISM: Artificial Sequence
<220> FEATURE:
<223> OTHER INFORMATION: Synthetic

<400> SEQUENCE: 1

```
gtcgactcaa gatgggaacg ggcacgggac gcacgttgca gggacgattg cggctctgga    60
taatgacgaa ggtgttgttg gcgtagcgcc aaatgcggat ctatacgccg ttaaagtgct   120
tagcgcatct ggctctggtt cgattagttc gattgcccaa gggcttgaat ggtctggcga   180
aaacggcatg gatattgcca atttgagtct tggcagctct gcaccaagcg caactcttga   240
acaagctgtt aacgcagcga catctcgtgg tgtacttgtt atcgcagcct ctggtaactc   300
cggcgctgga tccgttggtt atcctgcacg ttatgcgaat gcgatggcag taggtgcaac   360
tgatcaaaat aacaaccgtg caagctcctc tcaatacggt gcaggtcttg atattgtcgc   420
tcctggcgta ggtgttcaaa gcacatatcc agggaaccgt tatgcgagct tgaatggtac   480
ttcaatggca actcctcatg tcgccggcgt cgccgcacta gt                      522
```

<210> SEQ ID NO 2
<211> LENGTH: 522
<212> TYPE: DNA
<213> ORGANISM: Artificial Sequence
<220> FEATURE:
<223> OTHER INFORMATION: Synthetic

<400> SEQUENCE: 2

```
gtcgactcaa gatggcaatg ggcacgggac gcacgttgca ggaacagtgg cagctcttaa    60
```

| | |
|---|---|
| taactcaatc ggtgtgattg gtgtggcacc aagtgctgat ctatacgctg taaaagtact | 120 |
| tggagcaaat ggtagaggaa gcgttagtgg aattgctcaa ggtctagagt gggctgcagc | 180 |
| gaataacatg catattgcta acatgagtct cggtagtgat tttcctagct ctacacttga | 240 |
| gcgtgcagtc aactatgcga caagccaagg tgtactagtt attgcagcga ctggtaacaa | 300 |
| cggttccggt tcagtaggct atcctgctcg ttatgcaaac gcaatggctg taggagcgac | 360 |
| tgaccaaaac aacagacgtg caaacttttc tcagtacggt acaggaattg acatcgtagc | 420 |
| accaggggtt aatgtacaaa gtacgtatcc tggaaaccgc tatgcaagtt taaatggtac | 480 |
| atctatggct actccacacg tcgccggcgc cgccgcacta gt | 522 |

<210> SEQ ID NO 3
<211> LENGTH: 522
<212> TYPE: DNA
<213> ORGANISM: Artificial Sequence
<220> FEATURE:
<223> OTHER INFORMATION: Synthetic

<400> SEQUENCE: 3

| | |
|---|---|
| gtcgactcaa gatgggaatg ggcacgggac gcatgtagca ggaacaatag ccgctctaaa | 60 |
| caattcaata ggcgtacttg gtgttgcacc gaatgcagaa ttatatgctg ttaaagtact | 120 |
| cggagcaaat ggtagaggaa gcgttagtgg aattgctcaa ggtctagagt gggctgcagc | 180 |
| gaataacatg catattgcta acatgagtct cggtagtgat gcacctagta ctacacttga | 240 |
| gcgtgcagtc aactatgcga caagccaagg tgtactagtt attgcagcga ctggtaacaa | 300 |
| cggttctggt tcagtaggct atcctgctcg ttatgccaac gcaatggctg taggagcgac | 360 |
| tgaccaaaac aacagacgtg caaacttttc tcagtatggt acaggaattg acatcgtagc | 420 |
| acctggagtt aacgtacaaa gtacgtatcc aggaaaccgt tatgtgagta tgaatggtac | 480 |
| atctatggct actccacacg tcgccggcgt cgccgcacta gt | 522 |

<210> SEQ ID NO 4
<211> LENGTH: 522
<212> TYPE: DNA
<213> ORGANISM: Artificial Sequence
<220> FEATURE:
<223> OTHER INFORMATION: Synthetic

<400> SEQUENCE: 4

| | |
|---|---|
| gtcgactcaa gatgggaacg ggcacgggac gcacgtagca ggaacggttg cagctcttaa | 60 |
| taattcaatc ggtgtgattg gtgtggcacc aagtgctgat ctatacgctg taaaagtact | 120 |
| tggagcaaat ggtagaggaa gcgttagtgg aattgctcaa ggtctagagt gggctgcagc | 180 |
| gaataacatg catattgcta acatgagtct cggtagtgat gcacctagta ctacacttgg | 240 |
| gcgtgcagtc aactacgcga caagccaagg tgtactagtt attgcagcga ctggtaacaa | 300 |
| cggttccggt tcagttggct atcctgctcg ttatgcaaac gcaatggctg taggagcgac | 360 |
| tgaccaaaac aacagacgtg caaacttttc tcagtatggt acaggaattg acatcgtagc | 420 |
| accaggggtt aatgtacaaa gtacgtatcc tggaaaccgc tatgcaagtt taaatggtac | 480 |
| gtcgatggca actcctcacg tcgccggcgt cgccgcacta gt | 522 |

<210> SEQ ID NO 5
<211> LENGTH: 522
<212> TYPE: DNA
<213> ORGANISM: Artificial Sequence
<220> FEATURE:
<223> OTHER INFORMATION: Synthetic

<400> SEQUENCE: 5

```
gtcgactcaa gatgggaacg ggcacgggac gcatgtggcc ggaacagtag cagctcttaa      60
taactcaatc ggtgtgattg gtgtggcacc aagtgctgat ctatacgctg taaaagtact     120
tggagcaaat ggtagaggaa gcgttagtgg aattgctcga ggtctagagt gggctgcagc     180
gaataacatg catattgcta acatgagtct cggtagtgat gcacctagta ctacacttga    240
gcgtgcagtc aactacgcga caagccaagg tgtactagtt attgcagcga ctggtaacaa    300
cggttctggt tcagttggct atcctgctcg ttatgcaaac gcaatggctg taggagcgac    360
tgaccaaaac aacagacgtg caaacttttc tcagtatggt acaggaattg acatcgtagc    420
accaggggtt aatgtacaaa gtacgtatcc tggaaaccgc tatgcaagtt taaatggtac    480
atctatggct actccacacg tcgccggcgt cgccgcacta gt                        522
```

<210> SEQ ID NO 6
<211> LENGTH: 522
<212> TYPE: DNA
<213> ORGANISM: Artificial Sequence
<220> FEATURE:
<223> OTHER INFORMATION: Synthetic

<400> SEQUENCE: 6

```
gtcgactcaa gatggcaatg ggcatgggac gcacgttgca ggaacgattg cggcgctaaa      60
caataatgtt ggtgtacttg gtgttgcgcc taacgttgag ctttatggtg ttaaagtact     120
tggagcaagt ggttctggat caatcagtgg aattgcacaa gggttgcaat gggctggtaa    180
taatggaatg catatagcta atatgagcct tggtacttct gcaccaagcg caactcttga    240
acaagctgtt aacgcagcga catctcgtgg tgtacttgtt atcgcagcct ctggtaattc    300
tggtgctgga tcagttggtt atcctgcacg ttacgcgaat gcgatggctg taggagcgac    360
tgaccaaaac aacagacgtg caaacttttc tcagtatggt acaggaattg acatcgtagc    420
acctggagtt aacgtacaaa gtacgtatcc aggaaaccgt tatgtgagta tgaatggtac    480
atctatggcc actccacacg tcgccggcgt cgccgcacta gt                        522
```

<210> SEQ ID NO 7
<211> LENGTH: 522
<212> TYPE: DNA
<213> ORGANISM: Artificial Sequence
<220> FEATURE:
<223> OTHER INFORMATION: Synthetic

<400> SEQUENCE: 7

```
gtcgactcaa gatgggaatg ggcatgggac gcacgttgca ggaacagtgg cagctcttaa      60
taattcaatc ggtgtgattg gtgtggcacc aagtgctgat ctatacgctg taaaagtact     120
tggagcaaat ggtagaggaa gcgttagtgg aattgctcaa ggtctagagt gggctgcagc     180
gaataacatg catattgcta acatgagtct cggtagtgat gcacctagta ctacacttga    240
gcgtgcagtc aactatgcga caagccaagg tgtactagtt attgcagcga ctggtaacaa    300
cggttccggt tcagtaggct atcctgctcg ttatgccaac gcaatggctg taggagcgac    360
tgaccaaaac aacagacgtg caaacttttc tcagtatggt acaggaattg acatcgtagc    420
accaggggtt aatgtacaaa gtacgtatcc aggaaaccgt tatgtgagta tgagtggtac    480
atctatggcc actccacacg tcgccggcgc cgccgccctt gt                        522
```

<210> SEQ ID NO 8

```
<211> LENGTH: 522
<212> TYPE: DNA
<213> ORGANISM: Artificial Sequence
<220> FEATURE:
<223> OTHER INFORMATION: Synthetic
<221> NAME/KEY: misc_feature
<222> LOCATION: (60)..(60)
<223> OTHER INFORMATION: n in position 60 denotes an unknown nucleotide

<400> SEQUENCE: 8
gtcgactcaa gatgggaacg ggcacgggac gcacgttgca ggaacagtgg cagctcttan      60
taattcaatc ggtgtgattg gtgtggcacc aagtgctgat ctatacgctg taaaagtact     120
tggagcaaat ggtagaggaa gcgttagtgg aattgctcaa ggtctagagt gggctgcagc     180
gaataacatg catattgcta acatgagtct cggtagtgat gcacctagta ctacacttga     240
gcgtgcagtc aactatgcga caagccaagg tgtactagtt attgcagcga ctggtaacaa     300
cggttctggt tcagttggct atcctgctcg ttatgcaaac gcaatggctg taggagcgac     360
tgaccaaaac aacagacgtg caaacttttc tcagtatggt acaggaattg acatcgtagc     420
accaggggtt aatgtacaaa gtacgtatcc tggaaaccgt tatgtgagta tgaatggtac     480
atctatggcc actccacatg tcgccggcgc cgccgcacta gt                        522

<210> SEQ ID NO 9
<211> LENGTH: 522
<212> TYPE: DNA
<213> ORGANISM: Artificial Sequence
<220> FEATURE:
<223> OTHER INFORMATION: Syntehtic

<400> SEQUENCE: 9
gtcgactcaa gatgggaacg ggcatgggac gcacgtagca ggaacaatag ccgctctaaa      60
caattcagta ggcgtactgg gtgtcgcacc gaatgcagaa ttatatgcag ttaaagtact     120
tggagcaaat ggtagaggaa gcgttagtgg aattgctcaa ggtctagagt gggctgcagc     180
gaataacatg catattgcta acatgagtct cggtagtgat gcacctagta ctacacttga     240
gcgtgcagtc aactatgcga caagccaagg tgtactagtt attgcagcga ctggtaacaa     300
cggttctggt tcagttggct atcctgctcg ttatgccaac gcaatggctg taggagcgac     360
tgaccaaaac aacagacgtg caaacttttc tcagtatggt acaggaattg acatcgtagc     420
accaggggtt aatgtacaaa gtacgtatcc tggaacccgc tatgcaagtt taaatggtac     480
atctatggct actccacacg tcgccggcgc cgccgcacta gt                        522

<210> SEQ ID NO 10
<211> LENGTH: 522
<212> TYPE: DNA
<213> ORGANISM: Artificial Sequence
<220> FEATURE:
<223> OTHER INFORMATION: Synthetic

<400> SEQUENCE: 10
gtcgactcaa gatgggaacg ggcacgggac gcacgttgct ggaacgattg cggctcttga      60
taattcaatc ggtgtgattg gtgtggcacc aagtgctgat ctatacgctg taaaagtact     120
tggagcaaat ggtagaggaa gcgttagtgg aattgctcaa ggtctagagt gggctgcagc     180
gaataacatg catattgcta acatgagtct cggtagtgat gcacctagta ctacacttga     240
gcgtgcagtc aactacgcga caagccaagg tgtactagtt attgcagcga ctggtaacaa     300
cggttctggt tcagttggct atcctgctcg ttatgcaaac gcaatggctg taggagcgac     360
```

```
tgaccaaaac aacagacgtg caaacttttc tcagtatggt acaggaattg acatcgtagc    420
accaggggtt aatgtacaaa gtacgtatcc tggaaaccgc tatgcaagtt taaatggtac    480
atctatggct actccacacg tcgccggcgc cgccgcacta gt                      522

<210> SEQ ID NO 11
<211> LENGTH: 522
<212> TYPE: DNA
<213> ORGANISM: Artificial Sequence
<220> FEATURE:
<223> OTHER INFORMATION: Synthetic

<400> SEQUENCE: 11
gtcgactcaa gatgggaacg ggcatgggac gcacgttgca ggaacagtgg cagctcttaa     60
taactcaatc ggtgtgattg gtgtggcacc aagtgctgat ctatacgctg taaaagtact    120
tggagcaaat ggaagcggaa gtgtaagtgg gattgctcga ggtttagagt gggcggcaac    180
caataacatg catattgcga acatgagtct cggtagtgat tttcctagct ctacacttga    240
gcgtgcagtc aactatgcga caagccgtga tgtactagtt attgcagcga ctggtaacaa    300
cggttccggt tcagtaggct atccggcgcg ttatgccaac gcaatggctg taggagcgac    360
tgaccaaaac aacagacgtg caaacttttc tcagtatggt acaggaattg acatcgtagc    420
accaggggtt aatgtacaaa gtacgtatcc tggaaaccgt tatgcgagct tgaatggtac    480
ttcaatggca actcctcatg tcgccggcgc cgccgcacta gt                      522

<210> SEQ ID NO 12
<211> LENGTH: 522
<212> TYPE: DNA
<213> ORGANISM: Artificial Sequence
<220> FEATURE:
<223> OTHER INFORMATION: Synthetic

<400> SEQUENCE: 12
gtcgactcaa gatgggaacg ggcacgggac gcacgttgca ggaacagtgg cagctcttaa     60
taattcaatc ggtgtgattg gtgtggcacc aagtgctgat ctatacgctg taaaagtact    120
tggagcaaat ggtagaggaa gcgttagtgg aattgctcaa ggtctagagt gggctgcagc    180
gaataacatg catattgcta acatgagtct cggtagtgat gcacctagta ctacacttga    240
gcgtgcagtc aactacgcga caagccaagg tgtactagtt attgcagcga ctggtaacaa    300
cggttctggt tcagttggct atcctgctcg ttatgcaaac gcaatggctg taggagcgac    360
tgaccaaaac aacagacgtg caaacttttc tcagtatggt acaggaattg acatcgtagc    420
accaggggtt aatgtacaaa gtacgtatcc tggtaaccgt tatgcaagct taagtggtac    480
gtcaatggct acgcctcatg tcgccggcgt cgccgcacta gt                      522

<210> SEQ ID NO 13
<211> LENGTH: 522
<212> TYPE: DNA
<213> ORGANISM: Artificial Sequence
<220> FEATURE:
<223> OTHER INFORMATION: Synthetic

<400> SEQUENCE: 13
gtcgactcaa gatgggaacg ggcacgggac gcacgttgct ggaacagtgg cagctcttaa     60
taattcaatc ggtgtgattg gtgtggcacc aagtgctgat ctatacgctg taaaagtact    120
tggagcaaat ggtagaggaa gcgttagtgg aattgctcaa ggtctagagt gggctgcagc    180
gaataacatg catattgcta acatgagtct cggtagtgat tttcctagct ctacacttga    240
```

```
gcgtgcagtc aactatgcga caagtcgtga tgtactagtt attgcagcga ctggtaacaa    300
cggttctggt tcagtaggct atcctgctcg ttatgcaaac gcaatggctg taggagcgac    360
tgaccaaaac aacagacgcg caaacttttc tcagtatggt acaggaattg acatcgtagc    420
accaggggtt aatgtacaaa gtacgtatcc tggaaaccgc tatgcaagtt taaatggtac    480
atctatggct actccacacg tcgccggcgt cgccgcacta gt                       522

<210> SEQ ID NO 14
<211> LENGTH: 522
<212> TYPE: DNA
<213> ORGANISM: Artificial Sequence
<220> FEATURE:
<223> OTHER INFORMATION: Synthetic

<400> SEQUENCE: 14
gtcgactcaa gatgggaatg ggcatgggac gcacgttgca ggaacagtgg cagctcttaa    60
taattcaatc ggtgtgattg gtgtggcacc aagtgctgat ctatacgctg taaaagtact    120
tggagcaaat ggtagaggaa gcgttagtgg aattgctcaa ggtctagagt gggctgcagc    180
gaataacatg catattgcta acatgagtct cggtagtgat gcacctagta ctacacttga    240
gcgtgcagtc aactatgcga caagccgtga tgtactagtt attgcagcga ctggtaacaa    300
cggttccggt tcagtaggct atcctgctcg ttatgccaac gcaatggctg taggagcgac    360
tgaccaaaac aacagacgtg caaacttttc tcagtatggt acaggaattg acatcgtagc    420
accaggggtt aatgtacaaa gtacgtatcc tggaaaccgc tatgcaagct taagtggtac    480
ttcaatggct acgcctcacg tcgccggcgt cgccgcacta gt                       522

<210> SEQ ID NO 15
<211> LENGTH: 522
<212> TYPE: DNA
<213> ORGANISM: Artificial Sequence
<220> FEATURE:
<223> OTHER INFORMATION: Synthetic

<400> SEQUENCE: 15
gtcgactcaa gatgggaacg ggcatgggac gcacgttgca ggaacagtgg cagctcttaa    60
taactcaatc ggtgtgattg gtgtggcacc aagtgctgat ctatacgctg taaaagtact    120
tggagcaaat ggtagaggaa gcgttagtgg aattgctcaa ggtctagagt gggctgcagc    180
gaataacatg catattgcta acatgagtct cggtagtgat gcacctagta ctacacttga    240
gcgtgcagtc aactatgcga caagccaagg tgtactagtt attgcagcga ctggtaacaa    300
cggttctggt tcagttggct atcctgctcg ttatgcaaac gcaatggctg taggagcgac    360
tgaccaaaac aacagacgtg caaacttttc tcagtatggt acaggaattg acatcgtagc    420
accaggggtt aatgtacaaa gtacgtatcc tggaaaccgc tatgcaagtt taagtggcac    480
ttcaatggca actcctcatg tcgccggcgc cgccgcacta gt                       522

<210> SEQ ID NO 16
<211> LENGTH: 522
<212> TYPE: DNA
<213> ORGANISM: Artificial Sequence
<220> FEATURE:
<223> OTHER INFORMATION: Synthetic

<400> SEQUENCE: 16
gtcgactcaa gatgggaatg ggcatgggac gcacgttgca ggaacagtgg cagctcttaa    60
```

```
taattcaatc ggtgtgattg gtgtggcacc aagtgctgat ctatacgctg taaaagtact      120
tggagcaaat ggtagaggaa gcgttagtgg aattgctcaa ggtctagagt gggctgcagc      180
gaataacatg catattgcta acatgagtct cggtagtgat gcacctagta ctacacttga      240
gcgtgcagtc aactacgcga caagccaagg tgtactagtt attgcagcga ctggtaacaa      300
cggttctggt tcagttggct atcctgctcg ttatgcaaac gcaatggctg taggagcgac      360
tgaccaaaac aacagacgtg caaacttttc tcagtatggt acaggaattg acatcgtagc      420
acctggagtt aacgtacaaa gtacgtatcc aggaaaccgt tatgtgagta tgaatggtac      480
atcaatggca acgccacatg tcgccggcgt cgccgcacta gt                          522

<210> SEQ ID NO 17
<211> LENGTH: 522
<212> TYPE: DNA
<213> ORGANISM: Artificial Sequence
<220> FEATURE:
<223> OTHER INFORMATION: Synthetic

<400> SEQUENCE: 17
gtcgactcaa gatgggaatg ggcatgggac gcatgtagca gggacagttg cggcacttga       60
taactcagtc ggagtcctgg gtgtagcgcc agaggctgac ctttatgcag tgaaggtgct      120
tagcgcatct ggtgccggtt cgattagctc aattgcccaa gggcttgaat ggtctgcagc      180
gaataacatg catattgcta acatgagtct cggtagtgat gcacctagta ctacacttga      240
gcgtgcagtc aactacgcga caagccaagg tgtactagtt attgcagcga ctggtaacaa      300
cggttctggt tcagttggct atcctgctcg ttatgcaaac gcaatggctg taggagcgac      360
tgaccaaaac aacagacgtg caaacttttc tcagtatggt acaggaattg acatcgtagc      420 accagggggtt aatgtacaaa gtacgtatcc tggaaaccgc tatgcaagtt taaatggtac      480
atctatggcc actccacacg tcgccggcgt cgccgcacta gt                          522

<210> SEQ ID NO 18
<211> LENGTH: 522
<212> TYPE: DNA
<213> ORGANISM: Artificial Sequence
<220> FEATURE:
<223> OTHER INFORMATION: Synthetic

<400> SEQUENCE: 18
gtcgactcaa gatgggaatg ggcacgggac gcacgtagca ggaacaatag ccgctctaaa       60
caattcaatc ggtgtgattg gtgtggcacc aagtgctgat ctatacgctg taaaagtact      120
tggagcaaat ggtagaggaa gcgttagtgg aattgctcaa ggtctagagt gggctgcagc      180
gaataacatg catattgcta acatgagtct cggtagtgat gcacctagta ctacacttga      240
gcgtgcagtc aactacgcga caagccaagg tgtactagtt attgcagcga ctggtaacaa      300
cggttctggt tcagttggct atcctgctcg ttatgcaaac gcaatggctg taggagcgac      360
tgaccaaaac aacagacgtg caaacttttc tcagtatggt acaggaattg acatcgtagc      420
acctggagtt aacgtacaaa gtacgtatcc aggaaaccgt tatgtgagta tgaatggtac      480
atctatggcc actccacacg tcgccggcgc cgccgcacta gt                          522

<210> SEQ ID NO 19
<211> LENGTH: 522
<212> TYPE: DNA
<213> ORGANISM: Artificial Sequence
<220> FEATURE:
<223> OTHER INFORMATION: Synthetic
```

```
<400> SEQUENCE: 19
gtcgactcaa gatgggaacg ggcacgggac gcacgttgct ggaacgattg cggctctgga      60
taatgacgaa ggtgttgttg gcgtagcgcc aaatgcggat ctatacgccg ttaaagtgct     120
tagcgcatct ggctctggtt cgattagttc gattgcccaa gggcttgaat ggtctggcga     180
aaacggcatg gatattgcca atttgagtct tggcagctct gctccaagcg caacactcga     240
acaagctgtt aacgcagcaa catctcgtgg tgtacttgta attgctgcat ctggtaactc     300
cggcgctgga tccgttggtt atcctgcacg ttatgcgaat gcgatggcag tcggcgcaac     360
tgatcaaaat aacaaccgcg caagctttc tcaatacggt gctggtcttg atattgtcgc      420
tcctggagtt ggtgttcaaa gcacatatcc aggaaaccgt tatgctagtt taaatggtac     480
gtcgatggca actcctcacg tcgccggcgc cgccgcacta gt                        522

<210> SEQ ID NO 20
<211> LENGTH: 522
<212> TYPE: DNA
<213> ORGANISM: Artificial Sequence
<220> FEATURE:
<223> OTHER INFORMATION: Synthetic

<400> SEQUENCE: 20
gtcgactcaa gatgggaatg ggcacgggac gcacgtagca ggaacaatag ccgctctaaa      60
caattcaata ggcgtacttg gtgttgcacc gaatgctgac ttatatgctg ttaaagtact     120
cggagcaaat ggaagcggaa gtgtaagtgg gattgctcga ggtttagagt gggcggcaac     180
caataacatg catattgcga acatgagtct cggtagtgat gcacctagta ctacacttga     240
gcgtgcagtc aactacgcga caagccaagg tgtactagtt attgcagcga ctggtaacaa     300
cggttccggt tcagtaggct atcctgctcg ttatgccaac gcaatggctg taggagcgac     360
tgaccaaaac aacagacgcg caaacttttc tcagtacggt acaggaattg acatcgtagc     420
accaggggtt aatgtacaaa gtacgtatcc tggaaaccgc tatgcacgtt taaatggtac     480
atctatggct actccacacg tcgccggcgt cgccgcacta gt                        522

<210> SEQ ID NO 21
<211> LENGTH: 522
<212> TYPE: DNA
<213> ORGANISM: Artificial Sequence
<220> FEATURE:
<223> OTHER INFORMATION: Synthetic

<400> SEQUENCE: 21
gtcgactcaa gatgggaacg ggcacgggac gcatgttgct ggaacgattg cggctcttga      60
taactcaatc ggtgtgattg gtgtggcacc aagtgctgat ctatacgctg taaaagtact     120
tggagcaaat ggaagcggaa gtgtaagtgg gattgctcga ggtttagagt gggcggcaac     180
caataacatg catattgcta acatgagtct cggtagtgat gcacctagta ctacacttga     240
gcgtgcagtc aactacgcga caagccaagg tgtactagtt attgcagcga ctggtaacaa     300
cggttctggt tcagttggct atcctgctcg ttatgcgaac gcaatggctg taggagcgac     360
tgaccaaaac aacagacgcg caaacttttc tcagtatggt acaggaattg acatcgtagc     420
accaggggtt aatgtacaaa gtacgtatcc tggaaaccgc tatgcaagtt taaatggtac     480
ttcaatggca actcctcacg tcgccggcgc cgccgcacta gt                        522

<210> SEQ ID NO 22
```

-continued

```
<211> LENGTH: 522
<212> TYPE: DNA
<213> ORGANISM: Artificial Sequence
<220> FEATURE:
<223> OTHER INFORMATION: Synthetic

<400> SEQUENCE: 22
gtcgactcaa gatgggaacg ggcacgggac gcacgttgct ggaacgattg cggctcttga      60
taacgatgaa ggcgttgttg gcgtagcacc aaatgccgat ctttacgcag ttaaggtgct     120
tagcgcatct ggtgccggtt cgattagctc aattgcccaa gggcttgaat ggtctggcga     180
aaacggcatg gatattgcca atttgagtct tggcagctct gctccaagcg caactcttga     240
acaagctgtt aacgcagcga catctcgtgg tgtacttgtt atcgcagcct ctggtaattc     300
tggtgctgga tcagttggtt atcctgcacg ttacgcgaat gcgatggcag taggtgcaac     360
tgatcaaaat aacaaccgtg caagcttctc tcaatacggt gcaggtcttg atattgtcgc     420
tcctggcgta ggtgttcaaa gcacataccc aggttcaaca tatgccagct aaacggtac      480
atcgatggct actcctcacg tcgccggcgt cgccgcacta gt                        522

<210> SEQ ID NO 23
<211> LENGTH: 522
<212> TYPE: DNA
<213> ORGANISM: Artificial Sequence
<220> FEATURE:
<223> OTHER INFORMATION: Synthetic

<400> SEQUENCE: 23
gtcgactcaa gatgggaacg ggcacgggac gcacgttgca ggaacaatag ccgctctaaa      60
caattcaata ggcgtacttg gtgttgcacc gaatgcagaa ttatatgctg ttaaagtact     120
tggagcaagt ggttctggat caatcagtgg aattgctcaa ggtctagagt gggctgcagc     180
gaataacatg catattgcta acatgagtct cggtagtgat gcacctagta ctacacttga     240
gcgtgcagtc aactacgcga caagccaagg tgtactagtt attgcagcga ctggtaacaa     300
cggttccggt tcagtaggct atcctgctcg ttatgcaaac gcaatggctg taggagcgac     360
tgaccaaaac aacagacgtg caaacttttc tcagtatggt acaggaattg acatcgtagc     420
accaggggtt aatgtacaaa gtacgtatcc tggaaaccgc tatgcaagtt taaatggtac     480
atctatggct actccacatg tcgccggcgt cgccgcacta gt                        522

<210> SEQ ID NO 24
<211> LENGTH: 522
<212> TYPE: DNA
<213> ORGANISM: Artificial Sequence
<220> FEATURE:
<223> OTHER INFORMATION: Synthetic

<400> SEQUENCE: 24
gtcgactcaa gatgggaacg ggcacgggac gcacgttgca gggacaatcg ctgctctaaa      60
caattcaata ggcgtactgg gtgtcgcacc gaatgcagaa ttatatgcag ttaaagtact     120
tggtgcaaat ggtagaggaa gcgttagtgg aattgctcaa ggtctagagt gggctgcagc     180
gaataacatg catattgcta acatgagtct cggtagtgat gcacctagta ctacacttga     240
gcgtgcagtc aactacgcga caagccaagg tgtactagtt attgcagcga ctggtaacaa     300
cggttctggt tcagtaggct atcctgctcg ttatgccaac gcaatggctg taggagcgac     360
tgaccaaaac aacaaccgcg ctagcttttc acagtatgga gctgggcttg acattgtcgc     420
gccaggtgtc aatgtgcaga gcacataccc aggttcaaca tatgacagct aagtggcac      480
```
ttcaatggca acgcctcacg tcgccggcgt cgccgcacta gt         522

```
<210> SEQ ID NO 25
<211> LENGTH: 522
<212> TYPE: DNA
<213> ORGANISM: Artificial Sequence
<220> FEATURE:
<223> OTHER INFORMATION: Synthetic
```

<400> SEQUENCE: 25
gtcgactcaa gatgggaatg ggcacgggac gcatgtggcc ggaacagtag cagctcttaa    60
taattcaatc ggtgtgattg gtgtggcacc aagtgctgat ctatacgctg taaaagtact    120
tggagcaaat ggtagaggaa gcgttagtgg aattgctcaa ggtctagagt gggctgcagc    180
gaataacatg catattgcta acatgagtct cggtagtgat gcacctagta ctacacttga    240
gcgtgcagtc aactatgcga caagccaagg tgtactagtt attgcagcga ctggtaacaa    300
cggttccggt tcagtaggct atcctgctcg ttatgcaaac gcaatggctg taggagcgac    360
tgaccaaaac aacagacgtg caaacttttc tcagtatggt acaggaattg acatcgtagc    420
accaggggtt aatgtacaaa gtacgtatcc gggaggtcaa tacgctgagc taagcggaac    480
ctcaatggcc tcaccacacg tcgccggcgc cgccgcacta gt         522

```
<210> SEQ ID NO 26
<211> LENGTH: 522
<212> TYPE: DNA
<213> ORGANISM: Artificial Sequence
<220> FEATURE:
<223> OTHER INFORMATION: Synthetic
```

<400> SEQUENCE: 26
gtcgactcaa gatgggaacg ggcacgggac gcatgtggcc ggaacagtag cagctctaaa    60
caattcaata ggcgtacttg gtgttgcacc gaatgcagaa ttatatgctg ttaaagtact   120
tggagcaagt ggttctggat caatcagtgg aattgctcaa ggtctagagt gggctgcagc   180
gaataacatg catattgcta acatgagtct cggtagtgat gcacctagta ctacacttga   240
gcgtgcagtc aactacgcga caagccaagg tgtactagtt attgcagcga ctggtaacaa   300
cggttccggt tcagtaggct atcctgctcg ttatgccaac gcaatggctg taggagcgac   360
tgaccaaaac aacagacgtg caaacttttc tcagtatggt acaggaattg acatcgtagc   420
accaggggtt gaaattgaaa gcacctaccc aggaagctct tatgacagct aagaggcac   480 ttcaatggca acgcctcacg tcgccggcgc cgccgcacta gt         522

```
<210> SEQ ID NO 27
<211> LENGTH: 522
<212> TYPE: DNA
<213> ORGANISM: Artificial Sequence
<220> FEATURE:
<223> OTHER INFORMATION: Synthetic
```

<400> SEQUENCE: 27
gtcgactcaa gatgggaacg ggcacgggac gcacgttgca ggaacgattg cggctctgga    60
taatgacgaa ggtgttgttg gcgtagcgcc aaatgcggat ctatacgctg taaaagtact   120
tggagcaaat ggtagaggaa gcgttagtgg aattgctcaa ggtctagagt gggctgcagc   180
gaataacatg catattgcta acatgagtct cggtagtgat gcacctagta ctacacttga   240
gcgtgcagtc aactacgcga caagccaagg tgtactagtt attgcagcga ctggtaacaa   300

```
cggttccggt tcagttggct atcctgctcg ttatgcaaac gcaatggctg taggagcgac    360
tgaccaaaac aacagacgtg caaacttttc tcagtatggt acaggaattg acatcgtagc    420
accaggggtt aatgtacaaa gtacgtatcc tggaaaccgc tatgcaagtt taaatggtac    480
atctatggct actccacatg tcgccggcgt cgccgcacta gt                      522
```

<210> SEQ ID NO 28
<211> LENGTH: 522
<212> TYPE: DNA
<213> ORGANISM: Artificial Sequence
<220> FEATURE:
<223> OTHER INFORMATION: Synthetic

<400> SEQUENCE: 28

```
gtcgactcaa gatggcaatg ggcacgggac gcatgtagca ggaacaatag ccgctctaaa    60
caattcagta ggcgtactgg gtgtcgcacc gaatgcagat ctatacgctg taaaagtact    120
tggagcaaat ggtagaggaa gcgttagtgg aattgctcaa ggtctagagt gggctgcagc    180
gaataacatg catattgcta acatgagtct cggtagtgat gcacctagta ctacacttga    240
gcgtgcagtc aactatgcga caagccaagg tgtactagtt attgcagcga ctggtaacaa    300
cggttctggt tcagttggct atcctgctcg ttatgcaaac gcaatggctg taggagcgac    360
tgaccaaaac aacagacgtg caaacttttc tcagtatggt acaggaattg acattgttgc    420
acctggcgtt ggcgttcaga gcacataccc aggtaaccgt tatgcaagct taagtggtac    480
gtcaatggcc tctccgcacg tcgccggcgt cgccgcgcta gt                      522
```

<210> SEQ ID NO 29
<211> LENGTH: 522
<212> TYPE: DNA
<213> ORGANISM: Artificial Sequence
<220> FEATURE:
<223> OTHER INFORMATION: Synthetic

<400> SEQUENCE: 29

```
gtcgactcaa gatgggaacg ggcacgggac gcatgtagca ggaacaatag ccgctctaaa    60
caattcaata ggcgtacttg gtgttgcacc gaatgcagaa ttatatgctg ttaaagtact    120
tggagcaaat ggtagaggaa gcgttagtgg aattgctcaa ggtctagagt gggctgcagc    180
gaataacatg catattgcta acatgagtct cggtagtgat gcacctagta ctacacttaa    240
gcgtgcagtc aactatgcga caagccaagg tgtactagtt attgcagcga ctggtaacaa    300
cggttccggt tcagtaggct atcctgctcg ttatgccaac gcaatggctg taggagcgac    360
tgaccaaaac aacagacgtg caaacttttc tcagtatggt acaggaattg acatcgtagc    420
accaggggtt aatgtacaaa gtacgtatcc tggaaaccgc tatgcaagtt taaatggtac    480
atctatggct actcctcatg ttgcaggtgc ggccgcacta gt                      522
```

<210> SEQ ID NO 30
<211> LENGTH: 522
<212> TYPE: DNA
<213> ORGANISM: Artificial Sequence
<220> FEATURE:
<223> OTHER INFORMATION: Synthetic

<400> SEQUENCE: 30

```
gtcgactcaa gatgggaacg ggcacgggac gcacgttgct ggaacgattg cggctcttaa    60
taattcaatc ggtgtgattg gtgtggcacc gaatgctgac ttatatgctg ttaaagtact    120
cggagcaaat ggaagcggaa gtgtaagtgg gattgctcga ggtttagagt gggcggcaac    180
```

```
caataacatg catattgcga acatgagtct cggtagtgat tttcctagct ctacacttga      240
gcgtgcagtc aactatgcga caagccaagg tgtactagtt attgcagcga ctggtaacaa      300
cggttctggt tcagttggct atcctgctcg ttatgccaac gcaatggctg taggagcgac      360
tgaccaaaac aacagacgtg caaacttttc tcagtatggt acaggaattg acatcgtagc      420
accaggggtt aatgtacaaa gtacgtatcc tggaaaccgc tatgcaagtt taaatggtac      480
ttcaatggca actcctcacg tcgccggcgt cgccgcacta gt                         522
```

<210> SEQ ID NO 31
<211> LENGTH: 522
<212> TYPE: DNA
<213> ORGANISM: Artificial Sequence
<220> FEATURE:
<223> OTHER INFORMATION: Synthetic

<400> SEQUENCE: 31

```
gtcgactcaa gatgggaacg ggcacgggac gcacgttgca ggaacagtgg cagctcttaa      60
taactcaatc ggtgtgattg gtgtggcacc aagtgctgat ctatacgctg taaaagtact     120
tggagcaaat ggtagaggaa gcgttagtgg aattgctcaa ggtctagagt gggctgcagc     180
gaataacatg catattgcta acatgagtct cggtagtgat gcacctagta ctacacttga     240
gcgtgcagtc aactatgcga caagccaagg tgtactagtt attgcagcga ctggtaacaa     300
cggttctggt tcagtaggct atcctgctcg ttatgcaaac gcaatggctg taggagcgac     360
tgaccaaaac aacagacgtg caaacttttc tcagtatggt acaggaattg acatcgtagc     420
accaggggtt aatgtacaaa gtacgtatcc tggaaaccgc tatgcaagtt taaatggtac     480
atctatggca actcctcacg tcgccggcgt cgccgcacta gt                        522
```

<210> SEQ ID NO 32
<211> LENGTH: 522
<212> TYPE: DNA
<213> ORGANISM: Artificial Sequence
<220> FEATURE:
<223> OTHER INFORMATION: Synthetic

<400> SEQUENCE: 32

```
gtcgactcaa gatgggaacg ggcacgggac gcacgttgct ggaacgattg cggctcttga      60
taacgatgaa ggcgttgttg gcgtagcacc aaatgccgat ctttacgcag ttaaggtgct     120
tagcgcatct ggtgccggtt cgattagctc aattgcccaa gggcttgaat ggtctggcga     180
aaacggcatg gatattgcca atttgagtct tggcagctct gctccaagcg caactcttga     240
acaagctgtt aacgcagcga catctcgtgg tgtacttgtt atcgcagcct ctggtaattc     300
tggtgctgga tcagttggtt atcctgcacg ttacgcgaat gcgatggcag taggtgcaac     360
tgatcaaaat aacaaccgtg caagcttctc tcaatacggt gcaggtcttg atattgtcgc     420
tcctggcgta ggtgttcaaa gcacataccc aggttcaaca tatgccagct taaacggtac     480
atcgatggct actcctcacg tcgccggcgt cgccgcacta gt                        522
```

<210> SEQ ID NO 33
<211> LENGTH: 522
<212> TYPE: DNA
<213> ORGANISM: Artificial Sequence
<220> FEATURE:
<223> OTHER INFORMATION: Synthetic

<400> SEQUENCE: 33

```
gtcgactcaa gatggcaatg ggcatgggac gcacgttgca ggaacgattg cggcgctaaa       60
caataatgtt ggtgtacttg gtgttgcgcc taacgttgag ctttatggtg ttaaagtact      120
tggagcaagt ggttctggat caatcagtgg aattgcacaa gggttgcaat gggctggtaa      180
taatggaatg catatagcta atatgagcct tggtacttct gcaccaagcg caactcttga      240
acaagctgtt aacgcagcga catctcgtgg tgtacttgtt atcgcagcct ctggtaattc      300
tggtgctgga tcagttggtt atcctgcacg ttacgcgaat gcgatggctg taggagcgac      360
tgaccaaaac aacagacgtg caaacttttc tcagtatggt acaggaattg acatcgtagc      420
acctggagtt aacgtacaaa gtacgtatcc aggaaaccgt tatgtgagta tgaatggtac      480
atctatggcc actccacacg tcgccggcgt cgccgcacta gt                         522
```

<210> SEQ ID NO 34
<211> LENGTH: 522
<212> TYPE: DNA
<213> ORGANISM: Artificial Sequence
<220> FEATURE:
<223> OTHER INFORMATION: Synthetic

<400> SEQUENCE: 34

```
gtcgactcaa gatgggaatg ggcatgggac gcacgttgca ggaacagtgg cagctcttaa       60
taattcaatc ggtgtgattg gtgtggcacc aagtgctgat ctatacgctg taaaagtact      120
tggagcaaat ggtagaggaa gcgttagtgg aattgctcaa ggtctagagt gggctgcagc      180
gaataacatg catattgcta acatgagtct cggtagtgat gcacctagta ctacacttga      240
gcgtgcagtc aactacgcga caagccaagg tgtactagtt attgcagcga ctggtaacaa      300
cggttccggt tcagttggct atcctgctcg ttatgcaaac gcaatggctg taggagcgac      360
tgaccaaaac aacagacgtg caaacttttc tcagtatggt acaggaattg acatcgtagc      420
accaggggtt aatgtacaaa gtacgtatcc tggaaaccgc tatgcaagtt taaatggtac      480
atctatggct actccacacg tcgccggcgt cgccgcacta gt                         522
```

<210> SEQ ID NO 35
<211> LENGTH: 522
<212> TYPE: DNA
<213> ORGANISM: Artificial Sequence
<220> FEATURE:
<223> OTHER INFORMATION: Synthetic

<400> SEQUENCE: 35

```
gtcgactcaa gatgggaatg ggcatgggac gcacgttgca ggaacagtgg cagctcttaa       60
taattcaatc ggtgtgattg gtgtggcacc aagtgctgat ctatacgctg taaaagtact      120
tggagcaaat ggtagaggaa gcgttagtgg aattgctcaa ggtctagagt gggctgcagc      180
gaataacatg catattgcta acatgagtct cggtagtgat gcacctagta ctacacttga      240
gcgtgcagtc aactacgcga caagccaagg tgtactagtt attgcagcga ctggtaacaa      300
cggttccggt tcagtaggct atcctgctcg ttatgcaaac gcaatggctg taggagcgac      360
tgaccaaaac aacagacgtg caaacttttc tcagtatggt acaggaattg acatcgtagc      420
accaggggtt aatgtacaaa gtacgtatcc tggaaaccgc tatgcaagtt taaatggtac      480
ttcaatggca actcctcacg tcgccggcgt cgccgcacta gt                         522
```

<210> SEQ ID NO 36
<211> LENGTH: 522
<212> TYPE: DNA
<213> ORGANISM: Artificial Sequence

```
<220> FEATURE:
<223> OTHER INFORMATION: Synthetic

<400> SEQUENCE: 36
gtcgacacaa gatggcaatg gacatggcac acatgttgca ggcacagttg cagcactgaa      60
taataacgat ggcgttcttg gcgttgcacc gaacgttgat ctgtatgcag ttaaagttct     120
gggcgcaaac ggcagaggct caatttcagg cattgcacgg ggcctgcaat gggcagcaga     180
taatggcacg catgttgcaa atctgtcact gggcacagat caaccgtcaa caacactgga     240
acgggcagtt aattatgcaa catcacgggg cgttctggtt gttgcagcaa caggcaatac     300
cggctcaggc acagttagct atccggcaag atatgcaaat gcaatggcag ttggcgcaac     360
agatcaaaat aataatagag caaacttttc acaatatggc gcaggcattg atattgttgc     420
accgggcgtt aatgtccaat caacatatcc gggcaacaca tacgtttcac tgaacggcac     480
atcaatggca acaccgcatg ttgcaggcgc tgcagcacta gt                         522

<210> SEQ ID NO 37
<211> LENGTH: 522
<212> TYPE: DNA
<213> ORGANISM: Artificial Sequence
<220> FEATURE:
<223> OTHER INFORMATION: Synthetic

<400> SEQUENCE: 37
gtcgacacaa gatggcaatg gacatggcac acatgttgca ggcacagttg cagcactgaa      60
taatagcgtt ggcgttcttg gcgttgcacc gagcgttgaa ctgtatgcag ttaaagttct     120
gggcgcaaac ggcagaggct caatttcagg cattgcacag gcctggaat gggcaggagc      180 aaatggcatg catattgcaa atatgtcact gggcacatct gcaccgtcat caacactgga     240
acgggcagtt aattcagcag catcacgggg cgttctggtt gttgcagcat caggcaataa     300
cggcgcaggc tcagttagct atccggcaag atatgcaaat gcaatggcag ttggcgcaac     360
agatcaaaat aatagaagag caaacttttc acaatatggc gcaggccttg acattgttgc     420
accgggcgtt ggcgttcaat caacatatcc gggcagcaca tatgcttcac tgagcggcac     480
atcaatggca acaccgcatg ttgcaggcgc tgcagcacta gt                         522

<210> SEQ ID NO 38
<211> LENGTH: 522
<212> TYPE: DNA
<213> ORGANISM: Artificial sequence
<220> FEATURE:
<223> OTHER INFORMATION: Synthetic

<400> SEQUENCE: 38
gtcgacacaa gatggcaatg gacatggcac acatgttgca ggcacagttg cagcactgaa      60
taatagcgat ggcgttattg gcgttgcacc gagcgctgat ctgtatgcag ttaaagttct     120
gggcgcaaac ggcagaggct caatttcagg cattgcacgg gcttggaat gggcagcaaa      180 taatggcatg catgttgcaa atatgtcact gggcacagat caaccgtcag caacactgga     240
acgggcagtt aatcaagcaa catcacaggg cgttctggtt attgcagcaa caggcaataa     300
cggctcaggc tcagttagct atccggcaag atatgcaaat gcaatggcag ttggcgcaac     360
agatcaaaat aataatagag caagcttttc acaatatggc gcaggccttg atattgttgc     420
accgggcgtt ggcgttcaat caacatatcc gggcagcaga tatgcttcac tgaacggcac     480
atcaatggca acaccgcatg ttgcaggcgc tgcagcacta gt                         522
```

<210> SEQ ID NO 39
<211> LENGTH: 522
<212> TYPE: DNA
<213> ORGANISM: Artificial Sequence
<220> FEATURE:
<223> OTHER INFORMATION: Synthetic

<400> SEQUENCE: 39

| | | | | | |
|---|---|---|---|---|---|
| gtcgacacaa | gatggcaatg | gacatggcac | acatgttgca | ggcacaattg | cagcactgaa | 60 |
| taataacatt | ggcgttcttg | gcgttgcacc | gagcgttgaa | ctgtatggag | ttaaagttct | 120 |
| gggcgcaagc | ggcagaggct | caatttcagg | cattgcacgg | ggcctggaat | gggcaggaga | 180 |
| taatggcatg | catgttgcaa | atctgtcatt | gggcacagat | caaccgtcag | caacactgga | 240 |
| acgggcagtt | aatgcagcaa | catcacaggg | cgttctggtt | attgcagcaa | caggcaatag | 300 |
| cggctcaggc | tcagttagct | atccggcaag | atatgcaaat | gcaatggcag | ttggcgcaac | 360 |
| agatcaaaat | aataatagag | caagctcttc | acaatatggc | acaggccttg | atattgttgc | 420 |
| accgggcgtt | ggcgttcaat | caacatatcc | gggcagcaca | tatgtttcac | tgaacggcac | 480 |
| atcaatggca | acaccgcatg | ttgcaggcgc | tgcagcacta | gt | | 522 |

<210> SEQ ID NO 40
<211> LENGTH: 522
<212> TYPE: DNA
<213> ORGANISM: Artificial Sequence
<220> FEATURE:
<223> OTHER INFORMATION: Synthetic

<400> SEQUENCE: 40

| | | | | | |
|---|---|---|---|---|---|
| gtcgacacaa | gatggcaatg | gacatggcac | acatgttgca | ggcacagtcg | cagcactgaa | 60 |
| taataacatt | ggcgttcttg | gcgttgcacc | gagcgttgaa | ctgtatggag | ttaaagttct | 120 |
| gggcgcaagc | ggcagaggct | cagtttcagg | cattgctcgg | ggcctgcaat | ggacagcaga | 180 |
| taatggcatg | catattgcaa | atctgtcact | gggctcatct | tcaccgtcag | caacactgga | 240 |
| acgggcagtt | aattatgcaa | catcacgggg | cgttctggtt | attgcagcaa | caggcaatac | 300 |
| cggcgcaggc | acaattagct | atccggcaag | atatgcaaat | gcaatggcag | ttggcgcaac | 360 |
| agatcaaaat | aataatagag | caagcttttc | acaatatggc | acaggccttg | atattgttgc | 420 |
| accgggcgtt | ggcgttcaat | caacatatcc | gggcagcaca | tatgcttcac | tgaacggcac | 480 |
| atcaatggca | acaccgcatg | ttgcaggcgc | tgcagcacta | gt | | 522 |

<210> SEQ ID NO 41
<211> LENGTH: 522
<212> TYPE: DNA
<213> ORGANISM: Artificial Sequence
<220> FEATURE:
<223> OTHER INFORMATION: Synthetic

<400> SEQUENCE: 41

| | | | | | |
|---|---|---|---|---|---|
| gtcgacacaa | gatggcaatg | gacatggcac | acatgttgca | ggcacaattg | cagcactgaa | 60 |
| taatagcatt | ggcgttcttg | gcgttgcacc | gagcgctgat | ctgtatggag | ttaaagttct | 120 |
| gggcgcaagc | ggcagaggct | caatttcaag | cattgcacgg | ggcctgcaat | gggcagcaga | 180 |
| taatggcatg | catgttgcaa | atctgtcact | gggctcagat | tttccgtcag | caacactgga | 240 |
| acgggcagtt | aattcagcaa | catcacgggg | cgttctggtt | gttgcagcat | caggcaatag | 300 |
| cggcgcaggc | tcaattagct | atccggcaag | atatgcaaat | gcaatggcag | ttggcgcaac | 360 |
| agatcaaaat | aataatagag | caagcttttc | acattatggc | gcaggccttg | atattgttgc | 420 |

```
accgggcgtt ggcgttcaat caacatatcc gggcaacaca tatgcttcac tgaacggcac    480
atcaatggca accccgcatg ttgcaggcgt tgctgcacta gt                       522
```

<210> SEQ ID NO 42
<211> LENGTH: 522
<212> TYPE: DNA
<213> ORGANISM: Artificial Sequence
<220> FEATURE:
<223> OTHER INFORMATION: Synthetic

<400> SEQUENCE: 42

```
gtcgacacaa gatggcaatg gacatggcac acatgttgca ggcacagttg cagcactgaa     60
taataacgtt ggcgttcttg gcgttgcacc gagcgttgat ctgtatgcag ttaaagttct    120
gggcgcaagc ggcagaggct cagtttcaag cattgcacag ggcctggaat gggcagcaac    180
taataatatg catgttgcaa atctgtcact gggctcatct caaccgtcat caacactgga    240
acaggcagtg aatgcagcaa catcacgggg cgttctggtt attgcagcat caggcaataa    300
cggctcaggc acagttagct atccggcaag atatgcaaat gcaatggcag ttggcgcaac    360
agatcaaaat aataatagag caagcttttc acattatggc acaggccttg atattgttgc    420
accgggcgtt ggcgttcaat caacatatcc gggcagcaga tatgcttcac tgaacggcac    480
atcaatggca tcaccgcatg ttgcaggcgt tgcagcacta gt                       522
```

<210> SEQ ID NO 43
<211> LENGTH: 522
<212> TYPE: DNA
<213> ORGANISM: Artificial Sequence
<220> FEATURE:
<223> OTHER INFORMATION: Synthetic

<400> SEQUENCE: 43

```
gtcgacacaa gatggcaatg gacatggcac acatgttgca ggcacaattg cagcactgaa     60
taatagcgtt ggcgttcttg gcgttgcacc gagcgctgaa ctgtatgcag ttaaagttct    120
gggcgcaagc ggcagaggca cagtttcagg cattgcacgg ggcctgcaat gggcagcaga    180
taatggcatg catgttgcaa atctgtcact gggcacacct caaccgtcag caacactgga    240
acgggcagtt aatcaagcaa catcacgggg cgttctggtt attgcagcat caggcaatac    300
cggctcaggc acagttagct atccggcaag atatgcaaat gcaatggcag ttggcgcaac    360
agatcaaaat aatagaagag caaacttttc acaatatggc gcaggccttg atattgttgc    420
accgggcgtt ggcgttcaat caacatatcg ggcagcaca tatgcctcac tgagcggcac     480
atcaatggca tcaccgcatg ttgcaggcgt tgcagcacta gt                       522
```

<210> SEQ ID NO 44
<211> LENGTH: 522
<212> TYPE: DNA
<213> ORGANISM: Artificial Sequence
<220> FEATURE:
<223> OTHER INFORMATION: Synthetic

<400> SEQUENCE: 44

```
gtcgacacaa gatggcaatg gacatggcac acatgttgca ggcacaattg cagcactgaa     60
taatagcgtt ggcgttcttg gcgttgcacc gaacgctgat ctgtatggag ttaaagttct    120
gggcgcaagc ggcagaggca caatttcaag cattgcacgg ggcctggaat gggcaggagc    180
aaatggcatg catgttgcaa atctgtcact gggcacatct tcaccgtcat caacactgga    240
```

| acaggcagtt aatcaagcaa catcacgggg cgttctggtt gttgcagcat caggcaatac | 300 |
| cggctcaggc acagttagct atccggcaac atatgcaaat gcaatggcag ttggcgcaac | 360 |
| agatcaaaat aataatagag caaacttttc acaatatggc accggccttg atattgttgc | 420 |
| accgggcgtt ggcgttcaat caacatatcc gggcagcaga tatgcttctc tgaacggcac | 480 |
| atcaatggca tcaccgcatg ttgcaggcgc tgcagcacta gt | 522 |

<210> SEQ ID NO 45
<211> LENGTH: 522
<212> TYPE: DNA
<213> ORGANISM: Artificial Sequence
<220> FEATURE:
<223> OTHER INFORMATION: Synthetic

<400> SEQUENCE: 45

| gtcgacacaa gatggcaatg gacatggcac acatgttgca ggcacaattg cagcactgaa | 60 |
| taataacgtt ggcgttcttg gcgttgcacc gagcgctgaa ctgtatggag ttaaagttct | 120 |
| gggcgcaagc ggcagcggct caatttcagg cattgcacgg ggcctggaat gggcagcagc | 180 |
| aaatggcatg catgttgcaa atatgtcact gggcacacct tttccgtcag caacactgga | 240 |
| acaggcagtt aaagcagcaa catcacgggg cgttctggtt gttgcagcat caggcaatag | 300 |
| cggcgcaggc tcaattagct atccggcaag atatgcaaat gcaatggcag ttggcgcaac | 360 |
| agatcaaaat aataatagag caagcttttc acaatatggc acaggcattg atattgttgc | 420 |
| accgggcgtt ggcgttaaat caacatatcc gggcagcaca tatgtttcac tgagcggcac | 480 |
| atcaatggca tcaccgcatg ttgcaggcgt tgcagcacta gt | 522 |

<210> SEQ ID NO 46
<211> LENGTH: 522
<212> TYPE: DNA
<213> ORGANISM: Artificial Sequence
<220> FEATURE:
<223> OTHER INFORMATION: Synthetic

<400> SEQUENCE: 46

| gtcgacacag gatggcaatg gacatggcac acatgttgca ggcacagttg cagcactgaa | 60 |
| taataacgtt ggcgttcttg gcgttgcacc gagcgctgaa ctgtacgcag ttaaagttct | 120 |
| gggcgcaaac ggcagcggca cagtttcaag cattgcacag ggcctggaat gggcaggaaa | 180 |
| taatggcatg catgttgcaa atctgtcact gggcacagat caaccgtcag caacactgga | 240 |
| acgggcagtt aatgcagcaa catcacgggg cgttctggtt gttgcagcat caggcaatac | 300 |
| cggctcaggc tcagttggct atccggcaag atatgcaaat gcaatggcag ttggcgcaac | 360 |
| agatcaaaat aataatagag caaacttttc acaatatggc gcaggccttg atattgttgc | 420 |
| accgggcgtt ggcgttcaat caacatatcc gggcaacaga tatgcttcaa tgaacggcac | 480 |
| atcaatggca acaccgcatg ttgcaggcgc tgcagcacta gt | 522 |

<210> SEQ ID NO 47
<211> LENGTH: 522
<212> TYPE: DNA
<213> ORGANISM: Artificial Sequence
<220> FEATURE:
<223> OTHER INFORMATION: Synthetic

<400> SEQUENCE: 47

| gtcgacacaa gatggcaatg gacatggcac acatgttgca ggcacaattg cagcactgaa | 60 |
| taataacatt ggcgttcttg gcgttgcacc gagcgctgaa ctgtatgcag ttaaagttct | 120 |

| | |
|---|---|
| gggcgcaagc ggcagaggct cagtttcaag tattgcacag ggcctggaat gggcaggaga | 180 |
| taatggcatg catgttgcaa atctgtcact gggctcacct tttccgtcat caacactgga | 240 |
| acgggcagtt aatgcagcaa catcacgggg cgttctggtt attgcagcat caggcaatag | 300 |
| cggctcaggc tcaattagct atccggcaag atatgcgaat gcaatggcag ttggcgcaac | 360 |
| agatcaaaat aataatagag caaactcttc acaatatggc gcaggccttg agattgttgc | 420 |
| accgggcgtt ggcgttcaat caacatatcc gggcagcaca tatgtctcaa tgagcggcac | 480 |
| atcaatggca tcaccgcatg ttgcaggcgc tgcagcacta gt | 522 |

<210> SEQ ID NO 48
<211> LENGTH: 522
<212> TYPE: DNA
<213> ORGANISM: Artificial Sequence
<220> FEATURE:
<223> OTHER INFORMATION: Synthetic

<400> SEQUENCE: 48

| | |
|---|---|
| gtcgacacaa gatggcaatg gacatggcac acatgttgca ggcacaattg cagcactgaa | 60 |
| taataacgtt ggcgttattg gcgttgcacc gaacgttgaa ctgtatggag ttaaagttct | 120 |
| gggcgcaaac ggcagaggca caatttcaag cattgcacgg ggcctggaat gggcagcaaa | 180 |
| taatggcacg catattgcaa atctgtcact gggcacagat caaccgtcag caacactgga | 240 |
| acgggcagtt aatcaagcaa catcacaggg cgttctggtt attgcagcat caggcaatag | 300 |
| cggctcaggc tcagttagct atccggcaag atatgcaaat gcaatggcag ttggcgcaac | 360 |
| agatcaaaat aataatagag caagcttttc acattatggc acaggccttg atattgttgc | 420 |
| accgggcgtt ggcgttcaat caacatatcc gggcagcaga tatgcttcac tgaacggcac | 480 |
| atcaatggca tcaccgcatg ttgcaggcgt tgcagcacta gt | 522 |

<210> SEQ ID NO 49
<211> LENGTH: 522
<212> TYPE: DNA
<213> ORGANISM: Artificial Sequence
<220> FEATURE:
<223> OTHER INFORMATION: Synthetic

<400> SEQUENCE: 49

| | |
|---|---|
| gtcgacacaa gatggcaatg gacatggcac acatgttgca ggcacagttg cagcactgaa | 60 |
| taatagcgtt ggcgttcttg gcgttgcacc gagcgctgat ctgtatgcag ttaaagttct | 120 |
| gggcgcaagc ggcagaggca cagtttcaag cattgcacgg ggcctggaat gggcagcaga | 180 |
| taataatatg catattgcaa atctgtcact gggcacagat caaccgtcag caacactgga | 240 |
| acaggcagtt aatgcagcaa catcacaggg cgttctggtt gttgcagcat caggcaataa | 300 |
| cggctcaggc tcaattggct atccggcaag atatgcaaat gcaatggcag ttggcgcaac | 360 |
| agatcaaaat aataatagag caagcttttc acaatatggc acaggccttg atattgttgc | 420 |
| accgggcgtt ggcgttcaat caacatatcc gggcaacaca tatgtttcac tgagcggcac | 480 |
| atcaatggca acaccgcatg ttgcaggcgc tgcagcacta gt | 522 |

<210> SEQ ID NO 50
<211> LENGTH: 522
<212> TYPE: DNA
<213> ORGANISM: Artificial Sequence
<220> FEATURE:
<223> OTHER INFORMATION: Synthetic

```
<400> SEQUENCE: 50
gtcgacacaa gatggcaatg gacatggcac acatgttgca ggcacagttg cagcactgaa      60
taataacgtt ggcgttattg gcgttgcacc gagcgctgat ctgtatgcag ttaaagttct     120
gggcgcaagc ggcagaggca caatttcagg cattgcacag ggcctggaat gggcaggaga    180
taatggcatg catgttgcaa atctgtcact gggctcagat caaccgtcag caacactgga    240
acaggcagtt aatgcagcaa catcacaggg cgttctggtt gttgcagcat caggcaatag    300
cggctcaggc tcagttggct atccggcaag atatgcaaat gcaatggcag ttggcgcaac    360
agatcaaaat aataatagag caagcttttc acaatatggc caaggccttg atattgttgc    420
accgggcgtt ggcgttcaat cgacatatcc gggcagcaga tatgcttcaa tgagcggcac    480
atcaatggca tcaccgcatg ttgcaggcgt tgcagcacta gt                        522

<210> SEQ ID NO 51
<211> LENGTH: 522
<212> TYPE: DNA
<213> ORGANISM: Artificial Sequence
<220> FEATURE:
<223> OTHER INFORMATION: Synthetic

<400> SEQUENCE: 51
gtcgacacaa gatggcaatg gacatggcac acatgttgca ggcacagttg cagcactgaa     60
taatagcatt ggcgttcttg gcgttgcacc gagcgttgat ctgtatgcag ttaaagttct    120
gggcgcaaac ggcagaggca cagtttcagg cattgcacag ggcctggaat gggcagcaga   180
taaaggcatg catgttgcaa atctgtcact gggctcatct tcaccgtcaa caacactgga   240
acaggcggtt aatgcagcaa catcacaggg cgttctggtt attgcagcaa caggcaatag   300
cggcgcaggc tcaattagct atccggcaag atatgcaaat gcaatggcag ttggcgcaac   360
agatcaaaat aataatagag caagcttttc acaatatggc caaggccttg atattgttgc   420
accgggcgtt ggcgttcaat caacatatcc gggcagcaca tatgtttcac tgagcggcac   480
atcaatggca acaccgcatg ttgcaggcgc tgcagcacta gt                       522

<210> SEQ ID NO 52
<211> LENGTH: 522
<212> TYPE: DNA
<213> ORGANISM: Artificial Sequence
<220> FEATURE:
<223> OTHER INFORMATION: Synthetic

<400> SEQUENCE: 52
gtcgacacaa gatggcaatg gacatggcac acatgttgca ggcacaattg cagcactgaa     60
taataacgat ggcgttcttg gcgttgcacc gagcgttgaa ctgtatggag ttaaagttct    120
gggcgcaagc ggcagaggca cagtttcaag cattgcacga ggcctggaat gggcagcaaa   180
taatggcatg catgttgcaa atatgtcact gggcacacct gcaccgtcaa caacactgga   240
acgggcagtt aatcaagcaa catcacgggg cgttctggtt attgcagcat caggcaataa   300
cggctcaggc tcaattagct atccggcaag atatgcaaat gcaatggcag ttggcgcaac   360
agatcaaaat aatagaagag caagcttttc acaatatggc gcaggccttg atattgttgc   420
accgggcgtt ggcgttcaat caacatatcc gggcagcaga tatgcttcac tgagcggcac   480
atcaatggca tcaccgcatg ttgcaggcgt tgcagcacta gt                        522

<210> SEQ ID NO 53
<211> LENGTH: 522
```

<210> SEQ ID NO 53
<211> LENGTH: 522
<212> TYPE: DNA
<213> ORGANISM: Artificial Sequence
<220> FEATURE:
<223> OTHER INFORMATION: Synthetic

<400> SEQUENCE: 53

```
gtcgacacaa gatggcaatg gacatggcac acatgttgca ggcacagttg cagcactgaa      60
taatagcgtt ggcgtttttg gcgttgcacc gagcgttgat ctgtatgcag ttaaagttct     120
gggcgcaagc ggcagcggca cagtttcaag cgttgcacag ggcctgcaat gggcaggaga     180
taatggcatg catgttgcaa atctgtcact gggctcagat gcaccgtcag caacactgga     240
acaggcagtt aattcagcaa catcacgggg cgttctggtt gttgcagcat caggcaatac     300
cggcgcaggc acagttggct atccggcaag atatgcaaat gcaatggcag ttggcgcaac     360
agatcaaaat aatagaagag caaacttttc acaatatggc gcaggccttg atattgttgc     420
accgggcgtt ggcgttcaat caacatatcc gggcagcaca tatgcttcac tgaacggcac     480
atcaatggca acaccgcatg ttgcaggcgt tgcagcacta gt                        522
```

<210> SEQ ID NO 54
<211> LENGTH: 522
<212> TYPE: DNA
<213> ORGANISM: Artificial Sequence
<220> FEATURE:
<223> OTHER INFORMATION: Synthetic

<400> SEQUENCE: 54

```
gtcgacacaa gatggcaatg gacatggcac acatgttgca ggcacagttg cagcactgaa      60
taatagcgtt ggcgttcttg gcgttgcacc gagcgttgaa ctgtatgcag ttaaagttct     120
gggcgcaagc ggcagcggct caatttcagg cattgcacgg ggcctggaat gggcagcaga     180
taataatacg catgttgcaa atctgtcact gggctcagat tttccgtcag caacactgga     240
acgggcagtt aattatgcaa catcacgggg cgttctggtt gttgcagcat caggcaatac     300
cggctcaggc acaattggct atccggcaag atatgcaaat gcaatggcag ttggcgcaac     360
agatcaaaat aatagaagag caagcttttc acaatatggc acaggccttg atattgttgc     420
accgggcgtt ggcgttcaat cgacatatcc gggcagcaga tatgcttcac tgaacggcac     480
atcaatggca tcaccgcatg ttgcaggcgt tgcagcacta gt                        522
```

<210> SEQ ID NO 55
<211> LENGTH: 522
<212> TYPE: DNA
<213> ORGANISM: Artificial Sequence
<220> FEATURE:
<223> OTHER INFORMATION: Synthetic

<400> SEQUENCE: 55

```
gtcgacacaa gatggcaatg gacatggcac acatgttgca ggcacagttg cagcactgaa      60
taatagcgat ggcgttattg gcgttgcacc gagcgctgaa ctgtatgcag ttaaagttct     120
gggcgcaaac ggcagcggct cagtttcagg cattgcacgg ggcctggaat gggcaggagc     180
aaatggcatg catgttgcaa atctgtcact gggcacagat caaccgtcag caacactgga     240
acaggcagtt aatcaagcaa catcacgggg cgttctggtt gttgcagcat caggcaatag     300
cggctcaggc acagttggct atccggcaag atatgcaaat gcaatggcag ttggcgcaac     360
agatcaaaat aataatagag caagcttttc acaatatggc gcaggcattg atattgttgc     420
accgggcgtt ggcgttcaat caacatatcc gggcagcaga tatacttcac tgagcggcac     480
```

| atcaatggca acaccgcatg ttgcaggcgc tgcagcacta gt | 522 |

<210> SEQ ID NO 56
<211> LENGTH: 522
<212> TYPE: DNA
<213> ORGANISM: Artificial Sequence
<220> FEATURE:
<223> OTHER INFORMATION: Synthetic

<400> SEQUENCE: 56

| gtcgacacaa gatggcaatg gacatggcac acatgttgca ggcacagttg cagcactgaa | 60 |
| taataacatt ggcgttattg gcgttgcacc gaacgttgaa ctgtatgcag ttaaagttct | 120 |
| gggcgcaagc ggcagcggct cagtttcaag cattgcacgg gcctgcaat gggcagcaaa | 180 |
| taatggcatg catattgcaa atctgtcact gggctcatct gcaccgtcag caacactgga | 240 |
| acgggcagtt aatgcagcaa catcacgggg cgttctggtt gttgcagcat caggcaatag | 300 |
| cggcgcaggc tcaattggct atccggcaag atatgcaaat gcaatggcag ttggcgcaac | 360 |
| agatcaaaat aataatagag caagcttttc acaatatggc gcaggccttg atattcttgc | 420 |
| accgggcgtt ggcgttcaat caacatatcc gggcagcaca tatgcttcaa tgagcggcac | 480 |
| atcaatggca acaccgcatg ttgcaggcgc tgcagcacta gt | 522 |

<210> SEQ ID NO 57
<211> LENGTH: 522
<212> TYPE: DNA
<213> ORGANISM: Artificial Sequence
<220> FEATURE:
<223> OTHER INFORMATION: Synthetic

<400> SEQUENCE: 57

| gtcgacacaa gatggcaatg gacatggcac acatgttgca ggcacagttg cagcactgaa | 60 |
| taatagcgtt ggcgttcttg gcgttgcacc gagcgctgat ctgtatgcag ttaaagttct | 120 |
| gggcgcaagc ggcagaggct cagtttcagg cattgcacag ggtctggaat gggcagcaga | 180 |
| taatggcatg catgttgcaa atatgtcact gggcacagat tttccgtcag caacactgga | 240 |
| acaggcagtt aatgcagcaa catcacggga cgttctggtt gttgcagcaa caggcaatac | 300 |
| cggctcaggc acagttggct atccggcaag atatgcaaat gcaatggcag ttggcgcaac | 360 |
| agatcaaaat aataatagag caaacttttc acaatatggc acaggccttg atattgttgc | 420 |
| accgggcgtt ggcgttcaat caacatatcc gggcagcaga tatgtttcaa tgagcggcac | 480 |
| atcaatggca tcaccgcatg ttgcaggcgc tgcagcacta gt | 522 |

<210> SEQ ID NO 58
<211> LENGTH: 522
<212> TYPE: DNA
<213> ORGANISM: Artificial Sequence
<220> FEATURE:
<223> OTHER INFORMATION: Synthetic

<400> SEQUENCE: 58

| gtcgacacaa gatggcaatg gacatggcac acatgttgca ggcacaattg cagcactgaa | 60 |
| taatagcgtt ggcgttcttg gcgttgcacc gagcgctgat ctgtatgcag ttaaagttct | 120 |
| gggcgcaagc ggcagaggct cagtttcaag cattgcacgg gcctggaat gggcagcaaa | 180 |
| taatggcatg catgttgcaa atctgtcact gggctcacct tttccgtcat caacactgga | 240 |
| acgggcagtt aattatgcaa catcacggga cgttctggtt attgcagcaa caggcaatag | 300 |
| cggcgcaggc acagttggct atccggcaag atatgcaaat gcaatggcag ttggcgcaac | 360 |

| agatcaaaat aataatagag caagctcttc acaatatggc gcaggccttg atattgttgc | 420 |
| accgggcgtt ggcgttcaat caacatatcc gggcagcaca tatgcttcac tgaacggcac | 480 |
| atcaatggca tcaccgcatg ttgcaggcgc tgcagcacta gt | 522 |

<210> SEQ ID NO 59
<211> LENGTH: 522
<212> TYPE: DNA
<213> ORGANISM: Artificial Sequence
<220> FEATURE:
<223> OTHER INFORMATION: Synthetic

<400> SEQUENCE: 59

| gtcgacacaa gatggcaatg acatggcac acatgttgca ggcacagttg ctgcactgaa | 60 |
| taatagcatt ggcgttcttg gcgttgcacc gagcgctgat ctgtatggag ttaaagttct | 120 |
| gggcgcaagc ggcagaggct caatttcaag cattgcacgg ggcctggaat gggcaggaaa | 180 |
| taatggcatg catattgcaa atatgtcact gggctcagat caaccgtcag caacactgga | 240 |
| acgggcagtt aattcagcaa catcacgggg cgttctggtt gttgcagcat caggcaatag | 300 |
| cggcgcaggc tcagttacct atccggcaag atatgcaaat gcaatggcag ttggcgcaac | 360 |
| agatcaaaat aatagaagag caagcttttc acattatggc gcaggccttg atattgttgc | 420 |
| accgggcgtt ggcgttcaat caacatatcc gggcagcaga tatgcttcac tgagcggcac | 480 |
| atcaatggca tcaccgcatg ttgcaggcgt tgcagcacta gt | 522 |

<210> SEQ ID NO 60
<211> LENGTH: 522
<212> TYPE: DNA
<213> ORGANISM: Artificial Sequence
<220> FEATURE:
<223> OTHER INFORMATION: Synthetic

<400> SEQUENCE: 60

| gtcgacacaa gatggcaatg acatggcac acatgttgca ggcacagttg cagcactgaa | 60 |
| taataacgtt ggcgttattg gcgttgcacc gagcgctgaa ctgtatgcag ttaaagttct | 120 |
| gggcgcaagc ggcagcggca caatttcagg cattgcacag ggcctgcaat gggcagcaga | 180 |
| taatggcacg catgttgcaa atctgtcact gggctcagat tttccgtcat caacactgga | 240 |
| acaggcagtt aattcagcaa catcacgggg cgttctggtt gttgcagcat caggcaataa | 300 |
| tggctcaggc tcagttagct atccggcagg gtatgcaaat gcaatggcag ttggcgcaac | 360 |
| agatcaaaat aatagaagag caagctcttc acaatatggc gcaggccttg atattgtcgc | 420 |
| accgggcgtt ggcgttcaat caacatatcc gggcagcaga tatgcttcac tgagcggcac | 480 |
| atcaatggca acaccgcatg ttgcaggcgc tgcagcacta gt | 522 |

<210> SEQ ID NO 61
<211> LENGTH: 522
<212> TYPE: DNA
<213> ORGANISM: Artificial Sequence
<220> FEATURE:
<223> OTHER INFORMATION: Synthetic

<400> SEQUENCE: 61

| gtcgacacaa gatggcaatg acatggcac acatgttgca ggcacagttg cagcactgaa | 60 |
| taataacgat ggcgttcttg gcgttgcacc gagcgctgat ctgtatggag ttaaagttct | 120 |
| gggcgcaaac ggcagaggct cagtttcagg cattgcacgg ggcttggaat gggcagcaga | 180 |

| | |
|---|---|
| taatggcatg catgttgcaa atatgtcact gggcacatct gcaccgtcag caacactgga | 240 |
| acaggcagtt aatcaagcaa catcacgggg cgttctggtt gttgcagcat caggcaatag | 300 |
| cggcgcaggc acaattggct atccggcaag atatgcaaat gcaatggcag ttggcgcaac | 360 |
| agatcaaaat aataatagag caagcttttc acaatatggc gcaggccttg atattgttgc | 420 |
| accgggcgtt ggcgttcaat caacatatcc gggcagcaca tatgtttcac tcaacggcac | 480 |
| atcaatggca acaccgcatg ttgcaggcgt tgcagcacta gt | 522 |

<210> SEQ ID NO 62
<211> LENGTH: 522
<212> TYPE: DNA
<213> ORGANISM: Artificial Sequence
<220> FEATURE:
<223> OTHER INFORMATION: Synthetic

<400> SEQUENCE: 62

| | |
|---|---|
| gtcgacacaa gatggcaatg gacatggcac acatgttgca ggcacagttg cagcactgaa | 60 |
| taatagcatt ggcgttcttg gcgttgcacc gagcgctgat ctgtatgcag ttaaagttct | 120 |
| gggcgcaagc ggcagaggca cagtttcaag cattgcacag gcctggaat gggcagcaaa | 180 |
| taatggcacg catgttgcaa atctgtcact gggcacacct tcaccgtcaa caacactgga | 240 |
| acggcagtt aattatgcaa catcacgggg cgttctggtt gttgcagcat caggcaatag | 300 |
| cggcgcaggc tcagttagct atccggcaag atatgcaaat gcaatggcag ttggcgcaac | 360 |
| agatcaaaat aatagaagag caagcttttc acaatatggc gcaggccttg atattgttgc | 420 |
| accggccgtt aatgttcaat caacatatcc gggcagcaca tatgcttcaa tgagcggcac | 480 |
| atcaatggca tcaccgcatg ttgcaggcgc tgcagcacta gt | 522 |

<210> SEQ ID NO 63
<211> LENGTH: 522
<212> TYPE: DNA
<213> ORGANISM: Artificial Sequence
<220> FEATURE:
<223> OTHER INFORMATION: Synthetic

<400> SEQUENCE: 63

| | |
|---|---|
| gtcgacacaa gatggcaatg gacatggcac acatgttgca ggcacaattg cagcactgaa | 60 |
| taatagcgat ggcgttattg gcgttgcacc gaacgctgat ctgtatgcag ttaaagttct | 120 |
| gggcgcaagc ggcagaggca cagtttcagg cattgcacag gcctggaat gggcagcagc | 180 |
| aaatggcatg catgttgcaa atatgtcact gggcacacct caaccgtcag caacactgga | 240 |
| acggcagtt aatgcagcaa cctcacaggg cgttctggtt gttgcagcat caggcaataa | 300 |
| cggctcaggc tcaattagct atccggcaag atatgcaaat gcaatggcag ttggcgcaac | 360 |
| agatcaaaat aatagaagag caagctcttc acaatatggc acaggccttg atattgttgc | 420 |
| accgggcgtt ggcgttcaat caacatatcc gggcagcaga tatgcttcac tgaacggcac | 480 |
| atcaatggca tcaccgcatg ttgcaggcgt tgcagcacta gt | 522 |

<210> SEQ ID NO 64
<211> LENGTH: 522
<212> TYPE: DNA
<213> ORGANISM: Artificial Sequence
<220> FEATURE:
<223> OTHER INFORMATION: Synthetic

<400> SEQUENCE: 64

| | |
|---|---|
| gtcgacacaa gatggcaatg gacatggcac acatgttgca ggcacaattg cagcactgaa | 60 |

```
taatagcatt ggcgttcttg gcgttgctcc gaacgctgaa ctgtatggag ttaaagttct    120
gggcgcaagc ggcagcggca cagtttcagg cattgcacgg ggcctggaat gggcagcaaa    180
taatggcatg catattgcaa atatgtcact gggcacagat gcaccgtcat caacactgga    240
acaggcagtt aattcagcaa catcacaggg cgttctggtt attgcagcaa caggcaatag    300
cggcgcaggc acaattagct atccggcaag atatgcaaat gcaatggcag ttggcgcaac    360
agatcaaaat aatagaagag caagcttttc acaatatggc acaggcattg atattgttgc    420
accgggcgtt ggcgttcaat caacatatcc gggcagcaca tatgcttcac tgaacggcac    480
atcaatggca tcaccgcatg ttgcaggcgc tgcagcacta gt                      522

<210> SEQ ID NO 65
<211> LENGTH: 522
<212> TYPE: DNA
<213> ORGANISM: Artificial Sequence
<220> FEATURE:
<223> OTHER INFORMATION: Synthetic

<400> SEQUENCE: 65
gtcgacacaa gatggcaatg gacatggcac acatgttgca ggcacagttg cagcactgaa     60
taatagcatt ggcgttcttg gcgttgcacc gaacgctgaa ctgtatggag ttaaagttct    120
gggcgcaaac ggcagcggct caatttcagg catagcacgg ggcctggaat gggcaggaaa    180
taatggcatg catattgcaa atctgtcact gggcacagat tcaccgtcag caacactgga    240
acaggcagtt aattatgcaa catcacgggg cgttctggtt attgcagcat caggcaatag    300
cggctcaggc acagttggct atccggcaag atatgcaaat gcaatggcag ttggcgcaac    360
agatcaaaat aataatagag caagcttttc acaatatggc acaggccttg atattgttgc    420
accgggcgtt ggcgttcaat caacatatcc gggcagcaca tatgcttcac tgaacggcac    480
atcaatggca tcaccgcatg ttgcaggcgc tgcagcacta gt                      522

<210> SEQ ID NO 66
<211> LENGTH: 522
<212> TYPE: DNA
<213> ORGANISM: Artificial Sequence
<220> FEATURE:
<223> OTHER INFORMATION: Synthetic

<400> SEQUENCE: 66
gtcgacacaa gatggcaatg gacatggcac acatgttgca ggcacagttg cagcactgaa     60
taatagcgtt ggcgttattg gcgttgcacc gaacgctgat ctgtatgcag ttaaagttct    120
gggcgcaaac ggcagaggca caatttcaag cattgcacgg ggcctggaat gggcaggaga    180
taatggcatg catgttgcaa atctgtcact gggctcacct gcaccgtcag caacactgga    240
acaggcagtt aatcaagcaa catcacgggg cgttctggtt attgcagcat caggcaataa    300
cggctcaggc tcagttagct atccggcaag atatgcaaat gcaatggcag ttggcgcaac    360
agatcaaaat aataatagag caagctcttc acaatatggc gcaggccttg atattgttgc    420
accgggcgtt ggcgttcaat caacatatcc gggcagcaca tatgcttcac tgagcggcac    480
atcaatggca acaccgcatg ttgcaggcgc tgcagcacta gt                      522

<210> SEQ ID NO 67
<211> LENGTH: 522
<212> TYPE: DNA
<213> ORGANISM: Artificial sequence
<220> FEATURE:
```

<223> OTHER INFORMATION: Synthetic

<400> SEQUENCE: 67

```
gtcgacacaa gatggcaatg gacatggcac acatgttgca ggcacagttg cagcactgaa     60
taatagcgtt ggcgttcttg gcgttgcacc gagcgctgaa ctgtatgcag ttaaagttct    120
gggcgcaagc ggcagaggca caatttcagg cattgcacag gcctggaat gggcagcaga     180
taatggcatg catgttgcaa atctgtcact gggcacatct gcaccgtcag caacactgga    240
acgggcagtt aatgcagcaa catcacgggg cgttctggtt gttgcagcat caggcaatag    300
cggcgcaggc acagttagct atccggcaag atatgcaaat gcaatggcag ttggcgcaac    360
agatcaaaat aataatagag caagcttttc acaatatggc acaggccttg atattgttgc    420
acccggcgtt ggcgttcaat caacatatcc gggcaacaca tatgcttcaa tgagcggcac    480
atcaatggca tcaccgcatg ttgcaggcgc tgcagcacta gt                       522
```

<210> SEQ ID NO 68
<211> LENGTH: 522
<212> TYPE: DNA
<213> ORGANISM: Artificial Sequence
<220> FEATURE:
<223> OTHER INFORMATION: Synthetic

<400> SEQUENCE: 68

```
gtcgacacaa gatggcaatg gacatggcac acatgttgca ggcacagttg cagcactgaa     60
taataacgtt ggcgttcttg gcgttgcacc gagcgctgaa ctgtatgcag ttaaagttct    120
gggcgcaagc ggcagaggca cagtttcaag cattgcacgg gcctgcaat gggcaggaga     180
taatggcatg catgttgcaa atatgtcact gggcacatct tttccgtcag caacactgga    240
acaggcagtt aatgcagcaa catcacaggg cgttctggtt gttgcagcat caggcaatac    300
cggctcaggc tcagttggct atccggcaag atatgcaaat gcaatggcag ttggcgcaac    360
agatcaaaat aataatagag caaacttttc acaatatggc acaggcattg atattgttgc    420
accgggcgtt ggcgttcaat caacatatcc gggcagcaca tatgcttcac tgaacggcac    480
atcaatggca acaccgcatg ttgcaggcgc tgcagcacta gt                       522
```

<210> SEQ ID NO 69
<211> LENGTH: 522
<212> TYPE: DNA
<213> ORGANISM: Artificial Sequence
<220> FEATURE:
<223> OTHER INFORMATION: Synthetic

<400> SEQUENCE: 69

```
gtcgacacaa gatggcaatg gacatggcac acatgttgca ggcacaattg cagcactgaa     60
taatagcgtt ggcgttcttg gcgttgcacc gagcgttgat ctgtatggag ttaaagttct    120
gggcgcaagc ggcagaggct cagtttcagg cattgcacag gcctggaat gggcagcagc     180
aaatggcatg catgttgcaa atatgtcact gggctcagat gcaccgtcag caacactgga    240
acgggcagtt aatcagcaa catcacgggg cgttctggtt attgcagcaa caggcaataa     300
cggctcaggc tcaattagct atccggcaag atatgcaaat gcaatggcag ttggcgcaac    360
agatcaaaat aataatagag caagcttttc acaatatggc gcaggccttg atattgttgc    420
accgggcgtt aatgttcaat caacatatcc gggcagcaca tatgtttcac tgagcggcac    480
atcaatggca tcaccgcatg ttgcaggcgc tgcagcacta gt                       522
```

<210> SEQ ID NO 70
<211> LENGTH: 522
<212> TYPE: DNA
<213> ORGANISM: Artificial Sequence
<220> FEATURE:
<223> OTHER INFORMATION: Synthetic

<400> SEQUENCE: 70

```
gtcgacacaa gatggcaatg gacatggcac acatgttgca ggcacagttg cagcactgaa      60
taataacgat ggcgttcttg gcgttgcacc gaacgctgaa ctgtatgcag ttaaagttct     120
gggcgcaagc ggcagcggca cagtttcagg cattgcacag ggcctggaat gggcagcaga     180
taatggcacg catattgcaa atctgtcact gggcacacct caaccgtcag caacactgga     240
acgggcagtt aaatcagcaa catcacgggg cgttctggtt gttgcagcat caggcaatag     300
cggcgcaggc tcagttagct atccggcaag atatgcaaat gcaatggcag ttggcgcaac     360
agatcaaaat aataatagag caagcttttc acaatatggc gcaggcattg atattgttgc     420
accgggcgtt ggcgttcaat caacatatcc gggcagcaca tatgcttcaa tgagcggcac     480
atcaatggca acaccgcatg ttgcaggcgt tgcagcacta gt                        522
```

<210> SEQ ID NO 71
<211> LENGTH: 522
<212> TYPE: DNA
<213> ORGANISM: Artificial Sequence
<220> FEATURE:
<223> OTHER INFORMATION: Synthetic

<400> SEQUENCE: 71

```
gtcgacacaa gatggcaatg gacatggcac acatgttgca ggcacagttg cagcactgaa      60
taatagcgat ggcgttattg gcgttgcacc gagcgctgat ctgtatggag ttaaagttct     120
gggcgcaaac ggcagcggct caatttcagg cattgcacag ggcctggaat gggcagcagc     180
aaatggcatg catgttgcaa atatgtcact gggcacatct tttccgtcat caacactgga     240
acaggcagtt aatgcggcaa catcacgggg cgttctggtt gttgcagcat caggcaatag     300
cggcgcaggc acagttagct atccggcaag atatgcaaat gcaatggcag ttggcgcaac     360
agatcaaaat aataatagag caagcttttc acaatatggc gcaggcattg atattgttgc     420
accgggcgtt ggcgttcaat caacatatcc gggcaacaga tgtgtttcac tgagcggcac     480
atcaatggca acaccgcatg ttgcaggcgc tgcagcacta gt                        522
```

<210> SEQ ID NO 72
<211> LENGTH: 522
<212> TYPE: DNA
<213> ORGANISM: Artificial Sequence
<220> FEATURE:
<223> OTHER INFORMATION: Synthetic

<400> SEQUENCE: 72

```
gtcgacacaa gatggcaatg gacatggcac acatgttgca ggcacagttg cagcactgaa      60
taataacgtt ggcgttcttg gcgttgcacc gagcgttgat ctgtatgcag ttaaagttct     120
gggcgcaaac ggcagcggca caatttcagg cattgcacag ggcctggaat gggcagcaaa     180
taatggcatg catgttgcaa atatgtcact gggctcacct gcaccgtcag caacactgga     240
acgggcagtt aatcaagcaa catcacgggg cgttctggtt gttgcagcaa caggcaatag     300
cggctcaggc acagttggct atccggcaag atatgcaaat gcaatggcag ttggcgcaac     360
agatcaaaat aataatagag caagcttttc acaatatggc gcaggcattg atattgttgc     420
```

```
accgggcgtt ggcgttcaat caacatatcc gggcagcaga tatgtttcac tgagcggcac    480
atcaatggca tcaccgcatg ttgcaggcgt tgcagcacta gt                       522

<210> SEQ ID NO 73
<211> LENGTH: 522
<212> TYPE: DNA
<213> ORGANISM: Artificial Sequence
<220> FEATURE:
<223> OTHER INFORMATION: Synthetic

<400> SEQUENCE: 73
gtcgacacaa gatggcaatg gacatggcac acatgttgca ggcacagttg cagcactgaa     60
taataacgat ggcgttattg gcgttgcacc gagcgctgaa ctgtatgcag ttaaagttct    120
gggcgcaagc ggcagcggct caatttcaag cattgcacgg ggcctggaat gggcagcaga    180
taatggcacg catattgcaa atatgtcact gggcacacct caaccgtcag caacactgga    240
acgggcagtt aattcagcaa catcacgggg cgttctggtt gttgcagcat caggcaatag    300
cggctcaggc tcagttagct atccggcaag atatgcaaat gcaatggcag ttggcgcaac    360
agatcaaaat aataatagag caagcttttc acaatatggc gcaggccttg atattcttgc    420
accgggcgtt ggggttcaat caacatatcc gggcagcaca tatgcttcac tgaacggcac    480
atcaatggca tcaccgcatg ttgcaggcgt tgcagcacta gt                       522

<210> SEQ ID NO 74
<211> LENGTH: 522
<212> TYPE: DNA
<213> ORGANISM: Artificial Sequence
<220> FEATURE:
<223> OTHER INFORMATION: Synthetic

<400> SEQUENCE: 74
gtcgacacaa gatggcaatg gacatggcac acatgttgca ggcacagttg cagcactgaa     60
taatagcatt ggcgttcttg gcgttgtacc gagcgctgat ctgtatgcag ttaaagttct    120
gggcgcaagc ggcagaggca cagtttcagg cattgcacag ggcctggaat gggcaggaaa    180
taataatatg catgttgcaa atctgtcact gggctcagat tttccgtcat caacactgga    240
acgggcagtt aatgcagcaa catcacggga cgttctggtt gttgcagcat caggcaatac    300
cggctcaggc tcaattagct atccggcaag atatgcaaat gcaatggcag ttggcgcaac    360
agatcaaaat aataatagag caaacttttc acaatatggc caaggcattg atattgttgc    420
accgggcgtt ggcgttcaat caacatatcc gggcagcaga tatgcttcac tgagcggcac    480
atcaatggca tcaccgcatg ttgcaggcgt tgcagcacta gt                       522

<210> SEQ ID NO 75
<211> LENGTH: 522
<212> TYPE: DNA
<213> ORGANISM: Artificial Sequence
<220> FEATURE:
<223> OTHER INFORMATION: Synthetic

<400> SEQUENCE: 75
gtcgactcaa gatggcaatg gacatggcac acatgttgca ggcacagttg cagcactgaa     60
taatagcgat ggcgttcttg gcgttgcacc gagcgttgat ctgtatggag ttaaagttct    120
gggcgcaagc ggcagcggct caatttcagg cattgcacag ggcctgcaat gggcagcaga    180
taatggcatg catgttgcaa atctgtcact gggctcacct caaccgtcag caacactgga    240
acgggcagtt aattatgcaa catcacgggg cgttctggtt gttgcagcaa caggcaatac    300
```

```
cggcgcaggc tcagttggct atccggcaag atatgcaaat gcaatggcag ttggcgcaac    360
agatcaaaat aatagaagag caagcttttc acaatatggc gcaggccttg atattgttgc    420
accgggcgtt ggcgttcaat caacatatcc gggcaacaga tatgtttcac tgagcggcac    480
atcaatggca acaccgcatg ttgcaggcgc tgcagcacta gt                       522

<210> SEQ ID NO 76
<211> LENGTH: 522
<212> TYPE: DNA
<213> ORGANISM: Artificial Sequence
<220> FEATURE:
<223> OTHER INFORMATION: Synthetic

<400> SEQUENCE: 76
gtcgacacaa gatggcaatg gacatggcac acatgttgca ggcacaattg cagcactgaa     60
taataacatt ggcgttcttg gcgttgcacc gaacgttgat ctgtatggag ttaaagttct    120
gggcgcaagc ggcagaggct cagtttcagg cattgcacgg ggcctggaat gggcaggaga    180
taatggcatg catgttgcaa atctgtcact gggctcatct caaccgtcag caacactgga    240
acaggcagtt aattcagcaa catcacgggg cgttctggtt attgcagcaa caggcaatac    300
cggcgcaggc acagttagct atccggcaag atatgcaaat gcaatggcag ttggcgcaac    360
agatcaaaat aataatagag caaacttttc acaatatggc acaggccttg atattgttgc    420
accgggcgtt ggcgttcaat caacatatcc gggcagcaca tatgcttcaa tgaacggcac    480
atcaatggca acaccgcatg ttgcaggcgc tgcagcacta gt                       522

<210> SEQ ID NO 77
<211> LENGTH: 522
<212> TYPE: DNA
<213> ORGANISM: Artificial Sequence
<220> FEATURE:
<223> OTHER INFORMATION: Synthetic

<400> SEQUENCE: 77
gtcgacacaa gatggcaatg gacatggcac acatgttgca ggcacagttg cagcactgaa     60
taataacatt ggcgttcttg gcgttgcacc gagcgctgaa ctgtatggag ttaaagttct    120
gggcgcaagc ggcagaggca cagtttcagg cattgcacag gcctggaat gggcaggaga     180 taatggcatg catgttgcaa atctgtcact gggcacagat caaccgtcat caacactgga    240
acgggcagtt aatgcagcaa catcacgggg cgttctggtt gttgcagcat caggcaatac    300
cggcgcaggc tcaattggct atccggcaag atatgcaaat gcaatggcag ttggcgcaac    360
agatcaaaat aataatagag caaacttttc acaatatggc gcaggccttg atattgttgc    420
accgggcgtt ggcgttcaat caacatatcc gggcagcaga tatgcttcac tgaacggcac    480
atctatggca acaccgcatg ttgcaggcgt tgcagcacta gt                       522

<210> SEQ ID NO 78
<211> LENGTH: 522
<212> TYPE: DNA
<213> ORGANISM: Artificial Sequence
<220> FEATURE:
<223> OTHER INFORMATION: Synthetic

<400> SEQUENCE: 78
gtcgacacaa gatggcaatg gacatggcac acatgttgca ggcacagttg cagcactgaa     60
taataacgtt ggcgttcttg gcgttgcacc gagcgctgaa ctgtatgcag ttaaagttct    120
```

```
gggcgcaagc ggcagcggca caatttcaag cattgcacag ggcctggaat gggcaggaac    180
aaatggcacg catattgcaa atctgtcact gggcacagat caaccgtcag caacactgga    240
acgggcagtt aatgcagcaa catcacgggg cgttctggtt gttgcagcat caggcaataa    300
cggctcaggc tcagttagct atccggcaag atatgcaaat gcaatggcag ttggcgcaac    360
agatcaaaat aatagaagag caaacttttc acaatatggc gcaggccttg atattgttgc    420
accgggcgtt ggcgttcaat caacatgtcc gggcaacaga tatgtttcac tgagcggcac    480
atcaatggca tcaccgcatg ttgcaggcgt tgcagcacta gt                        522
```

<210> SEQ ID NO 79
<211> LENGTH: 522
<212> TYPE: DNA
<213> ORGANISM: Artificial Sequence
<220> FEATURE:
<223> OTHER INFORMATION: Synthetic

<400> SEQUENCE: 79

```
gtcgacacaa gatggcaatg gacatggcac acatgttgca ggcacaattg cagcactgaa     60
taatagcgtt ggcgttcttg gcgttgcacc gagcgctgaa ctgtatggag ttaaagttct    120
gggcgcaagc ggcagaggct cagtttcaag cattgcacag ggcctggaat gggcagcaga    180
taatggcatg catgttgcaa atatgtcact gggcacatct tttccgtcat caacactgga    240
acgggcagtt aatgcagcaa catcacgggg cgttctggtt attgcagcat caggcaatag    300
cggctcaggc acaattggct atccgggaag atatgcaaat gcaatggcag ttggcgcaac    360
agatcaaaat aataatagag caagcttttc acaatatggc actggcattg atattgttgc    420
accaggcgtt ggcgttcaat caacatatcc gggcagcaca tatgcttcac tgagcggcac    480
atcaatggca acaccgcatg ttgcaggcgc tgcagcacta gt                        522
```

<210> SEQ ID NO 80
<211> LENGTH: 522
<212> TYPE: DNA
<213> ORGANISM: Artificial Sequence
<220> FEATURE:
<223> OTHER INFORMATION: Synthetic

<400> SEQUENCE: 80

```
gtcgacacaa gatggcaatg gacatggcac acatgttgca ggcacaattg cagcactgaa     60
taataacgtt ggcgttcttg gcgttgcacc gagcgttgaa ctgtatgcag ttaaagttct    120
gggcgcaaac ggcagcggca caatttcagg cattgcacag ggcctggaat gggcagcaaa    180
taatggcacg catgttgcaa atctgtcact gggcacagat gcaccgtcag caacactgga    240
acgggcagtt aatcaagcaa catcacgggg cgttctggtt gttgcagcat caggcaatag    300
cggctcaggc acaattggct atccggcaag atatgcaaat gcaatggcag ttggcgcaac    360
agatcaaaat aataatagag caagcttttc acaatatggc gcaggcattg atattgttgc    420
accgggcgtt ggcgttcaat caacatatcc gggcagcaca tatgctttac tgagcggcac    480
atcaatggca acaccgcatg ttgcaggcgt tgcagcacta gt                        522
```

<210> SEQ ID NO 81
<211> LENGTH: 522
<212> TYPE: DNA
<213> ORGANISM: Artificial Sequence
<220> FEATURE:
<223> OTHER INFORMATION: Synthetic

<400> SEQUENCE: 81

```
gtcgacacaa gatggcaatg gacatggcac acatgttgca ggcacagttg cagcactgaa    60
taatagcatt ggcgttcttg gcgttgcacc gagcgctgaa ctgtatgcag ttaaagttct   120
gggcgcaagc ggcagaggct cagtttcaag cattgcacag ggcctggaat gggcaggagc   180
aaatggcatg catattgcaa atctgtcact gggctcacct gcaccgtcat caacactgga   240
acgggcagtt aattcagcaa catcacgggg cgttctggtt attgcagcaa caggcaatac   300
cggctcaggc tcaattagct atccggcaag atatgcaaat gcaatggcag ttggcgcaac   360
agatcaaaat aatagaagag caagcttttc acaatatggc gcaggcattg atattgttgc   420
accgggcgtt ggcgttcaat caacatatcc gggcaacaca tatgtttcaa tgagcggcac   480
atcaatggca acaccgcatg ttgcaggcgc tgcagcacta gt                      522
```

<210> SEQ ID NO 82
<211> LENGTH: 522
<212> TYPE: DNA
<213> ORGANISM: Artificial Sequence
<220> FEATURE:
<223> OTHER INFORMATION: Synthetic

<400> SEQUENCE: 82

```
gtcgacacaa gatggcaatg gacatggcac acatgttgca ggcacagttg cagcattgaa    60
taataacatt ggcgttcttg gcgttgcacc gaacgttggt ctgtatgcag ttaaagttct   120
gggcgcaagc ggcagaggca cagtttcagg cattgcacgg ggcctggaat gggcagcaac   180
aaatggcatg catgttgcaa atctgtcact gggctcagat gcaccgtcag caacactgga   240
acaggcagtt aatcaagcaa catcacgggg cgttctggtt gttgcagcaa caggcaatac   300
cggctcaggc acaattagct atccggcaag atatgcaaat gcaatggcag ttggcgcaac   360
agatcaaaat aatagaagag caaacttttc acaatatggc caaggccttg atattgttgc   420
accgggcgtt ggcgttcaat caacatatcc gggcaacaca tatgtttcaa tgagcggcac   480
atcaatggca tcaccgcatg ttgcaggcgt tgcagcacta gt                      522
```

<210> SEQ ID NO 83
<211> LENGTH: 522
<212> TYPE: DNA
<213> ORGANISM: Artificial Sequence
<220> FEATURE:
<223> OTHER INFORMATION: Synthetic

<400> SEQUENCE: 83

```
gtcgacacaa gatggcaatg gacatggcac acatgttgca ggcacagttg cagcactgaa    60
taatagcgat ggcgttcttg gcgttgcacc gagcgctgat ctgtatgcag ttaaagttct   120
gggcgcaagc ggcagaggct cagtttcaag cattgcacgg ggcctggaat gggcagcagc   180
aaatggcatg catgttgcaa atctgtcact gggctcagat caaccgtcat caacactgga   240
acgggcagtt aatgaagcaa catcacaggg cgttctggtt gttgcagcat caggcaataa   300
cggcgcaggc acagttggct atccggcaag atatgcaaat gcaatggcag ttggcgcaac   360
agatcaaaat aatagaagag caagcttttc acaatatggc gcaggcctcg atattgttgc   420
accgggcgtt ggcgttcaat caacatatcc gggcagcaca tatgcttcaa tgaacggcac   480
atcaatggca acaccgcatg ttgcaggcgc tgcagcacta gt                      522
```

<210> SEQ ID NO 84
<211> LENGTH: 522
<212> TYPE: DNA

<213> ORGANISM: Artificial Sequence
<220> FEATURE:
<223> OTHER INFORMATION: Synthetic

<400> SEQUENCE: 84

```
gtcgacacaa gatggcaatg gacatggcac acatgttgca ggcacagttg cagcactgaa      60
taatagcgtt ggcgttcttg gcgttgcacc gagcgttgaa ctgtatggag ttaaagttct     120
gggcgcaaac ggcagcggct caatttcaag cattgcacgg ggcctggaat gggcagcaga     180
taatggcatg catattgcaa atctgtcact gggctcatct tttccgtcag caacactgga     240
acaggcagtt aatcaagcaa catcacgggg cgttctggtt attgcggcaa caggcaatag     300
cggctcaggc acagttggct atccggcaag atatgcaaat gcaatggcag ttggcgcaac     360
agatcaaaat aataatagag caaacttttc acaatatggc gcaggccttg atattgttgc     420
accgggcgtt ggcgttcaat caacatatac gggcagcaca tatgcttcaa tgaacggcac     480
atcaatggca tcaccgcatg ttgcaggcgc tgcagcacta gt                        522
```

<210> SEQ ID NO 85
<211> LENGTH: 522
<212> TYPE: DNA
<213> ORGANISM: Artificial Sequence
<220> FEATURE:
<223> OTHER INFORMATION: Synthetic

<400> SEQUENCE: 85

```
gtcgacacaa gatggcaatg gacatggcac acatgttgca ggcacaattg cagcactgaa      60
taatagcgat ggcgttcttg gcgttgcacc gaacgttgat ctgtatggag ttaaagttct     120
gggcgcaaac ggcagcggca cagtttcagg cattgcacgg ggcctgcaat gggcaggaga     180
taatggcatg catgttgcaa atctgtcact gggcacagat gcaccgtcag caacactgga     240
acgggcagtt aatcaagcaa catcacgggg cgttctggtt gttgcagcat caggcaatac     300
cggcgcaggc tcaattagct atccggcaag atatgcaaat gcaatggcag ttggcgcaac     360
agatcaaaat aatagaagag caaacttttc acaatatggc gcaggccttg atattgttgc     420
accgggcgtt ggcgttcaat caacatatac gggcaacaga tatgtttcaa tgaacggcac     480
atcaatggca tcaccgcatg ttgcaggcgc tgcagcacta gt                        522
```

<210> SEQ ID NO 86
<211> LENGTH: 522
<212> TYPE: DNA
<213> ORGANISM: Artificial Sequence
<220> FEATURE:
<223> OTHER INFORMATION: Synthetic

<400> SEQUENCE: 86

```
gtcgacacaa gatggcaatg gacatggcac acatgttgca ggcacaattg cagcactgaa      60
taataacgct ggcgttcttg gcgttgcacc gaacgttgat ctgtatgcag ttaaagttct     120
gggcgcaaac ggcagcggct caatatcagg cattgcacgg ggcctggaat gggcaggaga     180
taatggcatg catgttgcaa atctgtcact gggctcacct caaccgtcag caacactgga     240
acgggcagtt aatgcagcaa catcacgggg cgttctggtt gttgcagcat caggcaataa     300
cggcgtaggc tcagttagct atccggcaag atatgcaaat gcaatggcag ttggcgcaac     360
agatcaaaat aataatagag caaacttttc acaatatggc acaggccttg atattgttgc     420
accgggcgtt ggcgttcaat caacatatcc gggcagcaga tttgcttcac tgaacggcac     480
atcaatggca tctccgcatg ttgcaggcgt tgcagcacta gt                        522
```

<210> SEQ ID NO 87
<211> LENGTH: 522
<212> TYPE: DNA
<213> ORGANISM: Artificial Sequence
<220> FEATURE:
<223> OTHER INFORMATION: Synthetic

<400> SEQUENCE: 87

| | | | | | | |
|---|---|---|---|---|---|---|
| gtcgacacaa | gatggcaatg | gacatggcac | acatgttgca | ggcacagttg | cagcactgaa | 60 |
| taataacgtt | ggcgttcttg | gcgttgcacc | gaacgctgaa | ctgtatgcag | ttaaagttct | 120 |
| gggcgcaaac | ggcagcggct | cagtttcagg | cattgcacag | ggcctggaat | gggcaggagc | 180 |
| aaatggcatg | catgttgcaa | atatgtcact | gggctcacct | tcaccgtcag | caacactgga | 240 |
| acgggcagtt | aatgcagcaa | catcacgggg | cgttctggtt | gttgcagcaa | caggcaatag | 300 |
| cggcgcaggc | tcagttagct | atccggcaag | atatgcaaat | gcaatggcag | ttggcgcaac | 360 |
| agatcaaaat | aataatagag | caagcttttc | acaatatggc | gcaggccttg | atattgttgc | 420 |
| accgggcgtt | ggcgttcaat | caacatatcc | gggcaacaca | tatgtttcac | tgaacggcac | 480 |
| atcaatggca | acaccgcatg | ttgcaggcgt | tgcagcacta | gt | | 522 |

<210> SEQ ID NO 88
<211> LENGTH: 522
<212> TYPE: DNA
<213> ORGANISM: Artificial Sequence
<220> FEATURE:
<223> OTHER INFORMATION: Synthetic

<400> SEQUENCE: 88

| | | | | | | |
|---|---|---|---|---|---|---|
| gtcgacacaa | gatggcaatg | gacatggcac | acatgttgca | ggcacagttg | cagcactgaa | 60 |
| taataacatt | ggcgttcttg | gcgttgcacc | gagcgctgat | ctgtatgcag | ttaaagttct | 120 |
| gggcgcaagc | ggcagcggca | caatttcaag | cattgctcag | ggcctggaat | gggcaggagc | 180 |
| aaatggcatg | catgttgcaa | atctgtcact | gggcacatct | tttccgtcaa | caacactgga | 240 |
| acgggcagtt | aattcagcaa | catcacgggg | cgttctggtt | attgcagcat | caggcaatag | 300 |
| cggctcaggc | acagttggct | atccggcaag | atatgcaaat | gcaatggcag | ttggcgcaac | 360 |
| agatcaaaat | aatagaagag | caagctcttc | acaatatggc | gcaggcctcg | atattgttgc | 420 |
| accgggcgtt | ggcgttcaat | caacatatac | gggcagcaca | tatgtttcac | tgagcggcac | 480 |
| atcaatggca | acacctcatg | ttgcaggcgt | tgcagcacta | gt | | 522 |

<210> SEQ ID NO 89
<211> LENGTH: 522
<212> TYPE: DNA
<213> ORGANISM: Artificial Sequence
<220> FEATURE:
<223> OTHER INFORMATION: Synthetic

<400> SEQUENCE: 89

| | | | | | | |
|---|---|---|---|---|---|---|
| gtcgacacaa | gatggcaatg | gacatggcac | acatgttgca | ggcacagttg | cagcactgaa | 60 |
| taatagcgtt | ggcgttattg | gcgttgcacc | gagcgctgaa | ctgtatgcag | ttaaagttct | 120 |
| gggcgcaagc | ggcagaggca | caatttcaag | cattgcacgg | ggcctggaat | gggcagcaaa | 180 |
| taatggcacg | catgttgcaa | atctgtcact | gggctcacct | gcaccgtcag | caacactgga | 240 |
| acgggcagtt | aattcagcaa | catcacgggg | cgttctggtt | gttgcagcaa | caggcaataa | 300 |
| cggctcaggc | acaattagct | atccggcaag | atatgcaaat | gcaatggcag | ttggcgcaac | 360 |

```
agatcaaaat aataatagag caaactcttc acaatatggc acaggccttg atattgttgc    420
accgggcgtt ggggttcaat caacatatcc gggcagcaca tatgcttcac tgagcggcac    480
atcaatggca acacctcatg ttgcaggcgc tgcagcacta gt                      522
```

<210> SEQ ID NO 90
<211> LENGTH: 522
<212> TYPE: DNA
<213> ORGANISM: Artificial Sequence
<220> FEATURE:
<223> OTHER INFORMATION: Synthetic

<400> SEQUENCE: 90

```
gtcgacacaa gatggcaatg gacatggcac acatgttgca ggcacagttg cagcactgaa     60
taatagcgat ggcgttcttg gcgttgcacc gagcgttgat ctgtatgcag ttaaagttct    120
gggcgcaagc ggcagcggca caatttcaag cattgcacgg ggcctggaat gggcaggaaa    180
taatggcatg catgttgcaa atatgtcact gggctcacct tcaccgtcag caacactgga    240
acgggcagtt aatcaagcaa catcacgggg cgttctggtt gttgcagcaa caggcaatac    300
cggcgcaggc acagttggct atccggcaag atatgcaaat gcaatggcag ttggcgcaac    360
agatcaaaat aataatagag caaacttttc acaatatggc gcaggccttg atattgttgc    420
accgggcgtt aatgttcaat caacatatcc gggcagcaga tatgcttcac tgaacggcac    480
atcaatggca tcaccgcatg ttgcaggcgt tgcagcacta gt                      522
```

<210> SEQ ID NO 91
<211> LENGTH: 522
<212> TYPE: DNA
<213> ORGANISM: Artificial Sequence
<220> FEATURE:
<223> OTHER INFORMATION: Synthetic

<400> SEQUENCE: 91

```
gtcgacacaa gatggcaatg gacatggcac acatattgca ggcacaattg cagcactgaa     60
taatagcgtt ggcgttcttg gcgttgcacc gagcgttgat ctgtatggag ttaaagttct    120
gggcgcaagc ggcagaggct cagtttcaag cattgcacag ggcctggaat gggcaggaga    180
taatggcatg catgttgcaa atctgtcact gggcacagat caaccgtcag caacactgga    240
acgggcagtt aattcagcaa catcacaggg cgttctggtt gttgcagcat caggcaatag    300
cggcgcaggc tcagttagct atccggcaag atatgcaaat gcaatggcag ttggcgcaac    360
agatcaaaat aatagaagag caagcttttc acaatatggc gcaggccttg atattgttgc    420
accgggcgtt ggcgttcaat caacatatcc gggcagcaga tatgcttcaa tgaacggcac    480
atcaatggca tcaccgcatg ttgcaggcgc tgcagcacta gt                      522
```

<210> SEQ ID NO 92
<211> LENGTH: 522
<212> TYPE: DNA
<213> ORGANISM: Artificial Sequence
<220> FEATURE:
<223> OTHER INFORMATION: Synthetic

<400> SEQUENCE: 92

```
gtcgacacaa gatggcaatg gacatggcac acatgttgca ggcacagttg cagcactgaa     60
taataacatt ggcgttcttg gcgttgcacc gaacgctgaa ctgtatgcag ttaaagttct    120
gggcgcaagc ggcagaggca cagtttcagg cattgcacgg ggcctggaat gggcaggaga    180
taatggcatg catgttgcaa atctgtcact gggcacatct tcaccgtcat caacactgga    240
```

-continued

```
acaggcagtt aattatgcaa catcacaggg cgttctggtt gttgcagcaa caggcaatag      300
cggctcaggc acaattagct atccggcaag atatgcaaat gcaatggcag ttggcgcaac      360
agatcaaaat aataatagag caagcttttc acaatatggc acaggccttg atattgttgc      420
accgggcgtt cgcgttcaat caacatatcc gggcaacaga tatgcttcac tgagcggcac      480
atcaatggca tcaccgcatg ttgcaggcgt tgcagcacta gt                         522
```

<210> SEQ ID NO 93
<211> LENGTH: 522
<212> TYPE: DNA
<213> ORGANISM: Artificial Sequence
<220> FEATURE:
<223> OTHER INFORMATION: Synthetic

<400> SEQUENCE: 93

```
gtcgacacaa gatggcaatg gacatggcac acatgttgca ggcacagttg cagcactgaa      60
taatagcgtt ggcgttcttg gcgttgcacc gaacgctgaa ctgtatggag ttaaagttct     120
gggcgcaaac ggcagaggca caatttcaag cattgcacgg ggcctggaat gggcaggagc     180
aaatggcatg catgttgcaa atctgtcact gggcacacct gcaccgtcag caacactgga     240
acaggcagtt aatcaagcaa catcacaggg cgttctggtt gttgcagcat caggcaatag     300
cggcgcaggc tcaattagct atccggcaag atatgcaaat gcaatggcag ttggcgcaac     360
agatcaaaat aatagaagag caagcttttc acaatatggc acaggccttg atattgttgc     420
accgggcgtt ggcgttcaat caacatatcc gggcagcaca tatgcttcac tgaacggcac     480
atcaatggca tcaccgcatg ttgcaggcgc tgcagcacta gt                         522
```

<210> SEQ ID NO 94
<211> LENGTH: 522
<212> TYPE: DNA
<213> ORGANISM: Artificial Sequence
<220> FEATURE:
<223> OTHER INFORMATION: Synthetic

<400> SEQUENCE: 94

```
gtcgacacaa gatggcaatg gacatggcac acatgttgca ggcacaattg cagcactgaa      60
taatagcgtt ggcgttcttg gcgttgcacc gaacgctgaa ctgtatgcag ttaaagttct     120
gggcgcaagc ggcagcggct cagtttcagg cattgcacgg ggcctggaat gggcaggaga     180
taatggcatg catgttgcaa atctgtcact gggctcacct tttccgtcag caacactgga     240
acaggcagtt aatgcagcaa catcacgggg cgttctggtt gttgcagcat caggcaatag     300
cggctcaggc acagttggct atccggcaag atatgcaaat gcaatggcag ttggcgcaac     360
agatcaaaat aataatagag caagcttttc agaatatggc gcaggccttg atattgttgc     420
accgggcgtt ggcgttcaat caacatatcc gggcagcaga tatgcttcac tgagcggcac     480
atctatggca tcaccgcatg ttgcaggcgc tgcagcacta gt                         522
```

<210> SEQ ID NO 95
<211> LENGTH: 522
<212> TYPE: DNA
<213> ORGANISM: Artificial Sequence
<220> FEATURE:
<223> OTHER INFORMATION: Synthetic

<400> SEQUENCE: 95

```
gtcgacacaa gatggcaatg gacatggcac acatgttgca ggcacagttg cagcactgaa      60
```

```
taataacgtt ggcgttattg gcgttgcacc gagcgctgaa ctgtatggag ttaaagttct      120
gggcgcaagc ggcagcggct caatttcaag cattgcacgg ggcctggaat gggcaggaaa      180
taatggcatg catgttgcaa atatgtcact gggcacagat gcaccgtcag caacactgga      240
acgggcagtt aatcaagcaa catcacgggg cgttctggtt gttgcagcaa caggcaatag      300
cggcgcaggc tcagttgcct atccggcaag atatgcaaat gcaatggcag ttggcgcaac      360
agatcaaaat aataatagag caaacttttc acaatatggc gcaggccttg atattgttgc      420
accgggcgtt ggcgttcaat caacatatcc gggcagcaca tatgcttcac tgaacggcac      480
atcaatggca acaccgcatg ttgcaggcgt tgcagcacta gt                        522
```

<210> SEQ ID NO 96
<211> LENGTH: 522
<212> TYPE: DNA
<213> ORGANISM: Artificial Sequence
<220> FEATURE:
<223> OTHER INFORMATION: Synthetic

<400> SEQUENCE: 96

```
gtcgacacaa gatggcaatg gacatggcac acatgttgca ggcacagttg cagcactgaa      60
taataacgtt ggcgttcttg gcgttgcacc gagcgctgat ctgtatgcag ttaaagttct      120
gggcgcaagc ggcagaggca cagtttcaag cattgcacgg ggtctgcaat gggcagcaaa      180
taatggcatg catgttgcaa atctgtcact gggctcagat caaccgtcaa caacactgga      240
acgggcagtt aattatgcaa catcacaggg cgttctggtt attgcagcat caggcaatac      300
cggctcaggc tcaattggct atccggcaag atatgcaaat gcaatggcag ttggcgcaac      360
agatcaaaat aataatagag caaacttttc acaatatggc gcaggccttg atattgttgc      420
accgggcgtt ggcgttcaat caacatatcc gggcagcaca tatgcttcaa tgaacggcac      480
atcaatggca tcaccgcatg ttgcaggcgc tgcagcacta gt                        522
```

<210> SEQ ID NO 97
<211> LENGTH: 522
<212> TYPE: DNA
<213> ORGANISM: Artificial Sequence
<220> FEATURE:
<223> OTHER INFORMATION: Synthetic

<400> SEQUENCE: 97

```
gtcgacacaa gatggcaatg gacatggcac acatgttgca ggcacagttg cagcactgaa      60
taataacgtt ggcgttcttg gcgttgcacc gaacgctgaa ctgtatgcag ttaaagttct      120
gggcgcaagc ggcagaggct cagtttcaag cgttgcacag ggcctggaat gggcagcaga      180
taatggcacg catgttgcaa atctgtcact gggctcagat tttccgtcag caacactgga      240
acgggcagtt aattcagcaa catcacgggg cgttctggtt gttgcagcaa caggcaataa      300
cggctcaggc acagttagct atccggcaag atatgcaaat gcaatggcag ttggcgcaac      360
agatcaaaat aataatagag caagcttttc acaatatggc gcaggccttg atattgttgc      420
accgggcgtt ggcgttcaat caacatatcc gggcagcaca tatgcttcac tgaacggcac      480
atcaatggca acaccgcatg ttgcaggcgc tgcagcacta gt                        522
```

<210> SEQ ID NO 98
<211> LENGTH: 522
<212> TYPE: DNA
<213> ORGANISM: Artificial Sequence
<220> FEATURE:
<223> OTHER INFORMATION: Synthetic

```
<400> SEQUENCE: 98
gtcgacacaa gatggcaatg gacatggcac acatgttgca ggcacaattg cagcactgaa      60
taatagcgtt ggcgttcttg gcgttgcacc gaacgctgat ctgtatggag ttaaagttct     120
gggcgcaagc ggcagaggct caatttcagg cattgcacag ggcctggaat gggcagcaac     180
aaatggcatg catgttgcaa atctgtcact gggcacagat caaccgtcag caacactgga     240
acgggcagtt aattatgcaa catcacgggg cgttctggtt gttgcagcat caggcaatac     300
cggctcaggc acaattggct atccggcaag atatgcaaat gcaatggcag ttggcgcaac     360
agatcaaaat aataatagag caagcttttc acaatatggc gcaggcattg atattgttgc     420
accgggcgtt ggcgttcaat caacatatac gggcagcaga tatgctctaa tgagcggcac     480
atcaatggca acaccgcatg ttgcaggcgt tgcagcacta gt                         522

<210> SEQ ID NO 99
<211> LENGTH: 522
<212> TYPE: DNA
<213> ORGANISM: Artificial Sequence
<220> FEATURE:
<223> OTHER INFORMATION: Synthetic

<400> SEQUENCE: 99
gtcgacacaa gatggcaatg gacatggcac acatgttgca ggcacagttg cagcactgaa      60
taataacgtt ggcgttcttg gcgttgcacc gagcgttgat ctgtatggag ttaaagttct     120
gggcgcaagc ggcagaggca cagtttcagg cattgtacgg ggcctggaat gggcagcaga     180
taatggcatg catgttgcaa atctgtcact gggcacacct tttccgtcag caacactgga     240
acgggcagtt aatgcagcaa catcacaggg cgttctggtt attgcagcat caggcaatag     300
cggctcaggc tcaattagct atccggcaag atatgcaaat gcaatggcag ttggcgcaac     360
agatcaaaat aataatagag caagcttttc acaatatggc gcaggcattg atattgttgc     420
accgggcgtt ggcgttcaat caacatatcc gggcaacaga tatgcttcac tgagcggcac     480
atcaatggca acaccgcatg ttgcaggcgc tgcagcacta gt                         522

<210> SEQ ID NO 100
<211> LENGTH: 522
<212> TYPE: DNA
<213> ORGANISM: Artificial Sequence
<220> FEATURE:
<223> OTHER INFORMATION: Synthetic

<400> SEQUENCE: 100
gtcgacacaa gatggcaatg gacatggcac acatgttgca ggcacagttg cagcactgaa      60
taatagcgat ggcgttattg gcgttgcacc gagcgttgaa ctgtatgcag ttaaagttct     120
gggcgcaaac ggcagaggct cagtttcagg cattgcacgg ggcctggaat gggcagcaaa     180
taataatatg catgttgcaa atctgtcact gggcacatct tcaccgtcat caacactgga     240
acgggcagtt aaagcagcaa catcacaggg cgttctggtt gttgcagcat caggcaataa     300
cggcgcaggc acaatttgct atccggcaag atatgcaaat gcaatggcag ttggcgcaac     360
agatcaaaat aataatagag caagcttttc acaatatggc gcaggccttg atattgttgc     420
accgggcgtt ggcgttcaat caacatatcc gggcaacaca tatgcttcac tgaacggcac     480
atcaatggca acaccgcatg ttgcaggcgt tgcagcacta gt                         522

<210> SEQ ID NO 101
```

<211> LENGTH: 522
<212> TYPE: DNA
<213> ORGANISM: Artificial Sequence
<220> FEATURE:
<223> OTHER INFORMATION: Synthetic

<400> SEQUENCE: 101

| | | | | |
|---|---|---|---|---|
| gtcgacacaa gatggcaatg gacatggcac acatgttgca ggcacagttg cagcactgaa | 60 |
| taataacgtt ggcgttcttg gcgttgcacc gagcgctgat ctgtatggag ttaaagttct | 120 |
| gggcgcaaac ggcagcggct cagtttcaag cattgcacgg ggcctggaat gggcagcagc | 180 |
| aaataatatg catgttgcaa atctgtcact gggctcacct caaccgtcag caacactgga | 240 |
| acgggcagtt aatgcagcaa catcacaggg cgttctggtt gttgcagcat caggcaatac | 300 |
| cggctcaggc atagttagct atccggcaag atatgcaaat gcaatggcag ttggcgcaac | 360 |
| agatcaaaat aataatagag caagcttttc acaatatggc acaggccttg atattgttgc | 420 |
| accgggcgtt ggcgttcaat caacatatcc gggcagcaga tatgcttcac tgagcggcac | 480 |
| atcaatggca acaccgcatg ttgcaggcgc tgcagcacta gt | 522 |

<210> SEQ ID NO 102
<211> LENGTH: 522
<212> TYPE: DNA
<213> ORGANISM: Artificial Sequence
<220> FEATURE:
<223> OTHER INFORMATION: Synthetic

<400> SEQUENCE: 102

| | | | | |
|---|---|---|---|---|
| gtcgacacaa gatggcaatg gacatggcac acatgttgca ggcacagttg cagcactgaa | 60 |
| taatagcatt ggcgttcttg gcgttgcacc gagcgttgaa ctgtatggag ttaaagttct | 120 |
| gggcgcaaac ggcagaggct caatttcagg cattgcacgg ggcctggaat gggcagcagc | 180 |
| aaatggcatg catattgcaa atctgtcact gggcacatct tttccgtcaa caacactgga | 240 |
| acgggcagtt aatcaagcaa catcacgggg cgttctggtt gttgcagcat caggcaataa | 300 |
| cggctcaggc acagttggct atccggcaac atatgcaaat gcaatggcag ttggcgcaac | 360 |
| agatcaaaat aatagaagag caaacttttc acaatatggc gcaggcattg atattgttgc | 420 |
| accgggcgtt ggcgttcaat caacatatac gggcaacaga tatgcttcac tgagcggcac | 480 |
| atcaatggca tctccgcatg ttgcaggcgc tgcagcacta gt | 522 |

<210> SEQ ID NO 103
<211> LENGTH: 522
<212> TYPE: DNA
<213> ORGANISM: Artificial Sequence
<220> FEATURE:
<223> OTHER INFORMATION: Synthetic

<400> SEQUENCE: 103

| | | | | |
|---|---|---|---|---|
| gtcgactcaa gatggcaatg gacatggcac acatgttgca ggcacagttg cagcactgaa | 60 |
| taataacgtt ggcgttattg gcgttgcacc gagcgttgaa ctgtatgcag ttaaagttct | 120 |
| gggcgcaaac ggcagcggca caatttcagg cattgcacgg ggcctggaat gggcaggagc | 180 |
| aaatggcatg catattgcaa atatgtcact gggcacagat tttccgtcat caacactgga | 240 |
| acgggcagtt aattatgcaa catcacaggg cgttctggtt attgcagcat caggcaatag | 300 |
| cggcgcaggc tcagttggct atccggcaag atatgcaaat gcaatggcag ttggcgcaac | 360 |
| agatcaaaat aatagaagag caaactcttc acaatatggc acaggccttg atattgttgc | 420 |
| accgggcgtt ggcgttcaat caacatatcc aggcagcaga tatgtttcac tgagcggcac | 480 |

| atcaatggca acaccgcatg ttgcaggcgt tgcagcacta gt | 522 |

<210> SEQ ID NO 104
<211> LENGTH: 522
<212> TYPE: DNA
<213> ORGANISM: Artificial Sequence
<220> FEATURE:
<223> OTHER INFORMATION: Synthetic

<400> SEQUENCE: 104

| gtcgacacaa gatggcaatg gacatggcac acatgttgca ggcacaattg cagcactgaa | 60 |
| taatagcgtt ggcgttcttg gcgttgcacc gagcgttgaa ctgtatgcag ttaaagttct | 120 |
| gggcgcaagc ggcagaggct caatttcagg cattgcacgg ggcctggaat gggcaggaaa | 180 |
| taatggcatg catgttgcaa atatgtcact gggctcacct tttccgtcag caacactgga | 240 |
| acgggcagtt aatcaagcaa catcacgggg cgttctggtt attgcagcat caggcaatag | 300 |
| cggcgcaggc tcagttagct atccggcaag atatgcaaat gcaatggcag ttggcgcaac | 360 |
| agatcaaaat aataatagag caagcttttc acaatatggc gcaggccttg atattgttgc | 420 |
| accgggcgtt ggcgttcaat caacatatcc gggcagcaca tatgcttcac tgagcggcac | 480 |
| atcaatggca tcaccgcatg ttgcaggcgc tgcagcacta gt | 522 |

<210> SEQ ID NO 105
<211> LENGTH: 522
<212> TYPE: DNA
<213> ORGANISM: Artificial Sequence
<220> FEATURE:
<223> OTHER INFORMATION: Synthetic

<400> SEQUENCE: 105

| gtcgacacaa gatggcaatg gacatggcac acatgttgca ggcacaattg cagcactgaa | 60 |
| taataacgtt ggcgttattg gcgttgcacc gaacgctgat ctgtatgcag ttaaagttct | 120 |
| gggcgcaagc ggcagaggca caatttcagg cattgcacgg ggcctggaat gggcaggagc | 180 |
| aaatggcatg catattgcaa atctgtcact gggcacacct tcaccgtcaa caacactgga | 240 |
| acgggcagtt aatgcagcaa catcacggga cgttctggtt gttgcagcat caggcaatgg | 300 |
| cggctcaggc tcaattggct atccggcaag atatgcaaat gcaatggcag ttggcgcaac | 360 |
| agatcaaaat aataatagag caagcttttc acaatatggc gcgggccttg atattgttgc | 420 |
| accgggcgtt ggcgttcaat caacatatcc gggcagcaca tatgcttcac tgaacggcac | 480 |
| atcaatggca tcaccgcatg ttgcaggcgt tgcagcacta gt | 522 |

<210> SEQ ID NO 106
<211> LENGTH: 522
<212> TYPE: DNA
<213> ORGANISM: Artificial Sequence
<220> FEATURE:
<223> OTHER INFORMATION: Synthetic

<400> SEQUENCE: 106

| gtcgacacaa gatggcaatg ggcatggcac acatgttgca ggcacagttg cagcactgaa | 60 |
| taatagcgtt ggcgttcttg gcgttgcacc gagcgctgaa ctgtatgcag ttaaagttct | 120 |
| gggcgcaagc ggcagcggca cagtttcaag cattgcacgg ggcctggaat gggcagcaga | 180 |
| taataatatg catattgcaa atatgtcact gggcacacct tcaccgtcag caacactgga | 240 |
| acgggcagtt aatcaagcaa catcacgggg cgttctggtt gttgcagcaa caggcaatag | 300 |

```
cggctcaggc tcaattggct atccggcaag atatgcaaat gcaatggcag ttggcgcaac    360
agatcaaaat aatagaagag caaacttttc acaatatggc acaggccttg atattgttgc    420
accgggcgtt ggcgttcaat caacatatcc gggcagcaga tatgtttcac tgagcggcac    480
atcaatggca acaccgcatg ttgcaggcgt tgcagcacta gt                       522

<210> SEQ ID NO 107
<211> LENGTH: 522
<212> TYPE: DNA
<213> ORGANISM: Artificial Sequence
<220> FEATURE:
<223> OTHER INFORMATION: Synthetic

<400> SEQUENCE: 107
gtcgacacaa gatggcaatg gacatggcac acatgttgca ggcacagttg cagcactgaa     60
taatagcgtt ggcgttcttg gcgttgcacc gagcgttgaa ctgtatgcag ttaaagttct    120
gggcgcaagc ggcagaggca cagtttcagg cattgcacag ggcctgcaat gggcagcagc    180
aaatggcatg catgttgcaa atctgtcact gggcacagat tttccgtcag caacactgga    240
acaggcagtt aatgcagcaa catcacgggg cgttctggtt gttgcagcat caggcaatag    300
cggctcaggc tcaattagct atccggcaag atatgcaaat gcaatggcag ttggcgcaac    360
agatcaaaat aataatagag caaacttttc acaatatggc ggaggccttg atattgttgc    420
accgggcgtt ggcgttcaat caacatatcc gggcagcaca tatgtttcac tgagcggcac    480
atcaatggca gtaccgcatg ttgcaggcgc tgcagcacta gt                       522

<210> SEQ ID NO 108
<211> LENGTH: 522
<212> TYPE: DNA
<213> ORGANISM: Artificial Sequence
<220> FEATURE:
<223> OTHER INFORMATION: Synthetic

<400> SEQUENCE: 108
gtcgacacaa gatggcaatg gacatggcac acatgttgca ggcacaattg cagcactgaa     60
taatagcgtt ggcgttattg gcgttgcacc gaacgttgat ctgtatggag ttaaagttct    120
gggcgcaagc ggcagcggca caatttcaag cattgcacag ggcctggaat gggcagcaga    180
taatggcatg catgttgcaa atctgtcact gggcacacct gcaccgtcat caacactgga    240
acgggcagtt aatgcagcaa catcacgggg cgttctggtt gttgcagcat caggcaatag    300
cggcgcaggc tcaattagct atccggcaag atatgcaaat gcaatggcag ttggcgcaac    360
agatcaaaat aataatagag caagcttttc acaatatggc acaggcattg atattgttgc    420
accgggcgtt ggcgttcaat caacatatcc gggcaacaca tatgcttcac tgaacggcac    480
atcaatggca tcaccgcatg ttgcaggcgc tgcagcacta gt                       522

<210> SEQ ID NO 109
<211> LENGTH: 522
<212> TYPE: DNA
<213> ORGANISM: Artificial Sequence
<220> FEATURE:
<223> OTHER INFORMATION: Synthetic

<400> SEQUENCE: 109
gtcgacacaa gatggcaatg gacatggcac acatgttgca ggcacagttg cagcactgaa     60
taatagcgtt ggcgttcttg gcgttgcacc gagcgttgaa ctgtatgcag ttaaagttct    120
gggcgcaagc ggcagaggca cagtttcaag cattgcacgg ggcctggaat gggcagcaaa    180
```

```
taatggcacg catgttgcaa atatgtcact gggcacatct caaccgtcag caacactgga      240
acaggcagtt aatgcagcaa catcacgggg cgttctggtt gttgcagcat caggcaatag      300
cggctcaggc acagttggct atccggcaag atatgcaaat gcaatggcag ttggcgcaac      360
agatcaaaat aataatagag caagcttttc acaatatggc acaggccttg atattgttgc      420
accgggcgtt ggcgttcaat caacatatcc gggcagcaga tatgcttcac tgagcggcac      480
atcaatggca tcaccgcatg ttgcaggcgt tgcagcacta gt                         522
```

<210> SEQ ID NO 110
<211> LENGTH: 522
<212> TYPE: DNA
<213> ORGANISM: Artificial Sequence
<220> FEATURE:
<223> OTHER INFORMATION: Synthetic

<400> SEQUENCE: 110

```
gtcgacacaa gatggcaatg gacatggcac acatgttgca ggcacaattg cagcactgaa       60
taatagcgat ggcgttattg gcgttgcacc gagcgctgat ctgtatgcag ttaaagttct      120
gggcgcaaac ggcagcggta cagtttcaag cattgcacgg ggcctgcaat gggcagcaaa      180
taatggcatg catgttgcaa atctgtcact gggctcagat caaccgtcag caacactgga      240
acgggcagtt aatgcagcaa catcacgggg cgttctggtt gttgcagcat caggcaatag      300
cggcgcaggc acagttggct atccggcaag atatgcaaat gcaatggcag ttggcgcaac      360
agatcaaaat aataatagag caagcttttc acaatatggc acaggccttg atattgttgc      420
accgggcgtt ggcgttcaat caacatatcc gggcaacaca tatgtttcaa tgagcggcac      480
atcaatggca tcaccgcatg ttgcaggcgt tgcagcacta gt                         522
```

<210> SEQ ID NO 111
<211> LENGTH: 522
<212> TYPE: DNA
<213> ORGANISM: Artificial Sequence
<220> FEATURE:
<223> OTHER INFORMATION: Synthetic

<400> SEQUENCE: 111

```
gtcgacacaa gatggcaatg gacatggcac acatgttgca ggcacagttg cagcactgaa       60
taataacgtt ggcgttattg gcgttgcacc gagcgttgat ctgtatgcag ttaaagttct      120
gggcgcaagc ggcagagggct cagtttcagg cattgcacgg ggcctgcaat gggcagcagc      180
aaatggcatg catattgcaa atctgtcact gggctcatct caaccgtcag caacactgga      240
acgggcagtt aattatgcaa catcacgggg cgttctggtt gttgcagcat caggcaatag      300
cggctcaggc acagttagct atccggcaag atatgcaaat gcaatggcag ttggcgcaac      360
agatcaaaat aataatagag caaactcttc acaatatggc acaggccttg atattgttgc      420
accgggcgtt ggcgttcaat caacatatcc gggcaacaca tatgcttcac tgagcggcac      480
atcaatggca acaccgcatg ttgcaggcgc tgcagcacta gt                         522
```

<210> SEQ ID NO 112
<211> LENGTH: 522
<212> TYPE: DNA
<213> ORGANISM: Artificial Sequence
<220> FEATURE:
<223> OTHER INFORMATION: Synthetic

<400> SEQUENCE: 112

```
gtcgacacaa gatggcaatg gacatggcac acatgttgca ggcacagttg cagcactgaa    60
taataacgtt ggcgttcttg gcgttgcacc gagcgctgaa ctgtatgcag ttaaagttct   120
gggcgcaaac ggcagaggca caatttcagg cattgcacag ggcctggaat gggcagcaaa   180
taatggcatg catgttgcaa atctgtcact gggctcacct tcaccgtcag caacactgga   240
acaggcagtt aatgcagcaa catcacgggg cgttctggtt gttgcagcat caggcaatag   300
cggcgcaggc acaattggct atccggcaac atatgcaaat gcaatggcag ttggcgcaac   360
agatcaaaat aataatagag caagcttttc acaatatggc acaggcattg atattgttgc   420
accgggcgtt ggcgttcaat caacatatcc gggcaacaga tatgcttcaa tgagcggcac   480
atcaatggca acaccgcatg ttgcaggcgc tgcagcacta gt                      522
```

<210> SEQ ID NO 113
<211> LENGTH: 522
<212> TYPE: DNA
<213> ORGANISM: Artificial Sequence
<220> FEATURE:
<223> OTHER INFORMATION: Synthetic

<400> SEQUENCE: 113

```
gtcgacacaa gatggcaatg gacatggcac acatgttgca ggcacagttg cagcactgaa    60
taataacatt ggcgttcttg gcgttgcacc gagcgctgat ctgtatgcag ttaaagttct   120
gggcacaagc ggcagcggca cagtttcaag cattgcacgg ggcctggaat gggcagcaag   180
taatggcatg catgttgcaa atatgtcact gggcacatct caaccgtcag caacactgga   240
acgggcagtt aatgcagcaa catcacgggg cgttctggtt gttgcagcaa caggcaatag   300
cggctcaggc acaattggct atccggcaag atatgcaaat gcaatggcag ttggcgcaac   360
agatcaaaat aatagaagag caagcttttc acaatatggc acaggccttg atattgttgc   420
accgggcgtt ggcgttaaat caacatatcc gggcagcaca tatgcttcac tgaacggcac   480
atcaatggca tcaccgcatg ttgcaggcgt tgcagcacta gt                      522
```

<210> SEQ ID NO 114
<211> LENGTH: 522
<212> TYPE: DNA
<213> ORGANISM: Artificial Sequence
<220> FEATURE:
<223> OTHER INFORMATION: Synthetic

<400> SEQUENCE: 114

```
gtcgacacaa gatggcaatg gacatggcac acatgttgca ggcacaattg cagcactgaa    60
taatagcatt ggcgttcttg gcgttgcacc gagcgttgaa ctgtatggag ttaaagttct   120
gggcgcaaac ggcagcggca caatttcaag cattgcacgg ggcctggaat gggcaggaaa   180
taatggcatg catgttgcaa atatgtcact gggctcagat tttccgtcat caacactgga   240
acaggcagtt aatgcagcaa catcacgggg cgttctggtt gttgcagcat caggcaatag   300
cggctcaggc tcagttggct atccggcaag atatgcaaat gcaatggcag ttggcgcaac   360
agatcaaaat aatagaagag caaactcttc acaatatggc gcaggccttg atattgttgc   420
accgggcgtt ggcgttcaat caacatatcc gggcagcaga tatgtttcac tgagcggcac   480
atcaatggca tcaccgcatg ttgcaggcgc tgcagcacta gt                      522
```

<210> SEQ ID NO 115
<211> LENGTH: 522
<212> TYPE: DNA
<213> ORGANISM: Artificial Sequence
<220> FEATURE:
<223> OTHER INFORMATION: Synthetic

<400> SEQUENCE: 115

| | | | | | |
|---|---|---|---|---|---|
| gtcgacacaa | gatggcaatg | gacatggcac | acatgttaca | ggcacaattg | cagcactgaa | 60 |
| taatagcatt | ggcgttattg | gcgttgcacc | gagcgttgaa | ctgtatggag | ttaaagttct | 120 |
| gggcgcaagc | ggcagaggct | caatttcagg | cattgcacgg | ggcctggaat | gggcagcaga | 180 |
| taatggcatg | catgttgcaa | atatgtcact | gggctcacct | caaccgtcag | caacactgga | 240 |
| acaggcagtt | aattcagcaa | catcacgggg | cgttctggtt | attgcagcaa | caggcaatag | 300 |
| cggctcaggc | acaattgcct | atccggcaag | atatccaaat | gcaatggcag | ttggcgcaac | 360 |
| agatcaaaat | aataatagag | caagcttttc | acaatatggc | caaggccttg | atattgttgc | 420 |
| accgggcgtt | ggcgttcaat | caacatatcc | gggcagcaga | tatgcttcac | tgaacggcac | 480 |
| atcaatggca | tcaccgcatg | ttgcaggcgc | tgcagcacta | gt | | 522 |

<210> SEQ ID NO 116
<211> LENGTH: 522
<212> TYPE: DNA
<213> ORGANISM: Artificial Sequence
<220> FEATURE:
<223> OTHER INFORMATION: Synthetic

<400> SEQUENCE: 116

| | | | | | |
|---|---|---|---|---|---|
| gtcgacacaa | gatggcaatg | gacatggcac | acatgttgca | ggcacaattg | cagcactgaa | 60 |
| taataacgat | ggcgttcttg | gcgttgcacc | gagcgttgat | ctgtatggag | ttaaagttct | 120 |
| gggcgcaagc | ggcagaggca | cagtttcaag | cattgcacag | ggcctgctat | gggcagcaaa | 180 |
| taatggcacg | catgttgcaa | atatgtcact | gggctcatct | gcaccgtcaa | caacactgga | 240 |
| acgggcagtt | aattatgcaa | catcacgggg | cgttctggtt | gttgcagcat | caggcaatag | 300 |
| cggctcaggc | acaattagct | atccggcaag | atatgcaaat | gcaatggcag | ttggcgcaac | 360 |
| agatcaaaat | aataatagag | caagcttttc | acaatatggc | gcaggcattg | atattgttgc | 420 |
| accgggcgtt | aatgttcaat | caacatatcc | gggcagcaca | tatgtttcac | tgagcggcac | 480 |
| atcaatggca | tcaccgcatg | ttgcaggcgt | tgcagcacta | gt | | 522 |

<210> SEQ ID NO 117
<211> LENGTH: 522
<212> TYPE: DNA
<213> ORGANISM: Artificial Sequence
<220> FEATURE:
<223> OTHER INFORMATION: Synthetic

<400> SEQUENCE: 117

| | | | | | |
|---|---|---|---|---|---|
| gtcgacacaa | gacggcaatg | gacatggcac | acatgttgca | ggcacaattg | cagcactgaa | 60 |
| taatagcgtt | ggcgttattg | gcgttgcacc | gagcgctgat | ctgtatgcag | ttaaagttct | 120 |
| gggcgcaagc | ggcagaggct | cagtttcagg | cattgcacgg | ggcctggaat | gggcagcaaa | 180 |
| taatggcatg | catgttgcaa | atctgtcact | gggctcacct | gcaccgtcag | caacactgga | 240 |
| acgggcagtt | aattatgcaa | catcacgggg | cgttctggtt | attgcagcat | caggcaatag | 300 |
| cggcgcaggc | tcagttggct | atccggcaag | atatgcaaat | gcaatggcag | ttggcgcaac | 360 |
| agatcaaaat | aataatagag | caagcttttc | acaacatggc | acaggccttg | atattgttgc | 420 |
| acccggcgtt | ggcgttcaat | caacatatcc | gggcagcaga | tatgcttcac | tgagcggcac | 480 |
| atcaatggca | tcaccgcatg | ttgcaggcgc | tgcagcgcta | gt | | 522 |

<210> SEQ ID NO 118
<211> LENGTH: 522
<212> TYPE: DNA
<213> ORGANISM: Artificial Sequence
<220> FEATURE:
<223> OTHER INFORMATION: Synthetic

<400> SEQUENCE: 118

| | | | | | |
|---|---|---|---|---|---|
| gtcgacacaa | gatggcaatg | gacatggcac | acatgttgca | ggcacagttg | cagcactgaa | 60 |
| taatagcgtt | ggcgttcttg | gcgttgcacc | gagcgctgat | ctgtatgcag | ttaaagttct | 120 |
| gggcgcaagc | ggcagcggca | caatttcagg | cattgcacag | ggcctggaat | gggcagcaaa | 180 |
| taatggcacg | catgttgcaa | atctgtcact | gggcacatct | caaccgtcag | caacactgga | 240 |
| acgggcagtt | aatgcagcaa | catcacaggg | cgttctggtt | gttgcagcaa | caggcaatac | 300 |
| cggcgcaggc | acaattggct | atccggcaag | atatgcaaat | gcaatggcag | ttggcgcaac | 360 |
| agatcaaaat | aataatagag | caagcttttc | acaatatggc | acaggccttg | atattgttgc | 420 |
| accgggggtt | ggcgttcaat | caacatatcc | gggcagcaga | tatgcttcac | tgagcggcac | 480 |
| atcaatggca | acaccgcatg | ttgcaggcgc | tgcagcacta | gt | | 522 |

<210> SEQ ID NO 119
<211> LENGTH: 522
<212> TYPE: DNA
<213> ORGANISM: Artificial Sequence
<220> FEATURE:
<223> OTHER INFORMATION: Synthetic

<400> SEQUENCE: 119

| | | | | | |
|---|---|---|---|---|---|
| gtcgacacaa | gatggcaatg | gacatggcac | acatgttgca | ggcacagttg | cagcactgaa | 60 |
| taatagcatt | ggcgttcttg | gcgtcgcacc | gagcgttgaa | ctgtatgcag | ttaaagttct | 120 |
| gggcgcaagc | ggcagaggct | caatttcaag | cattgcacgg | ggcctggaat | gggcaggaga | 180 |
| taatggcatg | catattgcaa | atatgtcact | gggcacagat | caaccgtcag | caacactgga | 240 |
| acaggcagtt | aatgcagcaa | catcacgggg | cgttctggtt | attgcagcaa | caggcaatac | 300 |
| cggcgcaggc | tcaattagct | atccggcaag | atatgcaaat | gcaatggcag | ttggcgcaac | 360 |
| agatcaaaat | aataatagag | cgaacttttc | tcaatatggc | gcaggccttg | atattgttgc | 420 |
| accggcgtt | ggcgttcaat | caacatatcc | gggcagcaga | tatgcttcaa | tgaacggcac | 480 |
| atcaatggca | acaccgcatg | ttgcaggcgt | tgcagcacta | gt | | 522 |

<210> SEQ ID NO 120
<211> LENGTH: 522
<212> TYPE: DNA
<213> ORGANISM: Artificial Sequence
<220> FEATURE:
<223> OTHER INFORMATION: Synthetic

<400> SEQUENCE: 120

| | | | | | |
|---|---|---|---|---|---|
| gtcgacacaa | gatggcaatg | gacatggcac | acatgttgca | ggcacagttg | cagcactgaa | 60 |
| taataacgat | ggcgttcttg | gcgttgcacc | gaacgttgat | ctgtatgcag | ttaaagttct | 120 |
| gggcgcaagc | ggcagaggct | cagtttcagg | cattgcacgg | ggcctggaat | gggcaggagc | 180 |
| aaatggcatg | catattgcaa | atatgtcact | gggcacatct | tttccgtcag | caacactgga | 240 |
| acaggcagtt | aatgcagcaa | catcacgggg | cgttctggtt | gttgcagcaa | caggcaataa | 300 |
| cggcgcaggc | acagttggct | atccggcaag | atatgcaaat | gcaatggcag | ttggcgcaac | 360 |
| agatcaaaat | aataatagag | caagctcttc | acaatatggc | gcaggccttg | atattgttgc | 420 |

```
accgggcgtt ggcgttcaat caacatatcc gggcagcaga tatgcttcac tgagcggcac    480
atcaatggca acaccgcatg ttgcaggcgc tgcagcacta gt                       522
```

<210> SEQ ID NO 121
<211> LENGTH: 522
<212> TYPE: DNA
<213> ORGANISM: Artificial Sequence
<220> FEATURE:
<223> OTHER INFORMATION: Synthetic

<400> SEQUENCE: 121

```
gtcgacacaa gatggcaatg gacatggcac acatgttgca ggcacagttg cagcactgaa     60
taatagcgat ggcgttattg gcgttgcacc gagcgttgat ctgtatggag ttaaagttct    120
gggcgcaagc ggcagaggct cagtttcaag cattgcacgg ggcctggaat gggcagcaga    180
taatggcatg catgttgcaa atctgtcact gggctcagat caactgtcaa caacactgga    240
acgggcagtt aatcaagcaa catcacgggg cgttctggtt gttgcagcat caggcaataa    300
cggctcaggc acagttagct atccggcaag atatgcaaat gcaatggcag ttggcgcaac    360
agatcaaaat aataatagag caagctcttc acaatatggc acaggccttg atattgttgc    420
accgggcgtt ggcgttcaat caacatatcc gggcagcaga tatgcttcac tgagcggcac    480
atcaatggca tcaccgcatg tcgcaggcgt tgcagcacta gt                       522
```

<210> SEQ ID NO 122
<211> LENGTH: 522
<212> TYPE: DNA
<213> ORGANISM: Artificial Sequence
<220> FEATURE:
<223> OTHER INFORMATION: Synthetic

<400> SEQUENCE: 122

```
gtcgacacaa gatggcaatg gacatggcac acatgttgca ggcacagttg cagcactgaa     60
taatagcatt ggcgttcttg gcgttgcacc gagcgctgaa ctgtatgcag ttaaagttct    120
gggcgcaagc ggcagaggct cagtttcagg cattgcacag ggcctggaat gggcaggaac    180
aaatggcatg catgttgcaa atatgtcact gggcacacct gcaccgtcag caacactgga    240
acaggcagtt aatgcagcaa catcacaggg cgttctggtt attgcagcat caggcaatag    300
cggctcaggc acagttagct atccggcaag atatgcaaat gcaatggcag ttggcgcaac    360
agatcaaaat aataatagag caagcttttc acaatatggc gcaggccttg atactgttgc    420
accgggcgtt ggcgttcaat caacatatcc gggcagcaca tatgcttcaa tgagcggcac    480
atcaatggca tcaccgcatg ttgcaggcgt tgcagcacta gt                       522
```

<210> SEQ ID NO 123
<211> LENGTH: 522
<212> TYPE: DNA
<213> ORGANISM: Artificial Sequence
<220> FEATURE:
<223> OTHER INFORMATION: Synthetic

<400> SEQUENCE: 123

```
gtcgacacaa gatggcaatg gacatggcac acatgttgca ggcacagttg cagcactgaa     60
taataacatt ggcgttcttg gcgttgcacc gagcgttgaa ctgtatggag ttaaagttct    120
gggcgcaagc ggcagcggct cagtttcaag cattgcacag ggcctggaat gggcagcaga    180
taatggcatg catgttgcaa atatgtcact gggctcacct tttccgtcat caacactgga    240
```

```
acaggcagtt aattcagcaa catcacgggg cgttctggtt gttgcagcat caggcaatag    300
cggctcaggc acagttggct atccggcaag atatgcaaat gcaatggcag ttggcgcaac    360
agatcaaaat aataatagag caagcttttc acaatatggc gcaggccttg atattgttgc    420
accgggcgtt ggcgttcaat caacatatcc gggcagcaga tatgcttcac tgagcggcac    480
atcaatggca acaccgcatg ttgcaggcgt tgcagcacta gt                       522
```

<210> SEQ ID NO 124
<211> LENGTH: 522
<212> TYPE: DNA
<213> ORGANISM: Artificial Sequence
<220> FEATURE:
<223> OTHER INFORMATION: Synthetic

<400> SEQUENCE: 124

```
gtcgacacaa gatggcaatg gacatggcac acatgttgca ggcacaattg cagcactgaa     60
taatagcatt ggcgttattg gcgttgcacc gagcgttgat ctgtatggag ttaaagttct    120
gggcgcaagc ggcagcggct cagtttcaag cattgcacgg gcctggaat gggcaggaga    180 taatggcatg catgttgcaa atctgtcact gggctcacct tcaccgtcag caacactgga    240
acaggcagtt aattcagcaa catcacgggg cgttctggtt attgcagcaa caggcaatac    300
cggcgcaggc acacttagct atccggcaag atatgcaaat gcaatggcag ttggcgcaac    360
agatcaaaat aataatagag caagcttttc acaatatggc accggccttg atattgttgc    420
accgggcgtt ggcgttcaat caacatatcc gggcagcaca tatgtttcac tgaacggcac    480
atcaatggca acaccgcatg ttgcaagcgc tgcagcacta gt                       522
```

<210> SEQ ID NO 125
<211> LENGTH: 522
<212> TYPE: DNA
<213> ORGANISM: Artificial Sequence
<220> FEATURE:
<223> OTHER INFORMATION: Synthetic

<400> SEQUENCE: 125

```
gtcgacacaa gatggcaatg gacatggcac acatgttgca ggcacaattg cagcactgaa     60
taatagcgtt ggcgttcttg gcgttgcacc gaacgttgaa ctgtatgcag ttaaagttct    120
gggcgcaagc ggcagaggca caatttcagg cattgcacag gcctggaat gggcagcaga    180 taatggcacg catattgcaa atctgtcact gggcacatct tttccgtcag caacactgga    240
acgggcagtt aattcagcaa catcacgggg cgttctggtt gttgcagcaa caggcaatac    300
cggcgcaggc tcaattagct atccggcaag atttgcaaat gcaatggcag ttggcgcaac    360
agatcaaaat aatagaagag caagcttttc acaatatggc gcaggccttg atattgttgg    420
accgggcgtt ggcgttcaat caacatatcc gggcagcaca tatgcttcac tgagcggcac    480
atcaatggca acaccgcatg ttgcaggcgc tgcagcacta gt                       522
```

<210> SEQ ID NO 126
<211> LENGTH: 522
<212> TYPE: DNA
<213> ORGANISM: Artificial Sequence
<220> FEATURE:
<223> OTHER INFORMATION: Synthetic

<400> SEQUENCE: 126

```
gtcgacacaa gatggcaatg gacatggcac acatgttgca ggcacagttg cagcactgaa     60
taatagcgat ggcgttattg gcgttgcacc gagcgctgat ctgtatgcag ttaaagttct    120
```

```
gggcgcaaac ggcagcggct cagtttcaag cattgcacag ggcctggaat gggcagcaga    180
taatggcatg catattgcaa atatgtcact gggcacatct tcaccgtcag taacactgga    240
acgggcagtt aatgcagcaa catcacaggg cgttctggtt gttgcagcat caggcaatac    300
cggcgcaggc tcaattggct atccggcaag atatgcaaat gcaatggcag ttggcgcaac    360
agatcaaaat aatagaagag caagcttttc acaatatggc gcaggccttg atattgttgc    420
accgggcgtt aatgttcaat caacatatcc gggcagcaga tatgcttcac tgagcggcac    480
atcaatggca tcaccgcatg ttgcaggcgc tgcagcacta gt                       522
```

<210> SEQ ID NO 127
<211> LENGTH: 522
<212> TYPE: DNA
<213> ORGANISM: Artificial Sequence
<220> FEATURE:
<223> OTHER INFORMATION: Synthetic

<400> SEQUENCE: 127

```
gtcgacacaa gatggcaatg gacatggcac acatgttgca ggcacagttg cagcactgaa    60
taatagcatt ggcgttattg gcgttgcacc gagcgctgaa ctgtatggag ttaaagttct    120
gggcgcaaac ggcagcggct cggtttcaag cattgcacgg ggcctggaat gggcaggaaa    180
taatggcatg catattgcaa atctgtcact gggctcagat tttccgtcag caacactgga    240
acaggcagtt aatgcagcaa catcacgggg cgttctggtt gttgcagcat caggcaataa    300
cggctcaggc tcagttggct atccggcaag atatgcaaat gcaatgggag ttggcgcaac    360
agatcaaaat aatagaagag caaacttttc acaatatggc gcaggccttg atattgttgc    420
accgggcgtt ggcgttcaat caacatatcc gggcaacaca tatgtttcac tgaacggcac    480
atcaatggca acaccacatg ttgcgggcgt tgcagcacta gt                       522
```

<210> SEQ ID NO 128
<211> LENGTH: 522
<212> TYPE: DNA
<213> ORGANISM: Artificial Sequence
<220> FEATURE:
<223> OTHER INFORMATION: Synthetic

<400> SEQUENCE: 128

```
gtcgacacaa gatggcaatg gacatggcac acatgttgca ggcacagttg cagcactgaa    60
taatagcgat ggcgttattg gcgttgcacc gaacgttgaa ctgtatggag ttaaagttct    120
gggcgcaaac ggcagaggca cagtttcagg cattgcacag ggcctggaat gggcagcagc    180
aaatggcatg catgttgcaa atctgtcact gggctcacct gcaccgtcag caacactgga    240
acaggcagtt aatgcagcaa catcacgggg cgttctggtt attgcagcat caggcaatag    300
cggcgcaggc acagttggct atccggcaag atatgcaaat gcaatggcag ttggcgcaac    360
agatcaaaat aataatagag caaacttttc acagtatggc gcaggccttg atattgttgc    420
accgggcgtt ggcgttcaat caacatatcc gggcaacaca tatacttcac tgagcggcac    480
atcaatggca tcaccgcatg ttgcaggcgt tgcagcacta gt                       522
```

<210> SEQ ID NO 129
<211> LENGTH: 522
<212> TYPE: DNA
<213> ORGANISM: Artificial Sequence
<220> FEATURE:
<223> OTHER INFORMATION: Synthetic

```
<400> SEQUENCE: 129
gtcgacacaa gatggcaatg gacatggcac acatgttgca ggcacaattg cagcactgaa        60
taataacgtt ggcgttcttg gcgttgcacc gagcgttgat ctgtatggag ttaaagttct       120
ggacgcaagc ggcagaggca caatttcagg cattgcacgg ggcctggaat gggcagcagc       180
aaatggcatg catattgcaa atatgtcact gggctcagat caaccgtcaa caacactgga       240
acgggcagtt aatgcagcaa catcacgggg cgttctggtt gttgcagcat caggcaatac       300
cggctcaggc acagttagct atccggcaag atatgcaaat gcaatggcag ttggcgcaac       360
agatcaaaat aataatagag caaactcttc acaatatggc gcaggccttg atattgttgc       420
accgggcgtt ggcgttcaat caacatatcc gggcagcaca tatgcttcac tgagcggcac       480
atcaatggca tcaccgcatg ttgcaggcgt tgcagcacta gt                          522

<210> SEQ ID NO 130
<211> LENGTH: 522
<212> TYPE: DNA
<213> ORGANISM: Artificial Sequence
<220> FEATURE:
<223> OTHER INFORMATION: Synthetic

<400> SEQUENCE: 130
gtcgacacaa gatggcaatg gacatggcac acatgttgca ggcacaattg cagcactgaa        60
taatagcgtt ggcgttattg gcgttgcacc gagcgctgaa ctgtatggag ttaaagttct       120
gggcgcaaac ggcagcggca cagtttcagg cattgcacgg ggcctggaat gggcagcaga       180
taatggcatg catgttgcaa atatgtcact gggctcatct gcaccgtcag caacactgga       240
acgggcagtt aattcagcaa catcacgggg cgttctggtt gttgcagcaa caggcaatag       300
cggcgcaggc tcaattagct atccggcaag atatgcaaat gcaatggcag ttggcgcaac       360
agatcaaaat aataatagag caagcttttc acaatatggc acaggccttg atattgttgc       420
accgggcgtt aatgttcaat caacatatcc gggcagcaga tatgcttcaa tgagcggcac       480
atcaatggca tcaccgcatg ttgcaggcgc tgcagcacta gt                          522

<210> SEQ ID NO 131
<211> LENGTH: 173
<212> TYPE: PRT
<213> ORGANISM: Artificial Sequence
<220> FEATURE:
<223> OTHER INFORMATION: Synthetic

<400> SEQUENCE: 131

Ser Thr Gln Asp Gly Asn Gly His Gly Thr His Val Ala Gly Thr Ile
1               5                   10                  15

Ala Ala Leu Asp Asn Asp Glu Gly Val Val Gly Val Ala Pro Asn Ala
                20                  25                  30

Asp Leu Tyr Ala Val Lys Val Leu Ser Ala Ser Gly Ser Gly Ser Ile
            35                  40                  45

Ser Ser Ile Ala Gln Gly Leu Glu Trp Ser Gly Glu Asn Gly Met Asp
        50                  55                  60

Ile Ala Asn Leu Ser Leu Gly Ser Ser Ala Pro Ser Ala Thr Leu Glu
65                  70                  75                  80

Gln Ala Val Asn Ala Ala Thr Ser Arg Gly Val Leu Val Ile Ala Ala
                85                  90                  95

Ser Gly Asn Ser Gly Ala Gly Ser Val Gly Tyr Pro Ala Arg Tyr Ala
                100                 105                 110
```

-continued

```
Asn Ala Met Ala Val Gly Ala Thr Asp Gln Asn Asn Asn Arg Ala Ser
            115                 120                 125

Ser Ser Gln Tyr Gly Ala Gly Leu Asp Ile Val Ala Pro Gly Val Gly
        130                 135                 140

Val Gln Ser Thr Tyr Pro Gly Asn Arg Tyr Ala Ser Leu Asn Gly Thr
145                 150                 155                 160

Ser Met Ala Thr Pro His Val Ala Gly Val Ala Ala Leu
                165                 170
```

<210> SEQ ID NO 132
<211> LENGTH: 173
<212> TYPE: PRT
<213> ORGANISM: Artificial Sequence
<220> FEATURE:
<223> OTHER INFORMATION: Synthetic

<400> SEQUENCE: 132

```
Ser Thr Gln Asp Gly Asn Gly His Gly Thr His Val Ala Gly Thr Val
1               5                   10                  15

Ala Ala Leu Asn Asn Ser Ile Gly Val Ile Gly Val Ala Pro Ser Ala
            20                  25                  30

Asp Leu Tyr Ala Val Lys Val Leu Gly Ala Asn Gly Arg Gly Ser Val
        35                  40                  45

Ser Gly Ile Ala Gln Gly Leu Glu Trp Ala Ala Asn Asn Met His
    50                  55                  60

Ile Ala Asn Met Ser Leu Gly Ser Asp Phe Pro Ser Ser Thr Leu Glu
65                  70                  75                  80

Arg Ala Val Asn Tyr Ala Thr Ser Gln Gly Val Leu Val Ile Ala Ala
                85                  90                  95

Thr Gly Asn Asn Gly Ser Gly Ser Val Gly Tyr Pro Ala Arg Tyr Ala
            100                 105                 110

Asn Ala Met Ala Val Gly Ala Thr Asp Gln Asn Asn Arg Arg Ala Asn
        115                 120                 125

Phe Ser Gln Tyr Gly Thr Gly Ile Asp Ile Val Ala Pro Gly Val Asn
    130                 135                 140

Val Gln Ser Thr Tyr Pro Gly Asn Arg Tyr Ala Ser Leu Asn Gly Thr
145                 150                 155                 160

Ser Met Ala Thr Pro His Val Ala Gly Ala Ala Leu
                165                 170
```

<210> SEQ ID NO 133
<211> LENGTH: 173
<212> TYPE: PRT
<213> ORGANISM: Artificial Sequence
<220> FEATURE:
<223> OTHER INFORMATION: Synthetic

<400> SEQUENCE: 133

```
Ser Thr Gln Asp Gly Asn Gly His Gly Thr His Val Ala Gly Thr Ile
1               5                   10                  15

Ala Ala Leu Asn Asn Ser Ile Gly Val Leu Gly Val Ala Pro Asn Ala
            20                  25                  30

Glu Leu Tyr Ala Val Lys Val Leu Gly Ala Asn Gly Arg Gly Ser Val
        35                  40                  45

Ser Gly Ile Ala Gln Gly Leu Glu Trp Ala Ala Asn Asn Met His
    50                  55                  60

Ile Ala Asn Met Ser Leu Gly Ser Asp Ala Pro Ser Thr Thr Leu Glu
65                  70                  75                  80
```

```
Arg Ala Val Asn Tyr Ala Thr Ser Gln Gly Val Leu Val Ile Ala Ala
                85                  90                  95

Thr Gly Asn Asn Gly Ser Gly Ser Val Gly Tyr Pro Ala Arg Tyr Ala
            100                 105                 110

Asn Ala Met Ala Val Gly Ala Thr Asp Gln Asn Asn Arg Arg Ala Asn
        115                 120                 125

Phe Ser Gln Tyr Gly Thr Gly Ile Asp Ile Val Ala Pro Gly Val Asn
    130                 135                 140

Val Gln Ser Thr Tyr Pro Gly Asn Arg Tyr Val Ser Met Asn Gly Thr
145                 150                 155                 160

Ser Met Ala Thr Pro His Val Ala Gly Val Ala Ala Leu
                165                 170
```

<210> SEQ ID NO 134
<211> LENGTH: 173
<212> TYPE: PRT
<213> ORGANISM: Artificial Sequence
<220> FEATURE:
<223> OTHER INFORMATION: Synthetic

<400> SEQUENCE: 134

```
Ser Thr Gln Asp Gly Asn Gly His Gly Thr His Val Ala Gly Thr Val
1               5                   10                  15

Ala Ala Leu Asn Asn Ser Ile Gly Val Ile Gly Val Ala Pro Ser Ala
                20                  25                  30

Asp Leu Tyr Ala Val Lys Val Leu Gly Ala Asn Gly Arg Gly Ser Val
            35                  40                  45

Ser Gly Ile Ala Gln Gly Leu Glu Trp Ala Ala Asn Asn Met His
    50                  55                  60

Ile Ala Asn Met Ser Leu Gly Ser Asp Ala Pro Ser Thr Thr Leu Gly
65                  70                  75                  80

Arg Ala Val Asn Tyr Ala Thr Ser Gln Gly Val Leu Val Ile Ala Ala
                85                  90                  95

Thr Gly Asn Asn Gly Ser Gly Ser Val Gly Tyr Pro Ala Arg Tyr Ala
            100                 105                 110

Asn Ala Met Ala Val Gly Ala Thr Asp Gln Asn Asn Arg Arg Ala Asn
        115                 120                 125

Phe Ser Gln Tyr Gly Thr Gly Ile Asp Ile Val Ala Pro Gly Val Asn
    130                 135                 140

Val Gln Ser Thr Tyr Pro Gly Asn Arg Tyr Ala Ser Leu Asn Gly Thr
145                 150                 155                 160

Ser Met Ala Thr Pro His Val Ala Gly Val Ala Ala Leu
                165                 170
```

<210> SEQ ID NO 135
<211> LENGTH: 172
<212> TYPE: PRT
<213> ORGANISM: Artificial Sequence
<220> FEATURE:
<223> OTHER INFORMATION: Synthetic

<400> SEQUENCE: 135

```
Ser Thr Gln Asp Gly Asn Gly His Gly Thr His Val Ala Gly Thr Val
1               5                   10                  15

Ala Ala Leu Asn Asn Ser Ile Gly Val Ile Gly Val Ala Pro Ser Ala
                20                  25                  30

Asp Leu Tyr Ala Val Lys Val Leu Gly Ala Asn Gly Arg Gly Ser Val
```

```
             35                  40                  45
Ser Gly Ile Ala Arg Gly Leu Glu Trp Ala Ala Asn Asn Met His
 50                  55                  60

Ile Ala Asn Met Ser Leu Gly Ser Asp Ala Pro Ser Thr Thr Leu Glu
 65                  70                  75                  80

Arg Ala Val Asn Tyr Ala Thr Ser Gln Gly Val Leu Val Ile Ala Ala
                 85                  90                  95

Thr Gly Asn Asn Gly Ser Gly Ser Val Gly Tyr Pro Ala Arg Tyr Ala
                100                 105                 110

Asn Ala Met Ala Val Gly Ala Thr Asp Gln Asn Asn Arg Arg Ala Asn
            115                 120                 125

Phe Ser Gln Tyr Gly Thr Gly Ile Asp Ile Val Ala Pro Gly Val Asn
        130                 135                 140

Val Gln Ser Thr Tyr Pro Gly Asn Arg Tyr Ala Ser Leu Asn Gly Thr
145                 150                 155                 160

Ser Met Ala Pro His Val Ala Gly Val Ala Ala Leu
                165                 170

<210> SEQ ID NO 136
<211> LENGTH: 173
<212> TYPE: PRT
<213> ORGANISM: Artificial Sequence
<220> FEATURE:
<223> OTHER INFORMATION: Synthetic

<400> SEQUENCE: 136

Ser Thr Gln Asp Gly Asn Gly His Gly Thr His Val Ala Gly Thr Ile
 1               5                  10                  15

Ala Ala Leu Asn Asn Asn Val Gly Val Leu Gly Val Ala Pro Asn Val
                 20                  25                  30

Glu Leu Tyr Gly Val Lys Val Leu Gly Ala Ser Gly Ser Gly Ser Ile
             35                  40                  45

Ser Gly Ile Ala Gln Gly Leu Gln Trp Ala Gly Asn Asn Gly Met His
 50                  55                  60

Ile Ala Asn Met Ser Leu Gly Thr Ser Ala Pro Ser Ala Thr Leu Glu
 65                  70                  75                  80

Gln Ala Val Asn Ala Ala Thr Ser Arg Gly Val Leu Val Ile Ala Ala
                 85                  90                  95

Ser Gly Asn Ser Gly Ala Gly Ser Val Gly Tyr Pro Ala Arg Tyr Ala
                100                 105                 110

Asn Ala Met Ala Val Gly Ala Thr Asp Gln Asn Asn Arg Arg Ala Asn
            115                 120                 125

Phe Ser Gln Tyr Gly Thr Gly Ile Asp Ile Val Ala Pro Gly Val Asn
        130                 135                 140

Val Gln Ser Thr Tyr Pro Gly Asn Arg Tyr Val Ser Met Asn Gly Thr
145                 150                 155                 160

Ser Met Ala Thr Pro His Val Ala Gly Val Ala Ala Leu
                165                 170

<210> SEQ ID NO 137
<211> LENGTH: 173
<212> TYPE: PRT
<213> ORGANISM: Artificial Sequence
<220> FEATURE:
<223> OTHER INFORMATION: Synthetic

<400> SEQUENCE: 137
```

```
Ser Thr Gln Asp Gly Asn Gly His Gly Thr His Val Ala Gly Thr Val
  1               5                  10                 15

Ala Ala Leu Asn Asn Ser Ile Gly Val Ile Gly Val Ala Pro Ser Ala
             20                  25                 30

Asp Leu Tyr Ala Val Lys Val Leu Gly Ala Asn Gly Arg Gly Ser Val
             35                  40                 45

Ser Gly Ile Ala Gln Gly Leu Glu Trp Ala Ala Asn Asn Met His
 50                  55                  60

Ile Ala Asn Met Ser Leu Gly Ser Asp Ala Pro Ser Thr Thr Leu Glu
 65                  70                  75                 80

Arg Ala Val Asn Tyr Ala Thr Ser Gln Gly Val Leu Val Ile Ala Ala
                 85                  90                 95

Thr Gly Asn Asn Gly Ser Gly Ser Val Gly Tyr Pro Ala Arg Tyr Ala
             100                 105                110

Asn Ala Met Ala Val Gly Ala Thr Asp Gln Asn Asn Arg Arg Ala Asn
             115                 120                125

Phe Ser Gln Tyr Gly Thr Gly Ile Asp Ile Val Ala Pro Gly Val Asn
         130                 135                140

Val Gln Ser Thr Tyr Pro Gly Asn Arg Tyr Val Ser Met Ser Gly Thr
145                 150                 155                160

Ser Met Ala Thr Pro His Val Ala Gly Ala Ala Ala Leu
             165                 170
```

<210> SEQ ID NO 138
<211> LENGTH: 173
<212> TYPE: PRT
<213> ORGANISM: Artificial Sequence
<220> FEATURE:
<223> OTHER INFORMATION: Synthetic
<221> NAME/KEY: misc_feature
<222> LOCATION: (20)..(20)
<223> OTHER INFORMATION: Xaa in position 20 denotes an unknown amino
      acid

<400> SEQUENCE: 138

```
Ser Thr Gln Asp Gly Asn Gly His Gly Thr His Val Ala Gly Thr Val
  1               5                  10                 15

Ala Ala Leu Xaa Asn Ser Ile Gly Val Ile Gly Val Ala Pro Ser Ala
             20                  25                 30

Asp Leu Tyr Ala Val Lys Val Leu Gly Ala Asn Gly Arg Gly Ser Val
             35                  40                 45

Ser Gly Ile Ala Gln Gly Leu Glu Trp Ala Ala Asn Asn Met His
 50                  55                  60

Ile Ala Asn Met Ser Leu Gly Ser Asp Ala Pro Ser Thr Thr Leu Glu
 65                  70                  75                 80

Arg Ala Val Asn Tyr Ala Thr Ser Gln Gly Val Leu Val Ile Ala Ala
                 85                  90                 95

Thr Gly Asn Asn Gly Ser Gly Ser Val Gly Tyr Pro Ala Arg Tyr Ala
             100                 105                110

Asn Ala Met Ala Val Gly Ala Thr Asp Gln Asn Asn Arg Arg Ala Asn
             115                 120                125

Phe Ser Gln Tyr Gly Thr Gly Ile Asp Ile Val Ala Pro Gly Val Asn
         130                 135                140

Val Gln Ser Thr Tyr Pro Gly Asn Arg Tyr Val Ser Met Asn Gly Thr
145                 150                 155                160

Ser Met Ala Thr Pro His Val Ala Gly Ala Ala Ala Leu
             165                 170
```

<210> SEQ ID NO 139
<211> LENGTH: 173
<212> TYPE: PRT
<213> ORGANISM: Artificial Sequence
<220> FEATURE:
<223> OTHER INFORMATION: Synthetic

<400> SEQUENCE: 139

```
Ser Thr Gln Asp Gly Asn Gly His Gly Thr His Val Ala Gly Thr Ile
1               5                   10                  15

Ala Ala Leu Asn Asn Ser Val Gly Val Leu Gly Val Ala Pro Asn Ala
            20                  25                  30

Glu Leu Tyr Ala Val Lys Val Leu Gly Ala Asn Gly Arg Gly Ser Val
        35                  40                  45

Ser Gly Ile Ala Gln Gly Leu Glu Trp Ala Ala Asn Asn Met His
    50                  55                  60

Ile Ala Asn Met Ser Leu Gly Ser Asp Ala Pro Ser Thr Thr Leu Glu
65                  70                  75                  80

Arg Ala Val Asn Tyr Ala Thr Ser Gln Gly Val Leu Val Ile Ala Ala
                85                  90                  95

Thr Gly Asn Asn Gly Ser Gly Ser Val Gly Tyr Pro Ala Arg Tyr Ala
            100                 105                 110

Asn Ala Met Ala Val Gly Ala Thr Asp Gln Asn Asn Arg Arg Ala Asn
        115                 120                 125

Phe Ser Gln Tyr Gly Thr Gly Ile Asp Ile Val Ala Pro Gly Val Asn
    130                 135                 140

Val Gln Ser Thr Tyr Pro Gly Thr Arg Tyr Ala Ser Leu Asn Gly Thr
145                 150                 155                 160

Ser Met Ala Thr Pro His Val Ala Gly Ala Ala Ala Leu
                165                 170
```

<210> SEQ ID NO 140
<211> LENGTH: 173
<212> TYPE: PRT
<213> ORGANISM: Artificial Sequence
<220> FEATURE:
<223> OTHER INFORMATION: Synthetic

<400> SEQUENCE: 140

```
Ser Thr Gln Asp Gly Asn Gly His Gly Thr His Val Ala Gly Thr Ile
1               5                   10                  15

Ala Ala Leu Asp Asn Ser Ile Gly Val Ile Gly Val Ala Pro Ser Ala
            20                  25                  30

Asp Leu Tyr Ala Val Lys Val Leu Gly Ala Asn Gly Arg Gly Ser Val
        35                  40                  45

Ser Gly Ile Ala Gln Gly Leu Glu Trp Ala Ala Asn Asn Met His
    50                  55                  60

Ile Ala Asn Met Ser Leu Gly Ser Asp Ala Pro Ser Thr Thr Leu Glu
65                  70                  75                  80

Arg Ala Val Asn Tyr Ala Thr Ser Gln Gly Val Leu Val Ile Ala Ala
                85                  90                  95

Thr Gly Asn Asn Gly Ser Gly Ser Val Gly Tyr Pro Ala Arg Tyr Ala
            100                 105                 110

Asn Ala Met Ala Val Gly Ala Thr Asp Gln Asn Asn Arg Arg Ala Asn
        115                 120                 125

Phe Ser Gln Tyr Gly Thr Gly Ile Asp Ile Val Ala Pro Gly Val Asn
```

```
                130                 135                 140
Val Gln Ser Thr Tyr Pro Gly Asn Arg Tyr Ala Ser Leu Asn Gly Thr
145                 150                 155                 160

Ser Met Ala Thr Pro His Val Ala Gly Ala Ala Leu
                165                 170

<210> SEQ ID NO 141
<211> LENGTH: 173
<212> TYPE: PRT
<213> ORGANISM: Artificial Sequence
<220> FEATURE:
<223> OTHER INFORMATION: Synthetic

<400> SEQUENCE: 141

Ser Thr Gln Asp Gly Asn Gly His Gly Thr His Val Ala Gly Thr Val
1               5                   10                  15

Ala Ala Leu Asn Asn Ser Ile Gly Val Ile Gly Val Ala Pro Ser Ala
                20                  25                  30

Asp Leu Tyr Ala Val Lys Val Leu Gly Ala Asn Gly Ser Gly Ser Val
            35                  40                  45

Ser Gly Ile Ala Arg Gly Leu Glu Trp Ala Ala Thr Asn Asn Met His
    50                  55                  60

Ile Ala Asn Met Ser Leu Gly Ser Asp Phe Pro Ser Ser Thr Leu Glu
65                  70                  75                  80

Arg Ala Val Asn Tyr Ala Thr Ser Arg Asp Val Leu Val Ile Ala Ala
                85                  90                  95

Thr Gly Asn Asn Gly Ser Gly Ser Val Gly Tyr Pro Ala Arg Tyr Ala
                100                 105                 110

Asn Ala Met Ala Val Gly Ala Thr Asp Gln Asn Asn Arg Arg Ala Asn
            115                 120                 125

Phe Ser Gln Tyr Gly Thr Gly Ile Asp Ile Val Ala Pro Gly Val Asn
        130                 135                 140

Val Gln Ser Thr Tyr Pro Gly Asn Arg Tyr Ala Ser Leu Asn Gly Thr
145                 150                 155                 160

Ser Met Ala Thr Pro His Val Ala Gly Ala Ala Leu
                165                 170

<210> SEQ ID NO 142
<211> LENGTH: 173
<212> TYPE: PRT
<213> ORGANISM: Artificial Sequence
<220> FEATURE:
<223> OTHER INFORMATION: Synthetic

<400> SEQUENCE: 142

Ser Thr Gln Asp Gly Asn Gly His Gly Thr His Val Ala Gly Thr Val
1               5                   10                  15

Ala Ala Leu Asn Asn Ser Ile Gly Val Ile Gly Val Ala Pro Ser Ala
                20                  25                  30

Asp Leu Tyr Ala Val Lys Val Leu Gly Ala Asn Gly Arg Gly Ser Val
            35                  40                  45

Ser Gly Ile Ala Gln Gly Leu Glu Trp Ala Ala Asn Asn Met His
    50                  55                  60

Ile Ala Asn Met Ser Leu Gly Ser Asp Ala Pro Ser Thr Thr Leu Glu
65                  70                  75                  80

Arg Ala Val Asn Tyr Ala Thr Ser Gln Gly Val Leu Val Ile Ala Ala
                85                  90                  95
```

```
Thr Gly Asn Asn Gly Ser Gly Ser Val Gly Tyr Pro Ala Arg Tyr Ala
            100                 105                 110

Asn Ala Met Ala Val Gly Ala Thr Asp Gln Asn Asn Arg Arg Ala Asn
        115                 120                 125

Phe Ser Gln Tyr Gly Thr Gly Ile Asp Ile Val Ala Pro Gly Val Asn
    130                 135                 140

Val Gln Ser Thr Tyr Pro Gly Asn Arg Tyr Ala Ser Leu Ser Gly Thr
145                 150                 155                 160

Ser Met Ala Thr Pro His Val Ala Gly Val Ala Ala Leu
                165                 170

<210> SEQ ID NO 143
<211> LENGTH: 173
<212> TYPE: PRT
<213> ORGANISM: Artificial Sequence
<220> FEATURE:
<223> OTHER INFORMATION: Synthetic

<400> SEQUENCE: 143

Ser Thr Gln Asp Gly Asn Gly His Gly Thr His Val Ala Gly Thr Val
1               5                   10                  15

Ala Ala Leu Asn Asn Ser Ile Gly Val Ile Gly Val Ala Pro Ser Ala
            20                  25                  30

Asp Leu Tyr Ala Val Lys Val Leu Gly Ala Asn Gly Arg Gly Ser Val
        35                  40                  45

Ser Gly Ile Ala Gln Gly Leu Glu Trp Ala Ala Asn Asn Met His
    50                  55                  60

Ile Ala Asn Met Ser Leu Gly Ser Asp Phe Pro Ser Ser Thr Leu Glu
65                  70                  75                  80

Arg Ala Val Asn Tyr Ala Thr Ser Arg Asp Val Leu Val Ile Ala Ala
                85                  90                  95

Thr Gly Asn Asn Gly Ser Gly Ser Val Gly Tyr Pro Ala Arg Tyr Ala
            100                 105                 110

Asn Ala Met Ala Val Gly Ala Thr Asp Gln Asn Asn Arg Arg Ala Asn
        115                 120                 125

Phe Ser Gln Tyr Gly Thr Gly Ile Asp Ile Val Ala Pro Gly Val Asn
    130                 135                 140

Val Gln Ser Thr Tyr Pro Gly Asn Arg Tyr Ala Ser Leu Asn Gly Thr
145                 150                 155                 160

Ser Met Ala Thr Pro His Val Ala Gly Val Ala Ala Leu
                165                 170

<210> SEQ ID NO 144
<211> LENGTH: 173
<212> TYPE: PRT
<213> ORGANISM: Artificial Sequence
<220> FEATURE:
<223> OTHER INFORMATION: Synthetic

<400> SEQUENCE: 144

Ser Thr Gln Asp Gly Asn Gly His Gly Thr His Val Ala Gly Thr Val
1               5                   10                  15

Ala Ala Leu Asn Asn Ser Ile Gly Val Ile Gly Val Ala Pro Ser Ala
            20                  25                  30

Asp Leu Tyr Ala Val Lys Val Leu Gly Ala Asn Gly Arg Gly Ser Val
        35                  40                  45

Ser Gly Ile Ala Gln Gly Leu Glu Trp Ala Ala Ala Asn Asn Met His
    50                  55                  60
```

```
Ile Ala Asn Met Ser Leu Gly Ser Asp Ala Pro Ser Thr Thr Leu Glu
 65                  70                  75                  80

Arg Ala Val Asn Tyr Ala Thr Ser Arg Asp Val Leu Val Ile Ala Ala
                 85                  90                  95

Thr Gly Asn Asn Gly Ser Gly Ser Val Gly Tyr Pro Ala Arg Tyr Ala
            100                 105                 110

Asn Ala Met Ala Val Gly Ala Thr Asp Gln Asn Asn Arg Arg Ala Asn
        115                 120                 125

Phe Ser Gln Tyr Gly Thr Gly Ile Asp Ile Val Ala Pro Gly Val Asn
    130                 135                 140

Val Gln Ser Thr Tyr Pro Gly Asn Arg Tyr Ala Ser Leu Ser Gly Thr
145                 150                 155                 160

Ser Met Ala Thr Pro His Val Ala Gly Val Ala Ala Leu
                165                 170

<210> SEQ ID NO 145
<211> LENGTH: 173
<212> TYPE: PRT
<213> ORGANISM: Artificial Sequence
<220> FEATURE:
<223> OTHER INFORMATION: Synthetic

<400> SEQUENCE: 145

Ser Thr Gln Asp Gly Asn Gly His Gly Thr His Val Ala Gly Thr Val
  1               5                  10                  15

Ala Ala Leu Asn Asn Ser Ile Gly Val Ile Gly Val Ala Pro Ser Ala
                 20                  25                  30

Asp Leu Tyr Ala Val Lys Val Leu Gly Ala Asn Gly Arg Gly Ser Val
             35                  40                  45

Ser Gly Ile Ala Gln Gly Leu Glu Trp Ala Ala Asn Asn Met His
     50                  55                  60

Ile Ala Asn Met Ser Leu Gly Ser Asp Ala Pro Ser Thr Thr Leu Glu
 65                  70                  75                  80

Arg Ala Val Asn Tyr Ala Thr Ser Gln Gly Val Leu Val Ile Ala Ala
                 85                  90                  95

Thr Gly Asn Asn Gly Ser Gly Ser Val Gly Tyr Pro Ala Arg Tyr Ala
            100                 105                 110

Asn Ala Met Ala Val Gly Ala Thr Asp Gln Asn Asn Arg Arg Ala Asn
        115                 120                 125

Phe Ser Gln Tyr Gly Thr Gly Ile Asp Ile Val Ala Pro Gly Val Asn
    130                 135                 140

Val Gln Ser Thr Tyr Pro Gly Asn Arg Tyr Ala Ser Leu Ser Gly Thr
145                 150                 155                 160

Ser Met Ala Thr Pro His Val Ala Gly Ala Ala Ala Leu
                165                 170

<210> SEQ ID NO 146
<211> LENGTH: 173
<212> TYPE: PRT
<213> ORGANISM: Artificial Sequence
<220> FEATURE:
<223> OTHER INFORMATION: Synthetic

<400> SEQUENCE: 146

Ser Thr Gln Asp Gly Asn Gly His Gly Thr His Val Ala Gly Thr Val
  1               5                  10                  15

Ala Ala Leu Asn Asn Ser Ile Gly Val Ile Gly Val Ala Pro Ser Ala
```

```
                20                  25                  30

Asp Leu Tyr Ala Val Lys Val Leu Gly Ala Asn Gly Arg Gly Ser Val
            35                  40                  45

Ser Gly Ile Ala Gln Gly Leu Glu Trp Ala Ala Asn Asn Met His
50                  55                  60

Ile Ala Asn Met Ser Leu Gly Ser Asp Ala Pro Ser Thr Thr Leu Glu
65                  70                  75                  80

Arg Ala Val Asn Tyr Ala Thr Ser Gln Gly Val Leu Val Ile Ala Ala
                85                  90                  95

Thr Gly Asn Asn Gly Ser Gly Ser Val Gly Tyr Pro Ala Arg Tyr Ala
            100                 105                 110

Asn Ala Met Ala Val Gly Ala Thr Asp Gln Asn Asn Arg Arg Ala Asn
            115                 120                 125

Phe Ser Gln Tyr Gly Thr Gly Ile Asp Ile Val Ala Pro Gly Val Asn
            130                 135                 140

Val Gln Ser Thr Tyr Pro Gly Asn Arg Tyr Val Ser Met Asn Gly Thr
145                 150                 155                 160

Ser Met Ala Thr Pro His Val Ala Gly Val Ala Ala Leu
                165                 170

<210> SEQ ID NO 147
<211> LENGTH: 173
<212> TYPE: PRT
<213> ORGANISM: Artificial Sequence
<220> FEATURE:
<223> OTHER INFORMATION: Synthetic

<400> SEQUENCE: 147

Ser Thr Gln Asp Gly Asn Gly His Gly Thr His Val Ala Gly Thr Val
1               5                   10                  15

Ala Ala Leu Asp Asn Ser Val Gly Val Leu Gly Val Ala Pro Glu Ala
            20                  25                  30

Asp Leu Tyr Ala Val Lys Val Leu Ser Ala Ser Gly Ala Gly Ser Ile
            35                  40                  45

Ser Ser Ile Ala Gln Gly Leu Glu Trp Ser Ala Ala Asn Asn Met His
50                  55                  60

Ile Ala Asn Met Ser Leu Gly Ser Asp Ala Pro Ser Thr Thr Leu Glu
65                  70                  75                  80

Arg Ala Val Asn Tyr Ala Thr Ser Gln Gly Val Leu Val Ile Ala Ala
                85                  90                  95

Thr Gly Asn Asn Gly Ser Gly Ser Val Gly Tyr Pro Ala Arg Tyr Ala
            100                 105                 110

Asn Ala Met Ala Val Gly Ala Thr Asp Gln Asn Asn Arg Arg Ala Asn
            115                 120                 125

Phe Ser Gln Tyr Gly Thr Gly Ile Asp Ile Val Ala Pro Gly Val Asn
            130                 135                 140

Val Gln Ser Thr Tyr Pro Gly Asn Arg Tyr Ala Ser Leu Asn Gly Thr
145                 150                 155                 160

Ser Met Ala Thr Pro His Val Ala Gly Val Ala Ala Leu
                165                 170

<210> SEQ ID NO 148
<211> LENGTH: 173
<212> TYPE: PRT
<213> ORGANISM: Artificial Sequence
<220> FEATURE:
<223> OTHER INFORMATION: Synthetic
```

```
<400> SEQUENCE: 148

Ser Thr Gln Asp Gly Asn Gly His Gly Thr His Val Ala Gly Thr Ile
1               5                   10                  15

Ala Ala Leu Asn Asn Ser Ile Gly Val Ile Gly Val Ala Pro Ser Ala
            20                  25                  30

Asp Leu Tyr Ala Val Lys Val Leu Gly Ala Asn Gly Arg Gly Ser Val
        35                  40                  45

Ser Gly Ile Ala Gln Gly Leu Glu Trp Ala Ala Asn Asn Met His
    50                  55                  60

Ile Ala Asn Met Ser Leu Gly Ser Asp Ala Pro Ser Thr Thr Leu Glu
65                  70                  75                  80

Arg Ala Val Asn Tyr Ala Thr Ser Gln Gly Val Leu Val Ile Ala Ala
                85                  90                  95

Thr Gly Asn Asn Gly Ser Gly Ser Val Gly Tyr Pro Ala Arg Tyr Ala
            100                 105                 110

Asn Ala Met Ala Val Gly Ala Thr Asp Gln Asn Asn Arg Arg Ala Asn
            115                 120                 125

Phe Ser Gln Tyr Gly Thr Gly Ile Asp Ile Val Ala Pro Gly Val Asn
    130                 135                 140

Val Gln Ser Thr Tyr Pro Gly Asn Arg Tyr Val Ser Met Asn Gly Thr
145                 150                 155                 160

Ser Met Ala Thr Pro His Val Ala Gly Ala Ala Ala Leu
                165                 170

<210> SEQ ID NO 149
<211> LENGTH: 173
<212> TYPE: PRT
<213> ORGANISM: Artificial Sequence
<220> FEATURE:
<223> OTHER INFORMATION: Synthetic

<400> SEQUENCE: 149

Ser Thr Gln Asp Gly Asn Gly His Gly Thr His Val Ala Gly Thr Ile
1               5                   10                  15

Ala Ala Leu Asp Asn Asp Glu Gly Val Val Gly Val Ala Pro Asn Ala
            20                  25                  30

Asp Leu Tyr Ala Val Lys Val Leu Ser Ala Ser Gly Ser Gly Ser Ile
        35                  40                  45

Ser Ser Ile Ala Gln Gly Leu Glu Trp Ser Gly Glu Asn Gly Met Asp
    50                  55                  60

Ile Ala Asn Leu Ser Leu Gly Ser Ser Ala Pro Ser Ala Thr Leu Glu
65                  70                  75                  80

Gln Ala Val Asn Ala Ala Thr Ser Arg Gly Val Leu Val Ile Ala Ala
                85                  90                  95

Ser Gly Asn Ser Gly Ala Gly Ser Val Gly Tyr Pro Ala Arg Tyr Ala
            100                 105                 110

Asn Ala Met Ala Val Gly Ala Thr Asp Gln Asn Asn Asn Arg Ala Ser
            115                 120                 125

Phe Ser Gln Tyr Gly Ala Gly Leu Asp Ile Val Ala Pro Gly Val Gly
    130                 135                 140

Val Gln Ser Thr Tyr Pro Gly Asn Arg Tyr Ala Ser Leu Asn Gly Thr
145                 150                 155                 160

Ser Met Ala Thr Pro His Val Ala Gly Ala Ala Ala Leu
                165                 170
```

<210> SEQ ID NO 150
<211> LENGTH: 173
<212> TYPE: PRT
<213> ORGANISM: Artificial Sequence
<220> FEATURE:
<223> OTHER INFORMATION: Synthetic

<400> SEQUENCE: 150

```
Ser Thr Gln Asp Gly Asn Gly His Gly Thr His Val Ala Gly Thr Ile
1               5                   10                  15

Ala Ala Leu Asn Asn Ser Ile Gly Val Leu Gly Val Ala Pro Asn Ala
            20                  25                  30

Asp Leu Tyr Ala Val Lys Val Leu Gly Ala Asn Gly Ser Gly Ser Val
        35                  40                  45

Ser Gly Ile Ala Arg Gly Leu Glu Trp Ala Ala Thr Asn Asn Met His
50                  55                  60

Ile Ala Asn Met Ser Leu Gly Ser Asp Ala Pro Ser Thr Thr Leu Glu
65                  70                  75                  80

Arg Ala Val Asn Tyr Ala Thr Ser Gln Gly Val Leu Val Ile Ala Ala
                85                  90                  95

Thr Gly Asn Asn Gly Ser Gly Ser Val Gly Tyr Pro Ala Arg Tyr Ala
            100                 105                 110

Asn Ala Met Ala Val Gly Ala Thr Asp Gln Asn Asn Arg Arg Ala Asn
        115                 120                 125

Phe Ser Gln Tyr Gly Thr Gly Ile Asp Ile Val Ala Pro Gly Val Asn
    130                 135                 140

Val Gln Ser Thr Tyr Pro Gly Asn Arg Tyr Ala Arg Leu Asn Gly Thr
145                 150                 155                 160

Ser Met Ala Thr Pro His Val Ala Gly Val Ala Ala Leu
                165                 170
```

<210> SEQ ID NO 151
<211> LENGTH: 173
<212> TYPE: PRT
<213> ORGANISM: Artificial Sequence
<220> FEATURE:
<223> OTHER INFORMATION: Synthetic

<400> SEQUENCE: 151

```
Ser Thr Gln Asp Gly Asn Gly His Gly Thr His Val Ala Gly Thr Ile
1               5                   10                  15

Ala Ala Leu Asp Asn Ser Ile Gly Val Ile Gly Val Ala Pro Ser Ala
            20                  25                  30

Asp Leu Tyr Ala Val Lys Val Leu Gly Ala Asn Gly Ser Gly Ser Val
        35                  40                  45

Ser Gly Ile Ala Arg Gly Leu Glu Trp Ala Ala Thr Asn Asn Met His
50                  55                  60

Ile Ala Asn Met Ser Leu Gly Ser Asp Ala Pro Ser Thr Thr Leu Glu
65                  70                  75                  80

Arg Ala Val Asn Tyr Ala Thr Ser Gln Gly Val Leu Val Ile Ala Ala
                85                  90                  95

Thr Gly Asn Asn Gly Ser Gly Ser Val Gly Tyr Pro Ala Arg Tyr Ala
            100                 105                 110

Asn Ala Met Ala Val Gly Ala Thr Asp Gln Asn Asn Arg Arg Ala Asn
        115                 120                 125

Phe Ser Gln Tyr Gly Thr Gly Ile Asp Ile Val Ala Pro Gly Val Asn
    130                 135                 140
```

```
Val Gln Ser Thr Tyr Pro Gly Asn Arg Tyr Ala Ser Leu Asn Gly Thr
145                 150                 155                 160

Ser Met Ala Thr Pro His Val Ala Gly Ala Ala Ala Leu
                165                 170
```

<210> SEQ ID NO 152
<211> LENGTH: 173
<212> TYPE: PRT
<213> ORGANISM: Artificial Sequence
<220> FEATURE:
<223> OTHER INFORMATION: Synthetic

<400> SEQUENCE: 152

```
Ser Thr Gln Asp Gly Asn Gly His Gly Thr His Val Ala Gly Thr Ile
1               5                   10                  15

Ala Ala Leu Asp Asn Asp Glu Gly Val Val Gly Val Ala Pro Asn Ala
                20                  25                  30

Asp Leu Tyr Ala Val Lys Val Leu Ser Ala Ser Gly Ala Gly Ser Ile
            35                  40                  45

Ser Ser Ile Ala Gln Gly Leu Glu Trp Ser Gly Glu Asn Gly Met Asp
50                  55                  60

Ile Ala Asn Leu Ser Leu Gly Ser Ser Ala Pro Ser Ala Thr Leu Glu
65                  70                  75                  80

Gln Ala Val Asn Ala Ala Thr Ser Arg Gly Val Leu Val Ile Ala Ala
                85                  90                  95

Ser Gly Asn Ser Gly Ala Gly Ser Val Gly Tyr Pro Ala Arg Tyr Ala
                100                 105                 110

Asn Ala Met Ala Val Gly Ala Thr Asp Gln Asn Asn Asn Arg Ala Ser
                115                 120                 125

Phe Ser Gln Tyr Gly Ala Gly Leu Asp Ile Val Ala Pro Gly Val Gly
            130                 135                 140

Val Gln Ser Thr Tyr Pro Gly Ser Thr Tyr Ala Ser Leu Asn Gly Thr
145                 150                 155                 160

Ser Met Ala Thr Pro His Val Ala Gly Val Ala Ala Leu
                165                 170
```

<210> SEQ ID NO 153
<211> LENGTH: 173
<212> TYPE: PRT
<213> ORGANISM: Artificial Sequence
<220> FEATURE:
<223> OTHER INFORMATION: Synthetic

<400> SEQUENCE: 153

```
Ser Thr Gln Asp Gly Asn Gly His Gly Thr His Val Ala Gly Thr Ile
1               5                   10                  15

Ala Ala Leu Asn Asn Ser Ile Gly Val Leu Gly Val Ala Pro Asn Ala
                20                  25                  30

Glu Leu Tyr Ala Val Lys Val Leu Gly Ala Ser Gly Ser Gly Ser Ile
            35                  40                  45

Ser Gly Ile Ala Gln Gly Leu Glu Trp Ala Ala Asn Asn Met His
50                  55                  60

Ile Ala Asn Met Ser Leu Gly Ser Asp Ala Pro Ser Thr Thr Leu Glu
65                  70                  75                  80

Arg Ala Val Asn Tyr Ala Thr Ser Gln Gly Val Leu Val Ile Ala Ala
                85                  90                  95

Thr Gly Asn Asn Gly Ser Gly Ser Val Gly Tyr Pro Ala Arg Tyr Ala
```

-continued

```
                100                 105                 110
Asn Ala Met Ala Val Gly Ala Thr Asp Gln Asn Asn Arg Arg Ala Asn
            115                 120                 125
Phe Ser Gln Tyr Gly Thr Gly Ile Asp Ile Val Ala Pro Gly Val Asn
        130                 135                 140
Val Gln Ser Thr Tyr Pro Gly Asn Arg Tyr Ala Ser Leu Asn Gly Thr
145                 150                 155                 160
Ser Met Ala Thr Pro His Val Ala Gly Val Ala Ala Leu
                165                 170

<210> SEQ ID NO 154
<211> LENGTH: 173
<212> TYPE: PRT
<213> ORGANISM: Artificial Sequence
<220> FEATURE:
<223> OTHER INFORMATION: Synthetic

<400> SEQUENCE: 154

Ser Thr Gln Asp Gly Asn Gly His Gly Thr His Val Ala Gly Thr Ile
1               5                   10                  15
Ala Ala Leu Asn Asn Ser Ile Gly Val Leu Gly Val Ala Pro Asn Ala
            20                  25                  30
Glu Leu Tyr Ala Val Lys Val Leu Gly Ala Asn Gly Arg Gly Ser Val
        35                  40                  45
Ser Gly Ile Ala Gln Gly Leu Glu Trp Ala Ala Asn Asn Met His
    50                  55                  60
Ile Ala Asn Met Ser Leu Gly Ser Asp Ala Pro Ser Thr Thr Leu Glu
65                  70                  75                  80
Arg Ala Val Asn Tyr Ala Thr Ser Gln Gly Val Leu Val Ile Ala Ala
                85                  90                  95
Thr Gly Asn Asn Gly Ser Gly Ser Val Gly Tyr Pro Ala Arg Tyr Ala
            100                 105                 110
Asn Ala Met Ala Val Gly Ala Thr Asp Gln Asn Asn Asn Arg Ala Ser
            115                 120                 125
Phe Ser Gln Tyr Gly Ala Gly Leu Asp Ile Val Ala Pro Gly Val Asn
        130                 135                 140
Val Gln Ser Thr Tyr Pro Gly Ser Thr Tyr Asp Ser Leu Ser Gly Thr
145                 150                 155                 160
Ser Met Ala Thr Pro His Val Ala Gly Val Ala Ala Leu
                165                 170

<210> SEQ ID NO 155
<211> LENGTH: 173
<212> TYPE: PRT
<213> ORGANISM: Artificial Sequence
<220> FEATURE:
<223> OTHER INFORMATION: Synthetic

<400> SEQUENCE: 155

Ser Thr Gln Asp Gly Asn Gly His Gly Thr His Val Ala Gly Thr Val
1               5                   10                  15
Ala Ala Leu Asn Asn Ser Ile Gly Val Ile Gly Val Ala Pro Ser Ala
            20                  25                  30
Asp Leu Tyr Ala Val Lys Val Leu Gly Ala Asn Gly Arg Gly Ser Val
        35                  40                  45
Ser Gly Ile Ala Gln Gly Leu Glu Trp Ala Ala Asn Asn Met His
    50                  55                  60
```

-continued

```
Ile Ala Asn Met Ser Leu Gly Ser Asp Ala Pro Ser Thr Thr Leu Glu
 65                  70                  75                  80

Arg Ala Val Asn Tyr Ala Thr Ser Gln Gly Val Leu Val Ile Ala Ala
                 85                  90                  95

Thr Gly Asn Asn Gly Ser Gly Ser Val Gly Tyr Pro Ala Arg Tyr Ala
            100                 105                 110

Asn Ala Met Ala Val Gly Ala Thr Asp Gln Asn Asn Arg Arg Ala Asn
        115                 120                 125

Phe Ser Gln Tyr Gly Thr Gly Ile Asp Ile Val Ala Pro Gly Val Asn
    130                 135                 140

Val Gln Ser Thr Tyr Pro Gly Gly Gln Tyr Ala Glu Leu Ser Gly Thr
145                 150                 155                 160

Ser Met Ala Ser Pro His Val Ala Gly Ala Ala Ala Leu
                165                 170
```

<210> SEQ ID NO 156
<211> LENGTH: 173
<212> TYPE: PRT
<213> ORGANISM: Artificial Sequence
<220> FEATURE:
<223> OTHER INFORMATION: Synthetic

<400> SEQUENCE: 156

```
Ser Thr Gln Asp Gly Asn Gly His Gly Thr His Val Ala Gly Thr Val
 1               5                  10                  15

Ala Ala Leu Asn Asn Ser Ile Gly Val Leu Gly Val Ala Pro Asn Ala
                20                  25                  30

Glu Leu Tyr Ala Val Lys Val Leu Gly Ala Ser Gly Ser Gly Ser Ile
            35                  40                  45

Ser Gly Ile Ala Gln Gly Leu Glu Trp Ala Ala Asn Asn Met His
        50                  55                  60

Ile Ala Asn Met Ser Leu Gly Ser Asp Ala Pro Ser Thr Thr Leu Glu
 65                  70                  75                  80

Arg Ala Val Asn Tyr Ala Thr Ser Gln Gly Val Leu Val Ile Ala Ala
                 85                  90                  95

Thr Gly Asn Asn Gly Ser Gly Ser Val Gly Tyr Pro Ala Arg Tyr Ala
            100                 105                 110

Asn Ala Met Ala Val Gly Ala Thr Asp Gln Asn Asn Arg Arg Ala Asn
        115                 120                 125

Phe Ser Gln Tyr Gly Thr Gly Ile Asp Ile Val Ala Pro Gly Val Glu
    130                 135                 140

Ile Glu Ser Thr Tyr Pro Gly Ser Ser Tyr Asp Ser Leu Arg Gly Thr
145                 150                 155                 160

Ser Met Ala Thr Pro His Val Ala Gly Ala Ala Ala Leu
                165                 170
```

<210> SEQ ID NO 157
<211> LENGTH: 173
<212> TYPE: PRT
<213> ORGANISM: Artificial Sequence
<220> FEATURE:
<223> OTHER INFORMATION: Synthetic

<400> SEQUENCE: 157

```
Ser Thr Gln Asp Gly Asn Gly His Gly Thr His Val Ala Gly Thr Ile
 1               5                  10                  15

Ala Ala Leu Asp Asn Asp Glu Gly Val Val Gly Val Ala Pro Asn Ala
                20                  25                  30
```

Asp Leu Tyr Ala Val Lys Val Leu Gly Ala Asn Gly Arg Gly Ser Val
             35                  40                  45

Ser Gly Ile Ala Gln Gly Leu Glu Trp Ala Ala Ala Asn Asn Met His
         50                  55                  60

Ile Ala Asn Met Ser Leu Gly Ser Asp Ala Pro Ser Thr Thr Leu Glu
 65                  70                  75                  80

Arg Ala Val Asn Tyr Ala Thr Ser Gln Gly Val Leu Val Ile Ala Ala
                 85                  90                  95

Thr Gly Asn Asn Gly Ser Gly Ser Val Gly Tyr Pro Ala Arg Tyr Ala
                100                 105                 110

Asn Ala Met Ala Val Gly Ala Thr Asp Gln Asn Asn Arg Arg Ala Asn
             115                 120                 125

Phe Ser Gln Tyr Gly Thr Gly Ile Asp Ile Val Ala Pro Gly Val Asn
         130                 135                 140

Val Gln Ser Thr Tyr Pro Gly Asn Arg Tyr Ala Ser Leu Asn Gly Thr
145                 150                 155                 160

Ser Met Ala Thr Pro His Val Ala Gly Val Ala Ala Leu
                165                 170

<210> SEQ ID NO 158
<211> LENGTH: 173
<212> TYPE: PRT
<213> ORGANISM: Artificial Sequence
<220> FEATURE:
<223> OTHER INFORMATION: Synthetic

<400> SEQUENCE: 158

Ser Thr Gln Asp Gly Asn Gly His Gly Thr His Val Ala Gly Thr Ile
 1               5                  10                  15

Ala Ala Leu Asn Asn Ser Val Gly Val Leu Gly Val Ala Pro Asn Ala
                 20                  25                  30

Asp Leu Tyr Ala Val Lys Val Leu Gly Ala Asn Gly Arg Gly Ser Val
             35                  40                  45

Ser Gly Ile Ala Gln Gly Leu Glu Trp Ala Ala Ala Asn Asn Met His
         50                  55                  60

Ile Ala Asn Met Ser Leu Gly Ser Asp Ala Pro Ser Thr Thr Leu Glu
 65                  70                  75                  80

Arg Ala Val Asn Tyr Ala Thr Ser Gln Gly Val Leu Val Ile Ala Ala
                 85                  90                  95

Thr Gly Asn Asn Gly Ser Gly Ser Val Gly Tyr Pro Ala Arg Tyr Ala
                100                 105                 110

Asn Ala Met Ala Val Gly Ala Thr Asp Gln Asn Asn Arg Arg Ala Asn
             115                 120                 125

Phe Ser Gln Tyr Gly Thr Gly Ile Asp Ile Val Ala Pro Gly Val Gly
         130                 135                 140

Val Gln Ser Thr Tyr Pro Gly Asn Arg Tyr Ala Ser Leu Ser Gly Thr
145                 150                 155                 160

Ser Met Ala Ser Pro His Val Ala Gly Val Ala Ala Leu
                165                 170

<210> SEQ ID NO 159
<211> LENGTH: 173
<212> TYPE: PRT
<213> ORGANISM: Artificial Sequence
<220> FEATURE:
<223> OTHER INFORMATION: Synthetic -continued

<400> SEQUENCE: 159

Ser Thr Gln Asp Gly Asn Gly His Gly Thr His Val Ala Gly Thr Ile
1               5                   10                  15

Ala Ala Leu Asn Asn Ser Ile Gly Val Leu Gly Val Ala Pro Asn Ala
            20                  25                  30

Glu Leu Tyr Ala Val Lys Val Leu Gly Ala Asn Gly Arg Gly Ser Val
        35                  40                  45

Ser Gly Ile Ala Gln Gly Leu Glu Trp Ala Ala Asn Asn Met His
    50                  55                  60

Ile Ala Asn Met Ser Leu Gly Ser Asp Ala Pro Ser Thr Thr Leu Lys
65                  70                  75                  80

Arg Ala Val Asn Tyr Ala Thr Ser Gln Gly Val Leu Val Ile Ala Ala
                85                  90                  95

Thr Gly Asn Asn Gly Ser Gly Ser Val Gly Tyr Pro Ala Arg Tyr Ala
            100                 105                 110

Asn Ala Met Ala Val Gly Ala Thr Asp Gln Asn Asn Arg Arg Ala Asn
            115                 120                 125

Phe Ser Gln Tyr Gly Thr Gly Ile Asp Ile Val Ala Pro Gly Val Asn
    130                 135                 140

Val Gln Ser Thr Tyr Pro Gly Asn Arg Tyr Ala Ser Leu Asn Gly Thr
145                 150                 155                 160

Ser Met Ala Thr Pro His Val Ala Gly Ala Ala Ala Leu
                165                 170

<210> SEQ ID NO 160
<211> LENGTH: 173
<212> TYPE: PRT
<213> ORGANISM: Artificial Sequence
<220> FEATURE:
<223> OTHER INFORMATION: Synthetic

<400> SEQUENCE: 160

Ser Thr Gln Asp Gly Asn Gly His Gly Thr His Val Ala Gly Thr Ile
1               5                   10                  15

Ala Ala Leu Asn Asn Ser Ile Gly Val Ile Gly Val Ala Pro Asn Ala
            20                  25                  30

Asp Leu Tyr Ala Val Lys Val Leu Gly Ala Asn Gly Ser Gly Ser Val
        35                  40                  45

Ser Gly Ile Ala Arg Gly Leu Glu Trp Ala Ala Thr Asn Asn Met His
    50                  55                  60

Ile Ala Asn Met Ser Leu Gly Ser Asp Phe Pro Ser Ser Thr Leu Glu
65                  70                  75                  80

Arg Ala Val Asn Tyr Ala Thr Ser Gln Gly Val Leu Val Ile Ala Ala
                85                  90                  95

Thr Gly Asn Asn Gly Ser Gly Ser Val Gly Tyr Pro Ala Arg Tyr Ala
            100                 105                 110

Asn Ala Met Ala Val Gly Ala Thr Asp Gln Asn Asn Arg Arg Ala Asn
            115                 120                 125

Phe Ser Gln Tyr Gly Thr Gly Ile Asp Ile Val Ala Pro Gly Val Asn
    130                 135                 140

Val Gln Ser Thr Tyr Pro Gly Asn Arg Tyr Ala Ser Leu Asn Gly Thr
145                 150                 155                 160

Ser Met Ala Thr Pro His Val Ala Gly Val Ala Ala Leu
                165                 170

```
<210> SEQ ID NO 161
<211> LENGTH: 173
<212> TYPE: PRT
<213> ORGANISM: Artificial Sequence
<220> FEATURE:
<223> OTHER INFORMATION: Synthetic

<400> SEQUENCE: 161

Ser Thr Gln Asp Gly Asn Gly His Gly Thr His Val Ala Gly Thr Val
1               5                   10                  15

Ala Ala Leu Asn Asn Ser Ile Gly Val Ile Gly Val Ala Pro Ser Ala
            20                  25                  30

Asp Leu Tyr Ala Val Lys Val Leu Gly Ala Asn Gly Arg Gly Ser Val
        35                  40                  45

Ser Gly Ile Ala Gln Gly Leu Glu Trp Ala Ala Asn Asn Met His
    50                  55                  60

Ile Ala Asn Met Ser Leu Gly Ser Asp Ala Pro Ser Thr Thr Leu Glu
65                  70                  75                  80

Arg Ala Val Asn Tyr Ala Thr Ser Gln Gly Val Leu Val Ile Ala Ala
                85                  90                  95

Thr Gly Asn Asn Gly Ser Gly Ser Val Gly Tyr Pro Ala Arg Tyr Ala
            100                 105                 110

Asn Ala Met Ala Val Gly Ala Thr Asp Gln Asn Asn Arg Arg Ala Asn
        115                 120                 125

Phe Ser Gln Tyr Gly Thr Gly Ile Asp Ile Val Ala Pro Gly Val Asn
    130                 135                 140

Val Gln Ser Thr Tyr Pro Gly Asn Arg Tyr Ala Ser Leu Asn Gly Thr
145                 150                 155                 160

Ser Met Ala Thr Pro His Val Ala Gly Val Ala Ala Leu
                165                 170

<210> SEQ ID NO 162
<211> LENGTH: 173
<212> TYPE: PRT
<213> ORGANISM: Artificial Sequence
<220> FEATURE:
<223> OTHER INFORMATION: Synthetic

<400> SEQUENCE: 162

Ser Thr Gln Asp Gly Asn Gly His Gly Thr His Val Ala Gly Thr Ile
1               5                   10                  15

Ala Ala Leu Asp Asn Asp Glu Gly Val Val Gly Val Ala Pro Asn Ala
            20                  25                  30

Asp Leu Tyr Ala Val Lys Val Leu Ser Ala Ser Gly Ala Gly Ser Ile
        35                  40                  45

Ser Ser Ile Ala Gln Gly Leu Glu Trp Ser Gly Glu Asn Gly Met Asp
    50                  55                  60

Ile Ala Asn Leu Ser Leu Gly Ser Ser Ala Pro Ser Ala Thr Leu Glu
65                  70                  75                  80

Gln Ala Val Asn Ala Ala Thr Ser Arg Gly Val Leu Val Ile Ala Ala
                85                  90                  95

Ser Gly Asn Ser Gly Ala Gly Ser Val Gly Tyr Pro Ala Arg Tyr Ala
            100                 105                 110

Asn Ala Met Ala Val Gly Ala Thr Asp Gln Asn Asn Asn Arg Ala Ser
        115                 120                 125

Phe Ser Gln Tyr Gly Ala Gly Leu Asp Ile Val Ala Pro Gly Val Gly
    130                 135                 140
```

```
Val Gln Ser Thr Tyr Pro Gly Ser Thr Tyr Ala Ser Leu Asn Gly Thr
145                 150                 155                 160

Ser Met Ala Thr Pro His Val Ala Gly Val Ala Ala Leu
                165                 170
```

<210> SEQ ID NO 163
<211> LENGTH: 173
<212> TYPE: PRT
<213> ORGANISM: Artificial Sequence
<220> FEATURE:
<223> OTHER INFORMATION: Synthetic

<400> SEQUENCE: 163

```
Ser Thr Gln Asp Gly Asn Gly His Gly Thr His Val Ala Gly Thr Ile
1               5                   10                  15

Ala Ala Leu Asn Asn Val Gly Val Leu Gly Val Ala Pro Asn Val
                20                  25                  30

Glu Leu Tyr Gly Val Lys Val Leu Gly Ala Ser Gly Ser Gly Ser Ile
            35                  40                  45

Ser Gly Ile Ala Gln Gly Leu Gln Trp Ala Gly Asn Asn Gly Met His
        50                  55                  60

Ile Ala Asn Met Ser Leu Gly Thr Ser Ala Pro Ser Ala Thr Leu Glu
65                  70                  75                  80

Gln Ala Val Asn Ala Ala Thr Ser Arg Gly Val Leu Val Ile Ala Ala
                85                  90                  95

Ser Gly Asn Ser Gly Ala Gly Ser Val Gly Tyr Pro Ala Arg Tyr Ala
                100                 105                 110

Asn Ala Met Ala Val Gly Ala Thr Asp Gln Asn Asn Arg Arg Ala Asn
            115                 120                 125

Phe Ser Gln Tyr Gly Thr Gly Ile Asp Ile Val Ala Pro Gly Val Asn
    130                 135                 140

Val Gln Ser Thr Tyr Pro Gly Asn Arg Tyr Val Ser Met Asn Gly Thr
145                 150                 155                 160

Ser Met Ala Thr Pro His Val Ala Gly Val Ala Ala Leu
                165                 170
```

<210> SEQ ID NO 164
<211> LENGTH: 173
<212> TYPE: PRT
<213> ORGANISM: Artificial Sequence
<220> FEATURE:
<223> OTHER INFORMATION: Synthetic

<400> SEQUENCE: 164

```
Ser Thr Gln Asp Gly Asn Gly His Gly Thr His Val Ala Gly Thr Val
1               5                   10                  15

Ala Ala Leu Asn Asn Ser Ile Gly Val Ile Gly Val Ala Pro Ser Ala
                20                  25                  30

Asp Leu Tyr Ala Val Lys Val Leu Gly Ala Asn Gly Arg Gly Ser Val
            35                  40                  45

Ser Gly Ile Ala Gln Gly Leu Glu Trp Ala Ala Asn Asn Met His
        50                  55                  60

Ile Ala Asn Met Ser Leu Gly Ser Asp Ala Pro Ser Thr Thr Leu Glu
65                  70                  75                  80

Arg Ala Val Asn Tyr Ala Thr Ser Gln Gly Val Leu Val Ile Ala Ala
                85                  90                  95

Thr Gly Asn Asn Gly Ser Gly Ser Val Gly Tyr Pro Ala Arg Tyr Ala
                100                 105                 110
```

Asn Ala Met Ala Val Gly Ala Thr Asp Gln Asn Asn Arg Arg Ala Asn
            115                 120                 125

Phe Ser Gln Tyr Gly Thr Gly Ile Asp Ile Val Ala Pro Gly Val Asn
        130                 135                 140

Val Gln Ser Thr Tyr Pro Gly Asn Arg Tyr Ala Ser Leu Asn Gly Thr
145                 150                 155                 160

Ser Met Ala Thr Pro His Val Ala Gly Val Ala Ala Leu
                165                 170

<210> SEQ ID NO 165
<211> LENGTH: 173
<212> TYPE: PRT
<213> ORGANISM: Artificial Sequence
<220> FEATURE:
<223> OTHER INFORMATION: Synthetic

<400> SEQUENCE: 165

Ser Thr Gln Asp Gly Asn Gly His Gly Thr His Val Ala Gly Thr Val
1               5                   10                  15

Ala Ala Leu Asn Asn Ser Ile Gly Val Ile Gly Val Ala Pro Ser Ala
            20                  25                  30

Asp Leu Tyr Ala Val Lys Val Leu Gly Ala Asn Gly Arg Gly Ser Val
        35                  40                  45

Ser Gly Ile Ala Gln Gly Leu Glu Trp Ala Ala Asn Asn Met His
    50                  55                  60

Ile Ala Asn Met Ser Leu Gly Ser Asp Ala Pro Ser Thr Thr Leu Glu
65                  70                  75                  80

Arg Ala Val Asn Tyr Ala Thr Ser Gln Gly Val Leu Val Ile Ala Ala
                85                  90                  95

Thr Gly Asn Asn Gly Ser Gly Ser Val Gly Tyr Pro Ala Arg Tyr Ala
            100                 105                 110

Asn Ala Met Ala Val Gly Ala Thr Asp Gln Asn Asn Arg Arg Ala Asn
            115                 120                 125

Phe Ser Gln Tyr Gly Thr Gly Ile Asp Ile Val Ala Pro Gly Val Asn
        130                 135                 140

Val Gln Ser Thr Tyr Pro Gly Asn Arg Tyr Ala Ser Leu Asn Gly Thr
145                 150                 155                 160

Ser Met Ala Thr Pro His Val Ala Gly Val Ala Ala Leu
                165                 170

<210> SEQ ID NO 166
<211> LENGTH: 173
<212> TYPE: PRT
<213> ORGANISM: Artificial Sequence
<220> FEATURE:
<223> OTHER INFORMATION: Synthetic

<400> SEQUENCE: 166

Ser Thr Gln Asp Gly Asn Gly His Gly Thr His Val Ala Gly Thr Val
1               5                   10                  15

Ala Ala Leu Asn Asn Asp Gly Val Leu Gly Val Ala Pro Asn Val
            20                  25                  30

Asp Leu Tyr Ala Val Lys Val Leu Gly Ala Asn Gly Arg Gly Ser Ile
        35                  40                  45

Ser Gly Ile Ala Arg Gly Leu Gln Trp Ala Ala Asp Asn Gly Thr His
    50                  55                  60

Val Ala Asn Leu Ser Leu Gly Thr Asp Gln Pro Ser Thr Thr Leu Glu

```
                65                  70                  75                  80
Arg Ala Val Asn Tyr Ala Thr Ser Arg Gly Val Leu Val Ala Ala
                        85                  90                  95
Thr Gly Asn Thr Gly Ser Gly Thr Val Ser Tyr Pro Ala Arg Tyr Ala
                100                 105                 110
Asn Ala Met Ala Val Gly Ala Thr Asp Gln Asn Asn Arg Ala Asn
            115                 120                 125
Phe Ser Gln Tyr Gly Ala Gly Ile Asp Ile Val Ala Pro Gly Val Asn
        130                 135                 140
Val Gln Ser Thr Tyr Pro Gly Asn Thr Tyr Val Ser Leu Asn Gly Thr
145                 150                 155                 160
Ser Met Ala Thr Pro His Val Ala Gly Ala Ala Ala Leu
                165                 170

<210> SEQ ID NO 167
<211> LENGTH: 173
<212> TYPE: PRT
<213> ORGANISM: Artificial Sequence
<220> FEATURE:
<223> OTHER INFORMATION: Synthetic

<400> SEQUENCE: 167

Ser Thr Gln Asp Gly Asn Gly His Gly Thr His Val Ala Gly Thr Val
1               5                   10                  15
Ala Ala Leu Asn Asn Ser Val Gly Val Leu Gly Val Ala Pro Ser Val
                20                  25                  30
Glu Leu Tyr Ala Val Lys Val Leu Gly Ala Asn Gly Arg Gly Ser Ile
            35                  40                  45
Ser Gly Ile Ala Gln Gly Leu Glu Trp Ala Gly Ala Asn Gly Met His
        50                  55                  60
Ile Ala Asn Met Ser Leu Gly Thr Ser Ala Pro Ser Ser Thr Leu Glu
65                  70                  75                  80
Arg Ala Val Asn Ser Ala Ala Ser Arg Gly Val Leu Val Val Ala Ala
                85                  90                  95
Ser Gly Asn Asn Gly Ala Gly Ser Val Ser Tyr Pro Ala Arg Tyr Ala
                100                 105                 110
Asn Ala Met Ala Val Gly Ala Thr Asp Gln Asn Asn Arg Arg Ala Asn
            115                 120                 125
Phe Ser Gln Tyr Gly Ala Gly Leu Asp Ile Val Ala Pro Gly Val Gly
        130                 135                 140
Val Gln Ser Thr Tyr Pro Gly Ser Thr Tyr Ala Ser Leu Ser Gly Thr
145                 150                 155                 160
Ser Met Ala Thr Pro His Val Ala Gly Ala Ala Ala Leu
                165                 170

<210> SEQ ID NO 168
<211> LENGTH: 173
<212> TYPE: PRT
<213> ORGANISM: Artificial Sequence
<220> FEATURE:
<223> OTHER INFORMATION: Synthetic

<400> SEQUENCE: 168

Ser Thr Gln Asp Gly Asn Gly His Gly Thr His Val Ala Gly Thr Val
1               5                   10                  15
Ala Ala Leu Asn Asn Ser Asp Gly Val Ile Gly Val Ala Pro Ser Ala
                20                  25                  30
```

```
Asp Leu Tyr Ala Val Lys Val Leu Gly Ala Asn Gly Arg Gly Ser Ile
        35                  40                  45

Ser Gly Ile Ala Arg Gly Leu Glu Trp Ala Ala Asn Asn Gly Met His
 50                  55                  60

Val Ala Asn Met Ser Leu Gly Thr Asp Gln Pro Ser Ala Thr Leu Glu
 65                  70                  75                  80

Arg Ala Val Asn Gln Ala Thr Ser Gln Gly Val Leu Val Ile Ala Ala
                 85                  90                  95

Thr Gly Asn Asn Gly Ser Gly Ser Val Ser Tyr Pro Ala Arg Tyr Ala
                100                 105                 110

Asn Ala Met Ala Val Gly Ala Thr Asp Gln Asn Asn Arg Ala Ser
                115                 120                 125

Phe Ser Gln Tyr Gly Ala Gly Leu Asp Ile Val Ala Pro Gly Val Gly
        130                 135                 140

Val Gln Ser Thr Tyr Pro Gly Ser Arg Tyr Ala Ser Leu Asn Gly Thr
145                 150                 155                 160

Ser Met Ala Thr Pro His Val Ala Gly Ala Ala Ala Leu
                165                 170

<210> SEQ ID NO 169
<211> LENGTH: 173
<212> TYPE: PRT
<213> ORGANISM: Artificial Sequence
<220> FEATURE:
<223> OTHER INFORMATION: Synthetic

<400> SEQUENCE: 169

Ser Thr Gln Asp Gly Asn Gly His Gly Thr His Val Ala Gly Thr Ile
1               5                  10                  15

Ala Ala Leu Asn Asn Asn Ile Gly Val Leu Gly Val Ala Pro Ser Val
                 20                  25                  30

Glu Leu Tyr Gly Val Lys Val Leu Gly Ala Ser Gly Arg Gly Ser Ile
        35                  40                  45

Ser Gly Ile Ala Arg Gly Leu Glu Trp Ala Gly Asp Asn Gly Met His
 50                  55                  60

Val Ala Asn Leu Ser Leu Gly Thr Asp Gln Pro Ser Ala Thr Leu Glu
 65                  70                  75                  80

Arg Ala Val Asn Ala Ala Thr Ser Gln Gly Val Leu Val Ile Ala Ala
                 85                  90                  95

Thr Gly Asn Ser Gly Ser Gly Ser Val Ser Tyr Pro Ala Arg Tyr Ala
                100                 105                 110

Asn Ala Met Ala Val Gly Ala Thr Asp Gln Asn Asn Asn Arg Ala Ser
                115                 120                 125

Ser Ser Gln Tyr Gly Thr Gly Leu Asp Ile Val Ala Pro Gly Val Gly
        130                 135                 140

Val Gln Ser Thr Tyr Pro Gly Ser Thr Tyr Val Ser Leu Asn Gly Thr
145                 150                 155                 160

Ser Met Ala Thr Pro His Val Ala Gly Ala Ala Ala Leu
                165                 170

<210> SEQ ID NO 170
<211> LENGTH: 173
<212> TYPE: PRT
<213> ORGANISM: Artificial Sequence
<220> FEATURE:
<223> OTHER INFORMATION: Synthetic

<400> SEQUENCE: 170
```

```
Ser Thr Gln Asp Gly Asn Gly His Gly Thr His Val Ala Gly Thr Val
1               5                   10                  15

Ala Ala Leu Asn Asn Asn Ile Gly Val Leu Gly Val Ala Pro Ser Val
            20                  25                  30

Glu Leu Tyr Gly Val Lys Val Leu Gly Ala Ser Gly Arg Gly Ser Val
            35                  40                  45

Ser Gly Ile Ala Arg Gly Leu Gln Trp Thr Ala Asp Asn Gly Met His
    50                  55                  60

Ile Ala Asn Leu Ser Leu Gly Ser Ser Pro Ser Ala Thr Leu Glu
65                  70                  75                  80

Arg Ala Val Asn Tyr Ala Thr Ser Arg Gly Val Leu Val Ile Ala Ala
                85                  90                  95

Thr Gly Asn Thr Gly Ala Gly Thr Ile Ser Tyr Pro Ala Arg Tyr Ala
                100                 105                 110

Asn Ala Met Ala Val Gly Ala Thr Asp Gln Asn Asn Asn Arg Ala Ser
                115                 120                 125

Phe Ser Gln Tyr Gly Thr Gly Leu Asp Ile Val Ala Pro Gly Val Gly
    130                 135                 140

Val Gln Ser Thr Tyr Pro Gly Ser Thr Tyr Ala Ser Leu Asn Gly Thr
145                 150                 155                 160

Ser Met Ala Thr Pro His Val Ala Gly Ala Ala Leu
                165                 170
```

<210> SEQ ID NO 171
<211> LENGTH: 173
<212> TYPE: PRT
<213> ORGANISM: Artificial Sequence
<220> FEATURE:
<223> OTHER INFORMATION: Synthetic

<400> SEQUENCE: 171

```
Ser Thr Gln Asp Gly Asn Gly His Gly Thr His Val Ala Gly Thr Ile
1               5                   10                  15

Ala Ala Leu Asn Asn Ser Ile Gly Val Leu Gly Val Ala Pro Ser Ala
            20                  25                  30

Asp Leu Tyr Gly Val Lys Val Leu Gly Ala Ser Gly Arg Gly Ser Ile
            35                  40                  45

Ser Ser Ile Ala Arg Gly Leu Gln Trp Ala Ala Asp Asn Gly Met His
    50                  55                  60

Val Ala Asn Leu Ser Leu Gly Ser Asp Phe Pro Ser Ala Thr Leu Glu
65                  70                  75                  80

Arg Ala Val Asn Ser Ala Thr Ser Arg Gly Val Leu Val Val Ala Ala
                85                  90                  95

Ser Gly Asn Ser Gly Ala Gly Ser Ile Ser Tyr Pro Ala Arg Tyr Ala
                100                 105                 110

Asn Ala Met Ala Val Gly Ala Thr Asp Gln Asn Asn Asn Arg Ala Ser
                115                 120                 125

Phe Ser His Tyr Gly Ala Gly Leu Asp Ile Val Ala Pro Gly Val Gly
    130                 135                 140

Val Gln Ser Thr Tyr Pro Gly Asn Thr Tyr Ala Ser Leu Asn Gly Thr
145                 150                 155                 160

Ser Met Ala Thr Pro His Val Ala Gly Val Ala Ala Leu
                165                 170
```

<210> SEQ ID NO 172

```
<211> LENGTH: 173
<212> TYPE: PRT
<213> ORGANISM: Artificial Sequence
<220> FEATURE:
<223> OTHER INFORMATION: Synthetic

<400> SEQUENCE: 172

Ser Thr Gln Asp Gly Asn Gly His Gly Thr His Val Ala Gly Thr Val
1               5                   10                  15

Ala Ala Leu Asn Asn Asn Val Gly Val Leu Gly Val Ala Pro Ser Val
            20                  25                  30

Asp Leu Tyr Ala Val Lys Val Leu Gly Ala Ser Gly Arg Gly Ser Val
        35                  40                  45

Ser Ser Ile Ala Gln Gly Leu Glu Trp Ala Ala Thr Asn Asn Met His
    50                  55                  60

Val Ala Asn Leu Ser Leu Gly Ser Ser Gln Pro Ser Ser Thr Leu Glu
65                  70                  75                  80

Gln Ala Val Asn Ala Ala Thr Ser Arg Gly Val Leu Val Ile Ala Ala
                85                  90                  95

Ser Gly Asn Asn Gly Ser Gly Thr Val Ser Tyr Pro Ala Arg Tyr Ala
            100                 105                 110

Asn Ala Met Ala Val Gly Ala Thr Asp Gln Asn Asn Asn Arg Ala Ser
        115                 120                 125

Phe Ser His Tyr Gly Thr Gly Leu Asp Ile Val Ala Pro Gly Val Gly
    130                 135                 140

Val Gln Ser Thr Tyr Pro Gly Ser Arg Tyr Ala Ser Leu Asn Gly Thr
145                 150                 155                 160

Ser Met Ala Ser Pro His Val Ala Gly Val Ala Ala Leu
                165                 170

<210> SEQ ID NO 173
<211> LENGTH: 173
<212> TYPE: PRT
<213> ORGANISM: Artificial Sequence
<220> FEATURE:
<223> OTHER INFORMATION: Synthetic

<400> SEQUENCE: 173

Ser Thr Gln Asp Gly Asn Gly His Gly Thr His Val Ala Gly Thr Ile
1               5                   10                  15

Ala Ala Leu Asn Asn Ser Val Gly Val Leu Gly Val Ala Pro Ser Ala
            20                  25                  30

Glu Leu Tyr Ala Val Lys Val Leu Gly Ala Ser Gly Arg Gly Thr Val
        35                  40                  45

Ser Gly Ile Ala Arg Gly Leu Gln Trp Ala Ala Asp Asn Gly Met His
    50                  55                  60

Val Ala Asn Leu Ser Leu Gly Thr Pro Gln Pro Ser Ala Thr Leu Glu
65                  70                  75                  80

Arg Ala Val Asn Gln Ala Thr Ser Arg Gly Val Leu Val Ile Ala Ala
                85                  90                  95

Ser Gly Asn Thr Gly Ser Gly Thr Val Ser Tyr Pro Ala Arg Tyr Ala
            100                 105                 110

Asn Ala Met Ala Val Gly Ala Thr Asp Gln Asn Asn Arg Arg Ala Asn
        115                 120                 125

Phe Ser Gln Tyr Gly Ala Gly Leu Asp Ile Val Ala Pro Gly Val Gly
    130                 135                 140

Val Gln Ser Thr Tyr Arg Gly Ser Thr Tyr Ala Ser Leu Ser Gly Thr
```

145                 150                 155                 160
Ser Met Ala Ser Pro His Val Ala Gly Val Ala Ala Leu
                165                 170

<210> SEQ ID NO 174
<211> LENGTH: 173
<212> TYPE: PRT
<213> ORGANISM: Artificial Sequence
<220> FEATURE:
<223> OTHER INFORMATION: Synthetic

<400> SEQUENCE: 174

Ser Thr Gln Asp Gly Asn Gly His Gly Thr His Val Ala Gly Thr Ile
1               5                   10                  15

Ala Ala Leu Asn Asn Ser Val Gly Val Leu Gly Val Ala Pro Asn Ala
                20                  25                  30

Asp Leu Tyr Gly Val Lys Val Leu Gly Ala Ser Gly Arg Gly Thr Ile
            35                  40                  45

Ser Ser Ile Ala Arg Gly Leu Glu Trp Ala Gly Ala Asn Gly Met His
    50                  55                  60

Val Ala Asn Leu Ser Leu Gly Thr Ser Ser Pro Ser Ser Thr Leu Glu
65                  70                  75                  80

Gln Ala Val Asn Gln Ala Thr Ser Arg Gly Val Leu Val Val Ala Ala
                85                  90                  95

Ser Gly Asn Thr Gly Ser Gly Thr Val Ser Tyr Pro Ala Thr Tyr Ala
                100                 105                 110

Asn Ala Met Ala Val Gly Ala Thr Asp Gln Asn Asn Asn Arg Ala Asn
            115                 120                 125

Phe Ser Gln Tyr Gly Thr Gly Leu Asp Ile Val Ala Pro Gly Val Gly
    130                 135                 140

Val Gln Ser Thr Tyr Pro Gly Ser Arg Tyr Ala Ser Leu Asn Gly Thr
145                 150                 155                 160

Ser Met Ala Ser Pro His Val Gly Ala Ala Ala Leu
                165                 170

<210> SEQ ID NO 175
<211> LENGTH: 173
<212> TYPE: PRT
<213> ORGANISM: Artificial Sequence
<220> FEATURE:
<223> OTHER INFORMATION: Synthetic

<400> SEQUENCE: 175

Ser Thr Gln Asp Gly Asn Gly His Gly Thr His Val Ala Gly Thr Ile
1               5                   10                  15

Ala Ala Leu Asn Asn Val Gly Val Leu Gly Val Ala Pro Ser Ala
                20                  25                  30

Glu Leu Tyr Gly Val Lys Val Leu Gly Ala Ser Gly Ser Gly Ser Ile
            35                  40                  45

Ser Gly Ile Ala Arg Gly Leu Glu Trp Ala Ala Asn Gly Met His
    50                  55                  60

Val Ala Asn Met Ser Leu Gly Thr Pro Phe Pro Ser Ala Thr Leu Glu
65                  70                  75                  80

Gln Ala Val Lys Ala Ala Thr Ser Arg Gly Val Leu Val Val Ala Ala
                85                  90                  95

Ser Gly Asn Ser Gly Ala Gly Ser Ile Ser Tyr Pro Ala Arg Tyr Ala
                100                 105                 110

```
Asn Ala Met Ala Val Gly Ala Thr Asp Gln Asn Asn Asn Arg Ala Ser
            115                 120                 125

Phe Ser Gln Tyr Gly Thr Gly Ile Asp Ile Val Ala Pro Gly Val Gly
        130                 135                 140

Val Lys Ser Thr Tyr Pro Gly Ser Thr Tyr Val Ser Leu Ser Gly Thr
145                 150                 155                 160

Ser Met Ala Ser Pro His Val Ala Gly Val Ala Ala Leu
                165                 170
```

<210> SEQ ID NO 176
<211> LENGTH: 173
<212> TYPE: PRT
<213> ORGANISM: Artificial Sequence
<220> FEATURE:
<223> OTHER INFORMATION: Synthetic

<400> SEQUENCE: 176

```
Ser Thr Gln Asp Gly Asn Gly His Gly Thr His Val Ala Gly Thr Val
1               5                   10                  15

Ala Ala Leu Asn Asn Asn Val Gly Val Leu Gly Val Ala Pro Ser Ala
            20                  25                  30

Glu Leu Tyr Ala Val Lys Val Leu Gly Ala Asn Gly Ser Gly Thr Val
        35                  40                  45

Ser Ser Ile Ala Gln Gly Leu Glu Trp Ala Gly Asn Asn Gly Met His
    50                  55                  60

Val Ala Asn Leu Ser Leu Gly Thr Asp Gln Pro Ser Ala Thr Leu Glu
65                  70                  75                  80

Arg Ala Val Asn Ala Ala Thr Ser Arg Gly Val Leu Val Ala Ala
                85                  90                  95

Ser Gly Asn Thr Gly Ser Gly Ser Val Gly Tyr Pro Ala Arg Tyr Ala
                100                 105                 110

Asn Ala Met Ala Val Gly Ala Thr Asp Gln Asn Asn Asn Arg Ala Asn
            115                 120                 125

Phe Ser Gln Tyr Gly Ala Gly Leu Asp Ile Val Ala Pro Gly Val Gly
        130                 135                 140

Val Gln Ser Thr Tyr Pro Gly Asn Arg Tyr Ala Ser Met Asn Gly Thr
145                 150                 155                 160

Ser Met Ala Thr Pro His Val Ala Gly Ala Ala Ala Leu
                165                 170
```

<210> SEQ ID NO 177
<211> LENGTH: 173
<212> TYPE: PRT
<213> ORGANISM: Artificial Sequence
<220> FEATURE:
<223> OTHER INFORMATION: Synthetic

<400> SEQUENCE: 177

```
Ser Thr Gln Asp Gly Asn Gly His Gly Thr His Val Ala Gly Thr Ile
1               5                   10                  15

Ala Ala Leu Asn Asn Asn Ile Gly Val Leu Gly Val Ala Pro Ser Ala
            20                  25                  30

Glu Leu Tyr Ala Val Lys Val Leu Gly Ala Ser Gly Arg Gly Ser Val
        35                  40                  45

Ser Ser Ile Ala Gln Gly Leu Glu Trp Ala Gly Asp Asn Gly Met His
    50                  55                  60

Val Ala Asn Leu Ser Leu Gly Ser Pro Phe Pro Ser Ser Thr Leu Glu
65                  70                  75                  80
```

```
Arg Ala Val Asn Ala Ala Thr Ser Arg Gly Val Leu Val Ile Ala Ala
                85                  90                  95

Ser Gly Asn Ser Gly Ser Gly Ser Ile Ser Tyr Pro Ala Arg Tyr Ala
            100                 105                 110

Asn Ala Met Ala Val Gly Ala Thr Asp Gln Asn Asn Asn Arg Ala Asn
        115                 120                 125

Ser Ser Gln Tyr Gly Ala Gly Leu Glu Ile Val Ala Pro Gly Val Gly
    130                 135                 140

Val Gln Ser Thr Tyr Pro Gly Ser Thr Tyr Val Ser Met Ser Gly Thr
145                 150                 155                 160

Ser Met Ala Ser Pro His Val Ala Gly Ala Ala Leu
                165                 170

<210> SEQ ID NO 178
<211> LENGTH: 173
<212> TYPE: PRT
<213> ORGANISM: Artificial Sequence
<220> FEATURE:
<223> OTHER INFORMATION: Synthetic

<400> SEQUENCE: 178

Ser Thr Gln Asp Gly Asn Gly His Gly Thr His Val Ala Gly Thr Ile
1               5                   10                  15

Ala Ala Leu Asn Asn Asn Val Gly Val Ile Gly Val Ala Pro Asn Val
            20                  25                  30

Glu Leu Tyr Gly Val Lys Val Leu Gly Ala Asn Gly Arg Gly Thr Ile
        35                  40                  45

Ser Ser Ile Ala Arg Gly Leu Glu Trp Ala Ala Asn Asn Gly Thr His
    50                  55                  60

Ile Ala Asn Leu Ser Leu Gly Thr Asp Gln Pro Ser Ala Thr Leu Glu
65                  70                  75                  80

Arg Ala Val Asn Gln Ala Thr Ser Gln Gly Val Leu Val Ile Ala Ala
                85                  90                  95

Ser Gly Asn Ser Gly Ser Gly Ser Val Ser Tyr Pro Ala Arg Tyr Ala
            100                 105                 110

Asn Ala Met Ala Val Gly Ala Thr Asp Gln Asn Asn Asn Arg Ala Ser
        115                 120                 125

Phe Ser His Tyr Gly Thr Gly Leu Asp Ile Val Ala Pro Gly Val Gly
    130                 135                 140

Val Gln Ser Thr Tyr Pro Gly Ser Arg Tyr Ala Ser Leu Asn Gly Thr
145                 150                 155                 160

Ser Met Ala Ser Pro His Val Ala Gly Val Ala Ala Leu
                165                 170

<210> SEQ ID NO 179
<211> LENGTH: 173
<212> TYPE: PRT
<213> ORGANISM: Artificial Sequence
<220> FEATURE:
<223> OTHER INFORMATION: Synthetic

<400> SEQUENCE: 179

Ser Thr Gln Asp Gly Asn Gly His Gly Thr His Val Ala Gly Thr Val
1               5                   10                  15

Ala Ala Leu Asn Asn Ser Val Gly Val Leu Gly Val Ala Pro Ser Ala
            20                  25                  30

Asp Leu Tyr Ala Val Lys Val Leu Gly Ala Ser Gly Arg Gly Thr Val
```

```
                35                  40                  45
Ser Ser Ile Ala Arg Gly Leu Glu Trp Ala Ala Asp Asn Asn Met His
     50                  55                  60

Ile Ala Asn Leu Ser Leu Gly Thr Asp Gln Pro Ser Ala Thr Leu Glu
 65                  70                  75                  80

Gln Ala Val Asn Ala Ala Thr Ser Gln Gly Val Leu Val Ala Ala
                 85                  90                  95

Ser Gly Asn Asn Gly Ser Gly Ser Ile Gly Tyr Pro Ala Arg Tyr Ala
                100                 105                 110

Asn Ala Met Ala Val Gly Ala Thr Asp Gln Asn Asn Asn Arg Ala Ser
                115                 120                 125

Phe Ser Gln Tyr Gly Thr Gly Leu Asp Ile Val Ala Pro Gly Val Gly
                130                 135                 140

Val Gln Ser Thr Tyr Pro Gly Asn Thr Tyr Val Ser Leu Ser Gly Thr
145                 150                 155                 160

Ser Met Ala Thr Pro His Val Ala Gly Ala Ala Leu
                165                 170

<210> SEQ ID NO 180
<211> LENGTH: 173
<212> TYPE: PRT
<213> ORGANISM: Artificial Sequence
<220> FEATURE:
<223> OTHER INFORMATION: Synthetic

<400> SEQUENCE: 180

Ser Thr Gln Asp Gly Asn Gly His Gly Thr His Val Ala Gly Thr Val
 1               5                  10                  15

Ala Ala Leu Asn Asn Asn Val Gly Val Ile Gly Val Ala Pro Ser Ala
                 20                  25                  30

Asp Leu Tyr Ala Val Lys Val Leu Gly Ala Ser Gly Arg Gly Thr Ile
                 35                  40                  45

Ser Gly Ile Ala Gln Gly Leu Glu Trp Ala Gly Asp Asn Gly Met His
     50                  55                  60

Val Ala Asn Leu Ser Leu Gly Ser Asp Gln Pro Ser Ala Thr Leu Glu
 65                  70                  75                  80

Gln Ala Val Asn Ala Ala Thr Ser Gln Gly Val Leu Val Val Ala Ala
                 85                  90                  95

Ser Gly Asn Ser Gly Ser Gly Ser Val Gly Tyr Pro Ala Arg Tyr Ala
                100                 105                 110

Asn Ala Met Ala Val Gly Ala Thr Asp Gln Asn Asn Asn Arg Ala Ser
                115                 120                 125

Phe Ser Gln Tyr Gly Gln Gly Leu Asp Ile Val Ala Pro Gly Val Gly
                130                 135                 140

Val Gln Ser Thr Tyr Pro Gly Ser Arg Tyr Ala Ser Met Ser Gly Thr
145                 150                 155                 160

Ser Met Ala Ser Pro His Val Ala Gly Val Ala Ala Leu
                165                 170

<210> SEQ ID NO 181
<211> LENGTH: 173
<212> TYPE: PRT
<213> ORGANISM: Artificial Sequence
<220> FEATURE:
<223> OTHER INFORMATION: Synthetic

<400> SEQUENCE: 181
```

```
Ser Thr Gln Asp Gly Asn Gly His Gly Thr His Val Ala Gly Thr Val
1               5                   10                  15

Ala Ala Leu Asn Asn Ser Ile Gly Val Leu Gly Val Ala Pro Ser Val
                20                  25                  30

Asp Leu Tyr Ala Val Lys Val Leu Gly Ala Asn Gly Arg Gly Thr Val
            35                  40                  45

Ser Gly Ile Ala Gln Gly Leu Glu Trp Ala Ala Asp Lys Gly Met His
50                      55                  60

Val Ala Asn Leu Ser Leu Gly Ser Ser Pro Ser Thr Thr Leu Glu
65                  70                  75                  80

Gln Ala Val Asn Ala Ala Thr Ser Gln Gly Val Leu Val Ile Ala Ala
                85                  90                  95

Thr Gly Asn Ser Gly Ala Gly Ser Ile Ser Tyr Pro Ala Arg Tyr Ala
                100                 105                 110

Asn Ala Met Ala Val Gly Ala Thr Asp Gln Asn Asn Asn Arg Ala Ser
                115                 120                 125

Phe Ser Gln Tyr Gly Gln Gly Leu Asp Ile Val Ala Pro Gly Val Gly
            130                 135                 140

Val Gln Ser Thr Tyr Pro Gly Ser Thr Tyr Val Ser Leu Ser Gly Thr
145                 150                 155                 160

Ser Met Ala Thr Pro His Val Ala Gly Ala Ala Ala Leu
                165                 170
```

<210> SEQ ID NO 182
<211> LENGTH: 173
<212> TYPE: PRT
<213> ORGANISM: Artificial Sequence
<220> FEATURE:
<223> OTHER INFORMATION: Synthetic

<400> SEQUENCE: 182

```
Ser Thr Gln Asp Gly Asn Gly His Gly Thr His Val Ala Gly Thr Ile
1               5                   10                  15

Ala Ala Leu Asn Asn Asn Asp Gly Val Leu Gly Val Ala Pro Ser Val
                20                  25                  30

Glu Leu Tyr Gly Val Lys Val Leu Gly Ala Ser Gly Arg Gly Thr Val
            35                  40                  45

Ser Ser Ile Ala Arg Gly Leu Glu Trp Ala Ala Asn Asn Gly Met His
50                      55                  60

Val Ala Asn Met Ser Leu Gly Thr Pro Ala Pro Ser Thr Thr Leu Glu
65                  70                  75                  80

Arg Ala Val Asn Gln Ala Thr Ser Arg Gly Val Leu Val Ile Ala Ala
                85                  90                  95

Ser Gly Asn Asn Gly Ser Gly Ser Ile Ser Tyr Pro Ala Arg Tyr Ala
                100                 105                 110

Asn Ala Met Ala Val Gly Ala Thr Asp Gln Asn Asn Arg Arg Ala Ser
                115                 120                 125

Phe Ser Gln Tyr Gly Ala Gly Leu Asp Ile Val Ala Pro Gly Val Gly
            130                 135                 140

Val Gln Ser Thr Tyr Pro Gly Ser Arg Tyr Ala Ser Leu Ser Gly Thr
145                 150                 155                 160

Ser Met Ala Ser Pro His Val Ala Gly Val Ala Ala Leu
                165                 170
```

<210> SEQ ID NO 183
<211> LENGTH: 173

```
<212> TYPE: PRT
<213> ORGANISM: Artificial Sequence
<220> FEATURE:
<223> OTHER INFORMATION: Synthetic

<400> SEQUENCE: 183

Ser Thr Gln Asp Gly Asn Gly His Gly Thr His Val Ala Gly Thr Val
1               5                   10                  15

Ala Ala Leu Asn Asn Ser Val Gly Val Phe Gly Val Ala Pro Ser Val
            20                  25                  30

Asp Leu Tyr Ala Val Lys Val Leu Gly Ala Ser Gly Ser Gly Thr Val
        35                  40                  45

Ser Ser Val Ala Gln Gly Leu Gln Trp Ala Gly Asp Asn Gly Met His
    50                  55                  60

Val Ala Asn Leu Ser Leu Gly Ser Asp Ala Pro Ser Ala Thr Leu Glu
65                  70                  75                  80

Gln Ala Val Asn Ser Ala Thr Ser Arg Gly Val Leu Val Val Ala Ala
                85                  90                  95

Ser Gly Asn Thr Gly Ala Gly Thr Val Gly Tyr Pro Ala Arg Tyr Ala
            100                 105                 110

Asn Ala Met Ala Val Gly Ala Thr Asp Gln Asn Asn Arg Arg Ala Asn
        115                 120                 125

Phe Ser Gln Tyr Gly Ala Gly Leu Asp Ile Val Ala Pro Gly Val Gly
    130                 135                 140

Val Gln Ser Thr Tyr Pro Gly Ser Thr Tyr Ala Ser Leu Asn Gly Thr
145                 150                 155                 160

Ser Met Ala Thr Pro His Val Ala Gly Val Ala Ala Leu
                165                 170

<210> SEQ ID NO 184
<211> LENGTH: 173
<212> TYPE: PRT
<213> ORGANISM: Artificial Sequence
<220> FEATURE:
<223> OTHER INFORMATION: Synthetic

<400> SEQUENCE: 184

Ser Thr Gln Asp Gly Asn Gly His Gly Thr His Val Ala Gly Thr Val
1               5                   10                  15

Ala Ala Leu Asn Asn Ser Val Gly Val Leu Gly Val Ala Pro Ser Val
            20                  25                  30

Glu Leu Tyr Ala Val Lys Val Leu Gly Ala Ser Gly Ser Gly Ser Ile
        35                  40                  45

Ser Gly Ile Ala Arg Gly Leu Glu Trp Ala Ala Asp Asn Asn Thr His
    50                  55                  60

Val Ala Asn Leu Ser Leu Gly Ser Asp Phe Pro Ser Ala Thr Leu Glu
65                  70                  75                  80

Arg Ala Val Asn Tyr Ala Thr Ser Arg Gly Val Leu Val Val Ala Ala
                85                  90                  95

Ser Gly Asn Thr Gly Ser Gly Thr Ile Gly Tyr Pro Ala Arg Tyr Ala
            100                 105                 110

Asn Ala Met Ala Val Gly Ala Thr Asp Gln Asn Asn Arg Arg Ala Ser
        115                 120                 125

Phe Ser Gln Tyr Gly Thr Gly Leu Asp Ile Val Ala Pro Gly Val Gly
    130                 135                 140

Val Gln Ser Thr Tyr Pro Gly Ser Arg Tyr Ala Ser Leu Asn Gly Thr
145                 150                 155                 160
```

Ser Met Ala Ser Pro His Val Ala Gly Val Ala Ala Leu
            165                 170

<210> SEQ ID NO 185
<211> LENGTH: 173
<212> TYPE: PRT
<213> ORGANISM: Artificial Sequence
<220> FEATURE:
<223> OTHER INFORMATION: Synthetic

<400> SEQUENCE: 185

Ser Thr Gln Asp Gly Asn Gly His Gly Thr His Val Ala Gly Thr Val
1               5                   10                  15

Ala Ala Leu Asn Asn Ser Asp Gly Val Ile Gly Val Ala Pro Ser Ala
            20                  25                  30

Glu Leu Tyr Ala Val Lys Val Leu Gly Ala Asn Gly Ser Gly Ser Val
        35                  40                  45

Ser Gly Ile Ala Arg Gly Leu Glu Trp Ala Gly Ala Asn Gly Met His
    50                  55                  60

Val Ala Asn Leu Ser Leu Gly Thr Asp Gln Pro Ser Ala Thr Leu Glu
65                  70                  75                  80

Gln Ala Val Asn Gln Ala Thr Ser Arg Gly Val Leu Val Ala Ala
            85                  90                  95

Ser Gly Asn Ser Gly Ser Gly Thr Val Gly Tyr Pro Ala Arg Tyr Ala
            100                 105                 110

Asn Ala Met Ala Val Gly Ala Thr Asp Gln Asn Asn Asn Arg Ala Ser
            115                 120                 125

Phe Ser Gln Tyr Gly Ala Gly Ile Asp Ile Val Ala Pro Gly Val Gly
        130                 135                 140

Val Gln Ser Thr Tyr Pro Gly Ser Arg Tyr Thr Ser Leu Ser Gly Thr
145                 150                 155                 160

Ser Met Ala Thr Pro His Val Ala Gly Ala Ala Ala Leu
            165                 170

<210> SEQ ID NO 186
<211> LENGTH: 173
<212> TYPE: PRT
<213> ORGANISM: Artificial Sequence
<220> FEATURE:
<223> OTHER INFORMATION: Synthetic

<400> SEQUENCE: 186

Ser Thr Gln Asp Gly Asn Gly His Gly Thr His Val Ala Gly Thr Val
1               5                   10                  15

Ala Ala Leu Asn Asn Asn Ile Gly Val Ile Gly Val Ala Pro Asn Val
            20                  25                  30

Glu Leu Tyr Ala Val Lys Val Leu Gly Ala Ser Gly Ser Gly Ser Val
        35                  40                  45

Ser Ser Ile Ala Arg Gly Leu Gln Trp Ala Ala Asn Asn Gly Met His
    50                  55                  60

Ile Ala Asn Leu Ser Leu Gly Ser Ser Ala Pro Ser Ala Thr Leu Glu
65                  70                  75                  80

Arg Ala Val Asn Ala Ala Thr Ser Arg Gly Val Leu Val Val Ala Ala
            85                  90                  95

Ser Gly Asn Ser Gly Ala Gly Ser Ile Gly Tyr Pro Ala Arg Tyr Ala
            100                 105                 110

Asn Ala Met Ala Val Gly Ala Thr Asp Gln Asn Asn Asn Arg Ala Ser

```
            115                 120                 125
Phe Ser Gln Tyr Gly Ala Gly Leu Asp Ile Leu Ala Pro Gly Val Gly
    130                 135                 140

Val Gln Ser Thr Tyr Pro Gly Ser Thr Tyr Ala Ser Met Ser Gly Thr
145                 150                 155                 160

Ser Met Ala Thr Pro His Val Ala Gly Ala Ala Leu
                165                 170

<210> SEQ ID NO 187
<211> LENGTH: 173
<212> TYPE: PRT
<213> ORGANISM: Artificial Sequence
<220> FEATURE:
<223> OTHER INFORMATION: Synthetic

<400> SEQUENCE: 187

Ser Thr Gln Asp Gly Asn Gly His Gly Thr His Val Ala Gly Thr Val
1               5                   10                  15

Ala Ala Leu Asn Asn Ser Val Gly Val Leu Gly Val Ala Pro Ser Ala
                20                  25                  30

Asp Leu Tyr Ala Val Lys Val Leu Gly Ala Ser Gly Arg Gly Ser Val
            35                  40                  45

Ser Gly Ile Ala Gln Gly Leu Glu Trp Ala Ala Asp Asn Gly Met His
        50                  55                  60

Val Ala Asn Met Ser Leu Gly Thr Asp Phe Pro Ser Ala Thr Leu Glu
65                  70                  75                  80

Gln Ala Val Asn Ala Ala Thr Ser Arg Asp Val Leu Val Val Ala Ala
                85                  90                  95

Thr Gly Asn Thr Gly Ser Gly Thr Val Gly Tyr Pro Ala Arg Tyr Ala
            100                 105                 110

Asn Ala Met Ala Val Gly Ala Thr Asp Gln Asn Asn Asn Arg Ala Asn
        115                 120                 125

Phe Ser Gln Tyr Gly Thr Gly Leu Asp Ile Val Ala Pro Gly Val Gly
    130                 135                 140

Val Gln Ser Thr Tyr Pro Gly Ser Arg Tyr Val Ser Met Ser Gly Thr
145                 150                 155                 160

Ser Met Ala Ser Pro His Val Ala Gly Ala Ala Leu
                165                 170

<210> SEQ ID NO 188
<211> LENGTH: 173
<212> TYPE: PRT
<213> ORGANISM: Artificial Sequence
<220> FEATURE:
<223> OTHER INFORMATION: Synthetic

<400> SEQUENCE: 188

Ser Thr Gln Asp Gly Asn Gly His Gly Thr His Val Ala Gly Thr Ile
1               5                   10                  15

Ala Ala Leu Asn Asn Ser Val Gly Val Leu Gly Val Ala Pro Ser Ala
                20                  25                  30

Asp Leu Tyr Ala Val Lys Val Leu Gly Ala Ser Gly Arg Gly Ser Val
            35                  40                  45

Ser Ser Ile Ala Arg Gly Leu Glu Trp Ala Ala Asn Asn Gly Met His
        50                  55                  60

Val Ala Asn Leu Ser Leu Gly Ser Pro Phe Pro Ser Ser Thr Leu Glu
65                  70                  75                  80
```

```
Arg Ala Val Asn Tyr Ala Thr Ser Arg Asp Val Leu Val Ile Ala Ala
                 85                  90                  95

Thr Gly Asn Ser Gly Ala Gly Thr Val Gly Tyr Pro Ala Arg Tyr Ala
                100                 105                 110

Asn Ala Met Ala Val Gly Ala Thr Asp Gln Asn Asn Arg Ala Ser
            115                 120                 125

Ser Ser Gln Tyr Gly Ala Gly Leu Asp Ile Val Ala Pro Gly Val Gly
        130                 135                 140

Val Gln Ser Thr Tyr Pro Gly Ser Thr Tyr Ala Ser Leu Asn Gly Thr
145                 150                 155                 160

Ser Met Ala Ser Pro His Val Ala Gly Ala Ala Leu
                165                 170
```

<210> SEQ ID NO 189
<211> LENGTH: 173
<212> TYPE: PRT
<213> ORGANISM: Artificial Sequence
<220> FEATURE:
<223> OTHER INFORMATION: Synthetic

<400> SEQUENCE: 189

```
Ser Thr Gln Asp Gly Asn Gly His Gly Thr His Val Ala Gly Thr Val
1               5                   10                  15

Ala Ala Leu Asn Asn Ser Ile Gly Val Leu Gly Val Ala Pro Ser Ala
            20                  25                  30

Asp Leu Tyr Gly Val Lys Val Leu Gly Ala Ser Gly Arg Gly Ser Ile
        35                  40                  45

Ser Ser Ile Ala Arg Gly Leu Glu Trp Ala Gly Asn Asn Gly Met His
    50                  55                  60

Ile Ala Asn Met Ser Leu Gly Ser Asp Gln Pro Ser Ala Thr Leu Glu
65                  70                  75                  80

Arg Ala Val Asn Ser Ala Thr Ser Arg Gly Val Leu Val Val Ala Ala
                85                  90                  95

Ser Gly Asn Ser Gly Ala Gly Ser Val Thr Tyr Pro Ala Arg Tyr Ala
                100                 105                 110

Asn Ala Met Ala Val Gly Ala Thr Asp Gln Asn Asn Arg Arg Ala Ser
            115                 120                 125

Phe Ser His Tyr Gly Ala Gly Leu Asp Ile Val Ala Pro Gly Val Gly
        130                 135                 140

Val Gln Ser Thr Tyr Pro Gly Ser Arg Tyr Ala Ser Leu Ser Gly Thr
145                 150                 155                 160

Ser Met Ala Ser Pro His Val Ala Gly Val Ala Ala Leu
                165                 170
```

<210> SEQ ID NO 190
<211> LENGTH: 173
<212> TYPE: PRT
<213> ORGANISM: Artificial Sequence
<220> FEATURE:
<223> OTHER INFORMATION: Synthetic

<400> SEQUENCE: 190

```
Ser Thr Gln Asp Gly Asn Gly His Gly Thr His Val Ala Gly Thr Val
1               5                   10                  15

Ala Ala Leu Asn Asn Asn Val Gly Val Ile Gly Val Ala Pro Ser Ala
            20                  25                  30

Glu Leu Tyr Ala Val Lys Val Leu Gly Ala Ser Gly Ser Gly Thr Ile
        35                  40                  45
```

```
Ser Gly Ile Ala Gln Gly Leu Gln Trp Ala Ala Asp Asn Gly Thr His
    50                  55                  60

Val Ala Asn Leu Ser Leu Gly Ser Asp Phe Pro Ser Ser Thr Leu Glu
 65                  70                  75                  80

Gln Ala Val Asn Ser Ala Thr Ser Arg Gly Val Leu Val Ala Ala
                85                  90                  95

Ser Gly Asn Asn Gly Ser Gly Ser Val Ser Tyr Pro Ala Gly Tyr Ala
                100                 105                 110

Asn Ala Met Ala Val Gly Ala Thr Asp Gln Asn Asn Arg Arg Ala Ser
                115                 120                 125

Ser Ser Gln Tyr Gly Ala Gly Leu Asp Ile Val Ala Pro Gly Val Gly
        130                 135                 140

Val Gln Ser Thr Tyr Pro Gly Ser Arg Tyr Ala Ser Leu Ser Gly Thr
145                 150                 155                 160

Ser Met Ala Thr Pro His Val Ala Gly Ala Ala Leu
                165                 170

<210> SEQ ID NO 191
<211> LENGTH: 173
<212> TYPE: PRT
<213> ORGANISM: Artificial Sequence
<220> FEATURE:
<223> OTHER INFORMATION: Synthetic

<400> SEQUENCE: 191

Ser Thr Gln Asp Gly Asn Gly His Gly Thr His Val Ala Gly Thr Val
  1               5                  10                  15

Ala Ala Leu Asn Asn Asn Asp Gly Val Leu Gly Val Ala Pro Ser Ala
                 20                  25                  30

Asp Leu Tyr Gly Val Lys Val Leu Gly Ala Asn Gly Arg Gly Ser Val
            35                  40                  45

Ser Gly Ile Ala Arg Gly Leu Glu Trp Ala Ala Asp Asn Gly Met His
    50                  55                  60

Val Ala Asn Met Ser Leu Gly Thr Ser Ala Pro Ser Ala Thr Leu Glu
 65                  70                  75                  80

Gln Ala Val Asn Gln Ala Thr Ser Arg Gly Val Leu Val Ala Ala
                85                  90                  95

Ser Gly Asn Ser Gly Ala Gly Thr Ile Gly Tyr Pro Ala Arg Tyr Ala
                100                 105                 110

Asn Ala Met Ala Val Gly Ala Thr Asp Gln Asn Asn Asn Arg Ala Ser
                115                 120                 125

Phe Ser Gln Tyr Gly Ala Gly Leu Asp Ile Val Ala Pro Gly Val Gly
        130                 135                 140

Val Gln Ser Thr Tyr Pro Gly Ser Thr Tyr Val Ser Leu Asn Gly Thr
145                 150                 155                 160

Ser Met Ala Thr Pro His Val Ala Gly Val Ala Ala Leu
                165                 170

<210> SEQ ID NO 192
<211> LENGTH: 173
<212> TYPE: PRT
<213> ORGANISM: Artificial Sequence
<220> FEATURE:
<223> OTHER INFORMATION: Synthetic

<400> SEQUENCE: 192

Ser Thr Gln Asp Gly Asn Gly His Gly Thr His Val Ala Gly Thr Val
```

```
                    1               5                   10                  15
Ala Ala Leu Asn Asn Ser Ile Gly Val Leu Gly Val Ala Pro Ser Ala
                20                  25                  30

Asp Leu Tyr Ala Val Lys Val Leu Gly Ala Ser Gly Arg Gly Thr Val
                35                  40                  45

Ser Ser Ile Ala Gln Gly Leu Glu Trp Ala Ala Asn Asn Gly Thr His
            50                  55                  60

Val Ala Asn Leu Ser Leu Gly Thr Pro Ser Pro Ser Thr Thr Leu Glu
 65                 70                  75                  80

Arg Ala Val Asn Tyr Ala Thr Ser Arg Gly Val Leu Val Val Ala Ala
                85                  90                  95

Ser Gly Asn Ser Gly Ala Gly Ser Val Ser Tyr Pro Ala Arg Tyr Ala
               100                 105                 110

Asn Ala Met Ala Val Gly Ala Thr Asp Gln Asn Asn Arg Arg Ala Ser
               115                 120                 125

Phe Ser Gln Tyr Gly Ala Gly Leu Asp Ile Val Ala Pro Ala Val Asn
           130                 135                 140

Val Gln Ser Thr Tyr Pro Gly Ser Thr Tyr Ala Ser Met Ser Gly Thr
145                 150                 155                 160

Ser Met Ala Ser Pro His Val Ala Gly Ala Ala Ala Leu
                165                 170
```

<210> SEQ ID NO 193
<211> LENGTH: 173
<212> TYPE: PRT
<213> ORGANISM: Artificial Sequence
<220> FEATURE:
<223> OTHER INFORMATION: Synthetic

<400> SEQUENCE: 193

```
Ser Thr Gln Asp Gly Asn Gly His Gly Thr His Val Ala Gly Thr Ile
 1               5                   10                  15

Ala Ala Leu Asn Asn Ser Asp Gly Val Ile Gly Val Ala Pro Asn Ala
                20                  25                  30

Asp Leu Tyr Ala Val Lys Val Leu Gly Ala Ser Gly Arg Gly Thr Val
                35                  40                  45

Ser Gly Ile Ala Gln Gly Leu Glu Trp Ala Ala Ala Asn Gly Met His
            50                  55                  60

Val Ala Asn Met Ser Leu Gly Thr Pro Gln Pro Ser Ala Thr Leu Glu
 65                 70                  75                  80

Arg Ala Val Asn Ala Ala Thr Ser Gln Gly Val Leu Val Val Ala Ala
                85                  90                  95

Ser Gly Asn Gly Ser Gly Ser Ile Ser Tyr Pro Ala Arg Tyr Ala
               100                 105                 110

Asn Ala Met Ala Val Gly Ala Thr Asp Gln Asn Asn Arg Arg Ala Ser
               115                 120                 125

Ser Ser Gln Tyr Gly Thr Gly Leu Asp Ile Val Ala Pro Gly Val Gly
           130                 135                 140

Val Gln Ser Thr Tyr Pro Gly Ser Arg Tyr Ala Ser Leu Asn Gly Thr
145                 150                 155                 160

Ser Met Ala Ser Pro His Val Ala Gly Val Ala Ala Leu
                165                 170
```

<210> SEQ ID NO 194
<211> LENGTH: 173
<212> TYPE: PRT

```
<213> ORGANISM: Artificial Sequence
<220> FEATURE:
<223> OTHER INFORMATION: Synthetic

<400> SEQUENCE: 194

Ser Thr Gln Asp Gly Asn Gly His Gly Thr His Val Ala Gly Thr Ile
1               5                   10                  15

Ala Ala Leu Asn Asn Ser Ile Gly Val Leu Gly Val Ala Pro Asn Ala
            20                  25                  30

Glu Leu Tyr Gly Val Lys Val Leu Gly Ala Ser Gly Ser Gly Thr Val
        35                  40                  45

Ser Gly Ile Ala Arg Gly Leu Glu Trp Ala Ala Asn Asn Gly Met His
    50                  55                  60

Ile Ala Asn Met Ser Leu Gly Thr Asp Ala Pro Ser Ser Thr Leu Glu
65                  70                  75                  80

Gln Ala Val Asn Ser Ala Thr Ser Gln Gly Val Leu Val Ile Ala Ala
                85                  90                  95

Thr Gly Asn Ser Gly Ala Gly Thr Ile Ser Tyr Pro Ala Arg Tyr Ala
            100                 105                 110

Asn Ala Met Ala Val Gly Ala Thr Asp Gln Asn Asn Arg Arg Ala Ser
            115                 120                 125

Phe Ser Gln Tyr Gly Thr Gly Ile Asp Ile Val Ala Pro Gly Val Gly
        130                 135                 140

Val Gln Ser Thr Tyr Pro Gly Ser Thr Tyr Ala Ser Leu Asn Gly Thr
145                 150                 155                 160

Ser Met Ala Ser Pro His Val Ala Gly Ala Ala Leu
                165                 170

<210> SEQ ID NO 195
<211> LENGTH: 173
<212> TYPE: PRT
<213> ORGANISM: Artificial Sequence
<220> FEATURE:
<223> OTHER INFORMATION: Synthetic

<400> SEQUENCE: 195

Ser Thr Gln Asp Gly Asn Gly His Gly Thr His Val Ala Gly Thr Val
1               5                   10                  15

Ala Ala Leu Asn Asn Ser Ile Gly Val Leu Gly Val Ala Pro Asn Ala
            20                  25                  30

Glu Leu Tyr Gly Val Lys Val Leu Gly Ala Asn Gly Ser Gly Ser Ile
        35                  40                  45

Ser Gly Ile Ala Arg Gly Leu Glu Trp Ala Gly Asn Asn Gly Met His
    50                  55                  60

Ile Ala Asn Leu Ser Leu Gly Thr Asp Ser Pro Ser Ala Thr Leu Glu
65                  70                  75                  80

Gln Ala Val Asn Tyr Ala Thr Ser Arg Gly Val Leu Val Ile Ala Ala
                85                  90                  95

Ser Gly Asn Ser Gly Ser Gly Thr Val Gly Tyr Pro Ala Arg Tyr Ala
            100                 105                 110

Asn Ala Met Ala Val Gly Ala Thr Asp Gln Asn Asn Asn Arg Ala Ser
            115                 120                 125

Phe Ser Gln Tyr Gly Thr Gly Leu Asp Ile Val Ala Pro Gly Val Gly
        130                 135                 140

Val Gln Ser Thr Tyr Pro Gly Ser Thr Tyr Ala Ser Leu Asn Gly Thr
145                 150                 155                 160
```

Ser Met Ala Ser Pro His Val Gly Ala Ala Ala Leu
            165                 170

<210> SEQ ID NO 196
<211> LENGTH: 173
<212> TYPE: PRT
<213> ORGANISM: Artificial Sequence
<220> FEATURE:
<223> OTHER INFORMATION: Synthetic

<400> SEQUENCE: 196

Ser Thr Gln Asp Gly Asn Gly His Gly Thr His Val Ala Gly Thr Val
1               5                   10                  15

Ala Ala Leu Asn Asn Ser Val Gly Val Ile Gly Val Ala Pro Asn Ala
            20                  25                  30

Asp Leu Tyr Ala Val Lys Val Leu Gly Ala Asn Gly Arg Gly Thr Ile
        35                  40                  45

Ser Ser Ile Ala Arg Gly Leu Glu Trp Ala Gly Asp Asn Gly Met His
    50                  55                  60

Val Ala Asn Leu Ser Leu Gly Ser Pro Ala Pro Ser Ala Thr Leu Glu
65                  70                  75                  80

Gln Ala Val Asn Gln Ala Thr Ser Arg Gly Val Leu Val Ile Ala Ala
                85                  90                  95

Ser Gly Asn Asn Gly Ser Gly Ser Val Ser Tyr Pro Ala Arg Tyr Ala
            100                 105                 110

Asn Ala Met Ala Val Gly Ala Thr Asp Gln Asn Asn Asn Arg Ala Ser
        115                 120                 125

Ser Ser Gln Tyr Gly Ala Gly Leu Asp Ile Val Ala Pro Gly Val Gly
    130                 135                 140

Val Gln Ser Thr Tyr Pro Gly Ser Thr Tyr Ala Ser Leu Ser Gly Thr
145                 150                 155                 160

Ser Met Ala Thr Pro His Val Ala Gly Ala Ala Ala Leu
            165                 170

<210> SEQ ID NO 197
<211> LENGTH: 173
<212> TYPE: PRT
<213> ORGANISM: Artificial Sequence
<220> FEATURE:
<223> OTHER INFORMATION: Synthetic

<400> SEQUENCE: 197

Ser Thr Gln Asp Gly Asn Gly His Gly Thr His Val Ala Gly Thr Val
1               5                   10                  15

Ala Ala Leu Asn Asn Ser Val Gly Val Leu Gly Val Ala Pro Ser Ala
            20                  25                  30

Glu Leu Tyr Ala Val Lys Val Leu Gly Ala Ser Gly Arg Gly Thr Ile
        35                  40                  45

Ser Gly Ile Ala Gln Gly Leu Glu Trp Ala Ala Asp Asn Gly Met His
    50                  55                  60

Val Ala Asn Leu Ser Leu Gly Thr Ser Ala Pro Ser Ala Thr Leu Glu
65                  70                  75                  80

Arg Ala Val Asn Ala Ala Thr Ser Arg Gly Val Leu Val Val Ala Ala
                85                  90                  95

Ser Gly Asn Ser Gly Ala Gly Thr Val Ser Tyr Pro Ala Arg Tyr Ala
            100                 105                 110

Asn Ala Met Ala Val Gly Ala Thr Asp Gln Asn Asn Asn Arg Ala Ser
        115                 120                 125

```
Phe Ser Gln Tyr Gly Thr Gly Leu Asp Ile Val Ala Pro Gly Val Gly
        130                 135                 140
Val Gln Ser Thr Tyr Pro Gly Asn Thr Tyr Ala Ser Met Ser Gly Thr
145                 150                 155                 160
Ser Met Ala Ser Pro His Val Ala Gly Ala Ala Ala Leu
                165                 170
```

<210> SEQ ID NO 198
<211> LENGTH: 173
<212> TYPE: PRT
<213> ORGANISM: Artificial Sequence
<220> FEATURE:
<223> OTHER INFORMATION: Synthetic

<400> SEQUENCE: 198

```
Ser Thr Gln Asp Gly Asn Gly His Gly Thr His Val Ala Gly Thr Val
1               5                   10                  15
Ala Ala Leu Asn Asn Val Gly Val Leu Gly Val Ala Pro Ser Ala
                20                  25                  30
Glu Leu Tyr Ala Val Lys Val Leu Gly Ala Ser Gly Arg Gly Thr Val
            35                  40                  45
Ser Ser Ile Ala Arg Gly Leu Gln Trp Ala Gly Asp Asn Gly Met His
        50                  55                  60
Val Ala Asn Met Ser Leu Gly Thr Ser Phe Pro Ser Ala Thr Leu Glu
65                  70                  75                  80
Gln Ala Val Asn Ala Ala Thr Ser Gln Gly Val Leu Val Val Ala Ala
                85                  90                  95
Ser Gly Asn Thr Gly Ser Gly Ser Val Gly Tyr Pro Ala Arg Tyr Ala
                100                 105                 110
Asn Ala Met Ala Val Gly Ala Thr Asp Gln Asn Asn Asn Arg Ala Asn
            115                 120                 125
Phe Ser Gln Tyr Gly Thr Gly Ile Asp Ile Val Ala Pro Gly Val Gly
        130                 135                 140
Val Gln Ser Thr Tyr Pro Gly Ser Thr Tyr Ala Ser Leu Asn Gly Thr
145                 150                 155                 160
Ser Met Ala Thr Pro His Val Ala Gly Ala Ala Ala Leu
                165                 170
```

<210> SEQ ID NO 199
<211> LENGTH: 173
<212> TYPE: PRT
<213> ORGANISM: Artificial Sequence
<220> FEATURE:
<223> OTHER INFORMATION: Synthetic

<400> SEQUENCE: 199

```
Ser Thr Gln Asp Gly Asn Gly His Gly Thr His Val Ala Gly Thr Ile
1               5                   10                  15
Ala Ala Leu Asn Asn Ser Val Gly Val Leu Gly Val Ala Pro Ser Val
                20                  25                  30
Asp Leu Tyr Gly Val Lys Val Leu Gly Ala Ser Gly Arg Gly Ser Val
            35                  40                  45
Ser Gly Ile Ala Gln Gly Leu Glu Trp Ala Ala Asn Gly Met His
        50                  55                  60
Val Ala Asn Met Ser Leu Gly Ser Asp Ala Pro Ser Ala Thr Leu Glu
65                  70                  75                  80
Arg Ala Val Asn Gln Ala Thr Ser Arg Gly Val Leu Val Ile Ala Ala
```

```
                        85                  90                  95
Thr Gly Asn Asn Gly Ser Gly Ser Ile Ser Tyr Pro Ala Arg Tyr Ala
                100                 105                 110

Asn Ala Met Ala Val Gly Ala Thr Asp Gln Asn Asn Arg Ala Ser
            115                 120                 125

Phe Ser Gln Tyr Gly Ala Gly Leu Asp Ile Val Ala Pro Gly Val Asn
        130                 135                 140

Val Gln Ser Thr Tyr Pro Gly Ser Thr Tyr Val Ser Leu Ser Gly Thr
145                 150                 155                 160

Ser Met Ala Ser Pro His Val Ala Gly Ala Ala Leu
                165                 170

<210> SEQ ID NO 200
<211> LENGTH: 173
<212> TYPE: PRT
<213> ORGANISM: Artificial Sequence
<220> FEATURE:
<223> OTHER INFORMATION: Synthetic

<400> SEQUENCE: 200

Ser Thr Gln Asp Gly Asn Gly His Gly Thr His Val Ala Gly Thr Val
1               5                   10                  15

Ala Ala Leu Asn Asn Asn Asp Gly Val Leu Gly Val Ala Pro Asn Ala
            20                  25                  30

Glu Leu Tyr Ala Val Lys Val Leu Gly Ala Ser Gly Ser Gly Thr Val
        35                  40                  45

Ser Gly Ile Ala Gln Gly Leu Glu Trp Ala Ala Asp Asn Gly Thr His
    50                  55                  60

Ile Ala Asn Leu Ser Leu Gly Thr Pro Gln Pro Ser Ala Thr Leu Glu
65                  70                  75                  80

Arg Ala Val Lys Ser Ala Thr Ser Arg Gly Val Leu Val Val Ala Ala
                85                  90                  95

Ser Gly Asn Ser Gly Ala Gly Ser Val Ser Tyr Pro Ala Arg Tyr Ala
                100                 105                 110

Asn Ala Met Ala Val Gly Ala Thr Asp Gln Asn Asn Asn Arg Ala Ser
            115                 120                 125

Phe Ser Gln Tyr Gly Ala Gly Ile Asp Ile Val Ala Pro Gly Val Gly
        130                 135                 140

Val Gln Ser Thr Tyr Pro Gly Ser Thr Tyr Ala Ser Met Ser Gly Thr
145                 150                 155                 160

Ser Met Ala Thr Pro His Val Ala Gly Val Ala Ala Leu
                165                 170

<210> SEQ ID NO 201
<211> LENGTH: 173
<212> TYPE: PRT
<213> ORGANISM: Artificial Sequence
<220> FEATURE:
<223> OTHER INFORMATION: Synthetic

<400> SEQUENCE: 201

Ser Thr Gln Asp Gly Asn Gly His Gly Thr His Val Ala Gly Thr Val
1               5                   10                  15

Ala Ala Leu Asn Asn Ser Asp Gly Val Ile Gly Val Ala Pro Ser Ala
            20                  25                  30

Asp Leu Tyr Gly Val Lys Val Leu Gly Ala Asn Gly Ser Gly Ser Ile
        35                  40                  45
```

```
Ser Gly Ile Ala Gln Gly Leu Glu Trp Ala Ala Asn Gly Met His
     50                  55                  60

Val Ala Asn Met Ser Leu Gly Thr Ser Phe Pro Ser Ser Thr Leu Glu
 65                  70                  75                  80

Gln Ala Val Asn Ala Ala Thr Ser Arg Gly Val Leu Val Val Ala Ala
                 85                  90                  95

Ser Gly Asn Ser Gly Ala Gly Thr Val Ser Tyr Pro Ala Arg Tyr Ala
            100                 105                 110

Asn Ala Met Ala Val Gly Ala Thr Asp Gln Asn Asn Asn Arg Ala Ser
            115                 120                 125

Phe Ser Gln Tyr Gly Ala Gly Ile Asp Ile Val Ala Pro Gly Val Gly
        130                 135                 140

Val Gln Ser Thr Tyr Pro Gly Asn Arg Cys Val Ser Leu Ser Gly Thr
145                 150                 155                 160

Ser Met Ala Thr Pro His Val Ala Gly Ala Ala Ala Leu
                165                 170

<210> SEQ ID NO 202
<211> LENGTH: 173
<212> TYPE: PRT
<213> ORGANISM: Artificial Sequence
<220> FEATURE:
<223> OTHER INFORMATION: Synthetic

<400> SEQUENCE: 202

Ser Thr Gln Asp Gly Asn Gly His Gly Thr His Val Ala Gly Thr Val
 1               5                  10                  15

Ala Ala Leu Asn Asn Asn Val Gly Val Leu Gly Val Ala Pro Ser Val
                 20                  25                  30

Asp Leu Tyr Ala Val Lys Val Leu Gly Ala Asn Gly Ser Gly Thr Ile
             35                  40                  45

Ser Gly Ile Ala Gln Gly Leu Glu Trp Ala Ala Asn Asn Gly Met His
     50                  55                  60

Val Ala Asn Met Ser Leu Gly Ser Pro Ala Pro Ser Ala Thr Leu Glu
 65                  70                  75                  80

Arg Ala Val Asn Gln Ala Thr Ser Arg Gly Val Leu Val Val Ala Ala
                 85                  90                  95

Thr Gly Asn Ser Gly Ser Gly Thr Val Gly Tyr Pro Ala Arg Tyr Ala
            100                 105                 110

Asn Ala Met Ala Val Gly Ala Thr Asp Gln Asn Asn Asn Arg Ala Ser
            115                 120                 125

Phe Ser Gln Tyr Gly Ala Gly Ile Asp Ile Val Ala Pro Gly Val Gly
        130                 135                 140

Val Gln Ser Thr Tyr Pro Gly Ser Arg Tyr Val Ser Leu Ser Gly Thr
145                 150                 155                 160

Ser Met Ala Ser Pro His Val Ala Gly Val Ala Ala Leu
                165                 170

<210> SEQ ID NO 203
<211> LENGTH: 173
<212> TYPE: PRT
<213> ORGANISM: Artificial Sequence
<220> FEATURE:
<223> OTHER INFORMATION: Synthetic

<400> SEQUENCE: 203

Ser Thr Gln Asp Gly Asn Gly His Gly Thr His Val Ala Gly Thr Val
 1               5                  10                  15
```

```
Ala Ala Leu Asn Asn Asn Asp Gly Val Ile Gly Val Ala Pro Ser Ala
            20                  25                  30

Glu Leu Tyr Ala Val Lys Val Leu Gly Ala Ser Gly Ser Gly Ser Ile
        35                  40                  45

Ser Ser Ile Ala Arg Gly Leu Glu Trp Ala Ala Asp Asn Gly Thr His
    50                  55                  60

Ile Ala Asn Met Ser Leu Gly Thr Pro Gln Pro Ser Ala Thr Leu Glu
65                  70                  75                  80

Arg Ala Val Asn Ser Ala Thr Ser Arg Gly Val Leu Val Ala Ala
                85                  90                  95

Ser Gly Asn Ser Gly Ser Gly Ser Val Ser Tyr Pro Ala Arg Tyr Ala
                100                 105                 110

Asn Ala Met Ala Val Gly Ala Thr Asp Gln Asn Asn Asn Arg Ala Ser
                115                 120                 125

Phe Ser Gln Tyr Gly Ala Gly Leu Asp Ile Leu Ala Pro Gly Val Gly
                130                 135                 140

Val Gln Ser Thr Tyr Pro Gly Ser Thr Tyr Ala Ser Leu Asn Gly Thr
145                 150                 155                 160

Ser Met Ala Ser Pro His Val Ala Gly Val Ala Ala Leu
                165                 170

<210> SEQ ID NO 204
<211> LENGTH: 173
<212> TYPE: PRT
<213> ORGANISM: Artificial Sequence
<220> FEATURE:
<223> OTHER INFORMATION: Synthetic

<400> SEQUENCE: 204

Ser Thr Gln Asp Gly Asn Gly His Gly Thr His Val Ala Gly Thr Val
1               5                   10                  15

Ala Ala Leu Asn Asn Ser Ile Gly Val Leu Gly Val Val Pro Ser Ala
            20                  25                  30

Asp Leu Tyr Ala Val Lys Val Leu Gly Ala Ser Gly Arg Gly Thr Val
        35                  40                  45

Ser Gly Ile Ala Gln Gly Leu Glu Trp Ala Gly Asn Asn Met His
    50                  55                  60

Val Ala Asn Leu Ser Leu Gly Ser Asp Phe Pro Ser Ser Thr Leu Glu
65                  70                  75                  80

Arg Ala Val Asn Ala Ala Thr Ser Arg Asp Val Leu Val Val Ala Ala
                85                  90                  95

Ser Gly Asn Thr Gly Ser Gly Ser Ile Ser Tyr Pro Ala Arg Tyr Ala
                100                 105                 110

Asn Ala Met Ala Val Gly Ala Thr Asp Gln Asn Asn Asn Arg Ala Asn
                115                 120                 125

Phe Ser Gln Tyr Gly Gln Gly Ile Asp Ile Val Ala Pro Gly Val Gly
                130                 135                 140

Val Gln Ser Thr Tyr Pro Gly Ser Arg Tyr Ala Ser Leu Ser Gly Thr
145                 150                 155                 160

Ser Met Ala Ser Pro His Val Ala Gly Val Ala Ala Leu
                165                 170

<210> SEQ ID NO 205
<211> LENGTH: 173
<212> TYPE: PRT
<213> ORGANISM: Artificial Sequence
```

-continued

```
<220> FEATURE:
<223> OTHER INFORMATION: Synthetic

<400> SEQUENCE: 205

Ser Thr Gln Asp Gly Asn Gly His Gly Thr His Val Ala Gly Thr Val
1               5                   10                  15

Ala Ala Leu Asn Asn Ser Asp Gly Val Leu Gly Val Ala Pro Ser Val
            20                  25                  30

Asp Leu Tyr Gly Val Lys Val Leu Gly Ala Ser Gly Ser Gly Ser Ile
        35                  40                  45

Ser Gly Ile Ala Gln Gly Leu Gln Trp Ala Ala Asp Asn Gly Met His
    50                  55                  60

Val Ala Asn Leu Ser Leu Gly Ser Pro Gln Pro Ser Ala Thr Leu Glu
65                  70                  75                  80

Arg Ala Val Asn Tyr Ala Thr Ser Arg Gly Val Leu Val Ala Ala
                85                  90                  95

Thr Gly Asn Thr Gly Ala Gly Ser Gly Tyr Pro Ala Arg Tyr Ala
                100                 105                 110

Asn Ala Met Ala Val Gly Ala Thr Asp Gln Asn Asn Arg Arg Ala Ser
            115                 120                 125

Phe Ser Gln Tyr Gly Ala Gly Leu Asp Ile Val Ala Pro Gly Val Gly
    130                 135                 140

Val Gln Ser Thr Tyr Pro Gly Asn Arg Tyr Val Ser Leu Ser Gly Thr
145                 150                 155                 160

Ser Met Ala Thr Pro His Val Ala Gly Ala Ala Ala Leu
                165                 170

<210> SEQ ID NO 206
<211> LENGTH: 173
<212> TYPE: PRT
<213> ORGANISM: Artificial Sequence
<220> FEATURE:
<223> OTHER INFORMATION: Synthetic

<400> SEQUENCE: 206

Ser Thr Gln Asp Gly Asn Gly His Gly Thr His Val Ala Gly Thr Ile
1               5                   10                  15

Ala Ala Leu Asn Asn Ser Ile Gly Val Leu Gly Val Ala Pro Asn Val
            20                  25                  30

Asp Leu Tyr Gly Val Lys Val Leu Gly Ala Ser Gly Arg Gly Ser Val
        35                  40                  45

Ser Gly Ile Ala Arg Gly Leu Glu Trp Ala Gly Asp Asn Gly Met His
    50                  55                  60

Val Ala Asn Leu Ser Leu Gly Ser Ser Gln Pro Ser Ala Thr Leu Glu
65                  70                  75                  80

Gln Ala Val Asn Ser Ala Thr Ser Arg Gly Val Leu Val Ile Ala Ala
                85                  90                  95

Thr Gly Asn Thr Gly Ala Gly Thr Val Ser Tyr Pro Ala Arg Tyr Ala
                100                 105                 110

Asn Ala Met Ala Val Gly Ala Thr Asp Gln Asn Asn Asn Arg Ala Asn
            115                 120                 125

Phe Ser Gln Tyr Gly Thr Gly Leu Asp Ile Val Ala Pro Gly Val Gly
    130                 135                 140

Val Gln Ser Thr Tyr Pro Gly Ser Thr Tyr Ala Ser Met Asn Gly Thr
145                 150                 155                 160

Ser Met Ala Thr Pro His Val Ala Gly Ala Ala Ala Leu
```

<210> SEQ ID NO 207
<211> LENGTH: 173
<212> TYPE: PRT
<213> ORGANISM: Artificial Sequence
<220> FEATURE:
<223> OTHER INFORMATION: Synthetic

<400> SEQUENCE: 207

```
Ser Thr Gln Asp Gly Asn Gly His Gly Thr His Val Ala Gly Thr Val
1               5                   10                  15
Ala Ala Leu Asn Asn Asn Ile Gly Val Leu Gly Val Ala Pro Ser Ala
            20                  25                  30
Glu Leu Tyr Gly Val Lys Val Leu Gly Ala Ser Gly Arg Gly Thr Val
        35                  40                  45
Ser Gly Ile Ala Gln Gly Leu Glu Trp Ala Gly Asp Asn Gly Met His
    50                  55                  60
Val Ala Asn Leu Ser Leu Gly Thr Asp Gln Pro Ser Ser Thr Leu Glu
65                  70                  75                  80
Arg Ala Val Asn Ala Ala Thr Ser Arg Gly Val Leu Val Val Ala Ala
                85                  90                  95
Ser Gly Asn Thr Gly Ala Gly Ser Ile Gly Tyr Pro Ala Arg Tyr Ala
            100                 105                 110
Asn Ala Met Ala Val Gly Ala Thr Asp Gln Asn Asn Asn Arg Ala Asn
        115                 120                 125
Phe Ser Gln Tyr Gly Ala Gly Leu Asp Ile Val Ala Pro Gly Val Gly
    130                 135                 140
Val Gln Ser Thr Tyr Pro Gly Ser Arg Tyr Ala Ser Leu Asn Gly Thr
145                 150                 155                 160
Ser Met Ala Thr Pro His Val Ala Gly Val Ala Ala Leu
                165                 170
```

<210> SEQ ID NO 208
<211> LENGTH: 173
<212> TYPE: PRT
<213> ORGANISM: Artificial Sequence
<220> FEATURE:
<223> OTHER INFORMATION: Synthetic

<400> SEQUENCE: 208

```
Ser Thr Gln Asp Gly Asn Gly His Gly Thr His Val Ala Gly Thr Val
1               5                   10                  15
Ala Ala Leu Asn Asn Asn Val Gly Val Leu Gly Val Ala Pro Ser Ala
            20                  25                  30
Glu Leu Tyr Ala Val Lys Val Leu Gly Ala Ser Gly Ser Gly Thr Ile
        35                  40                  45
Ser Ser Ile Ala Gln Gly Leu Glu Trp Ala Gly Thr Asn Gly Thr His
    50                  55                  60
Ile Ala Asn Leu Ser Leu Gly Thr Asp Gln Pro Ser Ala Thr Leu Glu
65                  70                  75                  80
Arg Ala Val Asn Ala Ala Thr Ser Arg Gly Val Leu Val Val Ala Ala
                85                  90                  95
Ser Gly Asn Asn Gly Ser Gly Ser Val Ser Tyr Pro Ala Arg Tyr Ala
            100                 105                 110
Asn Ala Met Ala Val Gly Ala Thr Asp Gln Asn Asn Arg Arg Ala Asn
        115                 120                 125
```

```
Phe Ser Gln Tyr Gly Ala Gly Leu Asp Ile Val Ala Pro Gly Val Gly
    130                 135                 140

Val Gln Ser Thr Cys Pro Gly Asn Arg Tyr Val Ser Leu Ser Gly Thr
145                 150                 155                 160

Ser Met Ala Ser Pro His Val Ala Gly Val Ala Ala Leu
                165                 170

<210> SEQ ID NO 209
<211> LENGTH: 173
<212> TYPE: PRT
<213> ORGANISM: Artificial Sequence
<220> FEATURE:
<223> OTHER INFORMATION: Synthetic

<400> SEQUENCE: 209

Ser Thr Gln Asp Gly Asn Gly His Gly Thr His Val Ala Gly Thr Ile
1               5                   10                  15

Ala Ala Leu Asn Asn Ser Val Gly Val Leu Gly Val Ala Pro Ser Ala
                20                  25                  30

Glu Leu Tyr Gly Val Lys Val Leu Gly Ala Ser Gly Arg Gly Ser Val
            35                  40                  45

Ser Ser Ile Ala Gln Gly Leu Glu Trp Ala Ala Asp Asn Gly Met His
    50                  55                  60

Val Ala Asn Met Ser Leu Gly Thr Ser Phe Pro Ser Ser Thr Leu Glu
65                  70                  75                  80

Arg Ala Val Asn Ala Ala Thr Ser Arg Gly Val Leu Val Ile Ala Ala
                85                  90                  95

Ser Gly Asn Ser Gly Ser Gly Thr Ile Gly Tyr Pro Gly Arg Tyr Ala
                100                 105                 110

Asn Ala Met Ala Val Gly Ala Thr Asp Gln Asn Asn Asn Arg Ala Ser
            115                 120                 125

Phe Ser Gln Tyr Gly Thr Gly Ile Asp Ile Val Ala Pro Gly Val Gly
    130                 135                 140

Val Gln Ser Thr Tyr Pro Gly Ser Thr Tyr Ala Ser Leu Ser Gly Thr
145                 150                 155                 160

Ser Met Ala Thr Pro His Val Ala Gly Ala Ala Ala Leu
                165                 170

<210> SEQ ID NO 210
<211> LENGTH: 173
<212> TYPE: PRT
<213> ORGANISM: Artificial Sequence
<220> FEATURE:
<223> OTHER INFORMATION: Synthetic

<400> SEQUENCE: 210

Ser Thr Gln Asp Gly Asn Gly His Gly Thr His Val Ala Gly Thr Ile
1               5                   10                  15

Ala Ala Leu Asn Asn Val Gly Val Leu Gly Val Ala Pro Ser Val
                20                  25                  30

Glu Leu Tyr Ala Val Lys Val Leu Gly Ala Asn Gly Ser Gly Thr Ile
            35                  40                  45

Ser Gly Ile Ala Gln Gly Leu Glu Trp Ala Ala Asn Asn Gly Thr His
    50                  55                  60

Val Ala Asn Leu Ser Leu Gly Thr Asp Ala Pro Ser Ala Thr Leu Glu
65                  70                  75                  80

Arg Ala Val Asn Gln Ala Thr Ser Arg Gly Val Leu Val Val Ala Ala
                85                  90                  95
```

```
Ser Gly Asn Ser Gly Ser Gly Thr Ile Gly Tyr Pro Ala Arg Tyr Ala
            100                 105                 110

Asn Ala Met Ala Val Gly Ala Thr Asp Gln Asn Asn Arg Ala Ser
            115                 120                 125

Phe Ser Gln Tyr Gly Ala Gly Ile Asp Ile Val Ala Pro Gly Val Gly
            130                 135                 140

Val Gln Ser Thr Tyr Pro Gly Ser Thr Tyr Ala Leu Leu Ser Gly Thr
145                 150                 155                 160

Ser Met Ala Thr Pro His Val Ala Gly Val Ala Ala Leu
                165                 170
```

<210> SEQ ID NO 211
<211> LENGTH: 173
<212> TYPE: PRT
<213> ORGANISM: Artificial Sequence
<220> FEATURE:
<223> OTHER INFORMATION: Synthetic

<400> SEQUENCE: 211

```
Ser Thr Gln Asp Gly Asn Gly His Gly Thr His Val Ala Gly Thr Val
1               5                   10                  15

Ala Ala Leu Asn Asn Ser Ile Gly Val Leu Gly Val Ala Pro Ser Ala
            20                  25                  30

Glu Leu Tyr Ala Val Lys Val Leu Gly Ala Ser Gly Arg Gly Ser Val
            35                  40                  45

Ser Ser Ile Ala Gln Gly Leu Glu Trp Ala Gly Ala Asn Gly Met His
            50                  55                  60

Ile Ala Asn Leu Ser Leu Gly Ser Pro Ala Pro Ser Ser Thr Leu Glu
65                  70                  75                  80

Arg Ala Val Asn Ser Ala Thr Ser Arg Gly Val Leu Val Ile Ala Ala
            85                  90                  95

Thr Gly Asn Thr Gly Ser Gly Ser Ile Ser Tyr Pro Ala Arg Tyr Ala
            100                 105                 110

Asn Ala Met Ala Val Gly Ala Thr Asp Gln Asn Asn Arg Arg Ala Ser
            115                 120                 125

Phe Ser Gln Tyr Gly Ala Gly Ile Asp Ile Val Ala Pro Gly Val Gly
            130                 135                 140

Val Gln Ser Thr Tyr Pro Gly Asn Thr Tyr Val Ser Met Ser Gly Thr
145                 150                 155                 160

Ser Met Ala Thr Pro His Val Ala Gly Ala Ala Ala Leu
                165                 170
```

<210> SEQ ID NO 212
<211> LENGTH: 173
<212> TYPE: PRT
<213> ORGANISM: Artificial Sequence
<220> FEATURE:
<223> OTHER INFORMATION: Synthetic

<400> SEQUENCE: 212

```
Ser Thr Gln Asp Gly Asn Gly His Gly Thr His Val Ala Gly Thr Val
1               5                   10                  15

Ala Ala Leu Asn Asn Asn Ile Gly Val Leu Gly Val Ala Pro Asn Val
            20                  25                  30

Gly Leu Tyr Ala Val Lys Val Leu Gly Ala Ser Gly Arg Gly Thr Val
            35                  40                  45

Ser Gly Ile Ala Arg Gly Leu Glu Trp Ala Ala Thr Asn Gly Met His
```

```
                50                  55                  60
Val Ala Asn Leu Ser Leu Gly Ser Asp Ala Pro Ser Ala Thr Leu Glu
 65                  70                  75                  80

Gln Ala Val Asn Gln Ala Thr Ser Arg Gly Val Leu Val Ala Ala
                 85                  90                  95

Thr Gly Asn Thr Gly Ser Gly Thr Ile Ser Tyr Pro Ala Arg Tyr Ala
                100                 105                 110

Asn Ala Met Ala Val Gly Ala Thr Asp Gln Asn Asn Arg Arg Ala Asn
                115                 120                 125

Phe Ser Gln Tyr Gly Gln Gly Leu Asp Ile Val Ala Pro Gly Val Gly
                130                 135                 140

Val Gln Ser Thr Tyr Pro Gly Asn Thr Tyr Val Ser Met Ser Gly Thr
145                 150                 155                 160

Ser Met Ala Ser Pro His Val Ala Gly Val Ala Ala Leu
                165                 170

<210> SEQ ID NO 213
<211> LENGTH: 173
<212> TYPE: PRT
<213> ORGANISM: Artificial Sequence
<220> FEATURE:
<223> OTHER INFORMATION: Synthetic

<400> SEQUENCE: 213

Ser Thr Gln Asp Gly Asn Gly His Gly Thr His Val Ala Gly Thr Val
 1                   5                  10                  15

Ala Ala Leu Asn Asn Ser Asp Gly Val Leu Gly Val Ala Pro Ser Ala
                 20                  25                  30

Asp Leu Tyr Ala Val Lys Val Leu Gly Ala Ser Gly Arg Gly Ser Val
                 35                  40                  45

Ser Ser Ile Ala Arg Gly Leu Glu Trp Ala Ala Asn Gly Met His
                 50                  55                  60

Val Ala Asn Leu Ser Leu Gly Ser Asp Gln Pro Ser Ser Thr Leu Glu
 65                  70                  75                  80

Arg Ala Val Asn Glu Ala Thr Ser Gln Gly Val Leu Val Val Ala Ala
                 85                  90                  95

Ser Gly Asn Asn Gly Ala Gly Thr Val Gly Tyr Pro Ala Arg Tyr Ala
                100                 105                 110

Asn Ala Met Ala Val Gly Ala Thr Asp Gln Asn Asn Arg Arg Ala Ser
                115                 120                 125

Phe Ser Gln Tyr Gly Ala Gly Leu Asp Ile Val Ala Pro Gly Val Gly
                130                 135                 140

Val Gln Ser Thr Tyr Pro Gly Ser Thr Tyr Ala Ser Met Asn Gly Thr
145                 150                 155                 160

Ser Met Ala Thr Pro His Val Ala Gly Ala Ala Ala Leu
                165                 170

<210> SEQ ID NO 214
<211> LENGTH: 173
<212> TYPE: PRT
<213> ORGANISM: Artificial Sequence
<220> FEATURE:
<223> OTHER INFORMATION: Synthetic

<400> SEQUENCE: 214

Ser Thr Gln Asp Gly Asn Gly His Gly Thr His Val Ala Gly Thr Val
 1                   5                  10                  15
```

Ala Ala Leu Asn Asn Ser Val Gly Val Leu Gly Val Ala Pro Ser Val
            20                  25                  30

Glu Leu Tyr Gly Val Lys Val Leu Gly Ala Asn Gly Ser Gly Ser Ile
        35                  40                  45

Ser Ser Ile Ala Arg Gly Leu Glu Trp Ala Ala Asp Asn Gly Met His
 50                  55                  60

Ile Ala Asn Leu Ser Leu Gly Ser Ser Phe Pro Ser Ala Thr Leu Glu
 65                  70                  75                  80

Gln Ala Val Asn Gln Ala Thr Ser Arg Gly Val Leu Val Ile Ala Ala
            85                  90                  95

Thr Gly Asn Ser Gly Ser Gly Thr Val Gly Tyr Pro Ala Arg Tyr Ala
            100                 105                 110

Asn Ala Met Ala Val Gly Ala Thr Asp Gln Asn Asn Asn Arg Ala Asn
            115                 120                 125

Phe Ser Gln Tyr Gly Ala Gly Leu Asp Ile Val Ala Pro Gly Val Gly
            130                 135                 140

Val Gln Ser Thr Tyr Thr Gly Ser Thr Tyr Ala Ser Met Asn Gly Thr
145                 150                 155                 160

Ser Met Ala Ser Pro His Val Ala Gly Ala Ala Ala Leu
                165                 170

<210> SEQ ID NO 215
<211> LENGTH: 173
<212> TYPE: PRT
<213> ORGANISM: Artificial Sequence
<220> FEATURE:
<223> OTHER INFORMATION: Synthetic

<400> SEQUENCE: 215

Ser Thr Gln Asp Gly Asn Gly His Gly Thr His Val Ala Gly Thr Ile
1               5                   10                  15

Ala Ala Leu Asn Asn Ser Asp Gly Val Leu Gly Val Ala Pro Asn Val
            20                  25                  30

Asp Leu Tyr Gly Val Lys Val Leu Gly Ala Asn Gly Ser Gly Thr Val
        35                  40                  45

Ser Gly Ile Ala Arg Gly Leu Gln Trp Ala Gly Asp Asn Gly Met His
 50                  55                  60

Val Ala Asn Leu Ser Leu Gly Thr Asp Ala Pro Ser Ala Thr Leu Glu
 65                  70                  75                  80

Arg Ala Val Asn Gln Ala Thr Ser Arg Gly Val Leu Val Val Ala Ala
            85                  90                  95

Ser Gly Asn Thr Gly Ala Gly Ser Ile Ser Tyr Pro Ala Arg Tyr Ala
            100                 105                 110

Asn Ala Met Ala Val Gly Ala Thr Asp Gln Asn Asn Arg Arg Ala Asn
            115                 120                 125

Phe Ser Gln Tyr Gly Ala Gly Leu Asp Ile Val Ala Pro Gly Val Gly
            130                 135                 140

Val Gln Ser Thr Tyr Thr Gly Asn Arg Tyr Val Ser Met Asn Gly Thr
145                 150                 155                 160

Ser Met Ala Ser Pro His Val Ala Gly Ala Ala Ala Leu
                165                 170

<210> SEQ ID NO 216
<211> LENGTH: 173
<212> TYPE: PRT
<213> ORGANISM: Artificial Sequence
<220> FEATURE:

<223> OTHER INFORMATION: Synthetic

<400> SEQUENCE: 216

```
Ser Thr Gln Asp Gly Asn Gly His Gly Thr His Val Ala Gly Thr Ile
1               5                   10                  15

Ala Ala Leu Asn Asn Asn Ala Gly Val Leu Gly Val Ala Pro Asn Val
            20                  25                  30

Asp Leu Tyr Ala Val Lys Val Leu Gly Ala Asn Gly Ser Gly Ser Ile
        35                  40                  45

Ser Gly Ile Ala Arg Gly Leu Glu Trp Ala Gly Asp Asn Gly Met His
    50                  55                  60

Val Ala Asn Leu Ser Leu Gly Ser Pro Gln Pro Ser Ala Thr Leu Glu
65                  70                  75                  80

Arg Ala Val Asn Ala Ala Thr Ser Arg Gly Val Leu Val Val Ala Ala
                85                  90                  95

Ser Gly Asn Asn Gly Val Gly Ser Val Ser Tyr Pro Ala Arg Tyr Ala
            100                 105                 110

Asn Ala Met Ala Val Gly Ala Thr Asp Gln Asn Asn Asn Arg Ala Asn
        115                 120                 125

Phe Ser Gln Tyr Gly Thr Gly Leu Asp Ile Val Ala Pro Gly Val Gly
    130                 135                 140

Val Gln Ser Thr Tyr Pro Gly Ser Arg Phe Ala Ser Leu Asn Gly Thr
145                 150                 155                 160

Ser Met Ala Ser Pro His Val Ala Gly Val Ala Ala Leu
                165                 170
```

<210> SEQ ID NO 217
<211> LENGTH: 173
<212> TYPE: PRT
<213> ORGANISM: Artificial Sequence
<220> FEATURE:
<223> OTHER INFORMATION: Synthetic

<400> SEQUENCE: 217

```
Ser Thr Gln Asp Gly Asn Gly His Gly Thr His Val Ala Gly Thr Val
1               5                   10                  15

Ala Ala Leu Asn Asn Asn Val Gly Val Leu Gly Val Ala Pro Asn Ala
            20                  25                  30

Glu Leu Tyr Ala Val Lys Val Leu Gly Ala Asn Gly Ser Gly Ser Val
        35                  40                  45

Ser Gly Ile Ala Gln Gly Leu Glu Trp Ala Gly Ala Asn Gly Met His
    50                  55                  60

Val Ala Asn Met Ser Leu Gly Ser Pro Ser Pro Ser Ala Thr Leu Glu
65                  70                  75                  80

Arg Ala Val Asn Ala Ala Thr Ser Arg Gly Val Leu Val Val Ala Ala
                85                  90                  95

Thr Gly Asn Ser Gly Ala Gly Ser Val Ser Tyr Pro Ala Arg Tyr Ala
            100                 105                 110

Asn Ala Met Ala Val Gly Ala Thr Asp Gln Asn Asn Asn Arg Ala Ser
        115                 120                 125

Phe Ser Gln Tyr Gly Ala Gly Leu Asp Ile Val Ala Pro Gly Val Gly
    130                 135                 140

Val Gln Ser Thr Tyr Pro Gly Asn Thr Tyr Val Ser Leu Asn Gly Thr
145                 150                 155                 160

Ser Met Ala Thr Pro His Val Ala Gly Val Ala Ala Leu
                165                 170
```

```
<210> SEQ ID NO 218
<211> LENGTH: 173
<212> TYPE: PRT
<213> ORGANISM: Artificial Sequence
<220> FEATURE:
<223> OTHER INFORMATION: Synthetic

<400> SEQUENCE: 218

Ser Thr Gln Asp Gly Asn Gly His Gly Thr His Val Ala Gly Thr Val
1               5                   10                  15

Ala Ala Leu Asn Asn Asn Ile Gly Val Leu Gly Val Ala Pro Ser Ala
            20                  25                  30

Asp Leu Tyr Ala Val Lys Val Leu Gly Ala Ser Gly Ser Gly Thr Ile
        35                  40                  45

Ser Ser Ile Ala Gln Gly Leu Glu Trp Ala Gly Ala Asn Gly Met His
    50                  55                  60

Val Ala Asn Leu Ser Leu Gly Thr Ser Phe Pro Ser Thr Thr Leu Glu
65                  70                  75                  80

Arg Ala Val Asn Ser Ala Thr Ser Arg Gly Val Leu Val Ile Ala Ala
                85                  90                  95

Ser Gly Asn Ser Gly Ser Gly Thr Val Gly Tyr Pro Ala Arg Tyr Ala
            100                 105                 110

Asn Ala Met Ala Val Gly Ala Thr Asp Gln Asn Asn Arg Arg Ala Ser
        115                 120                 125

Ser Ser Gln Tyr Gly Ala Gly Leu Asp Ile Val Ala Pro Gly Val Gly
    130                 135                 140

Val Gln Ser Thr Tyr Thr Gly Ser Thr Tyr Val Ser Leu Ser Gly Thr
145                 150                 155                 160

Ser Met Ala Thr Pro His Val Ala Gly Val Ala Ala Leu
                165                 170

<210> SEQ ID NO 219
<211> LENGTH: 173
<212> TYPE: PRT
<213> ORGANISM: Artificial Sequence
<220> FEATURE:
<223> OTHER INFORMATION: Synthetic

<400> SEQUENCE: 219

Ser Thr Gln Asp Gly Asn Gly His Gly Thr His Val Ala Gly Thr Val
1               5                   10                  15

Ala Ala Leu Asn Asn Ser Val Gly Val Ile Gly Val Ala Pro Ser Ala
            20                  25                  30

Glu Leu Tyr Ala Val Lys Val Leu Gly Ala Ser Gly Arg Gly Thr Ile
        35                  40                  45

Ser Ser Ile Ala Arg Gly Leu Glu Trp Ala Ala Asn Asn Gly Thr His
    50                  55                  60

Val Ala Asn Leu Ser Leu Gly Ser Pro Ala Pro Ser Ala Thr Leu Glu
65                  70                  75                  80

Arg Ala Val Asn Ser Ala Thr Ser Arg Gly Val Leu Val Val Ala Ala
                85                  90                  95

Thr Gly Asn Asn Gly Ser Gly Thr Ile Ser Tyr Pro Ala Arg Tyr Ala
            100                 105                 110

Asn Ala Met Ala Val Gly Ala Thr Asp Gln Asn Asn Asn Arg Ala Asn
        115                 120                 125

Ser Ser Gln Tyr Gly Thr Gly Leu Asp Ile Val Ala Pro Gly Val Gly
```

```
              130                 135                 140
Val Gln Ser Thr Tyr Pro Gly Ser Thr Tyr Ala Ser Leu Ser Gly Thr
145                 150                 155                 160

Ser Met Ala Thr Pro His Val Ala Gly Ala Ala Leu
                165                 170

<210> SEQ ID NO 220
<211> LENGTH: 173
<212> TYPE: PRT
<213> ORGANISM: Artificial Sequence
<220> FEATURE:
<223> OTHER INFORMATION: Synthetic

<400> SEQUENCE: 220

Ser Thr Gln Asp Gly Asn Gly His Gly Thr His Val Ala Gly Thr Val
1               5                   10                  15

Ala Ala Leu Asn Asn Ser Asp Gly Val Leu Gly Val Ala Pro Ser Val
                20                  25                  30

Asp Leu Tyr Ala Val Lys Val Leu Gly Ala Ser Gly Ser Gly Thr Ile
            35                  40                  45

Ser Ser Ile Ala Arg Gly Leu Glu Trp Ala Gly Asn Asn Gly Met His
        50                  55                  60

Val Ala Asn Met Ser Leu Gly Ser Pro Ser Pro Ser Ala Thr Leu Glu
65                  70                  75                  80

Arg Ala Val Asn Gln Ala Thr Ser Arg Gly Val Leu Val Val Ala Ala
                85                  90                  95

Thr Gly Asn Thr Gly Ala Gly Thr Val Gly Tyr Pro Ala Arg Tyr Ala
            100                 105                 110

Asn Ala Met Ala Val Gly Ala Thr Asp Gln Asn Asn Asn Arg Ala Asn
        115                 120                 125

Phe Ser Gln Tyr Gly Ala Gly Leu Asp Ile Val Ala Pro Gly Val Asn
    130                 135                 140

Val Gln Ser Thr Tyr Pro Gly Ser Arg Tyr Ala Ser Leu Asn Gly Thr
145                 150                 155                 160

Ser Met Ala Ser Pro His Val Ala Gly Val Ala Ala Leu
                165                 170

<210> SEQ ID NO 221
<211> LENGTH: 173
<212> TYPE: PRT
<213> ORGANISM: Artificial Sequence
<220> FEATURE:
<223> OTHER INFORMATION: Synthetic

<400> SEQUENCE: 221

Ser Thr Gln Asp Gly Asn Gly His Gly Thr His Ile Ala Gly Thr Ile
1               5                   10                  15

Ala Ala Leu Asn Asn Ser Val Gly Val Leu Gly Val Ala Pro Ser Val
                20                  25                  30

Asp Leu Tyr Gly Val Lys Val Leu Gly Ala Ser Gly Arg Gly Ser Val
            35                  40                  45

Ser Ser Ile Ala Gln Gly Leu Glu Trp Ala Gly Asp Asn Gly Met His
        50                  55                  60

Val Ala Asn Leu Ser Leu Gly Thr Asp Gln Pro Ser Ala Thr Leu Glu
65                  70                  75                  80

Arg Ala Val Asn Ser Ala Thr Ser Gln Gly Val Leu Val Val Ala Ala
                85                  90                  95
```

```
Ser Gly Asn Ser Gly Ala Gly Ser Val Ser Tyr Pro Ala Arg Tyr Ala
            100                 105                 110

Asn Ala Met Ala Val Gly Ala Thr Asp Gln Asn Asn Arg Arg Ala Ser
        115                 120                 125

Phe Ser Gln Tyr Gly Ala Gly Leu Asp Ile Val Ala Pro Gly Val Gly
    130                 135                 140

Val Gln Ser Thr Tyr Pro Gly Ser Arg Tyr Ala Ser Met Asn Gly Thr
145                 150                 155                 160

Ser Met Ala Ser Pro His Val Ala Gly Ala Ala Leu
                165                 170

<210> SEQ ID NO 222
<211> LENGTH: 173
<212> TYPE: PRT
<213> ORGANISM: Artificial Sequence
<220> FEATURE:
<223> OTHER INFORMATION: Synthetic

<400> SEQUENCE: 222

Ser Thr Gln Asp Gly Asn Gly His Gly Thr His Val Ala Gly Thr Val
1               5                   10                  15

Ala Ala Leu Asn Asn Asn Ile Gly Val Leu Gly Val Ala Pro Asn Ala
            20                  25                  30

Glu Leu Tyr Ala Val Lys Val Leu Gly Ala Ser Gly Arg Gly Thr Val
        35                  40                  45

Ser Gly Ile Ala Arg Gly Leu Glu Trp Ala Gly Asp Asn Gly Met His
    50                  55                  60

Val Ala Asn Leu Ser Leu Gly Thr Ser Ser Pro Ser Ser Thr Leu Glu
65                  70                  75                  80

Gln Ala Val Asn Tyr Ala Thr Ser Gln Gly Val Leu Val Val Ala Ala
                85                  90                  95

Thr Gly Asn Ser Gly Ser Gly Thr Ile Ser Tyr Pro Ala Arg Tyr Ala
            100                 105                 110

Asn Ala Met Ala Val Gly Ala Thr Asp Gln Asn Asn Asn Arg Ala Ser
        115                 120                 125

Phe Ser Gln Tyr Gly Thr Gly Leu Asp Ile Val Ala Pro Gly Val Arg
    130                 135                 140

Val Gln Ser Thr Tyr Pro Gly Asn Arg Tyr Ala Ser Leu Ser Gly Thr
145                 150                 155                 160

Ser Met Ala Ser Pro His Val Ala Gly Val Ala Ala Leu
                165                 170

<210> SEQ ID NO 223
<211> LENGTH: 173
<212> TYPE: PRT
<213> ORGANISM: Artificial Sequence
<220> FEATURE:
<223> OTHER INFORMATION: Synthetic

<400> SEQUENCE: 223

Ser Thr Gln Asp Gly Asn Gly His Gly Thr His Val Ala Gly Thr Val
1               5                   10                  15

Ala Ala Leu Asn Asn Ser Val Gly Val Leu Gly Val Ala Pro Asn Ala
            20                  25                  30

Glu Leu Tyr Gly Val Lys Val Leu Gly Ala Asn Gly Arg Gly Thr Ile
        35                  40                  45

Ser Ser Ile Ala Arg Gly Leu Glu Trp Ala Gly Ala Asn Gly Met His
    50                  55                  60
```

Val Ala Asn Leu Ser Leu Gly Thr Pro Ala Pro Ser Ala Thr Leu Glu
65                  70                  75                  80

Gln Ala Val Asn Gln Ala Thr Ser Gln Gly Val Leu Val Ala Ala
            85                  90                  95

Ser Gly Asn Ser Gly Ala Gly Ser Ile Ser Tyr Pro Ala Arg Tyr Ala
            100                 105                 110

Asn Ala Met Ala Val Gly Ala Thr Asp Gln Asn Asn Arg Arg Ala Ser
            115                 120                 125

Phe Ser Gln Tyr Gly Thr Gly Leu Asp Ile Val Ala Pro Gly Val Gly
            130                 135                 140

Val Gln Ser Thr Tyr Pro Gly Ser Thr Tyr Ala Ser Leu Asn Gly Thr
145                 150                 155                 160

Ser Met Ala Ser Pro His Val Ala Gly Ala Ala Ala Leu
                165                 170

<210> SEQ ID NO 224
<211> LENGTH: 173
<212> TYPE: PRT
<213> ORGANISM: Artificial Sequence
<220> FEATURE:
<223> OTHER INFORMATION: Synthetic

<400> SEQUENCE: 224

Ser Thr Gln Asp Gly Asn Gly His Gly Thr His Val Ala Gly Thr Ile
1               5                   10                  15

Ala Ala Leu Asn Asn Ser Val Gly Val Leu Gly Val Ala Pro Asn Ala
            20                  25                  30

Glu Leu Tyr Ala Val Lys Val Leu Gly Ala Ser Gly Ser Gly Ser Val
            35                  40                  45

Ser Gly Ile Ala Arg Gly Leu Glu Trp Ala Gly Asp Asn Gly Met His
        50                  55                  60

Val Ala Asn Leu Ser Leu Gly Ser Pro Phe Pro Ser Ala Thr Leu Glu
65                  70                  75                  80

Gln Ala Val Asn Ala Ala Thr Ser Arg Gly Val Leu Val Val Ala Ala
            85                  90                  95

Ser Gly Asn Ser Gly Ser Gly Thr Val Gly Tyr Pro Ala Arg Tyr Ala
            100                 105                 110

Asn Ala Met Ala Val Gly Ala Thr Asp Gln Asn Asn Asn Arg Ala Ser
            115                 120                 125

Phe Ser Glu Tyr Gly Ala Gly Leu Asp Ile Val Ala Pro Gly Val Gly
            130                 135                 140

Val Gln Ser Thr Tyr Pro Gly Ser Arg Tyr Ala Ser Leu Ser Gly Thr
145                 150                 155                 160

Ser Met Ala Ser Pro His Val Ala Gly Ala Ala Ala Leu
                165                 170

<210> SEQ ID NO 225
<211> LENGTH: 173
<212> TYPE: PRT
<213> ORGANISM: Artificial Sequence
<220> FEATURE:
<223> OTHER INFORMATION: Synthetic

<400> SEQUENCE: 225

Ser Thr Gln Asp Gly Asn Gly His Gly Thr His Val Ala Gly Thr Val
1               5                   10                  15

Ala Ala Leu Asn Asn Asn Val Gly Val Ile Gly Val Ala Pro Ser Ala

```
                20                  25                  30

Glu Leu Tyr Gly Val Lys Val Leu Gly Ala Ser Gly Ser Gly Ser Ile
        35                  40                  45

Ser Ser Ile Ala Arg Gly Leu Glu Trp Ala Gly Asn Asn Gly Met His
 50                  55                  60

Val Ala Asn Met Ser Leu Gly Thr Asp Ala Pro Ser Ala Thr Leu Glu
 65                  70                  75                  80

Arg Ala Val Asn Gln Ala Thr Ser Arg Gly Val Leu Val Ala Ala
                85                  90                  95

Thr Gly Asn Ser Gly Ala Gly Ser Val Ala Tyr Pro Ala Arg Tyr Ala
                100                 105                 110

Asn Ala Met Ala Val Gly Ala Thr Asp Gln Asn Asn Asn Arg Ala Asn
                115                 120                 125

Phe Ser Gln Tyr Gly Ala Gly Leu Asp Ile Val Ala Pro Gly Val Gly
                130                 135                 140

Val Gln Ser Thr Tyr Pro Gly Ser Thr Tyr Ala Ser Leu Asn Gly Thr
145                 150                 155                 160

Ser Met Ala Thr Pro His Val Ala Gly Val Ala Ala Leu
                165                 170

<210> SEQ ID NO 226
<211> LENGTH: 173
<212> TYPE: PRT
<213> ORGANISM: Artificial Sequence
<220> FEATURE:
<223> OTHER INFORMATION: Synthetic

<400> SEQUENCE: 226

Ser Thr Gln Asp Gly Asn Gly His Gly Thr His Val Ala Gly Thr Val
 1               5                  10                  15

Ala Ala Leu Asn Asn Asn Val Gly Val Leu Gly Val Ala Pro Ser Ala
                20                  25                  30

Asp Leu Tyr Ala Val Lys Val Leu Gly Ala Ser Gly Arg Gly Thr Val
            35                  40                  45

Ser Ser Ile Ala Arg Gly Leu Gln Trp Ala Ala Asn Asn Gly Met His
 50                  55                  60

Val Ala Asn Leu Ser Leu Gly Ser Asp Gln Pro Ser Thr Thr Leu Glu
 65                  70                  75                  80

Arg Ala Val Asn Tyr Ala Thr Ser Gln Gly Val Leu Val Ile Ala Ala
                85                  90                  95

Ser Gly Asn Thr Gly Ser Gly Ser Ile Gly Tyr Pro Ala Arg Tyr Ala
                100                 105                 110

Asn Ala Met Ala Val Gly Ala Thr Asp Gln Asn Asn Asn Arg Ala Asn
                115                 120                 125

Phe Ser Gln Tyr Gly Ala Gly Leu Asp Ile Val Ala Pro Gly Val Gly
                130                 135                 140

Val Gln Ser Thr Tyr Pro Gly Ser Thr Tyr Ala Ser Met Asn Gly Thr
145                 150                 155                 160

Ser Met Ala Ser Pro His Val Ala Gly Ala Ala Ala Leu
                165                 170

<210> SEQ ID NO 227
<211> LENGTH: 173
<212> TYPE: PRT
<213> ORGANISM: Artificial Sequence
<220> FEATURE:
<223> OTHER INFORMATION: Synthetic
```

-continued

```
<400> SEQUENCE: 227

Ser Thr Gln Asp Gly Asn Gly His Gly Thr His Val Ala Gly Thr Val
1               5                   10                  15

Ala Ala Leu Asn Asn Val Gly Val Leu Gly Val Ala Pro Asn Ala
            20                  25                  30

Glu Leu Tyr Ala Val Lys Val Leu Gly Ala Ser Gly Arg Gly Ser Val
        35                  40                  45

Ser Ser Val Ala Gln Gly Leu Glu Trp Ala Ala Asp Asn Gly Thr His
    50                  55                  60

Val Ala Asn Leu Ser Leu Gly Ser Asp Phe Pro Ser Ala Thr Leu Glu
65                  70                  75                  80

Arg Ala Val Asn Ser Ala Thr Ser Arg Gly Val Leu Val Ala Ala
                85                  90                  95

Thr Gly Asn Asn Gly Ser Gly Thr Val Ser Tyr Pro Ala Arg Tyr Ala
            100                 105                 110

Asn Ala Met Ala Val Gly Ala Thr Asp Gln Asn Asn Asn Arg Ala Ser
            115                 120                 125

Phe Ser Gln Tyr Gly Ala Gly Leu Asp Ile Val Ala Pro Gly Val Gly
        130                 135                 140

Val Gln Ser Thr Tyr Pro Gly Ser Thr Tyr Ala Ser Leu Asn Gly Thr
145                 150                 155                 160

Ser Met Ala Thr Pro His Val Ala Gly Ala Ala Ala Leu
                165                 170

<210> SEQ ID NO 228
<211> LENGTH: 173
<212> TYPE: PRT
<213> ORGANISM: Artificial Sequence
<220> FEATURE:
<223> OTHER INFORMATION: Synthetic

<400> SEQUENCE: 228

Ser Thr Gln Asp Gly Asn Gly His Gly Thr His Val Ala Gly Thr Ile
1               5                   10                  15

Ala Ala Leu Asn Asn Ser Val Gly Val Leu Gly Val Ala Pro Asn Ala
            20                  25                  30

Asp Leu Tyr Gly Val Lys Val Leu Gly Ala Ser Gly Arg Gly Ser Ile
        35                  40                  45

Ser Gly Ile Ala Gln Gly Leu Glu Trp Ala Ala Thr Asn Gly Met His
    50                  55                  60

Val Ala Asn Leu Ser Leu Gly Thr Asp Gln Pro Ser Ala Thr Leu Glu
65                  70                  75                  80

Arg Ala Val Asn Tyr Ala Thr Ser Arg Gly Val Leu Val Val Ala Ala
                85                  90                  95

Ser Gly Asn Thr Gly Ser Gly Thr Ile Gly Tyr Pro Ala Arg Tyr Ala
            100                 105                 110

Asn Ala Met Ala Val Gly Ala Thr Asp Gln Asn Asn Asn Arg Ala Ser
            115                 120                 125

Phe Ser Gln Tyr Gly Ala Gly Ile Asp Ile Val Ala Pro Gly Val Gly
        130                 135                 140

Val Gln Ser Thr Tyr Thr Gly Ser Arg Tyr Ala Leu Met Ser Gly Thr
145                 150                 155                 160

Ser Met Ala Thr Pro His Val Ala Gly Val Ala Ala Leu
                165                 170
```

<210> SEQ ID NO 229
<211> LENGTH: 173
<212> TYPE: PRT
<213> ORGANISM: Artificial Sequence
<220> FEATURE:
<223> OTHER INFORMATION: Synthetic

<400> SEQUENCE: 229

```
Ser Thr Gln Asp Gly Asn Gly His Gly Thr His Val Ala Gly Thr Val
1               5                   10                  15

Ala Ala Leu Asn Asn Asn Val Gly Val Leu Gly Val Ala Pro Ser Val
            20                  25                  30

Asp Leu Tyr Gly Val Lys Val Leu Gly Ala Ser Gly Arg Gly Thr Val
            35                  40                  45

Ser Gly Ile Val Arg Gly Leu Glu Trp Ala Ala Asp Asn Gly Met His
50                  55                  60

Val Ala Asn Leu Ser Leu Gly Thr Pro Phe Pro Ser Ala Thr Leu Glu
65                  70                  75                  80

Arg Ala Val Asn Ala Ala Thr Ser Gln Gly Val Leu Val Ile Ala Ala
                85                  90                  95

Ser Gly Asn Ser Gly Ser Gly Ser Ile Ser Tyr Pro Ala Arg Tyr Ala
            100                 105                 110

Asn Ala Met Ala Val Gly Ala Thr Asp Gln Asn Asn Asn Arg Ala Ser
            115                 120                 125

Phe Ser Gln Tyr Gly Ala Gly Ile Asp Ile Val Ala Pro Gly Val Gly
        130                 135                 140

Val Gln Ser Thr Tyr Pro Gly Asn Arg Tyr Ala Ser Leu Ser Gly Thr
145                 150                 155                 160

Ser Met Ala Thr Pro His Val Ala Gly Ala Ala Ala Leu
                165                 170
```

<210> SEQ ID NO 230
<211> LENGTH: 173
<212> TYPE: PRT
<213> ORGANISM: Artificial Sequence
<220> FEATURE:
<223> OTHER INFORMATION: Synthetic

<400> SEQUENCE: 230

```
Ser Thr Gln Asp Gly Asn Gly His Gly Thr His Val Ala Gly Thr Val
1               5                   10                  15

Ala Ala Leu Asn Asn Ser Asp Gly Val Ile Gly Val Ala Pro Ser Val
            20                  25                  30

Glu Leu Tyr Ala Val Lys Val Leu Gly Ala Asn Gly Arg Gly Ser Val
            35                  40                  45

Ser Gly Ile Ala Arg Gly Leu Glu Trp Ala Ala Asn Asn Asn Met His
50                  55                  60

Val Ala Asn Leu Ser Leu Gly Thr Ser Ser Pro Ser Ser Thr Leu Glu
65                  70                  75                  80

Arg Ala Val Lys Ala Ala Thr Ser Gln Gly Val Leu Val Val Ala Ala
                85                  90                  95

Ser Gly Asn Asn Gly Ala Gly Thr Ile Cys Tyr Pro Ala Arg Tyr Ala
            100                 105                 110

Asn Ala Met Ala Val Gly Ala Thr Asp Gln Asn Asn Asn Arg Ala Ser
            115                 120                 125

Phe Ser Gln Tyr Gly Ala Gly Leu Asp Ile Val Ala Pro Gly Val Gly
        130                 135                 140
```

Val Gln Ser Thr Tyr Pro Gly Asn Thr Tyr Ala Ser Leu Asn Gly Thr
145                 150                 155                 160

Ser Met Ala Thr Pro His Val Ala Gly Val Ala Ala Leu
                165                 170

<210> SEQ ID NO 231
<211> LENGTH: 173
<212> TYPE: PRT
<213> ORGANISM: Artificial Sequence
<220> FEATURE:
<223> OTHER INFORMATION: Synthetic

<400> SEQUENCE: 231

Ser Thr Gln Asp Gly Asn Gly His Gly Thr His Val Ala Gly Thr Val
1               5                   10                  15

Ala Ala Leu Asn Asn Asn Val Gly Val Leu Gly Val Ala Pro Ser Ala
                20                  25                  30

Asp Leu Tyr Gly Val Lys Val Leu Gly Ala Asn Gly Ser Gly Ser Val
            35                  40                  45

Ser Ser Ile Ala Arg Gly Leu Glu Trp Ala Ala Ala Asn Asn Met His
50                  55                  60

Val Ala Asn Leu Ser Leu Gly Ser Pro Gln Pro Ser Ala Thr Leu Glu
65                  70                  75                  80

Arg Ala Val Asn Ala Ala Thr Ser Gln Gly Val Leu Val Val Ala Ala
                85                  90                  95

Ser Gly Asn Thr Gly Ser Gly Ile Val Ser Tyr Pro Ala Arg Tyr Ala
                100                 105                 110

Asn Ala Met Ala Val Gly Ala Thr Asp Gln Asn Asn Asn Arg Ala Ser
            115                 120                 125

Phe Ser Gln Tyr Gly Thr Gly Leu Asp Ile Val Ala Pro Gly Val Gly
        130                 135                 140

Val Gln Ser Thr Tyr Pro Gly Ser Arg Tyr Ala Ser Leu Ser Gly Thr
145                 150                 155                 160

Ser Met Ala Thr Pro His Val Ala Gly Ala Ala Ala Leu
                165                 170

<210> SEQ ID NO 232
<211> LENGTH: 173
<212> TYPE: PRT
<213> ORGANISM: Artificial Sequence
<220> FEATURE:
<223> OTHER INFORMATION: Synthetic

<400> SEQUENCE: 232

Ser Thr Gln Asp Gly Asn Gly His Gly Thr His Val Ala Gly Thr Val
1               5                   10                  15

Ala Ala Leu Asn Asn Ser Ile Gly Val Leu Gly Val Ala Pro Ser Val
                20                  25                  30

Glu Leu Tyr Gly Val Lys Val Leu Gly Ala Asn Gly Arg Gly Ser Ile
            35                  40                  45

Ser Gly Ile Ala Arg Gly Leu Glu Trp Ala Ala Asn Gly Met His
50                  55                  60

Ile Ala Asn Leu Ser Leu Gly Thr Ser Phe Pro Ser Thr Thr Leu Glu
65                  70                  75                  80

Arg Ala Val Asn Gln Ala Thr Ser Arg Gly Val Leu Val Val Ala Ala
                85                  90                  95

Ser Gly Asn Asn Gly Ser Gly Thr Val Gly Tyr Pro Ala Thr Tyr Ala

```
                  100                 105                 110
Asn Ala Met Ala Val Gly Ala Thr Asp Gln Asn Asn Arg Arg Ala Asn
            115                 120                 125
Phe Ser Gln Tyr Gly Ala Gly Ile Asp Ile Val Ala Pro Gly Val Gly
        130                 135                 140
Val Gln Ser Thr Tyr Thr Gly Asn Arg Tyr Ala Ser Leu Ser Gly Thr
145                 150                 155                 160
Ser Met Ala Ser Pro His Val Ala Gly Ala Ala Leu
                165                 170
```

<210> SEQ ID NO 233
<211> LENGTH: 173
<212> TYPE: PRT
<213> ORGANISM: Artificial Sequence
<220> FEATURE:
<223> OTHER INFORMATION: Synthetic

<400> SEQUENCE: 233

```
Ser Thr Gln Asp Gly Asn Gly His Gly Thr His Val Ala Gly Thr Val
1               5                   10                  15
Ala Ala Leu Asn Asn Val Gly Val Ile Gly Val Ala Pro Ser Val
            20                  25                  30
Glu Leu Tyr Ala Val Lys Val Leu Gly Ala Asn Gly Ser Gly Thr Ile
        35                  40                  45
Ser Gly Ile Ala Arg Gly Leu Glu Trp Ala Gly Ala Asn Gly Met His
    50                  55                  60
Ile Ala Asn Met Ser Leu Gly Thr Asp Phe Pro Ser Ser Thr Leu Glu
65                  70                  75                  80
Arg Ala Val Asn Tyr Ala Thr Ser Gln Gly Val Leu Val Ile Ala Ala
                85                  90                  95
Ser Gly Asn Ser Gly Ala Gly Ser Val Gly Tyr Pro Ala Arg Tyr Ala
            100                 105                 110
Asn Ala Met Ala Val Gly Ala Thr Asp Gln Asn Asn Arg Arg Ala Asn
        115                 120                 125
Ser Ser Gln Tyr Gly Thr Gly Leu Asp Ile Val Ala Pro Gly Val Gly
    130                 135                 140
Val Gln Ser Thr Tyr Pro Gly Ser Arg Tyr Val Ser Leu Ser Gly Thr
145                 150                 155                 160
Ser Met Ala Thr Pro His Val Ala Gly Val Ala Ala Leu
                165                 170
```

<210> SEQ ID NO 234
<211> LENGTH: 173
<212> TYPE: PRT
<213> ORGANISM: Artificial Sequence
<220> FEATURE:
<223> OTHER INFORMATION: Synthetic

<400> SEQUENCE: 234

```
Ser Thr Gln Asp Gly Asn Gly His Gly Thr His Val Ala Gly Thr Ile
1               5                   10                  15
Ala Ala Leu Asn Asn Ser Val Gly Val Leu Gly Val Ala Pro Ser Val
            20                  25                  30
Glu Leu Tyr Ala Val Lys Val Leu Gly Ala Ser Gly Arg Gly Ser Ile
        35                  40                  45
Ser Gly Ile Ala Arg Gly Leu Glu Trp Ala Gly Asn Asn Gly Met His
    50                  55                  60
```

-continued

```
Val Ala Asn Met Ser Leu Gly Ser Pro Phe Pro Ser Ala Thr Leu Glu
 65                  70                  75                  80

Arg Ala Val Asn Gln Ala Thr Ser Arg Gly Val Leu Val Ile Ala Ala
                 85                  90                  95

Ser Gly Asn Ser Gly Ala Gly Ser Val Ser Tyr Pro Ala Arg Tyr Ala
            100                 105                 110

Asn Ala Met Ala Val Gly Ala Thr Asp Gln Asn Asn Asn Arg Ala Ser
        115                 120                 125

Phe Ser Gln Tyr Gly Ala Gly Leu Asp Ile Val Ala Pro Gly Val Gly
    130                 135                 140

Val Gln Ser Thr Tyr Pro Gly Ser Thr Tyr Ala Ser Leu Ser Gly Thr
145                 150                 155                 160

Ser Met Ala Ser Pro His Val Ala Gly Ala Ala Ala Leu
                165                 170
```

<210> SEQ ID NO 235
<211> LENGTH: 173
<212> TYPE: PRT
<213> ORGANISM: Artificial Sequence
<220> FEATURE:
<223> OTHER INFORMATION: Synthetic

<400> SEQUENCE: 235

```
Ser Thr Gln Asp Gly Asn Gly His Gly Thr His Val Ala Gly Thr Ile
  1               5                  10                  15

Ala Ala Leu Asn Asn Asn Val Gly Val Ile Gly Val Ala Pro Asn Ala
                 20                  25                  30

Asp Leu Tyr Ala Val Lys Val Leu Gly Ala Ser Gly Arg Gly Thr Ile
             35                  40                  45

Ser Gly Ile Ala Arg Gly Leu Glu Trp Ala Gly Ala Asn Gly Met His
     50                  55                  60

Ile Ala Asn Leu Ser Leu Gly Thr Pro Ser Pro Ser Thr Thr Leu Glu
 65                  70                  75                  80

Arg Ala Val Asn Ala Ala Thr Ser Arg Asp Val Leu Val Val Ala Ala
                 85                  90                  95

Ser Gly Asn Gly Gly Ser Gly Ser Ile Gly Tyr Pro Ala Arg Tyr Ala
            100                 105                 110

Asn Ala Met Ala Val Gly Ala Thr Asp Gln Asn Asn Asn Arg Ala Ser
        115                 120                 125

Phe Ser Gln Tyr Gly Ala Gly Leu Asp Ile Val Ala Pro Gly Val Gly
    130                 135                 140

Val Gln Ser Thr Tyr Pro Gly Ser Thr Tyr Ala Ser Leu Asn Gly Thr
145                 150                 155                 160

Ser Met Ala Ser Pro His Val Ala Gly Val Ala Ala Leu
                165                 170
```

<210> SEQ ID NO 236
<211> LENGTH: 173
<212> TYPE: PRT
<213> ORGANISM: Artificial Sequence
<220> FEATURE:
<223> OTHER INFORMATION: Synthetic

<400> SEQUENCE: 236

```
Ser Thr Gln Asp Gly Asn Gly His Gly Thr His Val Ala Gly Thr Val
  1               5                  10                  15

Ala Ala Leu Asn Asn Ser Val Gly Val Leu Gly Val Ala Pro Ser Ala
                 20                  25                  30
```

```
Glu Leu Tyr Ala Val Lys Val Leu Gly Ala Ser Gly Ser Gly Thr Val
            35                  40                  45

Ser Ser Ile Ala Arg Gly Leu Glu Trp Ala Ala Asp Asn Asn Met His
 50                  55                  60

Ile Ala Asn Met Ser Leu Gly Thr Pro Ser Pro Ser Ala Thr Leu Glu
 65                  70                  75                  80

Arg Ala Val Asn Gln Ala Thr Ser Arg Gly Val Leu Val Val Ala Ala
                85                  90                  95

Thr Gly Asn Ser Gly Ser Gly Ser Ile Gly Tyr Pro Ala Arg Tyr Ala
                100                 105                 110

Asn Ala Met Ala Val Gly Ala Thr Asp Gln Asn Asn Arg Arg Ala Asn
                115                 120                 125

Phe Ser Gln Tyr Gly Thr Gly Leu Asp Ile Val Ala Pro Gly Val Gly
                130                 135                 140

Val Gln Ser Thr Tyr Pro Gly Ser Arg Tyr Val Ser Leu Ser Gly Thr
145                 150                 155                 160

Ser Met Ala Thr Pro His Val Ala Gly Val Ala Ala Leu
                165                 170

<210> SEQ ID NO 237
<211> LENGTH: 173
<212> TYPE: PRT
<213> ORGANISM: Artificial Sequence
<220> FEATURE:
<223> OTHER INFORMATION: Synthetic

<400> SEQUENCE: 237

Ser Thr Gln Asp Gly Asn Gly His Gly Thr His Val Ala Gly Thr Val
 1               5                   10                  15

Ala Ala Leu Asn Asn Ser Val Gly Val Leu Gly Val Ala Pro Ser Val
                20                  25                  30

Glu Leu Tyr Ala Val Lys Val Leu Gly Ala Ser Gly Arg Gly Thr Val
            35                  40                  45

Ser Gly Ile Ala Gln Gly Leu Gln Trp Ala Ala Ala Asn Gly Met His
 50                  55                  60

Val Ala Asn Leu Ser Leu Gly Thr Asp Phe Pro Ser Ala Thr Leu Glu
 65                  70                  75                  80

Gln Ala Val Asn Ala Ala Thr Ser Arg Gly Val Leu Val Val Ala Ala
                85                  90                  95

Ser Gly Asn Ser Gly Ser Gly Ser Ile Ser Tyr Pro Ala Arg Tyr Ala
                100                 105                 110

Asn Ala Met Ala Val Gly Ala Thr Asp Gln Asn Asn Asn Arg Ala Asn
                115                 120                 125

Phe Ser Gln Tyr Gly Gly Leu Asp Ile Val Ala Pro Gly Val Gly
                130                 135                 140

Val Gln Ser Thr Tyr Pro Gly Ser Thr Tyr Val Ser Leu Ser Gly Thr
145                 150                 155                 160

Ser Met Ala Val Pro His Val Ala Gly Ala Ala Ala Leu
                165                 170

<210> SEQ ID NO 238
<211> LENGTH: 173
<212> TYPE: PRT
<213> ORGANISM: Artificial Sequence
<220> FEATURE:
<223> OTHER INFORMATION: Synthetic
```

```
<400> SEQUENCE: 238

Ser Thr Gln Asp Gly Asn Gly His Gly Thr His Val Ala Gly Thr Ile
1               5                   10                  15

Ala Ala Leu Asn Asn Ser Val Gly Val Ile Gly Val Ala Pro Asn Val
            20                  25                  30

Asp Leu Tyr Gly Val Lys Val Leu Gly Ala Ser Gly Ser Gly Thr Ile
            35                  40                  45

Ser Ser Ile Ala Gln Gly Leu Glu Trp Ala Ala Asp Asn Gly Met His
    50                  55                  60

Val Ala Asn Leu Ser Leu Gly Thr Pro Ala Pro Ser Ser Thr Leu Glu
65                  70                  75                  80

Arg Ala Val Asn Ala Ala Thr Ser Arg Gly Val Leu Val Ala Ala
                85                  90                  95

Ser Gly Asn Ser Gly Ala Gly Ser Ile Ser Tyr Pro Ala Arg Tyr Ala
            100                 105                 110

Asn Ala Met Ala Val Gly Ala Thr Asp Gln Asn Asn Asn Arg Ala Ser
            115                 120                 125

Phe Ser Gln Tyr Gly Thr Gly Ile Asp Ile Val Ala Pro Gly Val Gly
    130                 135                 140

Val Gln Ser Thr Tyr Pro Gly Asn Thr Tyr Ala Ser Leu Asn Gly Thr
145                 150                 155                 160

Ser Met Ala Ser Pro His Val Ala Gly Ala Ala Ala Leu
                165                 170

<210> SEQ ID NO 239
<211> LENGTH: 173
<212> TYPE: PRT
<213> ORGANISM: Artificial Sequence
<220> FEATURE:
<223> OTHER INFORMATION: Synthetic

<400> SEQUENCE: 239

Ser Thr Gln Asp Gly Asn Gly His Gly Thr His Val Ala Gly Thr Val
1               5                   10                  15

Ala Ala Leu Asn Asn Ser Val Gly Val Leu Gly Val Ala Pro Ser Val
            20                  25                  30

Glu Leu Tyr Ala Val Lys Val Leu Gly Ala Ser Gly Arg Gly Thr Val
            35                  40                  45

Ser Ser Ile Ala Arg Gly Leu Glu Trp Ala Ala Asn Asn Gly Thr His
    50                  55                  60

Val Ala Asn Met Ser Leu Gly Thr Ser Gln Pro Ser Ala Thr Leu Glu
65                  70                  75                  80

Gln Ala Val Asn Ala Ala Thr Ser Arg Gly Val Leu Val Val Ala Ala
                85                  90                  95

Ser Gly Asn Ser Gly Ser Gly Thr Val Gly Tyr Pro Ala Arg Tyr Ala
            100                 105                 110

Asn Ala Met Ala Val Gly Ala Thr Asp Gln Asn Asn Asn Arg Ala Ser
            115                 120                 125

Phe Ser Gln Tyr Gly Thr Gly Leu Asp Ile Val Ala Pro Gly Val Gly
    130                 135                 140

Val Gln Ser Thr Tyr Pro Gly Ser Arg Tyr Ala Ser Leu Ser Gly Thr
145                 150                 155                 160

Ser Met Ala Ser Pro His Val Ala Gly Val Ala Ala Leu
                165                 170
```

-continued

```
<210> SEQ ID NO 240
<211> LENGTH: 173
<212> TYPE: PRT
<213> ORGANISM: Artificial Sequence
<220> FEATURE:
<223> OTHER INFORMATION: Synthetic

<400> SEQUENCE: 240

Ser Thr Gln Asp Gly Asn Gly His Gly Thr His Val Ala Gly Thr Ile
1               5                   10                  15

Ala Ala Leu Asn Asn Ser Asp Gly Val Ile Gly Val Ala Pro Ser Ala
                20                  25                  30

Asp Leu Tyr Ala Val Lys Val Leu Gly Ala Asn Gly Ser Gly Thr Val
            35                  40                  45

Ser Ser Ile Ala Arg Gly Leu Gln Trp Ala Ala Asn Asn Gly Met His
    50                  55                  60

Val Ala Asn Leu Ser Leu Gly Ser Asp Gln Pro Ser Ala Thr Leu Glu
65                  70                  75                  80

Arg Ala Val Asn Ala Ala Thr Ser Arg Gly Val Leu Val Val Ala Ala
                85                  90                  95

Ser Gly Asn Ser Gly Ala Gly Thr Val Gly Tyr Pro Ala Arg Tyr Ala
                100                 105                 110

Asn Ala Met Ala Val Gly Ala Thr Asp Gln Asn Asn Asn Arg Ala Ser
            115                 120                 125

Phe Ser Gln Tyr Gly Thr Gly Leu Asp Ile Val Ala Pro Gly Val Gly
    130                 135                 140

Val Gln Ser Thr Tyr Pro Gly Asn Thr Tyr Val Ser Met Ser Gly Thr
145                 150                 155                 160

Ser Met Ala Ser Pro His Val Ala Gly Val Ala Ala Leu
                165                 170

<210> SEQ ID NO 241
<211> LENGTH: 173
<212> TYPE: PRT
<213> ORGANISM: Artificial Sequence
<220> FEATURE:
<223> OTHER INFORMATION: Synthetic

<400> SEQUENCE: 241

Ser Thr Gln Asp Gly Asn Gly His Gly Thr His Val Ala Gly Thr Val
1               5                   10                  15

Ala Ala Leu Asn Asn Asn Val Gly Val Ile Gly Val Ala Pro Ser Val
                20                  25                  30

Asp Leu Tyr Ala Val Lys Val Leu Gly Ala Ser Gly Arg Gly Ser Val
            35                  40                  45

Ser Gly Ile Ala Arg Gly Leu Gln Trp Ala Ala Ala Asn Gly Met His
    50                  55                  60

Ile Ala Asn Leu Ser Leu Gly Ser Ser Gln Pro Ser Ala Thr Leu Glu
65                  70                  75                  80

Arg Ala Val Asn Tyr Ala Thr Ser Arg Gly Val Leu Val Val Ala Ala
                85                  90                  95

Ser Gly Asn Ser Gly Ser Gly Thr Val Ser Tyr Pro Ala Arg Tyr Ala
                100                 105                 110

Asn Ala Met Ala Val Gly Ala Thr Asp Gln Asn Asn Asn Arg Ala Asn
            115                 120                 125

Ser Ser Gln Tyr Gly Thr Gly Leu Asp Ile Val Ala Pro Gly Val Gly
    130                 135                 140
```

-continued

Val Gln Ser Thr Tyr Pro Gly Asn Thr Tyr Ala Ser Leu Ser Gly Thr
145                 150                 155                 160

Ser Met Ala Thr Pro His Val Ala Gly Ala Ala Ala Leu
                165                 170

<210> SEQ ID NO 242
<211> LENGTH: 173
<212> TYPE: PRT
<213> ORGANISM: Artificial Sequence
<220> FEATURE:
<223> OTHER INFORMATION: Synthetic

<400> SEQUENCE: 242

Ser Thr Gln Asp Gly Asn Gly His Gly Thr His Val Ala Gly Thr Val
1               5                   10                  15

Ala Ala Leu Asn Asn Val Gly Val Leu Gly Val Ala Pro Ser Ala
                20                  25                  30

Glu Leu Tyr Ala Val Lys Val Leu Gly Ala Asn Gly Arg Gly Thr Ile
            35                  40                  45

Ser Gly Ile Ala Gln Gly Leu Glu Trp Ala Ala Asn Asn Gly Met His
        50                  55                  60

Val Ala Asn Leu Ser Leu Gly Ser Pro Ser Pro Ser Ala Thr Leu Glu
65                  70                  75                  80

Gln Ala Val Asn Ala Ala Thr Ser Arg Gly Val Leu Val Val Ala Ala
                85                  90                  95

Ser Gly Asn Ser Gly Ala Gly Thr Ile Gly Tyr Pro Ala Thr Tyr Ala
                100                 105                 110

Asn Ala Met Ala Val Gly Ala Thr Asp Gln Asn Asn Asn Arg Ala Ser
            115                 120                 125

Phe Ser Gln Tyr Gly Thr Gly Ile Asp Ile Val Ala Pro Gly Val Gly
        130                 135                 140

Val Gln Ser Thr Tyr Pro Gly Asn Arg Tyr Ala Ser Met Ser Gly Thr
145                 150                 155                 160

Ser Met Ala Thr Pro His Val Ala Gly Ala Ala Ala Leu
                165                 170

<210> SEQ ID NO 243
<211> LENGTH: 173
<212> TYPE: PRT
<213> ORGANISM: Artificial Sequence
<220> FEATURE:
<223> OTHER INFORMATION: Synthetic

<400> SEQUENCE: 243

Ser Thr Gln Asp Gly Asn Gly His Gly Thr His Val Ala Gly Thr Val
1               5                   10                  15

Ala Ala Leu Asn Asn Asn Ile Gly Val Leu Gly Val Ala Pro Ser Ala
                20                  25                  30

Asp Leu Tyr Ala Val Lys Val Leu Gly Thr Ser Gly Ser Gly Thr Val
            35                  40                  45

Ser Ser Ile Ala Arg Gly Leu Glu Trp Ala Ala Ser Asn Gly Met His
        50                  55                  60

Val Ala Asn Met Ser Leu Gly Thr Ser Gln Pro Ser Ala Thr Leu Glu
65                  70                  75                  80

Arg Ala Val Asn Ala Ala Thr Ser Arg Gly Val Leu Val Val Ala Ala
                85                  90                  95

Thr Gly Asn Ser Gly Ser Gly Thr Ile Gly Tyr Pro Ala Arg Tyr Ala
                100                 105                 110

```
Asn Ala Met Ala Val Gly Ala Thr Asp Gln Asn Asn Arg Arg Ala Ser
            115                 120                 125

Phe Ser Gln Tyr Gly Thr Gly Leu Asp Ile Val Ala Pro Gly Val Gly
        130                 135                 140

Val Lys Ser Thr Tyr Pro Gly Ser Thr Tyr Ala Ser Leu Asn Gly Thr
145                 150                 155                 160

Ser Met Ala Ser Pro His Val Ala Gly Val Ala Ala Leu
                165                 170

<210> SEQ ID NO 244
<211> LENGTH: 173
<212> TYPE: PRT
<213> ORGANISM: Artificial Sequence
<220> FEATURE:
<223> OTHER INFORMATION: Synthetic

<400> SEQUENCE: 244

Ser Thr Gln Asp Gly Asn Gly His Gly Thr His Val Ala Gly Thr Ile
1               5                   10                  15

Ala Ala Leu Asn Asn Ser Ile Gly Val Leu Gly Val Ala Pro Ser Val
            20                  25                  30

Glu Leu Tyr Gly Val Lys Val Leu Gly Ala Asn Gly Ser Gly Thr Ile
        35                  40                  45

Ser Ser Ile Ala Arg Gly Leu Glu Trp Ala Gly Asn Asn Gly Met His
    50                  55                  60

Val Ala Asn Met Ser Leu Gly Ser Asp Phe Pro Ser Ser Thr Leu Glu
65                  70                  75                  80

Gln Ala Val Asn Ala Ala Thr Ser Arg Gly Val Leu Val Val Ala Ala
                85                  90                  95

Ser Gly Asn Ser Gly Ser Gly Ser Val Gly Tyr Pro Ala Arg Tyr Ala
            100                 105                 110

Asn Ala Met Ala Val Gly Ala Thr Asp Gln Asn Asn Arg Arg Ala Asn
            115                 120                 125

Ser Ser Gln Tyr Gly Ala Gly Leu Asp Ile Val Ala Pro Gly Val Gly
        130                 135                 140

Val Gln Ser Thr Tyr Pro Gly Ser Arg Tyr Val Ser Leu Ser Gly Thr
145                 150                 155                 160

Ser Met Ala Ser Pro His Val Ala Gly Ala Ala Ala Leu
                165                 170

<210> SEQ ID NO 245
<211> LENGTH: 173
<212> TYPE: PRT
<213> ORGANISM: Artificial Sequence
<220> FEATURE:
<223> OTHER INFORMATION: Synthetic

<400> SEQUENCE: 245

Ser Thr Gln Asp Gly Asn Gly His Gly Thr His Val Thr Gly Thr Ile
1               5                   10                  15

Ala Ala Leu Asn Asn Ser Ile Gly Val Ile Gly Val Ala Pro Ser Val
            20                  25                  30

Glu Leu Tyr Gly Val Lys Val Leu Gly Ala Ser Gly Arg Gly Ser Ile
        35                  40                  45

Ser Gly Ile Ala Arg Gly Leu Glu Trp Ala Ala Asp Asn Gly Met His
    50                  55                  60

Val Ala Asn Met Ser Leu Gly Ser Pro Gln Pro Ser Ala Thr Leu Glu
```

-continued

```
                65                  70                  75                  80
Gln Ala Val Asn Ser Ala Thr Ser Arg Gly Val Leu Val Ile Ala Ala
                    85                  90                  95

Thr Gly Asn Ser Gly Ser Gly Thr Ile Ala Tyr Pro Ala Arg Tyr Pro
                100                 105                 110

Asn Ala Met Ala Val Gly Ala Thr Asp Gln Asn Asn Asn Arg Ala Ser
                115                 120                 125

Phe Ser Gln Tyr Gly Gln Gly Leu Asp Ile Val Ala Pro Gly Val Gly
                130                 135                 140

Val Gln Ser Thr Tyr Pro Gly Ser Arg Tyr Ala Ser Leu Asn Gly Thr
145                 150                 155                 160

Ser Met Ala Ser Pro His Val Ala Gly Ala Ala Ala Leu
                165                 170

<210> SEQ ID NO 246
<211> LENGTH: 173
<212> TYPE: PRT
<213> ORGANISM: Artificial Sequence
<220> FEATURE:
<223> OTHER INFORMATION: Synthetic

<400> SEQUENCE: 246

Ser Thr Gln Asp Gly Asn Gly His Gly Thr His Val Ala Gly Thr Ile
1               5                   10                  15

Ala Ala Leu Asn Asn Asn Asp Gly Val Leu Gly Val Ala Pro Ser Val
                20                  25                  30

Asp Leu Tyr Gly Val Lys Val Leu Gly Ala Ser Gly Arg Gly Thr Val
                35                  40                  45

Ser Ser Ile Ala Gln Gly Leu Leu Trp Ala Ala Asn Asn Gly Thr His
        50                  55                  60

Val Ala Asn Met Ser Leu Gly Ser Ser Ala Pro Ser Thr Thr Leu Glu
65                  70                  75                  80

Arg Ala Val Asn Tyr Ala Thr Ser Arg Gly Val Leu Val Val Ala Ala
                85                  90                  95

Ser Gly Asn Ser Gly Ser Gly Thr Ile Ser Tyr Pro Ala Arg Tyr Ala
                100                 105                 110

Asn Ala Met Ala Val Gly Ala Thr Asp Gln Asn Asn Asn Arg Ala Ser
                115                 120                 125

Phe Ser Gln Tyr Gly Ala Gly Ile Asp Ile Val Ala Pro Gly Val Asn
                130                 135                 140

Val Gln Ser Thr Tyr Pro Gly Ser Thr Tyr Val Ser Leu Ser Gly Thr
145                 150                 155                 160

Ser Met Ala Ser Pro His Val Ala Gly Val Ala Ala Leu
                165                 170

<210> SEQ ID NO 247
<211> LENGTH: 173
<212> TYPE: PRT
<213> ORGANISM: Artificial Sequence
<220> FEATURE:
<223> OTHER INFORMATION: Synthetic

<400> SEQUENCE: 247

Ser Thr Gln Asp Gly Asn Gly His Gly Thr His Val Ala Gly Thr Ile
1               5                   10                  15

Ala Ala Leu Asn Asn Ser Val Gly Val Ile Gly Val Ala Pro Ser Ala
                20                  25                  30
```

```
Asp Leu Tyr Ala Val Lys Val Leu Gly Ala Ser Gly Arg Gly Ser Val
            35                  40                  45

Ser Gly Ile Ala Arg Gly Leu Glu Trp Ala Ala Asn Asn Gly Met His
 50                  55                  60

Val Ala Asn Leu Ser Leu Gly Ser Pro Ala Pro Ser Ala Thr Leu Glu
 65                  70                  75                  80

Arg Ala Val Asn Tyr Ala Thr Ser Arg Gly Val Leu Val Ile Ala Ala
                 85                  90                  95

Ser Gly Asn Ser Gly Ala Gly Ser Val Gly Tyr Pro Ala Arg Tyr Ala
                100                 105                 110

Asn Ala Met Ala Val Gly Ala Thr Asp Gln Asn Asn Arg Ala Ser
                115                 120                 125

Phe Ser Gln His Gly Thr Gly Leu Asp Ile Val Ala Pro Gly Val Gly
            130                 135                 140

Val Gln Ser Thr Tyr Pro Gly Ser Arg Tyr Ala Ser Leu Ser Gly Thr
145                 150                 155                 160

Ser Met Ala Ser Pro His Val Ala Gly Ala Ala Ala Leu
                165                 170

<210> SEQ ID NO 248
<211> LENGTH: 173
<212> TYPE: PRT
<213> ORGANISM: Artificial Sequence
<220> FEATURE:
<223> OTHER INFORMATION: Synthetic

<400> SEQUENCE: 248

Ser Thr Gln Asp Gly Asn Gly His Gly Thr His Val Ala Gly Thr Val
 1               5                  10                  15

Ala Ala Leu Asn Asn Ser Val Gly Val Leu Gly Val Ala Pro Ser Ala
                 20                  25                  30

Asp Leu Tyr Ala Val Lys Val Leu Gly Ala Ser Gly Ser Gly Thr Ile
            35                  40                  45

Ser Gly Ile Ala Gln Gly Leu Glu Trp Ala Ala Asn Asn Gly Thr His
 50                  55                  60

Val Ala Asn Leu Ser Leu Gly Thr Ser Gln Pro Ser Ala Thr Leu Glu
 65                  70                  75                  80

Arg Ala Val Asn Ala Ala Thr Ser Gln Gly Val Leu Val Val Ala Ala
                 85                  90                  95

Thr Gly Asn Thr Gly Ala Gly Thr Ile Gly Tyr Pro Ala Arg Tyr Ala
                100                 105                 110

Asn Ala Met Ala Val Gly Ala Thr Asp Gln Asn Asn Asn Arg Ala Ser
                115                 120                 125

Phe Ser Gln Tyr Gly Thr Gly Leu Asp Ile Val Ala Pro Gly Val Gly
            130                 135                 140

Val Gln Ser Thr Tyr Pro Gly Ser Arg Tyr Ala Ser Leu Ser Gly Thr
145                 150                 155                 160

Ser Met Ala Thr Pro His Val Ala Gly Ala Ala Ala Leu
                165                 170

<210> SEQ ID NO 249
<211> LENGTH: 173
<212> TYPE: PRT
<213> ORGANISM: Artificial Sequence
<220> FEATURE:
<223> OTHER INFORMATION: Synthetic

<400> SEQUENCE: 249
```

Ser Thr Gln Asp Gly Asn Gly His Gly Thr His Val Ala Gly Thr Val
1               5                   10                  15

Ala Ala Leu Asn Asn Ser Ile Gly Val Leu Gly Val Ala Pro Ser Val
            20                  25                  30

Glu Leu Tyr Ala Val Lys Val Leu Gly Ala Ser Gly Arg Gly Ser Ile
            35                  40                  45

Ser Ser Ile Ala Arg Gly Leu Glu Trp Ala Gly Asp Asn Gly Met His
    50                  55                  60

Ile Ala Asn Met Ser Leu Gly Thr Asp Gln Pro Ser Ala Thr Leu Glu
65                  70                  75                  80

Gln Ala Val Asn Ala Ala Thr Ser Arg Gly Val Leu Val Ile Ala Ala
                85                  90                  95

Thr Gly Asn Thr Gly Ala Gly Ser Ile Ser Tyr Pro Ala Arg Tyr Ala
            100                 105                 110

Asn Ala Met Ala Val Gly Ala Thr Asp Gln Asn Asn Asn Arg Ala Asn
            115                 120                 125

Phe Ser Gln Tyr Gly Ala Gly Leu Asp Ile Val Ala Pro Gly Val Gly
    130                 135                 140

Val Gln Ser Thr Tyr Pro Gly Ser Arg Tyr Ala Ser Met Asn Gly Thr
145                 150                 155                 160

Ser Met Ala Thr Pro His Val Ala Gly Val Ala Ala Leu
            165                 170

<210> SEQ ID NO 250
<211> LENGTH: 173
<212> TYPE: PRT
<213> ORGANISM: Artificial Sequence
<220> FEATURE:
<223> OTHER INFORMATION: Synthetic

<400> SEQUENCE: 250

Ser Thr Gln Asp Gly Asn Gly His Gly Thr His Val Ala Gly Thr Val
1               5                   10                  15

Ala Ala Leu Asn Asn Asn Asp Gly Val Leu Gly Val Ala Pro Asn Val
            20                  25                  30

Asp Leu Tyr Ala Val Lys Val Leu Gly Ala Ser Gly Arg Gly Ser Val
            35                  40                  45

Ser Gly Ile Ala Arg Gly Leu Glu Trp Ala Gly Ala Asn Gly Met His
    50                  55                  60

Ile Ala Asn Met Ser Leu Gly Thr Ser Phe Pro Ser Ala Thr Leu Glu
65                  70                  75                  80

Gln Ala Val Asn Ala Ala Thr Ser Arg Gly Val Leu Val Val Ala Ala
                85                  90                  95

Thr Gly Asn Asn Gly Ala Gly Thr Val Gly Tyr Pro Ala Arg Tyr Ala
            100                 105                 110

Asn Ala Met Ala Val Gly Ala Thr Asp Gln Asn Asn Asn Arg Ala Ser
            115                 120                 125

Ser Ser Gln Tyr Gly Ala Gly Leu Asp Ile Val Ala Pro Gly Val Gly
    130                 135                 140

Val Gln Ser Thr Tyr Pro Gly Ser Arg Tyr Ala Ser Leu Ser Gly Thr
145                 150                 155                 160

Ser Met Ala Thr Pro His Val Ala Gly Ala Ala Ala Leu
            165                 170

<210> SEQ ID NO 251

```
<211> LENGTH: 173
<212> TYPE: PRT
<213> ORGANISM: Artificial Sequence
<220> FEATURE:
<223> OTHER INFORMATION: Synthetic

<400> SEQUENCE: 251
```

Ser Thr Gln Asp Gly Asn Gly His Gly Thr His Val Ala Gly Thr Val
1               5                   10                  15

Ala Ala Leu Asn Asn Ser Asp Gly Val Ile Gly Val Ala Pro Ser Val
            20                  25                  30

Asp Leu Tyr Gly Val Lys Val Leu Gly Ala Ser Gly Arg Gly Ser Val
        35                  40                  45

Ser Ser Ile Ala Arg Gly Leu Glu Trp Ala Ala Asp Asn Gly Met His
50                  55                  60

Val Ala Asn Leu Ser Leu Gly Ser Asp Gln Leu Ser Thr Thr Leu Glu
65                  70                  75                  80

Arg Ala Val Asn Gln Ala Thr Ser Arg Gly Val Leu Val Val Ala Ala
                85                  90                  95

Ser Gly Asn Asn Gly Ser Gly Thr Val Ser Tyr Pro Ala Arg Tyr Ala
            100                 105                 110

Asn Ala Met Ala Val Gly Ala Thr Asp Gln Asn Asn Asn Arg Ala Ser
        115                 120                 125

Ser Ser Gln Tyr Gly Thr Gly Leu Asp Ile Val Ala Pro Gly Val Gly
    130                 135                 140

Val Gln Ser Thr Tyr Pro Gly Ser Arg Tyr Ala Ser Leu Ser Gly Thr
145                 150                 155                 160

Ser Met Ala Ser Pro His Val Ala Gly Val Ala Ala Leu
                165                 170

```
<210> SEQ ID NO 252
<211> LENGTH: 173
<212> TYPE: PRT
<213> ORGANISM: Artificial Sequence
<220> FEATURE:
<223> OTHER INFORMATION: Synthetic

<400> SEQUENCE: 252
```

Ser Thr Gln Asp Gly Asn Gly His Gly Thr His Val Ala Gly Thr Val
1               5                   10                  15

Ala Ala Leu Asn Asn Ser Ile Gly Val Leu Gly Val Ala Pro Ser Ala
            20                  25                  30

Glu Leu Tyr Ala Val Lys Val Leu Gly Ala Ser Gly Arg Gly Ser Val
        35                  40                  45

Ser Gly Ile Ala Gln Gly Leu Glu Trp Ala Gly Thr Asn Gly Met His
50                  55                  60

Val Ala Asn Met Ser Leu Gly Thr Pro Ala Pro Ser Ala Thr Leu Glu
65                  70                  75                  80

Gln Ala Val Asn Ala Ala Thr Ser Gln Gly Val Leu Val Ile Ala Ala
                85                  90                  95

Ser Gly Asn Ser Gly Ser Gly Thr Val Ser Tyr Pro Ala Arg Tyr Ala
            100                 105                 110

Asn Ala Met Ala Val Gly Ala Thr Asp Gln Asn Asn Asn Arg Ala Ser
        115                 120                 125

Phe Ser Gln Tyr Gly Ala Gly Leu Asp Thr Val Ala Pro Gly Val Gly
    130                 135                 140

Val Gln Ser Thr Tyr Pro Gly Ser Thr Tyr Ala Ser Met Ser Gly Thr

```
                145                 150                 155                 160
Ser Met Ala Ser Pro His Val Ala Gly Val Ala Ala Leu
                165                 170

<210> SEQ ID NO 253
<211> LENGTH: 173
<212> TYPE: PRT
<213> ORGANISM: Artificial Sequence
<220> FEATURE:
<223> OTHER INFORMATION: Synthetic

<400> SEQUENCE: 253

Ser Thr Gln Asp Gly Asn Gly His Gly Thr His Val Ala Gly Thr Val
1               5                   10                  15

Ala Ala Leu Asn Asn Asn Ile Gly Val Leu Gly Val Ala Pro Ser Val
                20                  25                  30

Glu Leu Tyr Gly Val Lys Val Leu Gly Ala Ser Gly Ser Gly Ser Val
            35                  40                  45

Ser Ser Ile Ala Gln Gly Leu Glu Trp Ala Ala Asp Asn Gly Met His
        50                  55                  60

Val Ala Asn Met Ser Leu Gly Ser Pro Phe Pro Ser Ser Thr Leu Glu
65                  70                  75                  80

Gln Ala Val Asn Ser Ala Thr Ser Arg Gly Val Leu Val Val Ala Ala
                85                  90                  95

Ser Gly Asn Ser Gly Ser Gly Thr Val Gly Tyr Pro Ala Arg Tyr Ala
            100                 105                 110

Asn Ala Met Ala Val Gly Ala Thr Asp Gln Asn Asn Asn Arg Ala Ser
        115                 120                 125

Phe Ser Gln Tyr Gly Ala Gly Leu Asp Ile Val Ala Pro Gly Val Gly
    130                 135                 140

Val Gln Ser Thr Tyr Pro Gly Ser Arg Tyr Ala Ser Leu Ser Gly Thr
145                 150                 155                 160

Ser Met Ala Thr Pro His Val Ala Gly Val Ala Ala Leu
                165                 170

<210> SEQ ID NO 254
<211> LENGTH: 173
<212> TYPE: PRT
<213> ORGANISM: Artificial Sequence
<220> FEATURE:
<223> OTHER INFORMATION: Synthetic

<400> SEQUENCE: 254

Ser Thr Gln Asp Gly Asn Gly His Gly Thr His Val Ala Gly Thr Ile
1               5                   10                  15

Ala Ala Leu Asn Asn Ser Ile Gly Val Ile Gly Val Ala Pro Ser Val
                20                  25                  30

Asp Leu Tyr Gly Val Lys Val Leu Gly Ala Ser Gly Ser Gly Ser Val
            35                  40                  45

Ser Ser Ile Ala Arg Gly Leu Glu Trp Ala Gly Asp Asn Gly Met His
        50                  55                  60

Val Ala Asn Leu Ser Leu Gly Ser Pro Ser Pro Ser Ala Thr Leu Glu
65                  70                  75                  80

Gln Ala Val Asn Ser Ala Thr Ser Arg Gly Val Leu Val Ile Ala Ala
                85                  90                  95

Thr Gly Asn Thr Gly Ala Gly Thr Leu Ser Tyr Pro Ala Arg Tyr Ala
            100                 105                 110
```

```
Asn Ala Met Ala Val Gly Ala Thr Asp Gln Asn Asn Arg Ala Ser
        115                 120                 125

Phe Ser Gln Tyr Gly Thr Gly Leu Asp Ile Val Ala Pro Gly Val Gly
        130                 135                 140

Val Gln Ser Thr Tyr Pro Gly Ser Thr Tyr Val Ser Leu Asn Gly Thr
145                 150                 155                 160

Ser Met Ala Thr Pro His Val Ala Ser Ala Ala Leu
                165                 170

<210> SEQ ID NO 255
<211> LENGTH: 173
<212> TYPE: PRT
<213> ORGANISM: Artificial Sequence
<220> FEATURE:
<223> OTHER INFORMATION: Synthetic

<400> SEQUENCE: 255

Ser Thr Gln Asp Gly Asn Gly His Gly Thr His Val Ala Gly Thr Ile
1               5                   10                  15

Ala Ala Leu Asn Asn Ser Val Gly Val Leu Gly Val Ala Pro Asn Val
                20                  25                  30

Glu Leu Tyr Ala Val Lys Val Leu Gly Ala Ser Gly Arg Gly Thr Ile
            35                  40                  45

Ser Gly Ile Ala Gln Gly Leu Glu Trp Ala Ala Asp Asn Gly Thr His
        50                  55                  60

Ile Ala Asn Leu Ser Leu Gly Thr Ser Phe Pro Ser Ala Thr Leu Glu
65                  70                  75                  80

Arg Ala Val Asn Ser Ala Thr Ser Arg Gly Val Leu Val Ala Ala
                85                  90                  95

Thr Gly Asn Thr Gly Ala Gly Ser Ile Ser Tyr Pro Ala Arg Phe Ala
                100                 105                 110

Asn Ala Met Ala Val Gly Ala Thr Asp Gln Asn Asn Arg Arg Ala Ser
        115                 120                 125

Phe Ser Gln Tyr Gly Ala Gly Leu Asp Ile Val Gly Pro Gly Val Gly
        130                 135                 140

Val Gln Ser Thr Tyr Pro Gly Ser Thr Tyr Ala Ser Leu Ser Gly Thr
145                 150                 155                 160

Ser Met Ala Thr Pro His Val Ala Gly Ala Ala Leu
                165                 170

<210> SEQ ID NO 256
<211> LENGTH: 173
<212> TYPE: PRT
<213> ORGANISM: Artificial Sequence
<220> FEATURE:
<223> OTHER INFORMATION: Synthetic

<400> SEQUENCE: 256

Ser Thr Gln Asp Gly Asn Gly His Gly Thr His Val Ala Gly Thr Val
1               5                   10                  15

Ala Ala Leu Asn Asn Ser Asp Gly Val Ile Gly Val Ala Pro Ser Ala
                20                  25                  30

Asp Leu Tyr Ala Val Lys Val Leu Gly Ala Asn Gly Ser Gly Ser Val
            35                  40                  45

Ser Ser Ile Ala Gln Gly Leu Glu Trp Ala Ala Asp Asn Gly Met His
        50                  55                  60

Ile Ala Asn Met Ser Leu Gly Thr Ser Ser Pro Ser Val Thr Leu Glu
65                  70                  75                  80
```

```
Arg Ala Val Asn Ala Ala Thr Ser Gln Gly Val Leu Val Ala Ala
                85                  90                  95

Ser Gly Asn Thr Gly Ala Gly Ser Ile Gly Tyr Pro Ala Arg Tyr Ala
                100                 105                 110

Asn Ala Met Ala Val Gly Ala Thr Asp Gln Asn Asn Arg Arg Ala Ser
                115                 120                 125

Phe Ser Gln Tyr Gly Ala Gly Leu Asp Ile Val Ala Pro Gly Val Asn
            130                 135                 140

Val Gln Ser Thr Tyr Pro Gly Ser Arg Tyr Ala Ser Leu Ser Gly Thr
145                 150                 155                 160

Ser Met Ala Ser Pro His Val Ala Gly Ala Ala Ala Leu
                165                 170

<210> SEQ ID NO 257
<211> LENGTH: 173
<212> TYPE: PRT
<213> ORGANISM: Artificial Sequence
<220> FEATURE:
<223> OTHER INFORMATION: Synthetic

<400> SEQUENCE: 257

Ser Thr Gln Asp Gly Asn Gly His Gly Thr His Val Ala Gly Thr Val
1               5                   10                  15

Ala Ala Leu Asn Asn Ser Ile Gly Val Ile Gly Val Ala Pro Ser Ala
                20                  25                  30

Glu Leu Tyr Gly Val Lys Val Leu Gly Ala Asn Gly Ser Gly Ser Val
            35                  40                  45

Ser Ser Ile Ala Arg Gly Leu Glu Trp Ala Gly Asn Asn Gly Met His
        50                  55                  60

Ile Ala Asn Leu Ser Leu Gly Ser Asp Phe Pro Ser Ala Thr Leu Glu
65                  70                  75                  80

Gln Ala Val Asn Ala Ala Thr Ser Arg Gly Val Leu Val Val Ala Ala
                85                  90                  95

Ser Gly Asn Asn Gly Ser Gly Ser Val Gly Tyr Pro Ala Arg Tyr Ala
                100                 105                 110

Asn Ala Met Gly Val Gly Ala Thr Asp Gln Asn Asn Arg Arg Ala Asn
                115                 120                 125

Phe Ser Gln Tyr Gly Ala Gly Leu Asp Ile Val Ala Pro Gly Val Gly
            130                 135                 140

Val Gln Ser Thr Tyr Pro Gly Asn Thr Tyr Val Ser Leu Asn Gly Thr
145                 150                 155                 160

Ser Met Ala Thr Pro His Val Ala Gly Val Ala Ala Leu
                165                 170

<210> SEQ ID NO 258
<211> LENGTH: 173
<212> TYPE: PRT
<213> ORGANISM: Artificial Sequence
<220> FEATURE:
<223> OTHER INFORMATION: Synthetic

<400> SEQUENCE: 258

Ser Thr Gln Asp Gly Asn Gly His Gly Thr His Val Ala Gly Thr Val
1               5                   10                  15

Ala Ala Leu Asn Asn Ser Asp Gly Val Ile Gly Val Ala Pro Asn Val
                20                  25                  30

Glu Leu Tyr Gly Val Lys Val Leu Gly Ala Asn Gly Arg Gly Thr Val
```

-continued

```
                35                  40                  45

Ser Gly Ile Ala Gln Gly Leu Glu Trp Ala Ala Asn Gly Met His
         50                  55                  60

Val Ala Asn Leu Ser Leu Gly Ser Pro Ala Pro Ser Ala Thr Leu Glu
 65                  70                  75                  80

Gln Ala Val Asn Ala Ala Thr Ser Arg Gly Val Leu Val Ile Ala Ala
                 85                  90                  95

Ser Gly Asn Ser Gly Ala Gly Thr Val Gly Tyr Pro Ala Arg Tyr Ala
            100                 105                 110

Asn Ala Met Ala Val Gly Ala Thr Asp Gln Asn Asn Asn Arg Ala Asn
            115                 120                 125

Phe Ser Gln Tyr Gly Ala Gly Leu Asp Ile Val Ala Pro Gly Val Gly
            130                 135                 140

Val Gln Ser Thr Tyr Pro Gly Asn Thr Tyr Thr Ser Leu Ser Gly Thr
145                 150                 155                 160

Ser Met Ala Ser Pro His Val Ala Gly Val Ala Ala Leu
                165                 170

<210> SEQ ID NO 259
<211> LENGTH: 173
<212> TYPE: PRT
<213> ORGANISM: Artificial Sequence
<220> FEATURE:
<223> OTHER INFORMATION: Synthetic

<400> SEQUENCE: 259

Ser Thr Gln Asp Gly Asn Gly His Gly Thr His Val Ala Gly Thr Ile
 1               5                  10                  15

Ala Ala Leu Asn Asn Asn Val Gly Val Leu Gly Val Ala Pro Ser Val
                 20                  25                  30

Asp Leu Tyr Gly Val Lys Val Leu Asp Ala Ser Gly Arg Gly Thr Ile
             35                  40                  45

Ser Gly Ile Ala Arg Gly Leu Glu Trp Ala Ala Asn Gly Met His
         50                  55                  60

Ile Ala Asn Met Ser Leu Gly Ser Asp Gln Pro Ser Thr Thr Leu Glu
 65                  70                  75                  80

Arg Ala Val Asn Ala Ala Thr Ser Arg Gly Val Leu Val Val Ala Ala
                 85                  90                  95

Ser Gly Asn Thr Gly Ser Gly Thr Val Ser Tyr Pro Ala Arg Tyr Ala
            100                 105                 110

Asn Ala Met Ala Val Gly Ala Thr Asp Gln Asn Asn Asn Arg Ala Asn
            115                 120                 125

Ser Ser Gln Tyr Gly Ala Gly Leu Asp Ile Val Ala Pro Gly Val Gly
            130                 135                 140

Val Gln Ser Thr Tyr Pro Gly Ser Thr Tyr Ala Ser Leu Ser Gly Thr
145                 150                 155                 160

Ser Met Ala Ser Pro His Val Ala Gly Val Ala Ala Leu
                165                 170

<210> SEQ ID NO 260
<211> LENGTH: 173
<212> TYPE: PRT
<213> ORGANISM: Artificial Sequence
<220> FEATURE:
<223> OTHER INFORMATION: Synthetic

<400> SEQUENCE: 260
```

-continued

```
Ser Thr Gln Asp Gly Asn Gly His Gly Thr His Val Ala Gly Thr Ile
  1               5                  10                 15

Ala Ala Leu Asn Asn Ser Val Gly Val Ile Gly Val Ala Pro Ser Ala
             20                  25                 30

Glu Leu Tyr Gly Val Lys Val Leu Gly Ala Asn Gly Ser Gly Thr Val
             35                  40                 45

Ser Gly Ile Ala Arg Gly Leu Glu Trp Ala Ala Asp Asn Gly Met His
 50                  55                  60

Val Ala Asn Met Ser Leu Gly Ser Ser Ala Pro Ser Ala Thr Leu Glu
 65                  70                  75                 80

Arg Ala Val Asn Ser Ala Thr Ser Arg Gly Val Leu Val Val Ala Ala
             85                  90                 95

Thr Gly Asn Ser Gly Ala Gly Ser Ile Ser Tyr Pro Ala Arg Tyr Ala
            100                 105                110

Asn Ala Met Ala Val Gly Ala Thr Asp Gln Asn Asn Asn Arg Ala Ser
            115                 120                125

Phe Ser Gln Tyr Gly Thr Gly Leu Asp Ile Val Ala Pro Gly Val Asn
        130                 135                140

Val Gln Ser Thr Tyr Pro Gly Ser Arg Tyr Ala Ser Met Ser Gly Thr
145                 150                 155                160

Ser Met Ala Ser Pro His Val Ala Gly Ala Ala Ala Leu
            165                 170
```

<210> SEQ ID NO 261
<211> LENGTH: 380
<212> TYPE: PRT
<213> ORGANISM: Bacillus

<400> SEQUENCE: 261

```
Met Lys Lys Pro Leu Gly Lys Ile Val Ala Ser Thr Ala Leu Leu Ile
  1               5                  10                 15

Ser Val Ala Phe Ser Ser Ser Ile Ala Ser Ala Ala Glu Glu Ala Lys
             20                  25                 30

Glu Lys Tyr Leu Ile Gly Phe Asn Glu Gln Glu Ala Val Ser Glu Phe
             35                  40                 45

Val Glu Gln Val Glu Ala Asn Asp Glu Val Ala Ile Leu Ser Glu Glu
 50                  55                  60

Glu Glu Val Glu Ile Glu Leu Leu His Glu Phe Glu Thr Ile Pro Val
 65                  70                  75                 80

Leu Ser Val Glu Leu Ser Pro Glu Asp Val Asp Ala Leu Glu Leu Asp
             85                  90                 95

Pro Ala Ile Ser Tyr Ile Glu Glu Asp Ala Glu Val Thr Thr Met Ala
            100                 105                110

Gln Ser Val Pro Trp Gly Ile Ser Arg Val Gln Ala Pro Ala Ala His
        115                 120                 125

Asn Arg Gly Leu Thr Gly Ser Gly Val Lys Val Ala Val Leu Asp Thr
        130                 135                 140

Gly Ile Ser Thr His Pro Asp Leu Asn Ile Arg Gly Gly Ala Ser Phe
145                 150                 155                160

Val Pro Gly Glu Pro Ser Thr Gln Asp Gly Asn Gly His Gly Thr His
            165                 170                 175

Val Ala Gly Thr Ile Ala Ala Leu Asn Asn Ser Ile Gly Val Leu Gly
        180                 185                 190

Val Ala Pro Ser Ala Glu Leu Tyr Ala Val Lys Val Leu Gly Ala Ser
        195                 200                 205
```

-continued

```
Gly Ser Gly Ser Val Ser Ser Ile Ala Gln Gly Leu Glu Trp Ala Gly
    210                 215                 220

Asn Asn Gly Thr His Val Ala Asn Leu Ser Leu Gly Ser Pro Ser Pro
225                 230                 235                 240

Ser Ala Thr Leu Glu Gln Ala Val Asn Ser Ala Thr Ser Arg Gly Val
                245                 250                 255

Leu Val Val Ala Ala Ser Gly Asn Ser Gly Ala Gly Ser Ile Ser Tyr
                260                 265                 270

Pro Ala Arg Tyr Ala Asn Ala Met Ala Val Gly Ala Thr Asp Gln Asn
            275                 280                 285

Asn Asn Arg Ala Ser Phe Ser Gln Tyr Gly Ala Gly Leu Asp Ile Val
    290                 295                 300

Ala Pro Gly Val Asn Val Gln Ser Thr Tyr Pro Gly Ser Thr Tyr Ala
305                 310                 315                 320

Ser Leu Asn Gly Thr Ser Met Ala Thr Pro His Val Ala Gly Val Ala
                325                 330                 335

Ala Leu Val Lys Gln Lys Asn Pro Ser Trp Ser Asn Val Gln Ile Arg
            340                 345                 350

Asn His Leu Lys Asn Thr Ala Thr Ser Leu Gly Ser Thr Asn Leu Tyr
    355                 360                 365

Gly Ser Gly Leu Val Asn Ala Glu Ala Ala Thr Arg
    370                 375                 380

<210> SEQ ID NO 262
<211> LENGTH: 173
<212> TYPE: PRT
<213> ORGANISM: Artificial Sequence
<220> FEATURE:
<223> OTHER INFORMATION: Synthetic
<221> NAME/KEY: misc_feature
<222> LOCATION: (16)..(16)
<223> OTHER INFORMATION: Xaa denotes Ile or Val
<221> NAME/KEY: misc_feature
<222> LOCATION: (20)..(20)
<223> OTHER INFORMATION: Xaa denotes Asp or Asn
<221> NAME/KEY: misc_feature
<222> LOCATION: (22)..(22)
<223> OTHER INFORMATION: Xaa denotes Asp, Ser, or Asn
<221> NAME/KEY: misc_feature
<222> LOCATION: (23)..(23)
<223> OTHER INFORMATION: Xaa denotes Ile, Val or Glu
<221> NAME/KEY: misc_feature
<222> LOCATION: (26)..(26)
<223> OTHER INFORMATION: Xaa denotes Ile, Val or Leu
<221> NAME/KEY: misc_feature
<222> LOCATION: (31)..(31)
<223> OTHER INFORMATION: Xaa denotes Asn, Glu, or Ser
<221> NAME/KEY: misc_feature
<222> LOCATION: (32)..(32)
<223> OTHER INFORMATION: Xaa denotes Ala or Val
<221> NAME/KEY: misc_feature
<222> LOCATION: (33)..(33)
<223> OTHER INFORMATION: Xaa denotes Asp or Glu,
<221> NAME/KEY: misc_feature
<222> LOCATION: (36)..(36)
<223> OTHER INFORMATION: Xaa denotes Ala or Gly
<221> NAME/KEY: misc_feature
<222> LOCATION: (41)..(41)
<223> OTHER INFORMATION: Xaa denotes Gly, Ser or Arg
<221> NAME/KEY: misc_feature
<222> LOCATION: (43)..(43)
<223> OTHER INFORMATION: Xaa denotes Ser or Asn
<221> NAME/KEY: misc_feature
<222> LOCATION: (45)..(45)
<223> OTHER INFORMATION: Xaa denotes Ser, Ala or Arg
<221> NAME/KEY: misc_feature
<222> LOCATION: (48)..(48)
```

```
<223> OTHER INFORMATION: Xaa denotes Ile or Val
<221> NAME/KEY: misc_feature
<222> LOCATION: (50)..(50)
<223> OTHER INFORMATION: Xaa denotes Gly or Ser
<221> NAME/KEY: misc_feature
<222> LOCATION: (53)..(53)
<223> OTHER INFORMATION: Xaa denotes Arg or Gln
<221> NAME/KEY: misc_feature
<222> LOCATION: (56)..(56)
<223> OTHER INFORMATION: Xaa denotes Glu or Gln
<221> NAME/KEY: misc_feature
<222> LOCATION: (58)..(58)
<223> OTHER INFORMATION: Xaa denotes Ala or Ser
<221> NAME/KEY: misc_feature
<222> LOCATION: (59)..(59)
<223> OTHER INFORMATION: Xaa denotes Gly or Ala
<221> NAME/KEY: misc_feature
<222> LOCATION: (60)..(60)
<223> OTHER INFORMATION: Xaa denotes Glu, Ala, Thr, or Asn
<221> NAME/KEY: misc_feature
<222> LOCATION: (62)..(62)
<223> OTHER INFORMATION: Xaa denotes Gly or Asn
<221> NAME/KEY: misc_feature
<222> LOCATION: (64)..(64)
<223> OTHER INFORMATION: Xaa denotes Asp or His
<221> NAME/KEY: misc_feature
<222> LOCATION: (68)..(68)
<223> OTHER INFORMATION: Xaa denotes Leu or Met
<221> NAME/KEY: misc_feature
<222> LOCATION: (72)..(72)
<223> OTHER INFORMATION: Xaa denotes Ser or Thr
<221> NAME/KEY: misc_feature
<222> LOCATION: (73)..(73)
<223> OTHER INFORMATION: Xaa denotes Ser or Asp
<221> NAME/KEY: misc_feature
<222> LOCATION: (74)..(74)
<223> OTHER INFORMATION: Xaa denotes Ala or Phe
<221> NAME/KEY: misc_feature
<222> LOCATION: (77)..(77)
<223> OTHER INFORMATION: Xaa denotes Ala, Thr, or Ser
<221> NAME/KEY: misc_feature
<222> LOCATION: (80)..(80)
<223> OTHER INFORMATION: Xaa denotes Glu, Lys, or Gly
<221> NAME/KEY: misc_feature
<222> LOCATION: (81)..(81)
<223> OTHER INFORMATION: Xaa denotes Gln or Arg
<221> NAME/KEY: misc_feature
<222> LOCATION: (85)..(85)
<223> OTHER INFORMATION: Xaa denotes Ala or Tyr
<221> NAME/KEY: misc_feature
<222> LOCATION: (89)..(89)
<223> OTHER INFORMATION: Xaa denotes Arg or Gln
<221> NAME/KEY: misc_feature
<222> LOCATION: (90)..(90)
<223> OTHER INFORMATION: Xaa denotes Asp or Gly
<221> NAME/KEY: misc_feature
<222> LOCATION: (97)..(97)
<223> OTHER INFORMATION: Xaa denotes Ser or Thr
<221> NAME/KEY: misc_feature
<222> LOCATION: (100)..(100)
<223> OTHER INFORMATION: Xaa denotes Ser or Asn
<221> NAME/KEY: misc_feature
<222> LOCATION: (102)..(102)
<223> OTHER INFORMATION: Xaa denotes Ala or Ser
<221> NAME/KEY: misc_feature
<222> LOCATION: (125)..(125)
<223> OTHER INFORMATION: Xaa denotes Asn or Arg
<221> NAME/KEY: misc_feature
<222> LOCATION: (128)..(128)
<223> OTHER INFORMATION: Xaa denotes Ser or Asn
<221> NAME/KEY: misc_feature
<222> LOCATION: (134)..(134)
<223> OTHER INFORMATION: Xaa denotes Ala or Thr
<221> NAME/KEY: misc_feature
<222> LOCATION: (136)..(136)
<223> OTHER INFORMATION: Xaa denotes Leu or Ile
<221> NAME/KEY: misc_feature
<222> LOCATION: (144)..(144)
<223> OTHER INFORMATION: Xaa denotes Gly, Arg, or Asn
```

```
<221> NAME/KEY: misc_feature
<222> LOCATION: (145)..(145)
<223> OTHER INFORMATION: Xaa denotes Val or Leu
<221> NAME/KEY: misc_feature
<222> LOCATION: (146)..(146)
<223> OTHER INFORMATION: Xaa denotes Gln or Arg
<221> NAME/KEY: misc_feature
<222> LOCATION: (152)..(152)
<223> OTHER INFORMATION: Xaa denotes Gly, Asn, Ser, or Thr
<221> NAME/KEY: misc_feature
<222> LOCATION: (153)..(153)
<223> OTHER INFORMATION: Xaa denotes Arg, Ser, Thr, or Gln
<221> NAME/KEY: misc_feature
<222> LOCATION: (155)..(155)
<223> OTHER INFORMATION: Xaa denotes Val, Ala, or Asp
<221> NAME/KEY: misc_feature
<222> LOCATION: (156)..(156)
<223> OTHER INFORMATION: Xaa denotes Glu, Arg, or Ser
<221> NAME/KEY: misc_feature
<222> LOCATION: (157)..(157)
<223> OTHER INFORMATION: Xaa denotes Leu or Met
<221> NAME/KEY: misc_feature
<222> LOCATION: (158)..(158)
<223> OTHER INFORMATION: Xaa denotes Asn, Ser , or Arg
<221> NAME/KEY: misc_feature
<222> LOCATION: (164)..(164)
<223> OTHER INFORMATION: Xaa denotes Ser or Thr
<221> NAME/KEY: misc_feature
<222> LOCATION: (170)..(170)
<223> OTHER INFORMATION: Xaa denotes Ala or Val

<400> SEQUENCE: 262

Ser Thr Gln Asp Gly Asn Gly His Gly Thr His Val Ala Gly Thr Xaa
1               5                   10                  15

Ala Ala Leu Xaa Asn Xaa Xaa Gly Val Xaa Gly Val Ala Pro Xaa Xaa
            20                  25                  30

Xaa Leu Tyr Xaa Val Lys Val Leu Xaa Ala Xaa Gly Xaa Gly Ser Xaa
        35                  40                  45

Ser Xaa Ile Ala Xaa Gly Leu Xaa Trp Xaa Xaa Xaa Asn Xaa Met Xaa
    50                  55                  60

Ile Ala Asn Xaa Ser Leu Gly Xaa Xaa Xaa Pro Ser Xaa Thr Leu Xaa
65                  70                  75                  80

Xaa Ala Val Asn Xaa Ala Thr Ser Xaa Xaa Val Leu Val Ile Ala Ala
                85                  90                  95

Xaa Gly Asn Xaa Gly Xaa Gly Ser Val Gly Tyr Pro Ala Arg Tyr Ala
            100                 105                 110

Asn Ala Met Ala Val Gly Ala Thr Asp Gln Asn Asn Xaa Arg Ala Xaa
            115                 120                 125

Phe Ser Gln Tyr Gly Xaa Gly Xaa Asp Ile Val Ala Pro Gly Val Xaa
    130                 135                 140

Xaa Xaa Ser Thr Tyr Pro Gly Xaa Xaa Tyr Xaa Xaa Xaa Xaa Gly Thr
145                 150                 155                 160

Ser Met Ala Xaa Pro His Val Ala Gly Xaa Ala Ala Leu
                165                 170

<210> SEQ ID NO 263
<211> LENGTH: 15
<212> TYPE: DNA
<213> ORGANISM: Artificial Sequence
<220> FEATURE:
<223> OTHER INFORMATION: Synthetic

<400> SEQUENCE: 263
agtacccagg acgga                                                    15
```

```
<210> SEQ ID NO 264
<211> LENGTH: 10
<212> TYPE: PRT
<213> ORGANISM: Artificial Sequence
<220> FEATURE:
<223> OTHER INFORMATION: Synthetic

<400> SEQUENCE: 264

Ala Ala Leu Asn Asn Ser Ile Gly Val Leu
1               5                   10

<210> SEQ ID NO 265
<211> LENGTH: 10
<212> TYPE: PRT
<213> ORGANISM: Artificial Sequence
<220> FEATURE:
<223> OTHER INFORMATION: Synthetic

<400> SEQUENCE: 265

Ala Ala Leu Gln Asn Ala Leu Gly Val Val
1               5                   10

<210> SEQ ID NO 266
<211> LENGTH: 10
<212> TYPE: PRT
<213> ORGANISM: Artificial Sequence
<220> FEATURE:
<223> OTHER INFORMATION: Synthetic

<400> SEQUENCE: 266

Ala Ala Leu Gln Asn Thr Val Gly Val Met
1               5                   10

<210> SEQ ID NO 267
<211> LENGTH: 175
<212> TYPE: PRT
<213> ORGANISM: Artificial Sequence
<220> FEATURE:
<223> OTHER INFORMATION: Synthetic

<400> SEQUENCE: 267

Ser Thr Gln Asp Gly Asn Gly His Gly Thr His Val Ala Gly Thr Val
1               5                   10                  15

Ala Ala Leu Asn Asn Ser Ile Gly Val Ile Gly Val Ala Pro Ser Ala
                20                  25                  30

Asp Leu Tyr Ala Val Lys Val Leu Gly Ala Asn Gly Arg Gly Ser Val
            35                  40                  45

Ser Gly Ile Ala Gln Gly Leu Glu Trp Ala Ala Asn Asn Met His
        50                  55                  60

Ile Ala Asn Met Ser Leu Gly Ser Asp Ala Pro Ser Thr Thr Leu Glu
65                  70                  75                  80

Arg Ala Val Asn Tyr Ala Thr Ser Gln Gly Val Leu Val Ile Ala Ala
                85                  90                  95

Thr Gly Asn Asn Gly Ser Gly Ser Val Gly Tyr Pro Ala Arg Tyr Ala
            100                 105                 110

Asn Ala Met Ala Val Gly Ala Thr Asp Gln Asn Asn Arg Arg Ala Asn
        115                 120                 125

Phe Ser Gln Tyr Gly Thr Gly Ile Asp Ile Val Ala Pro Gly Val Asn
    130                 135                 140

Val Gln Ser Thr Tyr Pro Gly Asn Arg Tyr Ala Ser Leu Asn Gly Thr
145                 150                 155                 160

Ser Met Ala Thr Pro His Val Ala Gly Ala Ala Ala Leu Val Lys
```

165                 170                 175

<210> SEQ ID NO 268
<211> LENGTH: 193
<212> TYPE: PRT
<213> ORGANISM: Artificial Sequence
<220> FEATURE:
<223> OTHER INFORMATION: Synthetic

<400> SEQUENCE: 268

Gly Ala Ser Phe Val Pro Gly Glu Pro Ser Thr Gln Asp Gly Asn Gly
1               5                   10                  15

His Gly Thr His Val Ala Gly Thr Ile Ala Ala Leu Asp Asn Ser Glu
            20                  25                  30

Gly Val Leu Gly Val Ala Pro Asn Ala Asp Leu Tyr Ala Val Lys Val
        35                  40                  45

Leu Gly Ala Ser Gly Ser Gly Ser Ile Ser Gly Ile Ala Gln Gly Leu
    50                  55                  60

Glu Trp Ala Gly Glu Asn Gly Met His Ile Ala Asn Leu Ser Leu Gly
65                  70                  75                  80

Ser Ser Ala Pro Ser Ala Thr Leu Glu Gln Ala Val Asn Tyr Ala Thr
                85                  90                  95

Ser Gln Gly Val Leu Val Ile Ala Ala Ser Gly Asn Ser Gly Ala Gly
            100                 105                 110

Ser Val Gly Tyr Pro Ala Arg Tyr Ala Asn Ala Met Ala Val Gly Ala
        115                 120                 125

Thr Asp Gln Asn Asn Asn Arg Ala Ser Phe Ser Gln Tyr Gly Ala Gly
    130                 135                 140

Leu Asp Ile Val Ala Pro Gly Val Gly Val Gln Ser Thr Tyr Pro Gly
145                 150                 155                 160

Asn Arg Tyr Ala Ser Leu Asn Gly Thr Ser Met Ala Thr Pro His Val
                165                 170                 175

Ala Gly Val Ala Ala Leu Val Lys Gln Lys Asn Pro Ser Trp Ser Asn
            180                 185                 190

Val

<210> SEQ ID NO 269
<211> LENGTH: 193
<212> TYPE: PRT
<213> ORGANISM: Artificial Sequence
<220> FEATURE:
<223> OTHER INFORMATION: Synthetic

<400> SEQUENCE: 269

Gly Ala Ser Phe Val Pro Gly Glu Pro Ser Thr Gln Asp Gly Asn Gly
1               5                   10                  15

His Gly Thr His Val Ala Gly Thr Ile Ala Ala Leu Asn Asn Ser Ile
            20                  25                  30

Gly Val Leu Gly Val Ala Pro Asn Ala Asp Leu Tyr Ala Val Lys Val
        35                  40                  45

Leu Gly Ala Asn Gly Ser Gly Ser Val Ser Gly Ile Ala Gln Gly Leu
    50                  55                  60

Glu Trp Ala Ala Ala Asn Asn Met His Ile Ala Asn Met Ser Leu Gly
65                  70                  75                  80

Ser Asp Ala Pro Ser Ala Thr Leu Glu Gln Ala Val Asn Tyr Ala Thr
                85                  90                  95

Ser Arg Gly Val Leu Val Ile Ala Ala Thr Gly Asn Asn Gly Ser Gly

```
                     100                 105                 110
Ser Val Gly Tyr Pro Ala Arg Tyr Ala Asn Ala Met Ala Val Gly Ala
        115                 120                 125

Thr Asp Gln Asn Asn Arg Arg Ala Asn Phe Ser Gln Tyr Gly Thr Gly
    130                 135                 140

Ile Asp Ile Val Ala Pro Gly Val Asn Val Gln Ser Thr Tyr Pro Gly
145                 150                 155                 160

Asn Arg Tyr Ala Ser Leu Asn Gly Thr Ser Met Ala Thr Pro His Val
                165                 170                 175

Ala Gly Val Ala Ala Leu Val Lys Gln Lys Asn Pro Ser Trp Ser Asn
            180                 185                 190

Val

<210> SEQ ID NO 270
<211> LENGTH: 193
<212> TYPE: PRT
<213> ORGANISM: Bacillus

<400> SEQUENCE: 270

Gly Ala Ser Phe Val Pro Gly Glu Pro Ser Thr Gln Asp Gly Asn Gly
1               5                   10                  15

His Gly Thr His Val Ala Gly Thr Ile Ala Ala Leu Asn Asn Ser Ile
            20                  25                  30

Gly Val Leu Gly Val Ala Pro Ser Ala Glu Leu Tyr Ala Val Lys Val
        35                  40                  45

Leu Gly Ala Ser Gly Ser Gly Ser Val Ser Ser Ile Ala Gln Gly Leu
    50                  55                  60

Glu Trp Ala Gly Asn Asn Gly Met His Val Ala Asn Leu Ser Leu Gly
65                  70                  75                  80

Ser Pro Ser Pro Ser Ala Thr Leu Glu Gln Ala Val Asn Ser Ala Thr
                85                  90                  95

Ser Arg Gly Val Leu Val Val Ala Ala Ser Gly Asn Ser Gly Ala Gly
            100                 105                 110

Ser Ile Ser Tyr Pro Ala Arg Tyr Ala Asn Ala Met Ala Val Gly Ala
        115                 120                 125

Thr Asp Gln Asn Asn Arg Ala Ser Phe Ser Gln Tyr Gly Ala Gly
    130                 135                 140

Leu Asp Ile Val Ala Pro Gly Val Asn Val Gln Ser Thr Tyr Pro Gly
145                 150                 155                 160

Ser Thr Tyr Ala Ser Leu Asn Gly Thr Ser Met Ala Thr Pro His Val
                165                 170                 175

Ala Gly Ala Ala Ala Leu Val Lys Gln Lys Asn Pro Ser Trp Ser Asn
            180                 185                 190

Val
```

SUBTILISIN VARIANTS

CROSS REFERENCE TO RELATED APPLICATIONS

The present application claims priority to and benefit of U.S. Provisional Application No. 60/194,143, filed Apr. 3, 2000, the disclosure of which is incorporated herein in its entirety for all purposes.

COPYRIGHT NOTIFICATION

Pursuant to 37 C.F.R. 1.71(e), Applicants note that a portion of this disclosure contains material which is subject to copyright protection. The copyright owner has no objection to the facsimile reproduction by anyone of the patent document or patent disclosure, as it appears in the Patent and Trademark Office patent file or records, but otherwise reserves all copyright rights whatsoever.

BACKGROUND OF THE INVENTION

Sales of the serine protease subtilisin exceed $300 million annually, accounting for approximately 40% of the industrial enzyme market. For more than 30 years, proteases, including subtilisin, have been used as additives in laundry and other detergents. Subtilisin has a broad specificity for proteins that commonly soil clothing, including proteins found in blood, grass, soil and many food products.

Initially isolated from the bacteria *Bacillus subtilis*, subtilisin has become one of the most intensively studied and extensively engineered proteins known to date. A wide variety of subtilisins have been identified, and the amino acid sequences of a number of these subtilisins have been determined. In addition, structural investigations, including more than 100 crystal structures, have revealed that subtilisins share a common active site with other serine proteases, the Ser-His-Asp catalytic triad.

Despite such studies, structural features correlating with specific functional properties remain to be elucidated. Indeed, due both to the lack of structural predictability and to the need to optimize multiple characteristics simultaneously, the task of protein engineering remains difficult.

For example, in detergent applications, subtilisins are not only active under a variety of washing conditions, they are also stable in the presence of other detergent components and additives. Such additives may include, among other things, other enzymes such as cellulases, lipases and the like. Subtilisin should be stable in the presence of effective concentrations of such enzymes, and at the same time must not result in the degradation (proteolysis) of these enzymes. The subtilisin selected for such an application should also be active under a variety of specific conditions such as high or low temperature, acid, neutral or alkaline pH, or the presence of such additives as bleaching agents. Mutations or alterations in the nucleotide or amino acid sequences which would provide these benefits are difficult to predict, and therefore difficult to engineer.

Nonetheless, both random mutagenesis and targeted mutagenesis approaches have been applied to the goal of producing improved subtilisin homologues. However, attempts to develop proteases that are improved for multiple properties are hampered by the fact that random mutations are often deleterious, and attempts to rationally alter one property of an enzyme often disrupt other important existing characteristics (Patkar et al. (1998) *Chem Phys Lipids* 93:95; Shoichet et al. (1995) *Proc Natl Acad Sci U S A*. (1995) 92:452).

The present invention provides novel subtilisin homologues that are improved for a variety of specific properties including thermal stability, activity at low temperature, alkaline stability as well as other desirable properties and combinations of properties. These subtilisins are useful in a variety of detergent and other industrial and commercial applications.

SUMMARY OF THE INVENTION

The present invention provides novel subtilisin homologues with improved characteristics and combinations of characteristics, including thermotolerance (thermal stability), activity at alkaline, acid and/or neutral pH, activity at ambient temperatures and activity in organic solvents. In one aspect, the invention relates to isolated and recombinant nucleic acids corresponding to polynucleotides that are novel subtilisin homologues, encode novel subtilisin proteins, hybridize under highly stringent conditions to such novel subtilisin homologues or polynucleotides encoding novel subtilisin proteins, or are fragments thereof, encoding polypeptides with endo-protease activity.

Embodiments of the invention include polynucleotides which include a subsequence corresponding to one or more sequence selected from SEQ ID NO:1 to SEQ ID NO:130. Such polynucleotides encode polypeptides that are novel subtilisins incorporating the sequence elements of SEQ ID: 131 to SEQ ID NO:260. Fragments of nucleic acids comprising SEQ ID NO:1 to SEQ ID NO:130 encoding 20 or more contiguous amino acids of SEQ ID NO:131 to SEQ ID NO:260 are embodiments of the invention.

In some embodiments, the encoded polypeptide comprises at least 20, at least about 30, or at least about 50, or least about 75, or at least about 100, or at least about 150 contiguous amino acids of a sequence selected from SEQ ID NO:131 to SEQ ID NO:260. In one embodiment, the encoded polypeptide is about 269 amino acid residues in length. In other preferred embodiments the encoded polypeptide is a pre-pro peptide of about 380 amino acid residues.

In some embodiments, such polynucleotides encode polypeptides having a diversified region between amino acid positions 55 and 227 with respect to the mature subtilisin protein, with the amino acid sequence STQDGNGHGTHVAGT-$X_{70}$-AAL-$X_{74}$-N-$X_{76}X_{77}$-GV-$X_{80}$-GVAP-$X_{85}X_{86}X_{87}$-LY-$X_{90}$-VKVL-$X_{95}$-A-$X_{97}$-G-$X_{99}$-GS-$X_{102}$-IA-$X_{107}$-GL-$X_{110}$-W-$X_{112}X_{113}X_{114}$-N-$X_{116}$-M-$X_{118}$-IAN-$X_{122}$-SLG-$X_{126}X_{127}$X128-PS-$X_{131}$-TL-$X_{134}X_{135}$-AVN-$X_{139}$-ATS-$X_{143}X_{144}$-VLVIAA-$X_{151}$-GN-$X_{154}$-G-$X_{156}$-GSVGYPARYANA-MAVGATDQNN-$X_{179}$-RA-$X_{182}$-FSQYG-X188-G-$X_{190}$-DIVAPGV-$X_{198}X_{199}X_{200}$-STYPG-$X_{206}X_{207}$-Y-$X_{209}X_{210}X_{211}X_{212}$-GTSMA-$X_{218}$-PHVAG-$X_{224}$-AAL, or a substituted variation thereof, wherein $X_{70}$ is I or V; $X_{74}$ is D or N; $X_{76}$ is D, S or N; $X_{77}$ is I, V or E; $X_{80}$ is I, V or L; $X_{85}$ is N, E or S; $X_{86}$ is A or V; $X_{87}$ is D or E; $X_{90}$ is A or G; $X_{95}$ is G, S or R; $X_{97}$ is S or N; $X_{99}$ is S, A or R; $X_{102}$ is I or V; $X_{104}$ is G or S; $X_{107}$ is R or Q; $X_{110}$ is E or Q; $X_{112}$ is A or S; $X_{113}$ is G or A, $X_{114}$ is E, A, T or N; $X_{116}$ is G or N; $X_{118}$ is D or H; $X_{122}$ is L or M; $X_{126}$ is S or T; $X_{127}$ is S or D; $X_{128}$ is A or F; $X_{131}$ is A, T or S; $X_{134}$ is E, K or G; $X_{135}$ is Q or R; $X_{139}$ is A or Y; $X_{143}$ is R or Q; $X_{144}$ is D or G; $X_{151}$ is S or T; $X_{154}$ is S or N; $X_{156}$ is A or S; $X_{179}$ is N or R; $X_{182}$ is S or N; $X_{188}$ is A or T; $X_{190}$ is L or I; $X_{198}$ is G, R or N; $X_{199}$ is V or L; $X_{200}$ is Q or R; $X_{206}$ is G, N, S or T; $X_{207}$ is R, S, T or Q; $X_{209}$ is V, A or D; $X_{210}$ is E, R or S; $X_{211}$ is L or M; $X_{212}$ is N, S or R; $X_{218}$ is S or T; and $X_{224}$ is A or V (SEQ ID NO: 262).

The nucleic acids of the invention encode novel endo-proteases, for example, endo-proteases that are active at ambient, low or high temperatures, are thermotolerant (thermostable), are stable and active at high, low or neutral pH, or are active in organic solvents. Nucleic acids that encode endo-proteases with combinations of such desirable properties are also embodiments.

Nucleic acids encoding thermotolerant endo-proteases incorporating SEQ ID NOs: 3, 7, 8, 10, 12, 14, 15, 16, 18, 21 and 25 are embodiments of the invention. Similarly, nucleic acids encoding alkaline active endo-proteases incorporating the SEQ ID NOs: 1, 17, 19, 22, 23, 24, 25, 26, 27 and 32 are embodiments of the invention. Nucleic acids encoding endo-proteases that are active in organic solvents, such as dimethylformamide (DMF) incorporating SEQ ID NOs: 2, 4, 5, 6, 11, 13, 20, 29, 30 and 33 are also embodiments of the invention.

Compositions containing two or more such nucleic acids or encoded polypeptides are a feature of the invention. In some cases, these compositions are libraries of nucleic acids, preferably containing at least 10 such nucleic acids. Compositions produced by digesting the nucleic acids of the invention with a restriction endonuclease, a DNAse or an RNAse are also a feature of the invention, as are compositions produced by incubating a nucleic acid of the invention with deoxyribonucleotide triphosphates and a nucleic acid polymerase, including thermostable nucleic acid polymerases.

Another aspect of the invention is vectors incorporating a nucleic acid of the invention. Such vectors include plasmids, cosmids, phage, viruses, including chromosome integration vectors. In preferred embodiments, the vector is an expression vector. Cells transduced by such vectors, or which otherwise incorporate the nucleic acid of the invention are an aspect of the invention. In a preferred embodiment, the cells express a polypeptide encoded by the nucleic acid.

Isolated or recombinant polypeptides encoded by the nucleic acids of the invention are another aspect of the invention. Similarly, polypeptides comprising the sequence elements of SEQ ID NO:131 to SEQ ID NO:260 are an aspect of the invention. Such polypeptides are endo-proteases. Preferred embodiments include polypeptides that are endo-proteases with one or more properties selected from among: activity at ambient temperature, psychrophilic activity, thermotolerance or thermostability, activity at alkaline, acid and/or neutral pH, and activity in the presence of organic solvents, such as dimethylformamide (DMF). Certain embodiments are endo-proteases with combinations of desired properties. Other embodiments are endo-protease polypeptides with desired conditional properties, such as pH dependence, temperature dependence, dependence on ionic strength, activation by ligand binding, and inactivation by ligand binding. In some embodiments, the polypeptide has at least 70% sequence identity to at least one of SEQ ID NO:131 to SEQ ID NO:260 over a comparison window of at least 20 contiguous amino acids. In other embodiments, the polypeptide as at least 80%, at least 90%, at least 95%, 96%, 97%, 98% or 99% sequence identity to at least one of SEQ ID NO:131 to SEQ ID NO:260. In other embodiments the polypeptide maintains sequence identity over a comparison window of at least 30, at least about 50, at least about 100, or at least about 150 amino acids of one or more of SEQ ID NO:131 to SEQ ID NO:260.

In some embodiments, the polypeptide has an improved endo-protease activity selected from among increased thermotolerance, increased activity at ambient temperature, increased activity at alkaline pH, increased activity at acid pH, increased activity at neutral pH, and increased activity in the presence of organic solvents, relative to the subtilisin homologue polypeptide corresponding to SEQ ID NO:261, which polypeptide has at least 70% sequence identity to at least one of SEQ ID NO:131 to SEQ ID NO:260, over a comparison window of at least 20 contiguous amino acids. In some embodiments, the polypeptide has at least 80%, at least 90%, at least 95%, 96%, 97%, 98%, or 99% sequence identity to at least one of SEQ ID NO:131 to SEQ ID NO:260. In some embodiments, the polypeptide maintains sequence identity over a comparison window of at least about 30, at least about 50, at least about 100, or more amino acids. In an embodiment the polypeptide with an improved endo-protease activity comprises a sequence element selected from among SEQ ID NO:131 to SEQ ID NO:260.

Polypeptides 150 contiguous amino acids or greater in length that are encoded by a polynucleotide comprising SEQ ID NO:1 to SEQ ID NO:130, a polynucleotide encoding SEQ ID NO:131 to SEQ ID NO:260, or a polynucleotide sequence that hybridizes under highly stringent conditions to such a polynucleotide are embodiments of the invention. Such polypeptides exhibit endo-protease activity. In some embodiments, such polypeptides are at least about 250 amino acids, e.g., about 269 amino acids in length. Alternatively such polypeptides are at least about 350 amino acids in length, e.g., pre-pro peptides of about 380 amino acids in length.

Furthermore, polypeptides of the invention with secretion and/or localization sequences are a feature of the invention, as are such polypeptides with purification sequences, including epitope tags, FLAG tags, polyhistidine tags, and GST fusions. Similarly, the polypeptides of the invention bearing a methionine at the N-terminus or having one or more modified amino acids, e.g., glycosylated, PEGylated, farnesylated, acetylated or biotinylated amino acids, are features of the invention.

Compositions that include one or more polypeptide of the invention and a detergent are an aspect of the invention.

Methods of producing the polypeptides of the invention by introducing the nucleic acids encoding them into cells and then expressing and recovering them from the cells or culture medium are a feature of the invention. In preferred embodiments, the cells expressing the polypeptides of the invention are grown in a bulk fermentation vessel.

Polypeptides that are specifically bound by a polyclonal antisera that reacts against an antigen derived from SEQ ID NO:131 to SEQ ID NO:260, but not to a naturally occurring subtilisin polypeptide or a previously described the sequence of which was available in GenBank as of Apr. 3, 2000, as exemplified by P29600, P41362, P29599, P27693, P20724, P41363, P00780, P00781, P35835, P00783, P29142, P04189, P07518, P00782, P04072, P16396, P29140, P29139, P08594, P16588, P11018, P54423, P40903, P23314, P23653, P33295, P42780, and P80146 as well as antibodies which are produced by administering an antigen derived from any one of SEQ ID NO:131 to SEQ ID NO:260 and/or which bind specifically to such antigens and which do not specifically bind to a naturally occurring subtilisin polypeptide or a subtilisin polypeptide corresponding to one or more of, e.g., P29600, P41362, P29599, P27693, P20724, P41363, P00780, P00781, P35835, P00783, P29142, P04189, P07518, P00782, P04072, P16396, P29140, P29139, P08594, P16588, P11018, P54423, P40903, P23314, P23653, P33295, P42780, and P80146 are all features of the invention.

Another aspect of the invention relates to methods of producing novel subtilisin homologues by mutating or recombining, e.g., recursively recombining, the nucleic acids of the invention in vitro or in vivo. In an embodiment, the recursive recombination produces at least one library of recombinant subtilisin homologue nucleic acids. The libraries so produced are embodiments of the invention, as are cells comprising the libraries. Furthermore, methods of producing a modified subtilisin nucleic acid homologue by mutating a nucleic acid of the invention are embodiments of the invention. Recombinant and mutant subtilisin homologue nucleic acids produced by the methods of the invention are also embodiments of the invention.

In addition, nucleic acids which are unique subsequences of SEQ ID NO:1 to SEQ ID NO:130, (as compared to any subtilisin nucleic acid sequences available in GenBank, as of Apr. 3, 2000, as exemplified by, e.g., M65086, D13157, S48754, AB005792, D29688, and M28537), or are unique subsequences of polypeptides selected from among SEQ ID NO:131 to SEQ ID NO:260, (as compared to any subtilisin protein sequences available in GenBank, as of Apr. 3, 2000, as exemplified by: P29600, P41362, P29599, P27693, P20724, P41363, P00780, P00781, P35835, P00783, P29142, P04189, P07518, P00782, P04072, P16396, P29140, P29139, P08594, P16588, P11018, P54423, P40903, P23314, P23653, P33295, P42780, and P80146), or are target nucleic acids that hybridize to unique coding oligonucleotides that encode a unique subsequence in a polypeptide selected from SEQ ID NO:131 to SEQ ID NO:260, and that are unique as compared to a polypeptide encoded by a sequence available in GenBank as of Apr. 3, 2000 and exemplified by M65086, D13157, S48754, AB005792, D29688, and M28537, are all embodiments of the invention.

The invention also provides computers, computer readable medium and integrated systems, including databases that are composed of sequence records including character strings corresponding to SEQ ID NOs:1–260. Such integrated systems optionally include, one or more instruction set for selecting, aligning, translating, reverse-translating or viewing any one or more character strings corresponding to SEQ ID NOs:1–260, with each other and/or with any additional nucleic acid or amino acid sequence.

BRIEF DESCRIPTION ON THE FIGURES

FIG. 1. The Amino Acid Sequence of Savinase®(SEQ ID NO:261).

FIGS. 2A–C. Sequence diagrams illustrating putative motifs (SEQ ID NOS: 131–138, 140–157, 159, 160, 162, 163, and 267–270).

DETAILED DISCUSSION

Subtilisins (Bott et al. (1996) *Adv Exp Med Biol* 379:277; Rao et al. (1998) *J Biomol Struct Dyn* 15:1053) are commercially important serine endo-proteases whose broad specificity for peptide bonds and relative ease of production makes them highly valued for a range of applications including food and leather processing and as additives to laundry detergents for stain hydrolysis and solubilization. Because of their high value, subtilisins have been extensively studied, with over 100 crystal structures solved (Siezen et al. (1991) *Protein Eng* 4:719).

The present invention provides novel subtilisin homologues with improved properties as well as combinations of properties. Among these properties are enhanced thermostability in high or low temperatures, stability and activity at high and low pH, and stability in organic solvents.

Definitions

A "polynucleotide sequence" is a nucleic acid, e.g., DNA, RNA (which is a polymer of nucleotides (A,C,T,U,G, etc. or naturally occurring or artificial nucleotide analogues) or a character string representing a nucleic acid, depending on context. Either the given nucleic acid or the complementary nucleic acid can be determined from any specified polynucleotide sequence.

Similarly, an "amino acid sequence" is a polymer of amino acids (a protein, polypeptide, etc.) or a character string representing an amino acid polymer, depending on context.

A nucleic acid, protein or other component is "isolated" when it is partially or completely separated from components with which it is normally associated (other proteins, nucleic acids, cells, synthetic reagents, etc.). A nucleic acid or polypeptide is "recombinant" when it is artificial or engineered, or derived from an artificial or engineered protein or nucleic acid.

A "subsequence" or "fragment" is any portion of an entire sequence, up to and including the complete sequence.

Numbering of an amino acid or nucleotide polymer corresponds to numbering of a selected amino acid polymer or nucleic acid when the position of a given monomer component (amino acid residue, incorporated nucleotide, etc.) of the polymer corresponds to the same residue position in a selected reference polypeptide or polynucleotide. Unless otherwise specified, numbering is given with reference to the sequence of Savinase®, as provided in FIG. 1.

A vector is a composition for facilitating cell transduction by a selected nucleic acid, and/or expression of the nucleic acid in the cell. Vectors include, e.g., plasmids, cosmids, viruses, YACs, bacteria, poly-lysine, chromosome integration vectors, episomal vectors, etc.

"Substantially an entire length of a polynucleotide or amino acid sequence" refers to at least 70%, generally at least 80%, or typically 90% or more of a sequence.

As used herein, an "antibody" refers to a protein comprising one or more polypeptides substantially or partially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. A typical immunoglobulin (antibody) structural unit comprises a tetramer. Each tetramer is composed of two identical pairs of polypeptide chains, each pair having one "light" (about 25 kD) and one "heavy" chain (about 50–70 kD). The N-terminus of each chain defines a variable region of about 100 to 110 or more amino acids primarily responsible for antigen recognition. The terms variable light chain (VL) and variable heavy chain (VH) refer to these light and heavy chains respectively. Antibodies exist as intact immunoglobulins or as a number of well characterized fragments produced by digestion with various peptidases. Thus, for example, pepsin digests an antibody below the disulfide linkages in the hinge region to produce F(ab)'2, a dimer of Fab which itself is a light chain joined to VH-CH1 by a disulfide bond. The F(ab)'2 may be reduced under mild conditions to break the disulfide linkage in the hinge region thereby converting the (Fab')2 dimer into an Fab' monomer. The Fab' monomer is essentially an Fab with part of the hinge region (see, *Fundamental Immunology*, 4th Edition, W. E. Paul (ed.), Raven Press, N.Y. (1998), for a more detailed description of other antibody fragments). While various antibody fragments are defined in terms of the digestion of an intact antibody, one of skill will appreciate that such Fab' fragments may be synthesized de novo either chemically or by utilizing recombinant DNA methodology. Thus, the term antibody, as used herein also includes antibody fragments either produced by the modification of whole antibodies or synthesized de novo using recombinant DNA methodologies. Antibodies include single chain antibodies, including single chain Fv (sFv) antibodies in which a variable heavy and a variable light chain are joined together (directly or through a peptide linker) to form a continuous polypeptide.

A variety of additional terms are defined or otherwise characterized herein.

Polynucleotides

Subtilisin Homologue Sequences

The invention provides isolated or recombinant subtilisin homologue polypeptides, and isolated or recombinant polynucleotides encoding the polypeptides. For convenience, comparisons are made to the subtilisin Savinase® and/or the polynucleotide encoding it. The 380 amino acid Savinase® polypeptide consists of an 111 amino acid pre-pro-peptide and the 269 amino acid mature subtilisin, which is released by autolytic cleavage following secretion and folding. The primary structure of the Savinase® polypeptide [GenBank accession no. P29600] is illustrated in FIG. 1 (and in sequence listings 261).

Polynucleotides encoding the polypeptides of the invention were discovered in libraries of subtilisin related sequences. DNA fragments were cloned into a Bacillus expression vector to generate a library of "diversified" region clones, corresponding to amino acids 55 through 227 of the mature protein (as indicated in FIG. 1 in bold). Library members were screened for protease activity, and assayed for a variety of desirable characteristics, including thermal stability, alkaline stability and activity in organic solvents.

Briefly, small libraries, e.g., of 654 active clones in one exemplary trial, were tested for four properties: activity at 23° C., thermostability, solvent stability, and pH dependence. To characterize the library, colonies were grown on casein plates and protease activity was evaluated by the production of clearing halos. Active colonies were grown to stationary phase in LB medium, and the secreted protease was recovered from the medium and diluted 100–200 fold for assay procedures. The protease samples were assayed under five different conditions: pH10; pH5.5, pH7.5; pH7.5 with 35% DMF; and pH10 following heat treatment.

In each condition tested, clones were obtained that outperformed the commercially available subtilisin, Savinase®. The most dramatic increase in total activity was at pH 5.5, where progeny were obtained with a 2–4-fold greater activity than Savinase®. More significant than improvements in single properties, however, are the combinations of desirable properties provided by the proteases of the present invention.

In one set of assays, seventy-seven clones (12%) that performed as well or better than Savinase ® at 23° C. and pH 10 were assayed for the additional properties of residual activity in organic solvent and stability to heat treatment. Nucleic acids encoding proteases with up to three times more residual activity after heat treatment or up to 50% greater residual activity in 35% dimethylformamide (DMF) were obtained. In addition, many clones that produced proteases that were both more heat-stable and more active in organic solvent than Savinase® were also obtained. It will be appreciated that in addition to the properties described above, desirable properties such as psychrophilic activity (i.e., activity at low temperature), activity in the presence of compounds such as hypochlorite, supercritical carbon dioxide, etc., can be isolated from the present library.

Thus, the present invention provides polynucleotide sequences encoding and polypeptide sequences corresponding to subtilisin homologues with one or more desirable properties such as increased thermotolerance, increased activity at ambient temperature, increased activity at alkaline pH, increased activity at acid pH, increased activity at neutral pH, increased activity in the presence of organic solvents, and the like, relative to Savinase®. In some instances, the improved property is a conditional activity, or conditional property. For example, properties that facilitate large scale preparation and/or purification often can be described as conditional activities. Subtilisin homologues with high activity at, e.g., pH 10 relative to pH 7, or with high activity at pH 7 relative to pH10 can be purified at the inactive pH, and then provided in compositions, e.g., detergents, cleaning fluids, with a pH permissive of the high activity, reducing autoproteolysis in the preparation process. Similarly, heat activated or cold activated subtilisin homologues, as well as subtilisin homologues activated by, e.g., reduced ionic strength (as by dilution of a composition of high ionic strength containing a subtilisin homologue) or by binding of a ligand, e.g., a component of a detergent, cleaning solution or cosmetic, can be isolated from among the sequences described herein, or derived therefrom according to the methods described herein.

Exemplary recombinant, e.g., shuffled, nucleic acids which encode the diversified region of subtilisin homologue polypeptides having desirable properties or combinations of properties, or which can be screened to provide additional subtilisin homologues with these or other desirable properties, are provided in SEQ ID NO:1 to SEQ ID NO:130, which encode the diversified region polypeptides identified herein as SEQ ID NO:131 to SEQ ID NO:260. Under many circumstances, including the expression and screening procedures described herein, the diversified regions indicated in the sequence listings are expressed in the context of a mature subtilisin or pre-pro peptide. When expressed in the context of the mature subtilisin protein SEQ ID NO:131 to SEQ ID NO:260 correspond to amino acids 55–227, inclusive.

Making Polynucleotides

Polynucleotides and oligonucleotides of the invention can be prepared by standard solid-phase methods, according to known synthetic methods. Typically, fragments of up to about 100 bases are individually synthesized, then joined (e.g., by enzymatic or chemical ligation methods, or polymerase mediated recombination methods) to form essentially any desired continuous sequence. For example, the polynucleotides and oligonucleotides of the invention can be prepared by chemical synthesis using, e.g., the classical phosphoramidite method described by Beaucage et al. (1981) *Tetrahedron Letters* 22:1859–69, or the method described by Matthes et al. (1984) *EMBO J*. 3: 801–05., e.g., as is typically practiced in automated synthetic methods. According to the phosphoramidite method, oligonucleotides are synthesized, e.g., in an automatic DNA synthesizer, purified, annealed, ligated and cloned in appropriate vectors.

In addition, essentially any nucleic acid can be custom ordered from any of a variety of commercial sources, such as The Midland Certified Reagent Company (mcrc@oligos.com), The Great American Gene Company (http://www.genco.com), ExpressGen Inc. (www.expressgen.com), Operon Technologies Inc. (Alameda, Calif.) and many others. Similarly, peptides and antibodies can be custom ordered from any of a variety of sources, such as PeptidoGenic (pkim@ccnet.com), HTI Bioproducts, inc. (http://www.htibio.com), BMA Biomedicals Ltd (U.K.), Bio.Synthesis, Inc., and many others.

Certain polynucleotides of the invention may also be obtained by screening cDNA libraries (e.g., libraries generated by recombining homologous nucleic acids as in typical shuffling methods) using oligonucleotide probes which can hybridize to or PCR-amplify polynucleotides which encode the subtilisin homologue polypeptides and fragments of those polypeptides. Procedures for screening and isolating cDNA clones are well-known to those of skill in the art. Such techniques are described in, for example, Sambrook et al. (1989) infra, and Ausubel F M et al. (1989; supplemented through 1999) infra. Some polynucleotides of the invention can be obtained by altering a naturally occurring backbone, e.g., by mutagensis or oligonucleotide shuffling. In other cases, such polynucleotides can be made by in silico or oligonucleotide shuffling methods as described in the references cited below.

As described in more detail herein, the polynucleotides of the invention include sequences which encode novel mature subtilisin homologues and sequences complementary to the coding sequences, and novel fragments of coding sequence and complements thereof. The polynucleotides can be in the form of RNA or in the form of DNA, and include mRNA, cRNA, synthetic RNA and DNA, and cDNA. The polynucleotides can be double-stranded or single-stranded, and if single-stranded, can be the coding strand or the non-coding (anti-sense, complementary) strand. The polynucleotides optionally include the coding sequence of a subtilisin homologue (i) in isolation, (ii) in combination with additional coding sequence, so as to encode, e.g., a fusion protein, a pre-protein, a prepro-protein, or the like, (iii) in combination with non-coding sequences, such as introns, control elements such as a promoter, a terminator element, or 5' and/or 3' untranslated regions effective for expression of the coding sequence in a suitable host, and/or (iv) in a vector or host environment in which the subtilisin homologue coding sequence is a heterologous gene. Sequences can also be found in combination with typical compositional formulations of nucleic acids, including in the presence of carriers, buffers, adjuvants, excipients and the like.

Using Polynucleotides

The polynucleotides of the invention have a variety of uses in, for example: recombinant production (i.e., expression) of the subtilisin homologue polypeptides of the invention; as detergent components; in food processing; as immunogens; as diagnostic probes for the presence of complementary or partially complementary nucleic acids (including for detection of natural subtilisin coding nucleic acids; as substrates for further diversity generation, e.g., diversity generating reactions, such as shuffling reactions or mutation reactions, to produce new and/or improved subtilisin homologues, and the like.

EXPRESSION OF POLYPEPTIDES

In accordance with the present invention, polynucleotide sequences which encode novel mature subtilisin homologues, fragments of subtilisin proteins, related fusion proteins, or functional equivalents thereof, collectively referred to herein as "subtilisin homologue polypeptides," or, simply, "subtilisin homologues," are used in recombinant DNA molecules that direct the expression of the subtilisin homologue polypeptides in appropriate host cells, such as bacterial cells. Due to the inherent degeneracy of the genetic code, other nucleic acid sequences which encode substantially the same or a functionally equivalent amino acid sequence are also used to clone and express the subtilisin homologues.

Modified Coding Sequences

As will be understood by those of skill in the art, it can be advantageous to modify a coding sequence to enhance its expression in a particular host. The genetic code is redundant with 64 possible codons, but most organisms preferentially use a subset of these codons. The codons that are utilized most often in a species are called optimal codons, and those not utilized very often are classified as rare or low-usage codons (see, e.g., Zhang S P et al. (1991) *Gene* 105:61–72). Codons can be substituted to reflect the preferred codon usage of the host, a process sometimes called "codon optimization" or "controlling for species codon bias."

Optimized coding sequence containing codons preferred by a particular prokaryotic or eukaryotic host (see also, Murray, E. et al. (1989) *Nuc. Acids Res.* 17:477–508) can be prepared, for example, to increase the rate of translation or to produce recombinant RNA transcripts having desirable properties, such as a longer half-life, as compared with transcripts produced from a non-optimized sequence. Translation stop codons can also be modified to reflect host preference. For example, preferred stop codons for *S. cerevisiae* and mammals are UAA and UGA respectively. The preferred stop codon for monocotyledonous plants is UGA, whereas insects and *E. coli* prefer to use UAA as the stop codon (Dalphin M E et al. (1996) *Nuc. Acids Res.* 24: 216–218).

The polynucleotide sequences of the present invention can be engineered in order to alter a subtilisin homologue coding sequence for a variety of reasons, including but not limited to, alterations which modify the cloning, processing and/or expression of the gene product. For example, alterations may be introduced using techniques that are well known in the art, e.g., site-directed mutagenesis, to insert new restriction sites, alter glycosylation patterns, change codon preference, introduce splice sites, etc.

Vectors, Promoters and Expression Systems

The present invention also includes recombinant constructs comprising one or more of the nucleic acid sequences as broadly described above. The constructs comprise a vector, such as, a plasmid, a cosmid, a phage, a virus, a bacterial artificial chromosome (BAC), a yeast artificial chromosome (YAC), or the like, into which a nucleic acid sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available.

General texts which describe molecular biological techniques useful herein, including the use of vectors, promoters and many other relevant topics, include Berger and Kimmel, *Guide to Molecular Cloning Techniques, Methods in Enzymology* volume 152 Academic Press, Inc., San Diego, Calif. (Berger); Sambrook et al., *Molecular Cloning—A Laboratory Manual* (2nd Ed.), Vol. 1–3, Cold Spring Harbor Laboratory, Cold Spring Harbor, N.Y., 1989 ("Sambrook") and *Current Protocols in Molecular Biology*, F. M. Ausubel et al., eds., Current Protocols, a joint venture between Greene Publishing Associates, Inc. and John Wiley & Sons, Inc., (supplemented through 1999) ("Ausubel"). Examples of protocols sufficient to direct persons of skill through in vitro amplification methods, including the polymerase chain reaction (PCR) the ligase chain reaction (LCR), Qβ-replicase amplification and other RNA polymerase mediated techniques (e.g., NASBA), e.g., for the production of the homologous nucleic acids of the invention are found in Berger, Sambrook, and Ausubel, as well as Mullis et al. (1987) U.S. Pat. No. 4,683,202; *PCR Protocols A Guide to Methods and Applications* (Innis et al. eds) Academic Press Inc. San Diego, Calif. (1990) (Innis); Arnheim & Levinson (Oct. 1, 1990) *C&EN* 36–47; *The Journal Of NIH Research* (1991) 3:81–94; Kwoh et al. (1989) *Proc. Natl. Acad. Sci. USA* 86:1173; Guatelli et al. (1990) *Proc. Natl. Acad. Sci. USA* 87:1874; Lomell et al. (1989) *J. Clin. Chem* 35:1826; Landegren et al. (1988) *Science* 241:1077–1080; Van Brunt (1990) *Biotechnology* 8:291–294; Wu and Wallace (1989) *Gene* 4:560; Barringer et al. (1990) *Gene* 89:117, and Sooknanan and Malek (1995) *Biotechnology* 13:563–564. Improved methods for cloning in vitro amplified nucleic acids are described in Wallace et al., U.S. Pat. No. 5,426,039. Improved methods for amplifying large nucleic acids by PCR are summarized in Cheng et al. (1994) *Nature* 369:684–685 and the references cited therein, in which PCR amplicons of up to 40kb are generated. One of skill will appreciate that essentially any RNA can be converted into a double stranded DNA suitable for restriction digestion, PCR expansion and sequencing using reverse transcriptase and a polymerase. See, e.g., Ausubel, Sambrook and Berger, all supra.

The present invention also relates to engineered host cells that are transduced (transformed or transfected) with a vector of the invention (e.g., an invention cloning vector or an invention expression vector), as well as the production of polypeptides of the invention by recombinant techniques. The vector may be, for example, a plasmid, a viral particle, a phage, etc., or a non-replicating vector, such as liposomes, naked or conjugated DNA, DNA-microparticles, etc. The engineered host cells can be cultured in conventional nutrient media modified as appropriate for activating promoters, selecting transformants, or amplifying the subtilisin homologue gene. Culture conditions, such as temperature, pH and the like, are those previously used with the host cell selected for expression, and will be apparent to those skilled in the art and in the references cited herein, including, e.g., Sambrook, Ausubel and Berger, as well as e.g., Freshney (1994) *Culture of Animal Cells, a Manual of Basic Technique*, third edition, Wiley-Liss, New York and the references cited therein.

Subtilisin homologue proteins of the invention can be produced in non-animal cells such as plants, yeast, fungi, bacteria and the like. In addition to Sambrook, Berger and Ausubel, details regarding non-animal cell culture can be found in Payne et al. (1992) *Plant Cell and Tissue Culture in Liquid Systems* John Wiley & Sons, Inc. New York, N.Y.; Gamborg and Phillips (eds) (1995) *Plant Cell, Tissue and Organ Culture*; Fundamental Methods Springer Lab Manual, Springer-Verlag (Berlin Heidelberg N.Y.) and Atlas and Parks (eds) *The Handbook of Microbiological Media* (1993) CRC Press, Boca Raton, Fla.

Polynucleotides of the present invention can be incorporated into any one of a variety of expression vectors suitable for expressing a polypeptide. Suitable vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, pseudorabies, adenovirus, adeno-associated virus, retroviruses and many others. Any vector that transduces genetic material into a cell, and, if replication is desired, which is replicable and viable in the relevant host can be used.

When incorporated into an expression vector, the invention polynucleotide is operatively linked to an appropriate transcription control sequence (promoter) to direct mRNA synthesis. Examples of such transcription control sequences include: LTR or SV40 promoter, *E. coli* lac or trp promoter, phage lambda $P_L$ promoter, and other promoters known to control expression of genes in prokaryotic or eukaryotic cells or their viruses. This invention expression vector, optionally contains a ribosome binding site for translation initiation, and a transcription terminator. The vector also optionally includes appropriate sequences for amplifying expression, e.g., an enhancer. In addition, the expression vectors of the present invention optionally contain one or more selectable marker genes to provide a phenotypic trait for selection of transformed host cells, such as dihydrofolate reductase or neomycin resistance for eukaryotic cell culture, or such as tetracycline or ampicillin resistance in *E. coli*.

Vectors of the present invention can be employed to transform an appropriate host to permit the host to express an invention protein or polypeptide. Examples of appropriate expression hosts include: bacterial cells, such as *E. coli, B. subtilis*, Streptomyces, and *Salmonella typhimurium*; fungal cells, such as *Saccharomyces cerevisiae, Pichia pastoris*, and *Neurospora crassa*; insect cells such as Drosophila and *Spodoptera frugiperda*; mammalian cells such as CHO, COS, BHK, HEK 293 or Bowes melanoma; plant cells, etc. It is understood that not all cells or cell lines need to be capable of producing fully functional subtilisin homologues; for example, antigenic fragments of an subtilisin homologue may be produced. The invention is not limited by the host cells employed.

In bacterial systems, a number of expression vectors may be selected depending upon the use intended for the subtilisin homologue. For example, when large quantities of subtilisin homologue or fragments thereof are needed for commercial production or for induction of antibodies, vectors which direct high level expression of fusion proteins that are readily purified can be desirable. Such vectors include, but are not limited to, multifunctional *E. coli* cloning and expression vectors such as BLUESCRIPT (Stratagene), in which the subtilisin homologue coding sequence may be ligated into the vector in-frame with sequences for the amino-terminal Met and the subsequent 7 residues of beta-galactosidase so that a hybrid protein is produced; pIN vectors (Van Heeke & Schuster (1989) *J Biol Chem* 264:5503–5509); pET vectors (Novagen, Madison Wis.); and the like.

Similarly, in the yeast *Saccharomyces cerevisiae* a number of vectors containing constitutive or inducible promoters such as alpha factor, alcohol oxidase and PGH may be used for production of the subtilisin homologue polypeptides of the invention. For reviews, see Ausubel et al. (supra) and Grant et al. (1987) *Methods in Enzymology* 153:516–544).

In mammalian host cells, a variety of expression systems, including viral-based systems, may be utilized. In cases where an adenovirus is used as an expression vector, a coding sequence, e.g., of a subtilisin homologue polypeptide, is optionally ligated into an adenovirus transcription/translation complex consisting of the late promoter and tripartite leader sequence. Insertion of a subtilisin polypeptide coding region into a nonessential E1 or E3 region of the viral genome will result in a viable virus capable of expressing subtilisin homologue in infected host cells (Logan and Shenk (1984) *Proc Natl Acad Sci USA* 81:3655–3659). In addition, transcription enhancers, such as the rous sarcoma virus (RSV) enhancer, may be used to increase expression in mammalian host cells.

Additional Expression Elements

Specific initiation signals can aid in efficient translation of a subtilisin homologue coding sequence of the present invention. These signals can include, e.g., the ATG initiation codon and adjacent sequences. In cases where a subtilisin homologue coding sequence, its initiation codon and upstream sequences are inserted into an appropriate expression vector, no additional translational control signals may be needed. However, in cases where only coding sequence (e.g., a mature protein coding sequence), or a portion thereof, is inserted, exogenous transcriptional control signals including the ATG initiation codon must be provided. Furthermore, the initiation codon must be in the correct reading frame to ensure transcription of the entire insert. Exogenous transcriptional elements and initiation codons can be of various origins, both natural and synthetic. The efficiency of expression may be enhanced by the inclusion of enhancers appropriate to the cell system in use (Scharf et al. (1994) *Results Probl Cell Differ* 20:125–62; Bittner et al. (1987) *Methods in Enzymol.* 153:516–544).

Secretion/Localization Sequences

Polynucleotides of the invention can also be fused, for example, in-frame to nucleic acids encoding a secretion/localization sequence, to target polypeptide expression to a desired cellular compartment, membrane, or organelle of a mammalian cell, or to direct polypeptide secretion to the periplasmic space or into the cell culture media. Such sequences are known to those of skill, and include secretion leader peptides, organelle targeting sequences (e.g., nuclear localization sequences, ER retention signals, mitochondrial transit sequences, chloroplast transit sequences), membrane localization/anchor sequences (e.g., stop transfer sequences, GPI anchor sequences), and the like.

Expression Hosts

In a further embodiment, the present invention relates to host cells containing the above-described constructs. The host cell can be a eukaryotic cell, such as a mammalian cell, a yeast cell, or a plant cell, or the host cell can be a prokaryotic cell, such as a bacterial cell. Introduction of the construct into the host cell can be effected by calcium phosphate transfection, DEAE-Dextran mediated transfection, electroporation, or other common techniques (Davis et al. (1986) *Basic Methods in Molecular Biology*).

A host cell strain is optionally chosen for its ability to modulate the expression of the inserted sequences or to process the expressed protein in the desired fashion. Such modifications of the protein include, but are not limited to, acetylation, carboxylation, glycosylation, phosphorylation, lipidation and acylation. Post-translational processing which cleaves a "pre" or a "prepro" form of the protein may also be important for correct insertion, folding and/or function. Different host cells such as *E. coli*, Bacillus sp., yeast or mammalian cells such as CHO, HeLa, BHK, MDCK, 293, WI38, etc. have specific cellular machinery and characteristic mechanisms, e.g., for post-translational activities and may be chosen to ensure the desired modification and processing of the introduced, foreign protein.

For long-term, high-yield production of recombinant proteins, stable expression systems can be used. For example, cell lines which stably express a polypeptide of the invention are transduced using expression vectors which contain viral origins of replication or endogenous expression elements and a selectable marker gene. Following the introduction of the vector, cells may be allowed to grow for a period determined to be appropriate for the cell type, e.g., 1–2 days for mammalian cell, 1 or more hours for bacterial cells, in an enriched media before they are switched to selective media. The purpose of the selectable marker is to confer resistance to selection, and its presence allows growth and recovery of cells which successfully express the introduced sequences. For example, resistant clumps of stably transformed cells can be proliferated using tissue culture techniques appropriate to the cell type.

Host cells transformed with a nucleotide sequence encoding a polypeptide of the invention are optionally cultured under conditions suitable for the expression and recovery of the encoded protein from cell culture. The protein or fragment thereof produced by a recombinant cell may be secreted, membrane-bound, or contained intracellularly, depending on the sequence and/or the vector used. As will be understood by those of skill in the art, expression vectors containing polynucleotides encoding mature subtilisin homologues of the invention can be designed with signal sequences which direct secretion of the mature polypeptides through a prokaryotic or eukaryotic cell membrane.

Additional Polypeptide Sequences

Polynucleotides of the present invention may also comprise a coding sequence fused in-frame to a marker sequence which, e.g., facilitates purification of the encoded polypeptide. Such purification facilitating domains include, but are not limited to, metal chelating peptides such as histidine-tryptophan modules that allow purification on immobilized metals, a sequence which binds glutathione (e.g., GST), a hemagglutinin (HA) tag (corresponding to an epitope derived from the influenza hemagglutinin protein; Wilson et al. (1984) *Cell* 37:767), maltose binding protein sequences, the FLAG epitope utilized in the FLAGS extension/affinity purification system (Immunex Corp, Seattle, Wash.), and the like. The inclusion of a protease-cleavable polypeptide linker sequence between the purification domain and the subtilisin homologue sequence is useful to facilitate purification. One expression vector contemplated for use in the compositions and methods described herein provides for expression of a fusion protein comprising a polypeptide of the invention fused to a polyhistidine region separated by an enterokinase cleavage site. The histidine residues facilitate purification on IMIAC (immobilized metal ion affinity chromatography, as described in Porath et al. (1992) *Protein Expression and Purification* 3:263–281) while the enterokinase cleavage site provides a means for separating the subtilisin homologue polypeptide from the fusion protein. pGEX vectors (Promega; Madison, Wis.) may also be used to express foreign polypeptides as fusion proteins with glutathione S-transferase (GST). In general, such fusion proteins are soluble and can easily be purified from lysed cells by adsorption to ligand-agarose beads (e.g., glutathione-agarose in the case of GST-fusions) followed by elution in the presence of free ligand.

Polypeptide Production and Recovery

Following transduction of a suitable host strain and growth of the host strain to an appropriate cell density, the selected promoter is induced by appropriate means (e.g., temperature shift or chemical induction) and cells are cultured for an additional period. Cells are typically harvested by centrifugation, disrupted by physical or chemical means, and the resulting crude extract retained for further purification. Microbial cells employed in expression of proteins can be disrupted by any convenient method, including freeze-thaw cycling, sonication, mechanical disruption, or use of cell lysing agents, or other methods, which are well known to those skilled in the art.

As noted, many references are available for the culture and production of many cells, including cells of bacterial, plant, animal (especially mammalian) and archebacterial origin. See, e.g., Sambrook, Ausubel, and Berger (all supra), as well as Freshney (1994) *Culture of Animal Cells, a Manual of Basic Technique*, third edition, Wiley-Liss, New York and the references cited therein; Doyle and Griffiths (1997) *Mammalian Cell Culture: Essential Techniques* John Wiley and Sons, NY; Humason (1979) *Animal Tissue Techniques*, fourth edition W. H. Freeman and Company; and Ricciardelli, et al. (1989) *In vitro Cell Dev. Biol.* 25:1016–1024. For plant cell culture and regeneration, Payne et al. (1992) *Plant Cell and Tissue Culture in Liquid Systems* John Wiley & Sons, Inc. New York, N.Y.; Gamborg and Phillips (eds) (1995) *Plant Cell, Tissue and Organ Culture*; Fundamental Methods Springer Lab Manual, Springer-Verlag (Berlin Heidelberg N.Y.) and *Plant Molecular Biolgy* (1993) R. R. D. Croy, Ed. Bios Scientific Publishers, Oxford, U.K. ISBN 0 12 198370 6. Cell culture media in general are set forth in Atlas and Parks (eds) *The Handbook of Microbiological Media* (1993) CRC Press, Boca Raton, Fla. Additional information for cell culture is found in available commercial literature such as the *Life Science Research Cell Culture Catalogue* (1998) from Sigma-Aldrich, Inc (St Louis, Mo.) ("Sigma-LSRCCC") and, e.g., the *Plant Culture Catalogue* and supplement (1997) also from Sigma-Aldrich, Inc (St Louis, Mo.) ("Sigma-PCCS").

Polypeptides of the invention can be recovered and purified from recombinant cell cultures by any of a number of methods well known in the art, including ammonium sulfate or ethanol precipitation, acid extraction, anion or cation exchange chromatography, phosphocellulose chromatography, hydrophobic interaction chromatography, affinity chromatography (e.g., using any of the tagging systems noted herein), hydroxylapatite chromatography, and lectin chromatography. Protein refolding steps can be used, as desired, in completing the configuration of the mature protein. Finally, high performance liquid chromatography (HPLC) can be employed in the final purification steps. In addition to the references noted supra, a variety of purification methods are well known in the art, including, e.g., those set forth in Sandana (1997) *Bioseparation of Proteins*, Academic Press, Inc.; and Bollag et al. (1996) *Protein Methods, $2^{nd}$ Edition* Wiley-Liss, NY; Walker (1996) *The Protein Protocols Handbook* Humana Press, NJ, Harris and Angal (1990) *Protein Purification Applications: A Practical Approach* IRL Press at Oxford, Oxford, England; Harris and Angal *Protein Purification Methods: A Practical Approach* IRL Press at Oxford, Oxford, England; Scopes (1993) *Protein Purification: Principles and Practice $3^{rd}$ Edition* Springer Verlag, NY; Janson and Ryden (1998) *Protein Purification: Principles, High Resolution Methods and Applications, Second Edition* Wiley-VCH, NY; and Walker (1998) *Protein Protocols on CD-ROM* Humana Press, NJ.

In some cases it is desirable to produce the subtilisin homologues of the invention in a large scale suitable for industrial and/or commercial applications. In such cases bulk fermentation procedures are employed. Briefly, polynucleotides comprising any one of SEQ ID NO:1 to SEQ ID NO:130, or other nucleic acids encoding subtilisin homologues of the invention can be cloned into an expression vector. For example, U.S. Pat. No. 5,955,310 to Widner et al. "METHODS FOR PRODUCING A POLYPEPTIDE IN A BACILLUS CELL," describes a vector with tandem promoters, and stabilizing sequences operably linked to a polypeptide encoding sequence. After inserting the polynucleotide of interest into a vector, the vector is transformed into a bacterial, e.g., a *Bacillus subtilis* strain PL1801IIE (amyE, apr, npr, spoIIE::Tn917) host. The introduction of an expression vector into a Bacillus cell may, for instance, be effected by protoplast transformation (see, e.g., Chang and Cohen (1979) *Molecular General Genetics* 168:111), by using competent cells (see, e.g., Young and Spizizin (1961) *Journal of Bacteriology* 81:823, or Dubnau and Davidoff-Abelson (1971) *Journal of Molecular Biology* 56:209), by electroporation (see, e.g., Shigekawa and Dower (1988) *Biotechniques* 6:742), or by conjugation (see, e.g., Koehler and Thorne (1987)*Journal of Bacteriology* 169:5271), also Ausubel, Sambrook and Berger, all supra.

The transformed cells are cultivated in a nutrient medium suitable for production of the polypeptide using methods that are known in the art. For example, the cell may be cultivated by shake flask cultivation, small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). The secreted polypeptide can be recovered directly from the medium.

The resulting polypeptide may be isolated by methods known in the art. For example, the polypeptide may be isolated from the nutrient medium by conventional procedures including, but not limited to, centrifugation, filtration, extraction, spray-drying, evaporation, or precipitation. The isolated polypeptide may then be further purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), or extraction (see, e.g., Bollag et al. (1996) *Protein Methods, $2^{nd}$ Edition* Wiley-Liss, NY; Walker (1996) *The Protein Protocols Handbook* Humana Press, NJ; Bollag et al. (1996) *Protein Methods, $2^{nd}$ Edition* Wiley-Liss, NY; Walker (1996) *The Protein Protocols Handbook* Humana Press, NJ).

In Vitro Expression Systems

Cell-free transcription/translation systems can also be employed to produce polypeptides using DNAs or RNAs of the present invention. Several such systems are commercially available. A general guide to in vitro transcription and translation protocols is found in Tymms (1995) *In vitro Transcription and Translation Protocols: Methods in Molecular Biology* Volume 37, Garland Publishing, NY.

(ix) Modified Amino Acids: Polypeptides of the invention may contain one or more modified amino acid. The presence of modified amino acids may be advantageous in, for example, (a) increasing polypeptide serum half-life, (b)

reducing polypeptide antigenicity, (c) increasing polypeptide storage stability. Amino acid(s) are modified, for example, co-translationally or post-translationally during recombinant production (e.g., N-linked glycosylation at N-X-S/T motifs during expression in mammalian cells) or modified by synthetic means.

Non-limiting examples of a modified amino acid include a glycosylated amino acid, a sulfated amino acid, a prenlyated (e.g., farnesylated, geranylgeranylated) amino acid, an acetylated amino acid, an acylated amino acid, a PEG-ylated amino acid, a biotinylated amino acid, a carboxylated amino acid, a phosphorylated amino acid, and the like. References adequate to guide one of skill in the modification of amino acids are replete throughout the literature. Example protocols are found in Walker (1998) *Protein Protocols on CD-ROM* Human Press, Towata, N.J.

Use as Probes

Also contemplated are uses of polynucleotides, also referred to herein as oligonucleotides, typically having at least 12 bases, preferably at least 15, more preferably at least 20, 30, or 50 or more bases, which hybridize under highly stringent conditions to an subtilisin homologue polynucleotide sequence described above. The polynucleotides may be used as probes, primers, sense and antisense agents, and the like, according to methods as noted supra.

Sequence Variations

Silent Variations

It will be appreciated by those skilled in the art that due to the degeneracy of the genetic code, a multitude of nucleic acids sequences encoding subtilisin homologue polypeptides of the invention may be produced, some of which bear substantial identity to the nucleic acid sequences explicitly disclosed herein.

TABLE 1

Codon Table

| Amino acids | | | Codon | | | |
|---|---|---|---|---|---|---|
| Alanine | Ala | A | GCA | GCC | GCG | GCU |
| Cysteine | Cys | C | UGC | UGU | | |
| Aspartic acid | Asp | D | GAC | GAU | | |
| Glutamic acid | Glu | E | GAA | GAG | | |
| Phenylalanine | Phe | F | UUC | UUU | | |
| Glycine | Gly | G | GGA | GGC | GGG | GGU |
| Histidine | His | H | CAC | CAU | | |
| Isoleucine | Ile | I | AUA | AUC | AUU | |
| Lysine | Lys | K | AAA | AAG | | |
| Leucine | Leu | L | UUA | UUG | CUA CUC CUG CUU | |
| Methionine | Met | M | AUG | | | |
| Asparagine | Asn | N | AAC | AAU | | |
| Proline | Pro | P | CCA | CCC | CCG | CCU |
| Glutamine | Gln | Q | CAA | CAG | | |
| Arginine | Arg | R | AGA | AGG CGA CGC CGG CGU | | |
| Serine | Ser | S | AGC | AGU UCA UCC UCG UCU | | |
| Threonine | Thr | T | ACA | ACC | ACG | ACU |
| Valine | Val | V | GUA | GUC | GUG | GUU |
| Tryptophan | Trp | W | UGG | | | |
| Tyrosine | Tyr | Y | UAC | UAU | | |

For instance, inspection of the codon table (Table 1) shows that codons AGA, AGG, CGA, CGC, CGG, and CGU all encode the amino acid arginine.

Thus, at every position in the nucleic acids of the invention where an arginine is specified by a codon, the codon can be altered to any of the corresponding codons described above without altering the encoded polypeptide. It is understood that U in an RNA sequence corresponds to T in a DNA sequence.

Using, as an example, the nucleic acid sequence corresponding to nucleotides 2–16 of SEQ ID NO:1, TCG ACT CAA GAT GGG, a silent variation of this sequence includes AGT ACC CAG GAC GGA (SEQ ID NO: 263), both sequences which encode the amino acid sequence STQDG, corresponding to amino acids 1–5 of SEQ ID NO:131.

Such "silent variations" are one species of "conservatively modified variations", discussed below. One of skill will recognize that each codon in a nucleic acid (except AUG, which is ordinarily the only codon for methionine) can be modified by standard techniques to encode a functionally identical polypeptide. Accordingly, each silent variation of a nucleic acid which encodes a polypeptide is implicit in any described sequence. The invention provides each and every possible variation of nucleic acid sequence encoding a polypeptide of the invention that could be made by selecting combinations based on possible codon choices. These combinations are made in accordance with the standard triplet genetic code (e.g., as set forth in Table 1) as applied to the nucleic acid sequence encoding an subtilisin homologue polypeptide of the invention. All such variations of every nucleic acid herein are specifically provided and described by consideration of the sequence in combination with the genetic code. Any variant can be produced as noted herein.

Conservative Variations

"Conservatively modified variations" or, simply, "conservative variations" of a particular nucleic acid sequence refers to those nucleic acids which encode identical or essentially identical amino acid sequences, or, where the nucleic acid does not encode an amino acid sequence, to essentially identical sequences. One of skill will recognize that individual substitutions, deletions or additions which alter, add or delete a single amino acid or a small percentage of amino acids (typically less than about 5%, more typically less than about 4%, about 2% or about 1%) in an encoded sequence are "conservatively modified variations" where the alterations result in the deletion of an amino acid, addition of an amino acid, or substitution of an amino acid with a chemically similar amino acid.

Conservative substitution tables providing functionally similar amino acids are well known in the art. Table 2 sets forth six groups which contain amino acids that are "conservative substitutions" for one another.

TABLE 2

Conservative Substitution Groups

| | | | |
|---|---|---|---|
| 1 | Alanine (A) | Serine (S) | Threonine (T) |
| 2 | Aspartic acid (D) | Glutamic acid (E) | |
| 3 | Asparagine (N) | Glutamine (Q) | |
| 4 | Arginine (R) | Lysine (K) | |
| 5 | Isoleucine (I) | Leucine (L) | Methionine (M) Valine (V) |
| 6 | Phenylalanine (F) | Tyrosine (Y) | Tryptophan (W) |

Thus, "conservatively substituted variations" of a listed polypeptide sequence of the present invention include substitutions of a small percentage, typically less than about 5%, more typically less than about 2% and often less than about 1%, of the amino acids of the polypeptide sequence, with a conservatively selected amino acid of the same conservative substitution group.

For example, a conservatively substituted variation of the polypeptide identified herein as SEQ ID NO:131 will contain "conservative substitutions", according to the six groups defined above, in up to 8 residues (i.e., about 5% of the amino acids) in the 169 amino acid polypeptide.

In a further example, if four conservative substitutions were localized in the region corresponding to amino acids 25 to 35 of SEQ ID NO:131, examples of conservatively substituted variations of this region, AAL NNS IGV L (SEQ ID NO: 264), include:

AAL QNA LGV V (SEQ ID NO: 265) and

AAL QNT VGV M (SEQ ID NO: 266) and the like, in accordance with the conservative substitutions listed in Table 2 (in the above example, conservative substitutions are underlined). Listing of a protein sequence herein, in conjunction with the above substitution table, provides an express listing of all conservatively substituted proteins.

Finally, the addition of sequences which do not alter the encoded activity of a nucleic acid molecule, such as the addition of a non-functional or non-coding sequence, is a conservative variation of the basic nucleic acid.

One of skill will appreciate that many conservative variations of the nucleic acid constructs which are disclosed yield a functionally identical construct. For example, as discussed above, owing to the degeneracy of the genetic code, "silent substitutions" (i.e., substitutions in a nucleic acid sequence which do not result in an alteration in an encoded polypeptide) are an implied feature of every nucleic acid sequence which encodes an amino acid. Similarly, "conservative amino acid substitutions," in one or a few amino acids in an amino acid sequence are substituted with different amino acids with highly similar properties, are also readily identified as being highly similar to a disclosed construct. Such conservative variations of each disclosed sequence are a feature of the present invention.

Non Conservative Variations

Non-conservative modifications of a particular nucleic acid are those which substitute any amino acid not characterized as a conservative substitution. For example, any substitution which crosses the bounds of the six groups set forth in Table 2. These include substitutions of basic or acidic amino acids for neutral amino acids, (e.g., Asp, Glu, Asn, or Gln for Val, Ile, Leu or Met), aromatic amino acid for basic or acidic amino acids (e.g., Phe, Tyr or Trp for Asp, Asn, Glu or Gln) or any other substitution not replacing an amino acid with a like amino acid.

Percent Sequence Identity-Sequence Similarity

As noted above, the polypeptides and nucleic acids employed in the subject invention need not be identical, but can be substantially identical (or substantially similar), to the corresponding sequence of a subtilisin homologue molecule or related molecule. The polypeptides (and peptides) can be subject to various changes, such as insertions, deletions, and substitutions, either conservative or non-conservative, where such changes might provide for certain advantages in their use. The polypeptides of the invention can be modified in a number of ways so long as they comprise a sequence substantially similar or substantially identical (as defined below) to a sequence in a subtilisin homologue molecule.

Alignment and comparison of relatively short amino acid sequences (less than about 30 residues) is typically straightforward. Comparison of longer sequences can require more sophisticated methods to achieve optimal alignment of two sequences. Optimal alignment of sequences for aligning a comparison window can be conducted by the local homology algorithm of Smith and Waterman (1981) *Adv Appl Math* 2:482, by the homology alignment algorithm of Needleman and Wunsch (1970) *J Mol Biol* 48:443, by the search for similarity method of Pearson and Lipman (1988) *Proc Natl Acad Sci USA* 85:2444, by computerized implementations of these algorithms (GAP, BESTFIT, FASTA and TFASTA in the Wisconsin Genetics Software Package Release 7.0, Genetics Computer Group, 575 Science Dr., Madison, Wis.; and BLAST, see, e.g., Altschul et al., (1977) *Nuc Acids Res* 25:3389–3402 and Altschul et al., (1990) *J Mol Biol* 215:403–410), or by inspection, with the best alignment (i.e., resulting in the highest percentage of sequence similarity over the comparison window) generated by the various methods being selected.

The term "sequence identity" means that two polynucleotide sequences are identical (i.e., on a nucleotide-by-nucleotide basis) over a window of comparison. The term "percentage of sequence identity" or "percentage of sequence similarity" is calculated by comparing two optimally aligned sequences over the window of comparison, determining the number of positions at which the identical residues occur in both nucleotide sequences to yield the number of matched positions, dividing the number of matched positions by the total number of positions in the window of comparison (i.e., the window size), and multiplying the result by 100 to yield the percentage of sequence identity (or percentage of sequence similarity). With regard to polypeptide sequences, the term sequence identity likewise means that two polypeptide sequences are identical (on an amino acid-by-amino acid basis) over a window of comparison, and a percentage of amino acid residue sequence identity (or percentage of amino acid residue sequence similarity), also can be calculated. Maximum correspondence can be determined by using one of the sequence algorithms described herein (or other algorithms available to those of ordinary skill in the art) or by visual inspection.

As applied to polypeptides, the term substantial identity or substantial similarity means that two peptide sequences, when optimally aligned, such as by the programs BLAST, GAP or BESTFIT using default gap weights (described in detail below) or by visual inspection, share at least about 60 percent, 70 percent, or 80 percent sequence identity or sequence similarity, preferably at least about 90 percent amino acid residue sequence identity or sequence similarity, more preferably at least about 95 percent sequence identity or sequence similarity, or more (including, e.g., about 96, 97, 98, 98.5, 99, 99.5 or more percent amino acid residue sequence identity or sequence similarity). Similarly, as applied in the context of two nucleic acids, the term substantial identity or substantial similarity means that the two nucleic acid sequences, when optimally aligned, such as by the programs BLAST, GAP or BESTFIT using default gap weights (described in detail below) or by visual inspection, share at least about 60 percent, 70 percent, or 80 percent sequence identity or sequence similarity, preferably at least about 90 percent amino acid residue sequence identity or sequence similarity, more preferably at least about 95 percent sequence identity or sequence similarity, or more (including, e.g., about 96, 97, 98, 98.5, 99, 99.5 or more percent nucleotide sequence identity or sequence similarity).

In one aspect, the present invention provides subtilisin homologue nucleic acids having at least about 70%, 80%, 85%, 90%, 95%, 96%, 97%, 98%, 98.5%, 99%, 99.5% or more percent sequence identity or sequence similarity with the nucleic acid sequences of any of SEQ ID NOs: 1–130 or fragments thereof. In another aspect, the present invention provides subtilisin homologue polypeptides having at least about 70%, 80%, 85%, 90%, 95%, 96%, 97%, 98%, 98.5, 99%, 99.5% or more percent sequence identity or sequence similarity with the amino acid sequences of any of SEQ ID NOs: 131–260, or fragments thereof that exhibit endoprotease activity. In yet another aspect, the present invention provides subtilisin homologue polypeptides that are substantially identical or substantially similar over at least about 20 (or about 30, 40, 60, 80, 100 or more) contiguous amino acids of at least one of SEQ ID NOs: 131–260; some such polypeptides may exhibit improved properties such as thermostability, activity at low or neutral pH, or activity in organic solvents, and the like.

Alternatively, parameters are set such that one or more sequences of the invention are identified by alignment to a query sequence selected from among SEQ ID NO:1 to SEQ ID NO:130, while sequences corresponding to unrelated polypeptides, e.g., those encoded by nucleic acid sequence represented by GenBank accession numbers: M65086, D13157, S48754, AB005792, D29688, and M28537, are not identified.

Preferably, residue positions which are not identical differ by conservative amino acid substitutions. Conservative amino acid substitution refers to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine.

A preferred example of an algorithm that is suitable for determining percent sequence identity or sequence similarity is the FASTA algorithm, which is described in Pearson, W. R. & Lipman, D. J., (1988) *Proc Natl Acad Sci USA* 85:2444. See also, W. R. Pearson, (1996) *Methods Enzymology* 266:227–258. Preferred parameters used in a FASTA alignment of DNA sequences to calculate percent identity or percent similarity are optimized, BL50 Matrix 15: −5, k-tuple=2; joining penalty=40, optimization=28; gap penalty −12, gap length penalty=−2; and width=16.

Other preferred examples of algorithms that are suitable for determining percent sequence identity or sequence similarity are the BLAST and BLAST 2.0 algorithms, which are described in Altschul et al., (1977) *Nuc Acids Res* 25:3389–3402 and Altschul et al., (1990) *J Mol Biol* 215:403–410, respectively. BLAST and BLAST 2.0 are used, with the parameters described herein, to determine percent sequence identity or percent sequence similarity for the nucleic acids and polypeptides and proteins of the invention. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see, Henikoff & Henikoff, (1989) *Proc Natl Acad Sci USA* 89:10915) uses alignments (B) of 50, expectation (E) of 10, M=5, N=−4, and a comparison of both strands. Again, as with other suitable algorithms, the stringency of comparison can be increased until the program identifies only sequences that are more closely related to those in the sequence listings herein (i.e., SEQ ID NO:1 to SEQ ID NO:130 or, alternatively, SEQ ID NO:131 to SEQ ID NO:260), rather than sequences that are more closely related to other similar sequences such as, e.g., those nucleic acid sequences represented by GenBank accession numbers: M65086, D13157, S48754, AB005792, D29688, and M28537 or other similar molecules found in, e.g., GenBank. In other words, the stringency of comparison of the algorithms can be increased so that all known prior art (e.g., those represented by GenBank accession numbers: M65086, D13157, S48754, AB005792, D29688, and M28537 or other similar molecules found in, e.g., GenBank, as well as sequences represented by GenBank accession numbers: P29600, P41362, P29599, P27693, P20724, P41363, P00780, P00781, P35835, P00783, P29142, P04189, P07518, P00782, P04072, P16396, P29140, P29139, P08594, P16588, P11018, P54423, P40903, P23314, P23653, P33295, P42780, and P80146) is excluded.

The BLAST algorithm also performs a statistical analysis of the similarity or identity between two sequences (see, e.g., Karlin & Altschul, (1993) *Proc Natl Acad Sci USA* 90:5873–5787). One measure of similarity or identity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

Another example of a useful algorithm is PILEUP. PILEUP creates a multiple sequence alignment from a group of related sequences using progressive, pairwise alignments to show relationship and percent sequence identity or percent sequence similarity. It also plots a tree or dendogram showing the clustering relationships used to create the alignment. PILEUP uses a simplification of the progressive alignment method of Feng & Doolittle, (1987) *J Mol Evol* 35:351–360. The method used is similar to the method described by Higgins & Sharp, (1989) *CABIOS* 5:151–153. The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. Using PILEUP, a reference sequence is compared to other test sequences to determine the percent sequence identity (or percent sequence similarity) relationship using the following parameters: default gap weight (3.00), default gap length weight (0.10), and weighted end gaps. PILEUP can be obtained from the GCG sequence analysis software package, e.g., version 7.0 (Devereaux et al., (1984) *Nuc Acids Res* 12:387–395).

Another preferred example of an algorithm that is suitable for multiple DNA and amino acid sequence alignments is the CLUSTALW program (Thompson, J. D. et al., (1994) *Nuc Acids Res* 22:4673–4680). CLUSTALW performs multiple pairwise comparisons between groups of sequences and assembles them into a multiple alignment based on homology. Gap open and Gap extension penalties were 10 and 0.05 respectively. For amino acid alignments, the BLOSUM algorithm can be used as a protein weight matrix (Henikoff and Henikoff, (1992) *Proc Natl Acad Sci USA* 89:10915–10919).

It will be understood by one of ordinary skill in the art, that the above discussion of search and alignment algorithms also applies to identification and evaluation of polynucleotide sequences, with the substitution of query sequences comprising nucleotide sequences, and where appropriate, selection of nucleic acid databases.

Nucleic Acid Hybridization

Nucleic acids "hybridize" when they associate, typically in solution. Nucleic acids hybridize due to a variety of well characterized physico-chemical forces, such as hydrogen bonding, solvent exclusion, base stacking and the like. An extensive guide to the hybridization of nucleic acids is found in Tijssen (1993) *Laboratory Techniques in Biochemistry and Molecular Biology—Hybridization with Nucleic Acid Probes* part I chapter 2, "Overview of principles of hybridization and the strategy of nucleic acid probe assays," (Elsevier, N.Y.), as well as in Ausubel, supra. Hames and Higgins (1995) *Gene Probes* 1 IRL Press at Oxford University Press, Oxford, England, (Hames and Higgins 1) and Hames and Higgins (1995) *Gene Probes* 2 IRL Press at Oxford University Press, Oxford, England (Hames and Higgins 2) provide details on the synthesis, labeling, detection and quantification of DNA and RNA, including oligonucleotides.

"Stringent hybridization wash conditions" in the context of nucleic acid hybridization experiments such as Southern and northern hybridizations are sequence dependent, and are different under different environmental parameters. An extensive guide to the hybridization of nucleic acids is found in Tijssen (1993), supra. and in Hames and Higgins, 1 and 2.

For purposes of the present invention, generally, "highly stringent" hybridization and wash conditions are selected to be about 5° C. lower than the thermal melting point ($T_m$) for the specific sequence at a defined ionic strength and pH. The $T_m$ is the temperature (under defined ionic strength and pH) at which 50% of the test sequence hybridizes to a perfectly matched probe. Very stringent conditions are selected to be equal to the $T_m$ for a particular probe.

An example of stringent hybridization conditions for hybridization of complementary nucleic acids which have more than 100 complementary residues on a filter in a Southern or northern blot is 50% formalin with 1 mg of heparin at 42° C., with the hybridization being carried out overnight. An example of stringent wash conditions is a 0.2×SSC wash at 65° C. for 15 minutes (see, Sambrook, supra for a description of SSC buffer). Often the high stringency wash is preceded by a low stringency wash to remove background probe signal. An example low stringency wash is 2×SSC at 40° C. for 15 minutes. In general, a signal to noise ratio of 5× (or higher) than that observed for an unmatched probe (e.g., a publically available subtilisin coding nucleic acid with a sequence found in Genbank prior to the filing of the present application) in the particular hybridization assay indicates detection of a specific hybridization.

Comparative hybridization can be used to identify nucleic acids of the invention, and this comparative hybridization method is a preferred method of distinguishing nucleic acids of the invention.

In particular, detection of highly stringent hybridization in the context of the present invention indicates strong structural similarity to, e.g., the nucleic acids provided in the sequence listing herein. For example, it is desirable to identify test nucleic acids which hybridize to the exemplar nucleic acids herein under stringent conditions. One measure of stringent hybridization is the ability to hybridize to one of the listed nucleic acids (e.g., nucleic acid sequences SEQ ID NO:1 to SEQ ID NO:130, and complementary polynucleotide sequences thereof, or a subsequence thereof, (e.g., subsequences encoding amino acid positions 71–95, 86–110, 111–135, and/or 196–230) under highly stringent conditions. Stringent hybridization and wash conditions can easily be determined empirically for any test nucleic acid.

For example, in determining highly stringent hybridization and wash conditions, the hybridization and wash conditions are gradually increased (e.g., by increasing temperature, decreasing salt concentration, increasing detergent concentration and/or increasing the concentration of organic solvents such as formalin in the hybridization or wash), until a selected set of criteria are met. For example, the hybridization and wash conditions are gradually increased until a probe comprising one or more nucleic acid sequences selected from SEQ ID NO:1 to SEQ ID NO:130, or complementary polynucleotide sequences thereof, binds to a perfectly matched complementary target (again, a nucleic acid comprising one or more nucleic acid sequences selected from SEQ ID NO:1 to SEQ ID NO:130, and complementary polynucleotide sequences thereof), with a signal to noise ratio that is at least 5× as high as that observed for hybridization of the probe to an unmatched target, and is sometimes 10×, 20×, 50× or even higher, depending on the desired discrimination. In this case, the unmatched target is a nucleic acid corresponding to a known subtilisin homologue, e.g., an subtilisin homologue nucleic acid (other than those in the accompanying sequence listing) that is present in a public database such as GenBank™ at the time of filing of the subject application. Examples of such unmatched target nucleic acids include, e.g., those with the following GenBank accession numbers: M65086, D13157, S48754, AB005792, D29688, and M28537. Additional such sequences can be identified in GenBank by one of skill.

A test nucleic acid is said to specifically hybridize to a probe nucleic acid when it hybridizes at least ½ as well to the probe as to the perfectly matched complementary target, i.e., with a signal to noise ratio at least ½ as high as hybridization of the probe to the target under conditions in which the perfectly matched probe binds to the perfectly matched complementary target with a signal to noise ratio that is at least about 5×–10×, and occasionally 20×, 50× or greater than that observed for hybridization to any of the unmatched target nucleic acids M65086, D13157, S48754, AB005792, D29688, and M28537.

Ultra high-stringency hybridization and wash conditions are those in which the stringency of hybridization and wash conditions are increased until the signal to noise ratio for binding of the probe to the perfectly matched complementary target nucleic acid is at least 10×, sometimes 20×, and occasionally 50× as high as that observed for hybridization to any of the unmatched target nucleic acids M65086, D13157, S48754, AB005792, D29688, and M28537. A target nucleic acid which hybridizes to a probe under such conditions, with a signal to noise ratio of at least ½ that of the perfectly matched complementary target nucleic acid is said to bind to the probe under ultra-high stringency conditions.

Similarly, even higher levels of stringency can be determined by gradually increasing the hybridization and/or wash conditions of the relevant hybridization assay. For example, those in which the stringency of hybridization and wash conditions are increased until the signal to noise ratio for binding of the probe to the perfectly matched complementary target nucleic acid is at least 10×, 20×, 50×, 100×, or 500× or more as high as that observed for hybridization to any of the unmatched target nucleic acids M65086, D13157, S48754, AB005792, D29688, and M28537can be identified. A target nucleic acid which hybridizes to a probe under such conditions, with a signal to noise ratio of at least ½ that of the perfectly matched complementary target nucleic acid is said to bind to the probe under ultra-ultra-high stringency conditions. For example, the most similar sequences selected from among those available in GenBank, as of the filing date, can be used as the control sequences.

Target nucleic acids which hybridize to the nucleic acids represented by SEQ ID NO:1 to SEQ ID NO:130, under high, ultra-high and ultra-ultra high stringency conditions are a feature of the invention. Examples of such nucleic acids include those with one or a few silent or conservative nucleic acid substitutions as compared to a given nucleic acid sequence.

Nucleic acids which do not hybridize to each other under stringent conditions are still substantially identical if the polypeptides which they encode are substantially identical. This occurs, e.g., when a copy of a nucleic acid is created using the maximum codon degeneracy permitted by the genetic code, or when antisera generated against one or more of SEQ ID NO:131 to SEQ ID NO:260 which has been subtracted using the polypeptides encoded by the following subtilisin sequences in GenBank: M65086, D13157, S48754, AB005792, D29688, and M28537. Further details on immunological identification of polypeptides of the invention are found below.

In one aspect, the invention provides a nucleic acid which comprises a unique subsequence in a nucleic acid selected from SEQ ID NO:1 to SEQ ID NO:130. The unique subsequence is unique as compared to a nucleic acid corresponding to any of: M65086, D13157, S48754, AB005792, D29688, and M28537. Such unique subsequences can be determined by aligning any of SEQ ID NO:1 to SEQ ID NO:130 against the complete set of nucleic acids corresponding to M65086, D13157, S48754, AB005792, D29688, and M28537. Alignment can be performed using the BLAST algorithm set to default parameters. Any unique subsequence is useful, e.g., as a probe to identify the nucleic acids of the invention.

Similarly, the invention includes a polypeptide which comprises a unique subsequence in a polypeptide selected from: SEQ ID NO:131 to SEQ ID NO:260. Here, the unique subsequence is unique as compared to a polypeptide corresponding to any of (GenBank accession numbers): P29600, P41362, P29599, P27693, P20724, P41363, P00780, P00781, P35835, P00783, P29142, P04189, P07518, P00782, P04072, P16396, P29140, P29139, P08594, P16588, P11018, P54423, P40903, P23314, P23653, P33295, P42780, and P80146. Here again, the polypeptide is aligned against the complete set of polypeptides corresponding to P29600, P41362, P29599, P27693, P20724, P41363, P00780, P00781, P35835, P00783, P29142, P04189, P07518, P00782, P04072, P16396, P29140, P29139, P08594, P16588, P11018, P54423, P40903, P23314, P23653, P33295, P42780, and P80146 (note that where the sequence corresponds to a non-translated sequence such as a pseudo gene, the corresponding polypeptide is generated simply by in silico translation of the nucleic acid sequence into an amino acid sequence, where the reading frame is selected to correspond to the reading frame of homologous subtilisin nucleic acids.

The invention also provides for target nucleic acids which hybridizes under stringent conditions to a unique coding oligonucleotide which encodes a unique subsequence in a polypeptide selected from: SEQ ID NO:131 to SEQ ID NO:260, wherein the unique subsequence is unique as compared to a polypeptide corresponding to any of the control polypeptides. Unique sequences are determined as noted above.

In one example, the stringent conditions are selected such that a perfectly complementary oligonucleotide to the coding oligonucleotide hybridizes to the coding oligonucleotide with at least about a 5–10× higher signal to noise ratio than for hybridization of the perfectly complementary oligonucleotide to a control nucleic acid corresponding to any of the control polypeptides. Conditions can be selected such that higher ratios of signal to noise are observed in the particular assay which is used, e.g., about 15×, 20×, 30×, 50× or more. In this example, the target nucleic acid hybridizes to the unique coding oligonucleotide with at least a 2× higher signal to noise ratio as compared to hybridization of the control nucleic acid to the coding oligonucleotide. Again, higher signal to noise ratios can be selected, e.g., about 5×, 10×, 20×, 30×, 50× or more. The particular signal will depend on the label used in the relevant assay, e.g., a fluorescent label, a colorimetric label, a radio active label, or the like.

Substrates and Formats for Sequence Recombination

The polynucleotides of the invention are optionally used as substrates for a variety of diversity generating procedures, including recombination and recursive recombination (e.g., DNA shuffling) reactions, i.e., to produce additional subtilisin homologues with desired properties. In addition to standard cloning methods as set for the in, e.g., Sambrook, Ausubel and Berger, all supra, a variety of diversity generating protocols are available and described in the art. The procedures can be used separately, and/or in combination to produce one or more variants of a nucleic acid or set of nucleic acids, as well variants of encoded proteins. Individually and collectively, these procedures provide robust, widely applicable ways of generating diversified nucleic acids and sets of nucleic acids (including, e.g., nucleic acid libraries) useful, e.g., for the engineering or rapid evolution of nucleic acids, proteins, pathways, cells and/or organisms with new and/or improved characteristics.

While distinctions and classifications are made in the course of the ensuing discussion for clarity, it will be appreciated that the techniques are often not mutually exclusive. Indeed, the various methods can be used singly or in combination, in parallel or in series, to access diverse sequence variants.

The result of any of the diversity generating procedures described herein can be the generation of one or more nucleic acids, which can be selected or screened for nucleic acids with or which confer desirable properties, or that encode proteins with or which confer desirable properties. Following diversification by one or more of the methods herein, or otherwise available to one of skill, any nucleic acids that are produced can be selected for a desired activity or property, e.g. subtilisin homologues with improved thermostability, increased activity at neutral or low pH, increased activity in organic solvents, and the like. This can include identifying any activity that can be detected, for example, in an automated or automatable format, by any of the assays in the art, including the various methods for assessing protease activity described herein, and known in the art. A variety of related (or even unrelated) properties can be evaluated, in serial or in parallel, at the discretion of the practitioner.

Descriptions of a variety of diversity generating procedures suitable for generating modified nucleic acid sequences encoding subtilisin homologues with desired properties are found in the following publications and the references cited therein: Soong, N. et al. (2000) "Molecular breeding of viruses" *Nat Genet* 25(4):436–439; Stemmer, et al. (1999) "Molecular breeding of viruses for targeting and other clinical properties" *Tumor Targeting* 4:1–4; Ness et al. (1999) "DNA Shuffling of subgenomic sequences of subtilisin" *Nature Biotechnology* 17:893–896; Chang et al. (1999) "Evolution of a cytokine using DNA family shuffling" *Nature Biotechnology* 17:793–797; Minshull and Stemmer (1999) "Protein evolution by molecular breeding" *Current Opinion in Chemical Biology* 3:284–290; Christians et al. (1999) "Directed evolution of thymidine kinase for AZT phosphorylation using DNA family shuffling" *Nature Biotechnology* 17:259–264; Crameri et al. (1998) "DNA shuffling of a family of genes from diverse species accelerates directed evolution" *Nature* 391:288–291; Crameri et al. (1997) "Molecular evolution of an arsenate detoxification pathway by DNA shuffling," *Nature Biotechnology* 15:436–438; Zhang et al. (1997) "Directed evolution of an effective fucosidase from a galactosidase by DNA shuffling and screening" *Proc. Natl. Acad. Sci. USA* 94:4504–4509; Patten et al. (1997) "Applications of DNA Shuffling to Pharmaceuticals and Vaccines" *Current Opinion in Biotechnology* 8:724–733; Crameri et al. (1996) "Construction and evolution of antibody-phage libraries by DNA shuffling" *Nature Medicine* 2:100–103; Crameri et al. (1996) "Improved green fluorescent protein by molecular evolution using DNA shuffling" *Nature Biotechnology* 14:315–319; Gates et al. (1996) "Affinity selective isolation of ligands from peptide libraries through display on a lac repressor "headpiece dimer" *Journal of Molecular Biology* 255:373–386; Stemmer (1996) "Sexual PCR and Assembly PCR" In: *The Encyclopedia of Molecular Biology*. VCH Publishers, New York. pp.447–457; Crameri and Stemmer (1995) "Combinatorial multiple cassette mutagenesis creates all the permutations of mutant and wildtype cassettes" *BioTechniques* 18:194–195; Stemmer et al., (1995) "Single-step assembly of a gene and entire plasmid form large numbers of oligodeoxy-ribonucleotides" *Gene*, 164:49–53; Stemmer (1995) "The Evolution of Molecular Computation" *Science* 270: 1510; Stemmer (1995) "Searching Sequence Space" *Bio/Technology* 13:549–553; Stemmer (1994) "Rapid evolution of a protein in vitro by DNA shuffling" Nature 370:389–391; and Stemmer (1994) "DNA shuffling by random fragmentation and reassembly: In vitro recombination for molecular evolution." *Proc. Natl. Acad. Sci. USA* 91:10747–10751.

Mutational methods of generating diversity include, for example, site-directed mutagenesis (Ling et al. (1997) "Approaches to DNA mutagenesis: an overview" *Anal Biochem*. 254(2): 157–178; Dale et al. (1996) "Oligonucleotide-directed random mutagenesis using the phosphorothioate method" *Methods Mol. Biol.* 57:369–374; Smith (1985) "In vitro mutagenesis" *Ann. Rev. Genet.* 19:423–462; Botstein & Shortle (1985) "Strategies and applications of in vitro mutagenesis" *Science* 229:1193–1201; Carter (1986) "Site-directed mutagenesis" *Biochem. J.* 237:1–7; and Kunkel (1987) "The efficiency of oligonucleotide directed mutagenesis" in *Nucleic Acids & Molecular Biology* (Eckstein, F. and Lilley, D. M. J. eds., Springer Verlag, Berlin)); mutagenesis using uracil containing templates (Kunkel (1985) "Rapid and efficient site-specific mutagenesis without phenotypic selection" *Proc. Natl. Acad. Sci. USA* 82:488–492; Kunkel et al. (1987) "Rapid and efficient site-specific mutagenesis without phenotypic selection" *Methods in Enzymol*. 154, 367–382; and Bass et al. (1988) "Mutant Trp repressors with new DNA-binding specificities" Science 242:240–245); oligonucleotide-directed mutagenesis (*Methods in Enzymol.* 100: 468–500 (1983); *Methods in Enzymol*. 154: 329–350 (1987); Zoller & Smith (1982) "Oligonucleotide-directed mutagenesis using M13-derived vectors: an efficient and general procedure for the production of point mutations in any DNA fragment" *Nucleic Acids Res*. 10:6487–6500; Zoller & Smith (1983) "Oligonucleotide-directed mutagenesis of DNA fragments cloned into M13 vectors" *Methods in Enzymol.* 100:468–500; and Zoller & Smith (1987) "Oligonucleotide-directed mutagenesis: a simple method using two oligonucleotide primers and a single-stranded DNA template" *Methods in Enzymol.* 154:329–350); phosphorothioate-modified DNA mutagenesis (Taylor et al. (1985) "The use of phosphorothioate-modified DNA in restriction enzyme reactions to prepare nicked DNA" *Nucl. Acids Res.* 13: 8749–8764; Taylor et al. (1985) "The rapid generation of oligonucleotide-directed mutations at high frequency using phosphorothioate-modified DNA" *Nucl. Acids Res*. 13: 8765–8787 (1985); Nakamaye & Eckstein (1986) "Inhibition of restriction endonuclease Nci I cleavage by phosphorothioate groups and its application to oligonucleotide-directed mutagenesis" *Nucl. Acids Res.* 14: 9679–9698; Sayers et al. (1988) "Y-T Exonucleases in phosphorothioate-based oligonucleotide-directed mutagenesis" *Nucl. Acids Res.* 16:791–802; and Sayers et al. (1988) "Strand specific cleavage of phosphorothioate-containing DNA by reaction with restriction endonucleases in the presence of ethidium bromide" *Nucl. Acids Res*. 16: 803–814); mutagenesis using gapped duplex DNA (Kramer et al. (1984) "The gapped duplex DNA approach to oligonucleotide-directed mutation construction" *Nucl. Acids Res.* 12: 9441–9456; Kramer & Fritz (1987) *Methods in Enzymol*. "Oligonucleotide-directed construction of mutations via gapped duplex DNA" 154:350–367; Kramer et al. (1988) "Improved enzymatic in vitro reactions in the gapped duplex DNA approach to oligonucleotide-directed construction of mutations" *Nucl. Acids Res.* 16: 7207; and Fritz et al. (1988) "Oligonucleotide-directed construction of mutations: a gapped duplex DNA procedure without enzymatic reactions in vitro" *Nucl. Acids Res.* 16: 6987–6999).

Additional suitable methods include point mismatch repair (Kramer et al. (1984) "Point Mismatch Repair" *Cell* 38:879–887), mutagenesis using repair-deficient host strains (Carter et al. (1985) "Improved oligonucleotide site-directed mutagenesis using M13 vectors" *Nucl. Acids Res.* 13: 4431–4443; and Carter (1987) "Improved oligonucleotide-directed mutagenesis using M13 vectors" *Methods in Enzymol.* 154: 382–403), deletion mutagenesis (Eghtedarzadeh & Henikoff (1986) "Use of oligonucleotides to generate large deletions" *Nucl. Acids Res.* 14: 5115), restriction-selection and restriction-purification (Wells et al. (1986) "Importance of hydrogen-bond formation in stabilizing the transition state of subtilisin" *Phil. Trans. R. Soc. Lond.* A 317: 415–423), mutagenesis by total gene synthesis (Nambiar et al. (1984) "Total synthesis and cloning of a gene coding for the ribonuclease S protein" *Science* 223: 1299–1301; Sakamar and Khorana (1988) "Total synthesis and expression of a gene for the a-subunit of bovine rod outer segment guanine nucleotide-binding protein (transducin)" *Nucl. Acids Res.* 14: 6361–6372; Wells et al. (1985) "Cassette mutagenesis: an efficient method for generation of multiple mutations at defined sites" *Gene* 34:315–323; and Grundström et al. (1985) "Oligonucleotide-directed mutagenesis by microscale 'shotgun' gene synthesis" *Nucl. Acids Res.* 13: 3305–3316), double-strand break repair (Mandecki (1986) "Oligonucleotide-directed double-strand break repair in plasmids of *Escherichia coli*: a method for site-specific mutagenesis" *Proc. Natl. Acad. Sci. USA*, 83:7177–7181; and Arnold (1993) "Protein engineering for unusual environments" *Current Opinion in Biotechnology* 4:450455). Additional details on many of the above methods can be found in *Methods in Enzymology* Volume 154, which also describes useful controls for trouble-shooting problems with various mutagenesis methods.

Additional details regarding various diversity generating methods, e.g., DNA shuffling methods, can be found in the following U.S. patents, PCT publications and applications, and EPO publications: U.S. Pat. No. 5,605,793 to Stemmer (Feb. 25, 1997), "Methods for In Vitro Recombination;" U.S. Pat. No. 5,811,238 to Stemmer et al. (Sep. 22, 1998) "Methods for Generating Polynucleotides having Desired Characteristics by Iterative Selection and Recombination;" U.S. Pat. No. 5,830,721 to Stemmer et al. (Nov. 3, 1998), "DNA Mutagenesis by Random Fragmentation and Reassembly;" U.S. Pat. No. 5,834,252 to Stemmer, et al. (Nov. 10, 1998) "End-Complementary Polymerase Reaction;" U.S. Pat. No. 5,837,458 to Minshull, et al. (Nov. 17, 1998), "Methods and Compositions for Cellular and Metabolic Engineering;" WO 95/22625, Stemmer and Crameri, "Mutagenesis by Random Fragmentation and Reassembly;" WO 96/33207 by Stemmer and Lipschutz "End Complementary Polymerase Chain Reaction;" WO 97/20078 by Stemmer and Crameri "Methods for Generating Polynucleotides having Desired Characteristics by Iterative Selection and Recombination;" WO 97/35966 by Minshull and Stemmer, "Methods and Compositions for Cellular and Metabolic Engineering;" WO 99/41402 by Punnonen et al. "Targeting of Genetic Vaccine Vectors;" WO 99/41383 by Punnonen et al. "Antigen Library Immunization;" WO 99/41369 by Punnonen et al. "Genetic Vaccine Vector Engineering;" WO 99/41368 by Punnonen et al. "Optimization of Immunomodulatory Properties of Genetic Vaccines;" EP 752008 by Stemmer and Crameri, "DNA Mutagenesis by Random Fragmentation and Reassembly;" EP 0932670 by Stemmer "Evolving Cellular DNA Uptake by Recursive Sequence Recombination;" WO 99/23107 by Stemmer et al., "Modification of Virus Tropism and Host Range by Viral Genome Shuffling;" WO 99/21979 by Apt et al., "Human Papillomavirus Vectors;" WO 98/31837 by del Cardayre et al. "Evolution of Whole Cells and Organisms by Recursive Sequence Recombination;" WO 98/27230 by Patten and Stemmer, "Methods and Compositions for Polypeptide Engineering;" WO 98/27230 by Stemmer et al., "Methods for Optimization of Gene Therapy by Recursive Sequence Shuffling and Selection," WO 00/00632, "Methods for Generating Highly Diverse Libraries," WO 00/09679, "Methods for Obtaining in Vitro Recombined Polynucleotide Sequence Banks and Resulting Sequences," WO 98/42832 by Arnold et al., "Recombination of Polynucleotide Sequences Using Random or Defined Primers," WO 99/29902 by Arnold et al., "Method for Creating Polynucleotide and Polypeptide Sequences," WO 98/41653 by Vind, "An in Vitro Method for Construction of a DNA Library," WO 98/41622 by Borchert et al., "Method for Constructing a Library Using DNA Shuffling," and WO 98/42727 by Pati and Zarling, "Sequence Alterations using Homologous Recombination;" WO 00/18906 by Patten et al., "Shuffling of Codon-Altered Genes;" WO 00/04190 by del Cardayre et al. "Evolution of Whole Cells and Organisms by Recursive Recombination;" WO 00/42561 by Crameri et al., "Oligonucleotide Mediated Nucleic Acid Recombination;" WO 00/42559 by Selifonov and Stemmer "Methods of Populating Data Structures for Use in Evolutionary Simulations;" WO 00/42560 by Selifonov et al., "Methods for Making Character Strings, Polynucleotides & Polypeptides Having Desired Characteristics;" PCT/US00/26708 by Welch et al., "Use of Codon-Varied Oligonucleotide Synthesis for Synthetic Shuffling;" and PCT/US01106775 "Single-Stranded Nucleic Acid Template-Mediated Recombination and Nucleic Acid Fragment Isolation" by Affholter.

In brief, several different general classes of sequence modification methods, such as mutation, recombination, etc. are applicable to the present invention and set forth, e.g., in the references above. That is, any of the methods cited above can be adapted to the present invention to evolve the subtilisin homologues discussed herein to produce new endo-proteases with improved properties. Both the methods of making such subtilisins and the subtilisins produced by these methods are a feature of the invention.

The following exemplify some of the different types of preferred formats for diversity generation in the context of the present invention, including, e.g., certain recombination based diversity generation formats.

Nucleic acids can be recombined in vitro by any of a variety of techniques discussed in the references above, including e.g., DNAse digestion of nucleic acids to be recombined followed by ligation and/or PCR reassembly of the nucleic acids. For example, sexual PCR mutagenesis can be used in which random (or pseudo random, or even non-random) fragmentation of the DNA molecule is followed by recombination, based on sequence similarity, between DNA molecules with different but related DNA sequences, in vitro, followed by fixation of the crossover by extension in a polymerase chain reaction. This process and many process variants is described in several of the references above, e.g., in Stemmer (1994) *Proc. Natl. Acad. Sci. USA* 91:10747–10751. Thus, any of the subtilisin homologue nucleic acids described herein can be recombined in vitro to generate additional subtilisin homologues with desired properties.

Similarly, nucleic acids can be recursively recombined in vivo, e.g., by allowing recombination to occur between nucleic acids in cells. Many such in vivo recombination formats are set forth in the references noted above. Such formats optionally provide direct recombination between nucleic acids of interest, or provide recombination between vectors, viruses, plasmids, etc., comprising the nucleic acids of interest, as well as other formats. Details regarding such procedures are found in the references noted above. Accordingle, any of the subtilisin homologue encoding nucleic acids can be recombined in vivo to produce novel subtilisin homologues with desired properties.

Whole genome recombination methods can also be used in which whole genomes of cells or other organisms are recombined, optionally including spiking of the genomic recombination mixtures with desired library components (e.g., genes corresponding to the pathways of the present invention). These methods have many applications, including those in which the identity of a target gene is not known. Details on such methods are found, e.g., in WO 98/31837 by del Cardayre et al. "Evolution of Whole Cells and Organisms by Recursive Sequence Recombination;" and in, e.g., PCT/US99/15972 by del Cardayre et al., also entitled "Evolution of Whole Cells and Organisms by Recursive Sequence Recombination." Any of the subtilisin homologue nucleic acids of the invention can, thus, be recombined using whole genome recombination methods to generate additional subtilisin homologues with advantageous characteristics.

Synthetic recombination methods can also be used, in which oligonucleotides corresponding to targets of interest, e.g., the subtilisin homologues provided herein, are synthesized and reassembled in PCR or ligation reactions which include, for example, oligonucleotides which correspond to more than one parental nucleic acid, oligonucleotides corresponding to consensus sequences for a plurality of parental nucleic acids, (optionally incorporating one or more variable nucleotide positions), oligonucleotides incorporating proven or putative functional motifs, etc., thereby generating new recombined nucleic acids. Oligonucleotides can be made by standard nucleotide addition methods, or can be made, e.g., by tri-nucleotide synthetic approaches. Details regarding such approaches are found in the references noted above, including, e.g., WO 00/42561 by Crameri et al., "Olgonucleotide Mediated Nucleic Acid Recombination;" PCT/US00/26708 by Welch et al., "Use of Codon-Varied Oligonucleotide Synthesis for Synthetic Shuffling;" WO 00/42560 by Selifonov et al., "Methods for Making Character Strings, Polynucleotides and Polypeptides Having Desired Characteristics;" and WO 00/42559 by Selifonov and Stemmer "Methods of Populating Data Structures for Use in Evolutionary Simulations."

In silico methods of recombination can be effected in which genetic algorithms are used in a computer to recombine sequence strings which correspond to homologous (or even non-homologous) nucleic acids. The resulting recombined sequence strings are optionally converted into nucleic acids by synthesis of nucleic acids which correspond to the recombined sequences, e.g., in concert with oligonucleotide synthesis/gene reassembly techniques. This approach can generate random, partially random or designed variants. Many details regarding in silico recombination, including the use of genetic algorithms, genetic operators and the like in computer systems, combined with generation of corresponding nucleic acids (and/or proteins), as well as combinations of designed nucleic acids and/or proteins (e.g., based on cross-over site selection) as well as designed, pseudo-random or random recombination methods are described in WO 00/42560 by Selifonov et al., "Methods for Making Character Strings, Polynucleotides and Polypeptides Having Desired Characteristics" and WO 00/42559 by Selifonov and Stemmer "Methods of Populating Data Structures for Use in Evolutionary Simulations." Extensive details regarding in silico recombination methods are found in these applications. This methodology is generally applicable to the present invention in providing for recombination of subtilisin homologues in silico and/or the generation of corresponding nucleic acids or proteins.

Many methods of accessing natural diversity, e.g., by hybridization of diverse nucleic acids or nucleic acid fragments to single-stranded templates, followed by polymerization and/or ligation to regenerate full-length sequences, optionally followed by degradation of the templates and recovery of the resulting modified nucleic acids can be similarly used. In one method employing a single-stranded template, the fragment population derived from the genomic library(ies) is annealed with partial, or, often approximately full length ssDNA or RNA corresponding to the opposite strand. Assembly of complex chimeric genes from this population is then mediated by nuclease-base removal of non-hybridizing fragment ends, polymerization to fill gaps between such fragments and subsequent single stranded ligation. The parental polynucleotide strand can be removed by digestion (e.g., if RNA or uracil-containing), magnetic separation under denaturing conditions (if labeled in a manner conducive to such separation) and other available separation/purification methods. Alternatively, the parental strand is optionally co-purified with the chimeric strands and removed during subsequent screening and processing steps. Additional details regarding this approach are found, e.g., in "Single-Stranded Nucleic Acid Template-Mediated Recombination and Nucleic Acid Fragment Isolation" by Affholter, PCT/US01/06775.

In another approach, single-stranded molecules are converted to double-stranded DNA (dsDNA) and the dsDNA molecules are bound to a solid support by ligand-mediated binding. After separation of unbound DNA, the selected DNA molecules are released from the support and introduced into a suitable host cell to generate a library enriched sequences which hybridize to the probe. A library produced in this manner provides a desirable substrate for further diversification using any of the procedures described herein.

Any of the preceding general recombination formats can be practiced in a reiterative fashion (e.g., one or more cycles of mutation/recombination or other diversity generation methods, optionally followed by one or more selection methods) to generate a more diverse set of recombinant nucleic acids.

Mutagenesis employing polynucleotide chain termination methods have also been proposed (see e.g., U.S. Pat. No. 5,965,408, "Method of DNA reassembly by interrupting synthesis" to Short, and the references above), and can be applied to the present invention. In this approach, double stranded DNAs corresponding to one or more genes sharing regions of sequence similarity are combined and denatured, in the presence or absence of primers specific for the gene. The single stranded polynucleotides are then annealed and incubated in the presence of a polymerase and a chain terminating reagent (e.g., ultraviolet, gamma or X-ray irradiation; ethidium bromide or other intercalators; DNA binding proteins, such as single strand binding proteins, transcription activating factors, or histones; polycyclic aromatic hydrocarbons; trivalent chromium or a trivalent chromium salt; or abbreviated polymerization mediated by rapid thermocycling; and the like), resulting in the production of partial duplex molecules. The partial duplex molecules, e.g., containing partially extended chains, are then denatured and reannealed in subsequent rounds of replication or partial replication resulting in polynucleotides which share varying degrees of sequence similarity and which are diversified with respect to the starting population of DNA molecules. Optionally, the products, or partial pools of the products, can be amplified at one or more stages in the process. Polynucleotides produced by a chain termination method, such as described above, are suitable substrates for any other described recombination format.

Diversity also can be generated in nucleic acids or populations of nucleic acids using a recombinational procedure termed "incremental truncation for the creation of hybrid enzymes" ("ITCHY") described in Ostermeier et al. (1999) "A combinatorial approach to hybrid enzymes independent of DNA homology" *Nature Biotech* 17:1205. This approach can be used to generate an initial a library of variants which can optionally serve as a substrate for one or more in vitro or in vivo recombination methods. See, also, Ostermeier et al. (1999) "Combinatorial Protein Engineering by Incremental Truncation," *Proc. Natl. Acad. Sci. USA*, 96: 3562–67; Ostermeier et al. (1999), "Incremental Truncation as a Strategy in the Engineering of Novel Biocatalysts," *Biological and Medicinal Chemistry*, 7: 2139–44.

Mutational methods which result in the alteration of individual nucleotides or groups of contiguous or non-contiguous nucleotides can be favorably employed to introduce nucleotide diversity into one or more parental subtilisin homologues. Many mutagenesis methods are found in the above-cited references; additional details regarding mutagenesis methods can be found in following, which can also be applied to the present invention.

For example, error-prone PCR can be used to generate nucleic acid variants. Using this technique, PCR is performed under conditions where the copying fidelity of the DNA polymerase is low, such that a high rate of point mutations is obtained along the entire length of the PCR product. Examples of such techniques are found in the references above and, e.g., in Leung et al. (1989) *Technique* 1:11–15 and Caldwell et al. (1992) *PCR Methods Applic.* 2:28–33. Similarly, assembly PCR can be used, in a process which involves the assembly of a PCR product from a mixture of small DNA fragments. A large number of different PCR reactions can occur in parallel in the same reaction mixture, with the products of one reaction priming the products of another reaction.

Oligonucleotide directed mutagenesis can be used to introduce site-specific mutations in a nucleic acid sequence of interest. Examples of such techniques are found in the references above and, e.g., in Reidhaar-Olson et al. (1988) *Science*, 241:53–57. Similarly, cassette mutagenesis can be used in a process that replaces a small region of a double stranded DNA molecule with a synthetic oligonucleotide cassette that differs from the native sequence. The oligonucleotide can contain, e.g., completely and/or partially randomized native sequence(s).

Recursive ensemble mutagenesis is a process in which an algorithm for protein mutagenesis is used to produce diverse populations of phenotypically related mutants, members of which differ in amino acid sequence. This method uses a feedback mechanism to monitor successive rounds of combinatorial cassette mutagenesis. Examples of this approach are found in Arkin & Youvan (1992) *Proc. Natl. Acad. Sci. USA* 89:7811–7815.

Exponential ensemble mutagenesis can be used for generating combinatorial libraries with a high percentage of unique and functional mutants. Small groups of residues in a sequence of interest are randomized in parallel to identify, at each altered position, amino acids which lead to functional proteins. Examples of such procedures are found in Delegrave & Youvan (1993) *Biotechnology Research* 11:1548–1552.

In vivo mutagenesis can be used to generate random mutations in any cloned DNA of interest by propagating the DNA, e.g., in a strain of *E. coli* that carries mutations in one or more of the DNA repair pathways. These "mutator" strains have a higher random mutation rate than that of a wild-type parent. Propagating the DNA in one of these strains will eventually generate random mutations within the DNA. Such procedures are described in the references noted above.

Other procedures for introducing diversity into a genome, e.g. a bacterial, fungal, animal or plant genome can be used in conjunction with the above described and/or referenced methods. For example, in addition to the methods above, techniques have been proposed which produce nucleic acid multimers suitable for transformation into a variety of species (see, e.g., Schellenberger U.S. Pat. No. 5,756,316 and the references above). Transformation of a suitable host with such multimers, consisting of genes that are divergent with respect to one another, (e.g., derived from natural diversity or through application of site directed mutagenesis, error prone PCR, passage through mutagenic bacterial strains, and the like), provides a source of nucleic acid diversity for DNA diversification, e.g., by an in vivo recombination process as indicated above.

Alternatively, a multiplicity of monomeric polynucleotides sharing regions of partial sequence similarity can be transformed into a host species and recombined in vivo by the host cell. Subsequent rounds of cell division can be used to generate libraries, members of which, include a single, homogenous population, or pool of monomeric polynucleotides. Alternatively, the monomeric nucleic acid can be recovered by standard techniques, e.g., PCR and/or cloning, and recombined in any of the recombination formats, including recursive recombination formats, described above.

Methods for generating multispecies expression libraries have been described (in addition to the reference noted above, see, e.g., Peterson et al. (1998) U.S. Pat. No. 5,783, 431 "Methods for Generating and Screening Novel Metabolic Pathways" and Thompson, et al. (1998) U.S. Pat. No. 5,824,485 " Methods for Generating and Screening Novel Metabolic Pathways) and their use to identify protein activities of interest has been proposed (In addition to the references noted above, see, Short (1999) U.S. Pat. No. 5,958, 672 "Protein Activity Screening of Clones Having DNA from Uncultivated Microorganisms"). Multispecies expression libraries include, in general, libraries comprising cDNA or genomic sequences from a plurality of species or strains, operably linked to appropriate regulatory sequences, in an expression cassette. The cDNA and/or genomic sequences are optionally randomly ligated to further enhance diversity. The vector can be a shuttle vector suitable for transformation and expression in more than one species of host organism, e.g., bacterial species, eukaryotic cells. In some cases, the library is biased by preselecting sequences which encode a protein of interest, or which hybridize to a nucleic acid of interest. Any such libraries can be provided as substrates for any of the methods herein described.

The above described procedures have been largely directed to increasing nucleic acid and/or encoded protein diversity. However, in many cases, not all of the diversity is useful, e.g., functional, and contributes merely to increasing the background of variants that must be screened or selected to identify the few favorable variants. In some applications, it is desirable to preselect or prescreen libraries (e.g., an amplified library, a genomic library, a cDNA library, a normalized library, etc.) or other substrate nucleic acids prior to diversification, e.g., by recombination-based mutagenesis procedures, or to otherwise bias the substrates towards nucleic acids that encode functional products. For example, in the case of antibody engineering, it is possible to bias the diversity generating process toward antibodies with functional antigen binding sites by taking advantage of in vivo recombination events prior to manipulation by any of the described methods. For example, recombined CDRs derived from B cell cDNA libraries can be amplified and assembled into framework regions (e.g., Jirholt et al. (1998) "Exploiting sequence space: shuffling in vivo formed complementarity determining regions into a master framework" *Gene* 215: 471) prior to diversifying according to any of the methods described herein.

Libraries can be biased towards nucleic acids which encode proteins with desirable enzyme activities. For example, after identifying a clone from a library which exhibits a specified activity, the clone can be mutagenized using any known method for introducing DNA alterations. A library comprising the mutagenized homologues is then screened for a desired activity, which can be the same as or different from the initially specified activity. An example of such a procedure is proposed in Short (1999) U.S. Pat. No. 5,939,250 for "Production of Enzymes Having Desired Activities by Mutagenesis." Desired activities can be identified by any method known in the art. For example, WO 99/10539 proposes that gene libraries can be screened by combining extracts from the gene library with components obtained from metabolically rich cells and identifying combinations which exhibit the desired activity. It has also been proposed (e.g., WO 98/58085) that clones with desired activities can be identified by inserting bioactive substrates into samples of the library, and detecting bioactive fluorescence corresponding to the product of a desired activity using a fluorescent analyzer, e.g., a flow cytometry device, a CCD, a fluorometer, or a spectrophotometer.

Libraries can also be biased towards nucleic acids which have specified characteristics, e.g., hybridization to a selected nucleic acid probe. For example, application WO 99/10539 proposes that polynucleotides encoding a desired activity (e.g., an enzymatic activity, for example: a lipase, an esterase, a protease, a glycosidase, a glycosyl transferase, a phosphatase, a kinase, an oxygenase, a peroxidase, a hydrolase, a hydratase, a nitrilase, a transaminase, an amidase or an acylase) can be identified from among genomic DNA sequences in the following manner. Single stranded DNA molecules from a population of genomic DNA are hybridized to a ligand-conjugated probe. The genomic DNA can be derived from either a cultivated or uncultivated microorganism, or from an environmental sample. Alternatively, the genomic DNA can be derived from a multicellular organism, or a tissue derived therefrom. Second strand synthesis can be conducted directly from the hybridization probe used in the capture, with or without prior release from the capture medium or by a wide variety of other strategies known in the art. Alternatively, the isolated single-stranded genomic DNA population can be fragmented without further cloning and used directly in, e.g., a recombination-based approach, that employs a single-stranded template, as described above.

"Non-Stochastic" methods of generating nucleic acids and polypeptides are alleged in Short "Non-Stochastic Generation of Genetic Vaccines and Enzymes" WO 00/46344. These methods, including proposed non-stochastic polynucleotide reassembly and site-saturation mutagenesis methods be applied to the present invention as well. Random or semi-random mutagenesis using doped or degenerate oligonucleotides is also described in, e.g., Arkin and Youvan (1992) "Optimizing nucleotide mixtures to encode specific subsets of amino acids for semi-random mutagenesis" *Biotechnology* 10:297–300; Reidhaar-Olson et al. (1991) "Random mutagenesis of protein sequences using oligonucleotide cassettes" *Methods Enzymol*. 208:564–86; Lim and Sauer (1991) "The role of internal packing interactions in determining the structure and stability of a protein" *J. Mol. Biol*. 219:359–76; Breyer and Sauer (1989) "Mutational analysis of the fine specificity of binding of monoclonal antibody 51F to lambda repressor" *J. Biol. Chem*. 264:13355–60); and "Walk-Through Mutagenesis" (Crea, R; U.S. Pat. Nos. 5,830,650 and 5,798,208, and EP Patent 0527809 B1.

It will readily be appreciated that any of the above described techniques suitable for enriching a library prior to diversification can also be used to screen the products, or libraries of products, produced by the diversity generating methods.

Kits for mutagenesis, library construction and other diversity generation methods are also commercially available. For example, kits are available from, e.g., Stratagene (e.g., QuickChange™ site-directed mutagenesis kit; and Chameleon™ double-stranded, site-directed mutagenesis kit), Bio/Can Scientific, Bio-Rad (e.g., using the Kunkel method described above), Boehringer Mannheim Corp., Clonetech Laboratories, DNA Technologies, Epicentre Technologies (e.g., 5 prime 3 prime kit); Genpak Inc, Lemargo Inc, Life Technologies (Gibco BRL), New England Biolabs, Pharmacia Biotech, Promega Corp., Quantum Biotechnologies, Amersham International plc (e.g., using the Eckstein method above), and Anglian Biotechnology Ltd (e.g., using the Carter/Winter method above).

The above references provide many mutational formats, including recombination, recursive recombination, recursive mutation and combinations or recombination with other forms of mutagenesis, as well as many modifications of these formats. Regardless of the diversity generation format that is used, the nucleic acids of the invention can be recombined (with each other, or with related (or even unrelated) sequences) to produce a diverse set of recombinant nucleic acids, including, e.g., sets of homologous nucleic acids, as well as corresponding polypeptides.

Other Polynucleotide Compositions

The invention also includes compositions comprising two or more polynucleotides of the invention (e.g., as substrates for recombination). The composition can comprise a library of recombinant nucleic acids, where the library contains at least 2, 3, 5, 10, 20, or 50 or more, e.g., at least about 100, at least about 1000, at least about 10,000, or more, nucleic acids. The nucleic acids are optionally cloned into expression vectors, providing expression libraries.

The invention also includes compositions produced by digesting one or more polynucleotide of the invention with a restriction endonuclease, an RNAse, or a DNAse (e.g., as is performed in certain of the recombination formats noted above); and compositions produced by fragmenting or shearing one or more polynucleotide of the invention by mechanical means (e.g., sonication, vortexing, and the like), which can also be used to provide substrates for recombination in the methods above. Similarly, compositions comprising sets of oligonucleotides corresponding to more than one nucleic acid of the invention are useful as recombination substrates and are a feature of the invention. For convenience, these fragmented, sheared, or oligonucleotide synthesized mixtures are referred to as fragmented nucleic acid sets.

Also included in the invention are compositions produced by incubating one or more of the fragmented nucleic acid sets in the presence of ribonucleotide- or deoxyribonucleotide triphosphates and a nucleic acid polymerase. This resulting composition forms a recombination mixture for many of the recombination formats noted above. The nucleic acid polymerase may be an RNA polymerase, a DNA polymerase, or an RNA-directed DNA polymerase (e.g., a "reverse transcriptase"); the polymerase can be, e.g., a thermostable DNA polymerase (such as, VENT, TAQ, or the like).

Subtilisin Homologue Polypeptides

The invention provides isolated or recombinant subtilisin homologue polypeptides, referred to herein as "subtilisin homologue polypeptides" or simply "subtilisin homologues." An isolated or recombinant subtilisin homologue polypeptide of the invention includes a polypeptide comprising a sequence selected from SEQ ID NO:131 to SEQ ID NO:260, and conservatively modified variations therof.

Several conclusions may be drawn from comparison of exemplary sequences exhibiting desirable functional attributes to the subtilisin homologue, Savinase®. While the amino acids substituted demonstrate a certain amount of variability, and while the same amino acids are not universally substituted in all the homologues sharing a functional characteristic, patterns of substitutions, or motifs, corresponding to functional attributes can be discerned. For example, distinct but overlapping amino acid substitutions are correlated with the selected properties of thermal stability, aklakine stability and stability in organic solvents, e.g., dimethylformamide (DMF). Exemplary sequence alignments are illustrated in FIGS. 2A–C.

Thermal Stability

A comparison of exemplary subtilisin homologues with enhanced thermal stability reveals a number of variable amino acid positions. In comparison to Savinase®, several features are remarkable (FIG. 2A). The vast majority of novel subtilisin homologues with enhanced thermal stability have substituted Arg for Ser99 (all amino acid comparisons are made relative to the mature Savinase® protein), Ala for Asn114, Asn for Ser 206, and Arg for Thr207. In addition a cluster of variable residues is observed at positions 209–212. Notably, the amino acid substitutions at positions 99, 114, 206 and 207 are non-conservative substitutions.

pH Shifting

Again, a number of variable positions are observed among exemplary subtilisin homologues with activity at shifted pH, and among these there are striking substitutions relative to Savinase® (FIG. 2B). For example, Asp for Asn74, Glu for Ile77, Asn for Ser85, Asp for Glu87, Ser or Asp for Pro127, Ala or Tyr for Ser139 and Gly for Asn198 are found in the majority of subtilisin homologues with activities at altered pH. Substitutions at amino acid positions 74, 77, 85, 127, and 198 are non-conservative substitutions.

Activity in Organic Solvents

Exemplary subtilisins demonstrating improved residual activity in the organic solvent, dimethylformamide (DMF), typically also have a number of notable amino acid substitutions (FIG. 2C). For example, Asp for Glu132, Asn for Ser97, Ala for Gly113, Ala or Thr for Asn114, Asn for Gly116, Asp or Ser for Pro127, Ala for Ser128, Tyr for Ser139, Asn for Ser154 and Ser for Ala156.

Amino acid comparisons, such as those listed above, provide rational grounds for subsequent attempts at protein engineering of subtilisin homologues.

Making Polypeptides

Recombinant methods for producing and isolating subtilisin homologue polypeptides of the invention are described above. In addition to recombinant production, the polypeptides may be produced by direct peptide synthesis using solid-phase techniques (Stewart et al. (1969) Solid-Phase Peptide Synthesis, WH Freeman Co, San Francisco; Merrifield (1963) J. Am. Chem. Soc. 85:2149–2154). Peptide synthesis may be performed using manual techniques or by automation. Automated synthesis may be achieved, for example, using Applied Biosystems 431A Peptide Synthesizer (Perkin Elmer, Foster City, Calif.) in accordance with the instructions provided by the manufacturer. For example, subsequences may be chemically synthesized separately and combined using chemical methods to provide full-length subtilisin homologues. Peptides can also be ordered from a variety of sources.

Using Polypeptides

Antibodies

In another aspect of the invention, a subtilisin homologue polypeptide of the invention is used to produce antibodies which have, for example, diagnostic uses, e.g., related to the activity, distribution, and expression of subtilisin homologues.

Antibodies to subtilisin homologues of the invention may be generated by methods well known in the art. Such antibodies may include, but are not limited to, polyclonal, monoclonal, chimeric, humanized, single chain, Fab fragments and fragments produced by an Fab expression library.

Subtilisin homologue polypeptides for antibody induction do not require biological activity; however, the polypeptide or oligopeptide must be antigenic. Peptides used to induce specific antibodies may have an amino acid sequence consisting of at least 10 amino acids, preferably at least 15 or 20 amino acids. Short stretches of a subtilisin homologue polypeptide may be fused with another protein, such as keyhole limpet hemocyanin, and antibody produced against the chimeric molecule.

Methods of producing polyclonal and monoclonal antibodies are known to those of skill in the art, and many antibodies are available. See, e.g., Coligan (1991) Current Protocols in Immunology Wiley/Greene, NY; and Harlow and Lane (1989) Antibodies: A Laboratory Manual Cold Spring Harbor Press, NY; Stites et al. (eds.) Basic and Clinical Immunology (4th ed.) Lange Medical Publications, Los Altos, Calif., and references cited therein; Goding (1986) Monoclonal Antibodies: Principles and Practice (2d ed.) Academic Press, New York, N.Y.; and Kohler and Milstein (1975) Nature 256: 495–497. Other suitable techniques for antibody preparation include selection of libraries of recombinant antibodies in phage or similar vectors. See, Huse et al. (1989) Science 246: 1275–1281; and Ward, et al. (1989) Nature 341: 544–546. Specific monoclonal and polyclonal antibodies and antisera will usually bind with a $K_D$ of at least about 0.1 $\mu$M, preferably at least about 0.01 $\mu$M or better, and most typically and preferably, 0.001 $\mu$M or better.

Additional details antibody production and engineering techniques can be found in Borrebaeck (ed) (1995) Antibody Engineering, $2^{nd}$ Edition Freeman and Company, NY (Borrebaeck); McCafferty et al. (1996) Antibody Engineering, A Practical Approach IRL at Oxford Press, Oxford, England (McCafferty), and Paul (1995) Antibody Engineering Protocols Humana Press, Towata, N.J. (Paul).

Sequence Variations

Conservatively Modified Variations

Subtilisin homologue polypeptides of the present invention include conservatively modified variations of the sequences disclosed herein as SEQ ID NO:131 to SEQ ID NO:260. Such conservatively modified variations comprise substitutions, additions or deletions which alter, add or delete a single amino acid or a small percentage of amino acids (typically less than about 5%, more typically less than about 4%, about 2%, or about 1%) in any of SEQ ID NO:131 to SEQ ID NO:260.

For example, a conservatively modified variation (e.g., deletion) of the 173 amino acid polypeptide identified herein as SEQ ID NO:131 will have a length of at least 164 amino acids, preferably at least 166 amino acids, more preferably at least 170 amino acids, and still more preferably at least 171 amino acids, corresponding to a deletion of less than about 5%, about 4%, about 2% or about 1%, or less of the polypeptide sequence.

Another example of a conservatively modified variation (e.g., a "conservatively substituted variation") of the polypeptide identified herein as SEQ ID NO:131 will contain "conservative substitutions", according to the six substitution groups set forth in Table 2 (supra), in up to about 9 residues (i.e., less than about 5%) of the 173 amino acid polypeptide.

The subtilisin polypeptide sequence homologues of the invention, including conservatively substituted sequences, can be present as part of larger polypeptide sequences such as occur in a mature subtilisin protease, in a pre-pro subtilisin peptide or upon the addition of one or more domains for purification of the protein (e.g., poly Histidine (His) segments, FLAG tag segments, etc.). In the latter case, the additional functional domains have little or no effect on the activity of the subtilisin portion of the protein, or where the additional domains can be removed by post synthesis processing steps such as by treatment with a protease.

Defining Polypeptides By Immunoreactivity

Because the polypeptides of the invention provide a variety of new polypeptide sequences as compared to other subtilisin homologues, the polypeptides also provide new structural features which can be recognized, e.g., in immunological assays. The generation of antisera which specifically binds the polypeptides of the invention, as well as the polypeptides which are bound by such antisera, are a feature of the invention.

The invention includes subtilisin homologue proteins that specifically bind to or that are specifically immunoreactive with an antibody or antisera generated against an immunogen comprising an amino acid sequence selected from one or more of SEQ ID NO: SEQ ID NO:131 to SEQ ID NO:260. To eliminate cross-reactivity with other subtilisin homologues, the antibody or antisera is subtracted with available subtilisins, such as those represented by the proteins or peptides corresponding to GenBank accession numbers available as of Apr. 3, 2000 and exemplified by P29600, P41362, P29599, P27693, P20724, P41363, P00780, P00781, P35835, P00783, P29142, P04189, P07518, P00782, P04072, P16396, P29140, P29139, P08594, P16588, P11018, P54423, P40903, P23314, P23653, P33295, P42780, and P80146. Where the accession number corresponds to a nucleic acid, a polypeptide encoded by the nucleic acid is generated and used for antibody/antisera subtraction purposes.

In one typical format, the immunoassay uses a polyclonal antiserum which was raised against one or more polypeptide comprising one or more of the sequences corresponding to one or more of: SEQ ID NO:131 to SEQ ID NO:260, or a substantial subsequence thereof (i.e., at least about 30% of the full length sequence provided). The full set of potential polypeptide immunogens derived from SEQ ID NO:131 to SEQ ID NO:260 are collectively referred to below as "the immunogenic polypeptides." The resulting antisera is optionally selected to have low cross-reactivity against the control subtilisin homologues, other known subtilisin homologues and any such cross-reactivity is removed by immunoabsorbtion with one or more of the control subtilisin homologues, prior to use of the polyclonal antiserum in the immunoassay.

In order to produce antisera for use in an immunoassay, one or more of the immunogenic polypeptides is produced and purified as described herein. For example, recombinant protein may be produced in a bacterial cell line. An inbred strain of mice (used in this assay because results are more reproducible due to the virtual genetic identity of the mice) is immunized with the immunogenic protein(s) in combination with a standard adjuvant, such as Freund's adjuvant, and a standard mouse immunization protocol (see, Harlow and Lane (1988) *Antibodies A Laboratory Manual*, Cold Spring Harbor Publications, New York, for a standard description of antibody generation, immunoassay formats and conditions that can be used to determine specific immunoreactivity). Alternatively, one or more synthetic or recombinant polypeptide derived from the sequences disclosed herein is conjugated to a carrier protein and used as an immunogen.

Polyclonal sera are collected and titered against the immunogenic polypeptide in an immunoassay, for example, a solid phase immunoassay with one or more of the immunogenic proteins immobilized on a solid support. Polyclonal antisera with a titer of $10^6$ or greater are selected, pooled and subtracted with the control subtilisin polypeptides, e.g., those identified from GenBank as noted, to produce subtracted pooled titered polyclonal antisera.

The subtracted pooled titered polyclonal antisera are tested for cross reactivity against the control subtilisin homologues. Preferably at least two of the immunogenic subtilisins are used in this determination, preferably in conjunction with at least two of the control subtilisin homologues, to identify antibodies which are specifically bound by the immunogenic protein(s).

In this comparative assay, discriminatory binding conditions are determined for the subtracted titered polyclonal antisera which result in at least about a 5–10 fold higher signal to noise ratio for binding of the titered polyclonal antisera to the immunogenic subtilisin homologues as compared to binding to the control subtilisin homologues. That is, the stringency of the binding reaction is adjusted by the addition of non-specific competitors such as albumin or non-fat dry milk, or by adjusting salt conditions, temperature, or the like. These binding conditions are used in subsequent assays for determining whether a test polypeptide is specifically bound by the pooled subtracted polyclonal antisera. In particular, test polypeptides which show at least a 2–5×higher signal to noise ratio than the control polypeptides under discriminatory binding conditions, and at least about a ½ signal to noise ratio as compared to the immunogenic polypeptide(s), shares substantial structural similarity with the immunogenic polypeptide as compared to known subtilisin, and is, therefore a polypeptide of the invention.

In another example, immunoassays in the competitive binding format are used for detection of a test polypeptide. For example, as noted, cross-reacting antibodies are removed from the pooled antisera mixture by immunoabsorbtion with the control subtilisin polypeptides. The immunogenic polypeptide(s) are then immobilized to a solid support which is exposed to the subtracted pooled antisera. Test proteins are added to the assay to compete for binding to the pooled subtracted antisera. The ability of the test protein(s) to compete for binding to the pooled subtracted antisera as compared to the immobilized protein(s) is compared to the ability of the immunogenic polypeptide(s) added to the assay to compete for binding (the immunogenic polypeptides compete effectively with the immobilized immunogenic polypeptides for binding to the pooled antisera). The percent cross-reactivity for the test proteins is calculated, using standard calculations.

In a parallel assay, the ability of the control proteins to compete for binding to the pooled subtracted antisera is determined as compared to the ability of the immunogenic polypeptide(s) to compete for binding to the antisera. Again, the percent cross-reactivity for the control polypeptides is calculated, using standard calculations. Where the percent cross-reactivity is at least 5–10× as high for the test polypeptides, the test polypeptides are said to specifically bind the pooled subtracted antisera.

In general, the immunoabsorbed and pooled antisera can be used in a competitive binding immunoassay as described herein to compare any test polypeptide to the immunogenic polypeptide(s). In order to make this comparison, the two polypeptides are each assayed at a wide range of concentrations and the amount of each polypeptide required to inhibit 50% of the binding of the subtracted antisera to the immobilized protein is determined using standard techniques. If the amount of the test polypeptide required is less than twice the amount of the immunogenic polypeptide that is required, then the test polypeptide is said to specifically bind to an antibody generated to the immunogenic protein, provided the amount is at least about 5–10× as high as for a control polypeptide.

As a final determination of specificity, the pooled antisera is optionally fully immunosorbed with the immunogenic polypeptide(s) (rather than the control polypeptides) until little or no binding of the resulting immunogenic polypeptide subtracted pooled antisera to the immunogenic polypeptide(s) used in the immunosorbtion is detectable. This fully immunosorbed antisera is then tested for reactivity with the test polypeptide. If little or no reactivity is observed (i.e., no more than 2× the signal to noise ratio observed for binding of the fully immunosorbed antisera to the immunogenic polypeptide), then the test polypeptide is specifically bound by the antisera elicited by the immunogenic protein.

Cleaning Solutions

The subtilisin homologues of the invention are favorably used in compositions that serve as cleaning solutions in wide variety of applications, including laundry detergents, contact lens cleansing solutions, and dry cleaning, among others.

For example, the present invention provides the use of the novel subtilisin homologues of the invention in cleaning and detergent compositions, as well as such compositions containing mutant subtilisin enzymes. Such cleaning and detergent compositions can in principle have any physical form, but the subtilisin homologues are preferably incorporated in liquid detergent compositions or in detergent compositions in the form of bars, tablets, sticks and the like for direct application, wherein they exhibit improved enzyme stability or performance.

Among the liquid compositions of the present invention are aqueous liquid detergents having for example a homogeneous physical character, e.g. they can consist of a micellar solution of surfactants in a continuous aqueous phase, so-called isotropic liquids. Alternatively, they can have a heterogeneous physical phase and they can be structured, containing suspended solid particles such as particles of builder materials e.g. of the kinds mentioned below. In addition, the liquid detergents according to the present invention can include an enzyme stabilization system, comprising calcium ion, boric acid, propylene glycol and/or short chain carboxylic acids. Optionally, the detergents include additional enzyme components including cellulase, lipases, or proteases.

In addition, powder detergent compositions can include, in addition to any one or more of the subtilisin homologues of the invention as described herein, such components as builders (such as phosphate or zeolite builders), surfactants (such as anionic, cationic, non-ionic or zwitterionic type surfactants), polymers (such as acrylic or equivalent polymers), bleach systems (such as perborate- or amino-containing bleach precursors or activators), structurants (such as silicate structurants), alkali or acid to adjust pH, humectants, and/or neutral inorganic salts. Furthermore, a number of other ingredients are normally present in the compositions of the invention, such as cosurfactants, tartrate succinate builder, neutralization system, suds suppressor, other enzymes and other optional components.

Integrated Systems

The present invention provides computers, computer readable media and integrated systems comprising character strings corresponding to the sequence information herein for the polypeptides and nucleic acids herein, including, e.g., those sequences listed herein and the various silent substitutions and conservative substitutions thereof.

Various methods and genetic algorithms (GOs) known in the art can be used to detect homology or similarity between different character strings, or can be used to perform other desirable functions such as to control output files, provide the basis for making presentations of information including the sequences and the like. Examples include BLAST, discussed supra.

Thus, different types of homology and similarity of various stringency and length can be detected and recognized in the integrated systems herein. For example, many homology determination methods have been designed for comparative analysis of sequences of biopolymers, for spell-checking in word processing, and for data retrieval from various databases. With an understanding of double-helix pair-wise complement interactions among 4 principal nucleobases in natural polynucleotides, models that simulate annealing of complementary homologous polynucleotide strings can also be used as a foundation of sequence alignment or other operations typically performed on the character strings corresponding to the sequences herein (e.g., word-processing manipulations, construction of figures comprising sequence or subsequence character strings, output tables, etc.). An example of a software package with GOs for calculating sequence similarity is BLAST, which can be adapted to the present invention by inputting character strings corresponding to the sequences herein.

Similarly, standard desktop applications such as word processing software (e.g., Microsoft Word™ or Corel WordPerfect™) and database software (e.g., spreadsheet software such as Microsoft Excel™, Corel Quattro Pro™, or database programs such as Microsoft Access™ or Paradox™) can be adapted to the present invention by inputting a character string corresponding to the subtilisin homologues of the invention (either nucleic acids or proteins, or both). For example, the integrated systems can include the foregoing software having the appropriate character string information, e.g., used in conjunction with a user interface (e.g., a GUI in a standard operating system such as a Windows, Macintosh or LINUX system) to manipulate strings of characters. As noted, specialized alignment programs such as BLAST can also be incorporated into the systems of the invention for alignment of nucleic acids or proteins (or corresponding character strings).

Integrated systems for analysis in the present invention typically include a digital computer with GO software for aligning sequences, as well as data sets entered into the software system comprising any of the sequences herein. The computer can be, e.g., a PC (Intel x86 or Pentium chip-compatible DOS™, OS2™ WINDOWS™ WINDOWS NT™, WINDOWS95™, WINDOWS98™ LINUX based machine, a MACINTOSH™, Power PC, or a UNIX based (e.g., SUN™ work station) machine) or other commercially common computer which is known to one of skill. Software for aligning or otherwise manipulating sequences is available, or can easily be constructed by one of skill using a standard programming language such as Visualbasic, Fortran, Basic, Java, or the like.

Any controller or computer optionally includes a monitor which is often a cathode ray tube ("CRT") display, a flat panel display (e.g., active matrix liquid crystal display, liquid crystal display), or others. Computer circuitry is often placed in a box which includes numerous integrated circuit chips, such as a microprocessor, memory, interface circuits, and others. The box also optionally includes a hard disk drive, a floppy disk drive, a high capacity removable drive such as a writeable CD-ROM, and other common peripheral elements. Inputting devices such as a keyboard or mouse optionally provide for input from a user and for user selection of sequences to be compared or otherwise manipulated in the relevant computer system.

The computer typically includes appropriate software for receiving user instructions, either in the form of user input into a set parameter fields, e.g., in a GUI, or in the form of preprogrammed instructions, e.g., preprogrammed for a variety of different specific operations. The software then converts these instructions to appropriate language for instructing the operation of the fluid direction and transport controller to carry out the desired operation.

The software can also include output elements for controlling nucleic acid synthesis (e.g., based upon a sequence or an alignment of a sequences herein) or other operations which occur downstream from an alignment or other operation performed using a character string corresponding to a sequence herein.

In an additional aspect, the present invention provides kits embodying the methods, composition, systems and apparatus herein. Kits of the invention optionally comprise one or more of the following: (1) an apparatus, system, system component or apparatus component as described herein; (2) instructions for practicing the methods described herein, and/or for operating the apparatus or apparatus components herein and/or for using the compositions herein; (3) one or more subtilisin composition or component; (4) a container for holding components or compositions, and, (5) packaging materials.

In a further aspect, the present invention provides for the use of any apparatus, apparatus component, composition or kit herein, for the practice of any method or assay herein, and/or for the use of any apparatus or kit to practice any assay or method herein.

EXAMPLES

Recombinant, (e.g., shuffled) library sequences corresponding to the diversified region (amino acids 55–227) in the context of Savinase® protease in an expression vector were cloned into a Bacillus 168 apr nprB strain (Harwood and Cutting (1990) *Molecular Biological Methods for Bacillus*, J. Wiley and Sons, New York) for expression and screening. Activity was compared to that of Savinase®. Genes were sequenced using an Applied Biosystems 310 Sequencer according to the manufacturers directions.

Bacillus colonies comprising library produced clearing halos on casein plates were grown to stationary phase in LB medium. The supernatant from this medium contained secreted protease and was diluted 100-fold (for pH 5.5 and pH 10 reactions) or 200-fold (for pH 7.5 reactions) into the reaction mixture. Protease activities in the culture supernatants were assayed using BODIPY FL casein as a substrate (Jones et al. (1997) *Anal Biochem* 251: 144). Fluorescence of this multi-fluorophore casein derivative is internally quenched when the protein is intact. Proteolysis causes separation of neighboring fluorophores, relieving quenching, so activity is measured as an increase in fluorescence with time. The reaction mixture contained 5 μg/ml BODIPY FL casein, 1 mM $CaCl_2$, and either 50 mM sodium borate (pH 10), 50 mM Tris-HCl (pH 7.5), or 50 mM MES (pH 5.5). All reactions were performed at room temperature for 40–70 minutes. Fluorescence was monitored at 535 nm using an excitation wavelength of 485 nm (BMG Fluostar). The cv(%) observed for independent determinations with the Savinase® strain was ≦15 under all conditions. All activities are expressed relative to that of Savinase®.

The pH dependence of the exemplary clones was determined by measuring activity at pH's 5.5, 7.5, and 10. Thermostability was measured as the residual activity at pH 10 after incubation at 70° C. for 5 minutes. Function in organic solvent was assayed as activity in 35% DMF at pH 7.5. Representative values are given in Table 3. Assay values obtained for additional clones are provided in Table 4.

The most dramatic increase in activity was at pH 5.5, where clones encoding subtilisin homologues with between 2 and 4-fold greater activity than Savinase® were obtained.

Combinations of properties were evaluated by simultaneously comparing the activities of the recovered clones for pairs of properties. Seventy-seven of the clones demonstrating the highest activity at 23° C. and pH10 were evaluated for the additional properties of residual activity in organic solvent and stabliity to heat treatment. The seventy-seven clones that were highly active at pH 10 show a broad distribution of properties under these two additional reaction conditions. Enzymes with up to nearly four times more residual after heat treatment or up to 50% greater residual activity in 35% DMF (at pH 7.5) were obtained. Many individuals were also obtained that were both more heat-stable and more active in organic solvent than Savinase® or any of the naturally occurring subtilisins.

The subtilisin homologue library was tested for combinations of properties by plotting the activities of a large number (i.e., greater than 650) active clones for pairs of properties. Activities are expressed relative to Savinase®. In every case, proteases with higher activities that Savinase® were obtained. For example, Clones 3A3, 3B3 and 4C6 possess activity levels significantly higher than Savinase® at pH10, while maintaining heat stability. Other clones show novel activities: 7C6 is active at both pH 10 and pH 5.5; 6A4, 7A2, 4D7 and 5E1 all showed a much greater activity at pH 5.5 than at pH10 as compared to Savinase®.

While the foregoing invention has been described in some detail for purposes of clarity and understanding, it will be clear to one skilled in the art from a reading of this disclosure that various changes in form and detail can be made without departing from the true scope of the invention. For example, all the techniques, methods, compositions, apparatus and systems described above may be used in various combinations. All publications, patents, patent applications, or other documents cited in this application are incorporated by reference in their entirety for all purposes to the same extent as if each individual publication, patent, patent application, or other document were individually indicated to be incorporated by reference for all purposes.

TABLE 4-continued

| clone | pH 10 | pH 7 | Th | pH 7/pH 10 |
|---|---|---|---|---|
| 16c | 0.439 | 0.305 | 0.475 | 1.441748972 |
| 17c | 0.990 | 0.478 | 0.472 | 2.072226061 |
| 18c | 0.910 | 0.547 | 0.421 | 1.665155865 |
| 19c | 0.661 | 0.460 | 0.507 | 1.437709426 |
| 20c | 1.182 | 0.468 | 0.825 | 2.524636577 |
| 21c | 2.080 | 0.566 | 0.393 | 3.677708955 |
| 22c | 0.996 | 0.654 | 0.450 | 1.524065973 |
| 23c | 1.122 | 0.528 | 0.462 | 2.12541356 |
| 24c | 1.220 | 0.462 | 0.388 | 2.637815727 |
| 25c | 1.329 | 0.340 | 0.485 | 3.910712051 |
| 26c | 1.144 | 0.542 | 0.563 | 2.111840839 |
| 27c | 1.740 | 0.601 | 0.428 | 2.895997498 |
| 28c | 2.026 | 1.022 | 0.475 | 1.981824139 |

TABLE 3

| Clone | pH 10 | pH 5.5 | pH 10 + heat | pH 7.5, DMF | PH 7.5 | 5.5/10 | heat/no ht | DMF/No DMF |
|---|---|---|---|---|---|---|---|---|
| 3d11 | 0.783 | 0.269 | 0.558 | 1.211 | 0.156 | 0.343 | 0.713 | 7.764 |
| 2b4 | 0.645 | 0.102 | −0.040 | 1.677 | 0.281 | 0.158 | −0.061 | 5.968 |
| 2b8 | 0.835 | 0.310 | 0.192 | 1.267 | 0.194 | 0.371 | 0.230 | 6.528 |
| 2g6 | 1.358 | 0.227 | −0.011 | 1.452 | 0.246 | 0.167 | −0.008 | 5.906 |
| 3g9 | 1.027 | 0.294 | 0.334 | 1.415 | 0.242 | 0.286 | 0.325 | 5.845 |
| 5f4 | 1.247 | 0.316 | 0.089 | 2.345 | 0.411 | 0.254 | 0.071 | 5.710 |
| 9e3 | 1.145 | 0.303 | 0.074 | 1.572 | 0.296 | 0.265 | 0.064 | 5.316 |
| 1c4 | 1.634 | 0.637 | 0.373 | 2.122 | 0.414 | 0.390 | 0.228 | 5.127 |
| 8c2 | 1.259 | 0.456 | 0.204 | 1.912 | 0.463 | 0.362 | 0.162 | 4.133 |
| 8h2 | 2.176 | 0.862 | 0.389 | 3.367 | 0.899 | 0.396 | 0.179 | 3.743 |
| 5e1 | 0.486 | 2.424 | 0.176 | 0.200 | 0.295 | 4.985 | 0.363 | 0.679 |
| 6a4 | 0.220 | 2.096 | 0.066 | 0.266 | 0.753 | 9.545 | 0.299 | 0.354 |
| 1c10 | 0.202 | 1.434 | 0.052 | 0.119 | 0.463 | 7.099 | 0.257 | 0.257 |
| 7a2 | 0.125 | 1.093 | 0.107 | 0.087 | 0.144 | 8.710 | 0.855 | 0.606 |
| 4d7 | 0.507 | 1.084 | 0.155 | 0.340 | 0.875 | 2.139 | 0.307 | 0.389 |
| 6b6 | 0.417 | 0.917 | 0.013 | 0.554 | 0.610 | 2.198 | 0.032 | 0.907 |
| 6g6 | 0.545 | 0.660 | 0.836 | 0.557 | 0.545 | 1.212 | 1.535 | 1.022 |
| 7c6 | 1.780 | 1.266 | 1.157 | 1.496 | 1.332 | 0.711 | 0.650 | 1.123 |
| 6b11 | 1.036 | 1.157 | 0.367 | 1.054 | 0.687 | 1.117 | 0.354 | 1.535 |
| 3a3 | 1.388 | 0.442 | 1.925 | 1.654 | 0.474 | 0.318 | 1.387 | 3.492 |
| 3b2 | 1.768 | 0.772 | 0.053 | 2.091 | 0.814 | 0.437 | 0.030 | 2.568 |
| 3b3 | 1.677 | 0.808 | 2.052 | 1.886 | 0.832 | 0.482 | 1.224 | 2.267 |
| 3e2 | 3.131 | 1.500 | 3.003 | ND | ND | 0.479 | 0.959 | # VALUE! |
| 1f6 | 2.512 | 1.202 | 1.505 | 2.704 | 0.778 | 0.479 | 0.599 | 3.477 |
| 4c2 | 2.129 | 0.879 | 1.083 | 1.461 | 0.394 | 0.413 | 0.509 | 3.706 |
| 4f1 | 2.865 | 1.166 | 0.765 | 2.421 | 0.844 | 0.407 | 0.267 | 2.867 |
| 7f11 | 2.780 | 1.374 | 0.111 | 0.394 | 0.131 | 0.494 | 0.040 | 3.004 |
| 4c6 | 2.024 | 0.823 | 2.183 | 2.107 | 0.571 | 0.407 | 1.079 | 3.690 |
| 5h9 | 1.645 | 0.962 | 1.664 | 2.171 | 0.841 | 0.585 | 1.012 | 2.581 |
| 3a7 | 2.073 | 0.708 | 2.042 | 2.429 | 0.783 | 0.342 | 0.985 | 3.102 |
| 5b11 | 1.788 | 0.650 | 1.394 | 1.719 | 0.494 | 0.363 | 0.780 | 3.479 |
| 4d10 | 2.294 | 0.839 | 1.671 | 0.844 | 0.236 | 0.366 | 0.729 | 3.579 |
| Savinase | 1.000 | 1.000 | 1.000 | 1.000 | 1.000 | 1.000 | 1.000 | 1.000 |

TABLE 4

| clone | pH 10 | pH 7 | Th | pH 7/pH 10 |
|---|---|---|---|---|
| 1c | 0.945 | 0.384 | 0.428 | 2.464871042 |
| 2c | 1.267 | 0.538 | 0.367 | 2.357121395 |
| 4c | 1.341 | 0.599 | 0.421 | 2.237961923 |
| 5c | 1.087 | 0.847 | 0.460 | 1.283307044 |
| 6c | 0.744 | 0.545 | 0.412 | 1.365116663 |
| 7c | 0.876 | 0.311 | 0.472 | 2.819113153 |
| 8c | 1.385 | 0.904 | 0.378 | 1.532625359 |
| 9c | 1.004 | 0.296 | 0.450 | 3.393937588 |
| 10c | 1.182 | 0.377 | 0.418 | 3.137727106 |
| 11c | 0.742 | 0.874 | 0.436 | 0.849157019 |
| 12c | 0.565 | 0.575 | 0.399 | 0.981293336 |
| 13c | 0.400 | 0.230 | 0.529 | 1.741343493 |
| 14c | 0.441 | 0.286 | 0.372 | 1.545070426 |
| 15c | 1.261 | 0.333 | 0.463 | 3.793101512 |

TABLE 4-continued

| clone | pH 10 | pH 7 | Th | pH 7/pH 10 |
|---|---|---|---|---|
| 29c | 1.785 | 0.544 | 0.458 | 3.280859182 |
| 30c | 0.824 | 0.512 | 0.423 | 1.607893876 |
| 31c | 0.966 | 0.534 | 0.460 | 1.80773113 |
| 32c | 2.601 | 1.533 | 0.491 | 1.696982514 |
| 33c | 1.790 | 0.879 | 0.460 | 2.03667039 |
| 34c | 0.935 | 0.309 | 0.430 | 3.026028227 |
| 35c | 1.123 | 0.792 | 0.416 | 1.418322797 |
| 36c | 3.113 | 1.146 | 0.426 | 2.715383 |
| 37c | 2.434 | 0.805 | 0.598 | 3.022963419 |
| 38c | 0.706 | 0.330 | 0.549 | 2.139036202 |
| 39c | 0.914 | 0.468 | 0.459 | 1.952518093 |
| 40c | 1.673 | 0.486 | 1.000 | 3.44170834 |
| 41c | 0.553 | 0.372 | 0.437 | 1.485071884 |
| 42c | 0.445 | 0.299 | 0.407 | 1.486460895 |

TABLE 4-continued

| clone | pH 10 | pH 7 | Th | pH 7/pH 10 |
|---|---|---|---|---|
| 43c | 0.697 | 0.272 | 0.441 | 2.567107146 |
| 44c | 1.296 | 0.695 | 0.406 | 1.864715807 |
| 45c | 0.501 | 0.303 | 0.392 | 1.655828162 |
| 46c | 1.317 | 0.415 | 0.399 | 3.175523932 |
| 47c | 0.230 | 0.208 | 0.404 | 1.10382509 |
| 48c | 0.252 | 0.202 | 0.412 | 1.248118252 |
| 97c | 1.158 | 0.647 | 0.420 | 1.790715127 |
| 98c | 2.899 | 1.680 | 0.443 | 1.725812631 |
| 99c | 0.952 | 0.629 | 0.537 | 1.512413746 |
| 100c | 1.009 | 0.346 | 0.438 | 2.915262747 |
| 101c | 2.051 | 0.735 | 0.440 | 2.791564999 |
| 102c | 1.137 | 1.087 | 1.679 | 1.045594976 |
| 103c | 0.354 | 0.358 | 0.416 | 0.990052245 |
| 104c | 1.128 | 0.284 | 0.409 | 3.973877024 |
| 105c | 1.045 | 0.492 | 0.414 | 2.123430622 |
| 106c | 0.987 | 0.506 | 0.410 | 1.952792112 |
| 107c | 1.166 | 0.424 | 0.450 | 2.750345337 |
| 108c | 1.068 | 0.552 | 0.476 | 1.936666893 |
| 109c | 1.009 | 0.347 | 0.443 | 2.908928888 |
| 110c | 1.467 | 1.057 | 0.399 | 1.388293853 |
| 112c | 0.794 | 0.458 | 0.442 | 1.734063931 |
| 113c | 0.445 | 0.284 | 0.445 | 1.564472964 |
| 114c | 1.761 | 0.670 | 0.411 | 2.63030704 |
| 115c | 1.176 | 0.659 | 0.491 | 1.784133206 |
| 116c | 1.718 | 0.422 | 1.529 | 4.068626315 |
| 117c | 1.649 | 0.637 | 0.411 | 2.589845625 |
| 118c | 0.736 | 0.438 | 0.440 | 1.680625308 |
| 119c | 0.404 | 0.299 | 0.406 | 1.348669155 |
| 121c | 0.685 | 0.300 | 0.440 | 2.28149295 |
| 122c | 0.589 | 0.484 | 0.434 | 1.216040763 |
| 123c | 0.589 | 0.370 | 0.449 | 1.594784354 |
| 124c | 0.508 | 0.422 | 0.406 | 1.204990859 |
| 125c | 0.175 | 0.217 | 0.416 | 0.807323532 |
| 126c | 0.743 | 0.510 | 0.433 | 1.458465033 |
| 127c | 0.970 | 0.299 | 0.431 | 3.243561131 |
| 128c | 1.894 | 1.194 | 0.484 | 1.586054628 |
| 129c | 0.636 | 0.528 | 0.428 | 1.205199814 |
| 130c | 0.684 | 0.461 | 0.409 | 1.483384371 |
| 131c | 2.915 | 0.730 | 2.988 | 3.991692678 |
| 132c | 1.051 | 0.433 | 0.400 | 2.428608904 |
| 133c | 1.274 | 0.554 | 1.022 | 2.29910642 |
| 134c | 1.162 | 0.372 | 0.406 | 3.123039477 |
| 135c | 0.935 | 0.542 | 0.386 | 1.724927616 |
| 136c | 2.854 | 1.159 | 0.426 | 2.461828522 |
| 137c | 1.341 | 0.870 | 0.397 | 1.54213239 |
| 190c | 0.728 | 0.608 | 0.412 | 1.198083789 |
| 191c | 2.152 | 0.493 | 1.598 | 4.36548397 |
| 192c | 1.517 | 0.325 | 2.686 | 4.669483412 |
| 193c | 1.616 | 0.904 | 0.457 | 1.788108104 |
| 195c | 0.773 | 0.466 | 0.385 | 1.659682628 |
| 196c | 1.237 | 0.338 | 0.395 | 3.657539014 |
| 197c | 1.180 | 0.491 | 0.392 | 2.404256665 |
| 199c | 1.726 | 0.883 | 0.469 | 1.95410316 |
| 200c | 1.703 | 0.862 | 0.375 | 1.9760179 |
| 201c | 1.088 | 0.363 | 0.383 | 3.00038898 |

Sequence Listings

The coding sequences shown start at bp 495 and end at bp 1011 relative to a nucleotide sequence encoding the Savinase® subtilisin. The amino acid sequences shown start at aa 166 and end at aa 338 of the Savinase® polypeptide. The amino acid of the Savinase® polypeptide is shown in SEQ ID NO:261.

| SEQ ID | Clone ID | Sequence |
|---|---|---|
| SEQ ID NO:1 | 1C10 | GTCGACTCAAGATGGGAACGGGCACGGGACGCACGTTGCAG |
| | | GGACGATTGCGGCTCTGGATAATGACGAAGGTGTTGTTGGC |
| | | GTAGCGCCAAATGCGGATCTATACGCCGTTAAAGTGCTTAG |
| | | CGCATCTGGCTCTGGTTCGATTAGTTCGATTGCCCAAGGGC |
| | | TTGAATGGTCTGGCGAAAACGGCATGGATATTGCCAATTTG |
| | | AGTCTTGGCAGCTCTGCACCAAGCGCAACTCTTGAACAAGC |
| | | TGTTAACGCAGCGACATCTCGTGGTGTACTTGTTATCGCAG |
| | | CCTCTGGTAACTCCGGCGCTGGATCCGTTGGTTATCCTGCA |
| | | CGTTATGCGAATGCGATGGCAGTAGGTGCAACTGATCAAAA |
| | | TAACAACCGTGCAAGCTCCTCTCAATACGGTGCAGGTCTTG |
| | | ATATTGTCGCTCCTGGCGTAGGTGTTCAAAGCACATATCCA |
| | | GGGAACCGTTATGCGAGCTTGAATGGTACTTCAATGGCAAC |
| | | TCCTCATGTCGCCGGCGTCGCCGCACTAGT |
| SEQ ID NO:2 | 1C4 | GTCGACTCAAGATGGCAATGGGCACGGGACGCACGTTGCAG |
| | | GAACAGTGGCAGCTCTTAATAACTCAATCGGTGTGATTGGT |
| | | GTGGCACCAAGTGCTGATCTATACGCTGTAAAAGTACTTGG |
| | | AGCAAATGGTAGAGGAAGCGTTAGTGGAATTGCTCAAGGTC |
| | | TAGAGTGGGCTGCAGCGAATAACATGCATATTGCTAACATG |

-continued

| SEQ ID | Clone ID | Sequence |
|---|---|---|
| | | AGTCTCGGTAGTGATTTTCCTAGCTCTACACTTGAGCGTGC |
| | | AGTCAACTATGCGACAAGCCAAGGTGTACTAGTTATTGCAG |
| | | CGACTGGTAACAACGGTTCCGGTTCAGTAGGCTATCCTGCT |
| | | CGTTATGCAAACGCAATGGCTGTAGGAGCGACTGACCAAAA |
| | | CAACAGACGTGCAAACTTTTCTCAGTACGGTACAGGAATTG |
| | | ACATCGTAGCACCAGGGGTTAATGTACAAAGTACGTATCCT |
| | | GGAAACCGCTATGCAAGTTTAAATGGTACATCTATGGCTAC |
| | | TCCACACGTCGCCGGCGCCGCCGC<u>ACTAGT</u> |
| SEQ ID NO:3 | 1F6 | <u>GTCGAC</u>TCAAGATGGGAATGGGCACGGGACGCATGTAGCAG |
| | | GAACAATAGCCGCTCTAAACAATTCAATAGGCGTACTTGGT |
| | | GTTGCACCGAATGCAGAATTATATGCTGTTAAAGTACTCGG |
| | | AGCAAATGGTAGAGGAAGCGTTAGTGGAATTGCTCAAGGTC |
| | | TAGAGTGGGCTGCAGCGAATAACATGCATATTGCTAACATG |
| | | AGTCTCGGTAGTGATGCACCTAGTACTACACTTGAGCGTGC |
| | | AGTCAACTATGCGACAAGCCAAGGTGTACTAGTTATTGCAG |
| | | CGACTGGTAACAACGGTTCTGGTTCAGTAGGCTATCCTGCT |
| | | CGTTATGCCAACGCAATGGCTGTAGGAGCGACTGACCAAAA |
| | | CAACAGACGTGCAAACTTTTCTCAGTATGGTACAGGAATTG |
| | | ACATCGTAGCACCTGGAGTTAACGTACAAAGTACGTATCCA |
| | | GGAAACCGTTATGTGAGTATGAATGGTACATCTATGGCTAC |
| | | TCCACACGTCGCCGGCGTCGCCGC<u>ACTAGT</u> |
| SEQ ID NO:4 | 2B4 | <u>GTCGAC</u>TCAAGATGGGAACGGGCACGGGACGCACGTAGCAG |
| | | GAACGGTTGCAGCTCTTAATAATTCAATCGGTGTGATTGGT |
| | | GTGGCACCAAGTGCTGATCTATACGCTGTAAAAGTACTTGG |
| | | AGCAAATGGTAGAGGAAGCGTTAGTGGAATTGCTCAAGGTC |
| | | TAGAGTGGGCTGCAGCGAATAACATGCATATTGCTAACATG |
| | | AGTCTCGGTAGTGATGCACCTAGTACTACACTTGGGCGTGC |
| | | AGTCAACTACGCGACAAGCCAAGGTGTACTAGTTATTGCAG |
| | | CGACTGGTAACAACGGTTCCGGTTCAGTTGGCTATCCTGCT |
| | | CGTTATGCAAACGCAATGGCTGTAGGAGCGACTGACCAAAA |
| | | CAACAGACGTGCAAACTTTTCTCAGTATGGTACAGGAATTG |
| | | ACATCGTAGCACCAGGGGTTAATGTACAAAGTACGTATCCT |
| | | GGAAACCGCTATGCAAGTTTAAATGGTACGTCGATGGCAAC |
| | | TCCTCACGTCGCCGGCGTCGCCGC<u>ACTAGT</u> |
| SEQ ID NO:5 | 2B8 | <u>GTCGAC</u>TCAAGATGGGAACGGGCACGGGACGCATGTGGCCC |
| | | GAACAGTACCAGCTCTTAATAACTCAATCGGTGTGATTGGT |
| | | GTGGCACCAAGTGCTGATCTATACGCTGTAAAAGTACTTGG |
| | | AGCAAATGGTAGAGGAAGCGTTAGTGGAATTGCTCGAGGTC |

| SEQ ID | Clone ID | Sequence |
|---|---|---|
| | | TAGAGTGGGCTGCAGCGAATAACATGCATATTGCTAACATG |
| | | AGTCTCGGTAGTGATGCACCTAGTACTACACTTGAGCGTGC |
| | | AGTCAACTACGCGACAAGCCAAGGTGTACTAGTTATTGCAG |
| | | CGACTGGTAACAACGGTTCTGGTTCAGTTGGCTATCCTGCT |
| | | CGTTATGCAAACGCAATGGCTGTAGGAGCGACTGACCAAAA |
| | | CAACAGACGTGCAAACTTTTCTCAGTATGGTACAGGAATTG |
| | | ACATCGTAGCACCAGGGGTTAATGTACAAAGTACGTATCCT |
| | | GGAAACCGCTATGCAAGTTTAAATGGTACATCTATGGCTAC |
| | | TCCACACGTCGCCGGCGTCGCCGCACTAGT |
| SEQ ID NO:6 | 2G6 | GTCGACTCAAGATGGCAATGGGCATGGGACGCACGTTGCAG |
| | | GAACGATTGCGGCGCTAAACAATAATGTTGGTGTACTTGGT |
| | | GTTGCGCCTAACGTTGAGCTTTATGGTGTTAAAGTACTTGG |
| | | AGCAAGTGGTTCTGGATCAATCAGTGGAATTGCACAAGGGT |
| | | TGCAATGGGCTGGTAATAATGGAATGCATATAGCTAATATG |
| | | AGCCTTGGTACTTCTGCACCAAGCGCAACTCTTGAACAAGC |
| | | TGTTAACGCAGCGACATCTCGTGGTGTACTTGTTATCGCAG |
| | | CCTCTGGTAATTCTGGTGCTGGATCAGTTGGTTATCCTGCA |
| | | CGTTACGCGAATGCGATGGCTGTAGGAGCGACTGACCAAAA |
| | | CAACAGACGTGCAAACTTTTCTCAGTATGGTACAGGAATTG |
| | | ACATCGTAGCACCTGGAGTTAACGTACAAAGTACGTATCCA |
| | | GGAAACCGTTATGTGAGTATGAATGGTACATCTATGGCCAC |
| | | TCCACACGTCGCCGGCGTCGCCGCACTAGT |
| SEQ ID NO:7 | 3A3 | GTCGACTCAAGATGGGAATGGGCATGGGACGCACGTTGCAG |
| | | GAACAGTGGCAGCTCTTAATAATTCAATCGGTGTGATTGGT |
| | | GTGGCACCAAGTGCTGATCTATACGCTGTAAAAGTACTTGG |
| | | AGCAAATGGTAGAGGAAGCGTTAGTGGAATTGCTCAAGGTC |
| | | TAGAGTGGGCTGCAGCGAATAACATGCATATTGCTAACATG |
| | | AGTCTCGGTAGTGATGCACCTACTACTACACTTGAGCGTGC |
| | | AGTCAACTATGCGACAAGCCAAGGTGTACTAGTTATTGCAG |
| | | CGACTGGTAACAACGGTTCCGGTTCAGTAGGCTATCCTGCT |
| | | CGTTATGCCAACGCAATGGCTGTAGGAGCGACTGACCAAAA |
| | | CAACAGACGTGCAAACTTTTCTCAGTATGGTACAGGAATTG |
| | | ACATCGTAGCACCAGGGGTTAATGTACAAAGTACGTATCCA |
| | | GGAAACCGTTATGTGAGTATGAGTGGTACATCTATGGCCAC |
| | | TCCACACGTCGCCGGCGCCGCCGCCCTTGT |
| SEQ ID NO:8 | 3A7 | GTCGACTCAAGATGGGAACGGGCACGGGACGCACGTTGCAG |
| | | GAACAGTGGCAGCTCTTANTAATTCAATCGGTGTGATTGGT |
| | | GTGGCACCAAGTGCTGATCTATACGCTGTAAAAGTACTTGG |

-continued

| SEQ ID | Clone ID | Sequence |
|---|---|---|
| | | AGCAAATGGTAGAGGAAGCGTTAGTGGAATTGCTCAAGGTC |
| | | TAGAGTGGGCTGCAGCGAATAACATGCATATTGCTAACATG |
| | | AGTCTCGGTAGTGATGCACCTAGTACTACACTTGAGCGTGC |
| | | AGTCAACTATGCGACAAGCCAAGGTGTACTAGTTATTGCAG |
| | | CGACTGGTAACAACGGTTCTGGTTCAGTTGGCTATCCTGCT |
| | | CGTTATGCAAACGCAATGGCTGTAGGAGCGACTGACCAAAA |
| | | CAACAGACGTGCAAACTTTTCTCAGTATGGTACAGGAATTG |
| | | ACATCGTAGCACCAGGGGTTAATGTACAAAGTACGTATCCT |
| | | GGAAACCGTTATGTGAGTATGAATGGTACATCTATGGCCAC |
| | | TCCACATGTCGCCGGCGCCGCCGC<u>ACTAGT</u> |
| SEQ ID NO:9 | 3E2 | <u>GTCGAC</u>TCAAGATGGGAACGGGCATGGGACGCACGTAGCAG |
| | | GAACAATAGCCGCTCTAAACAATTCAGTAGGCGTACTGGGT |
| | | GTCGCACCGAATGCAGAATTATATGCAGTTAAAGTACTTGG |
| | | AGCAAATGGTAGAGGAAGCGTTAGTGGAATTGCTCAAGGTC |
| | | TAGAGTGGGCTGCAGCGAATAACATGCATATTGCTAACATG |
| | | AGTCTCGGTAGTGATGCACCTAGTACTACACTTGAGCGTGC |
| | | AGTCAACTATGCGACAAGCCAAGGTGTACTAGTTATTGCAG |
| | | CGACTGGTAACAACGGTTCTGGTTCAGTTGGCTATCCTGCT |
| | | CGTTATGCCAACGCAATGGCTGTAGGAGCGACTGACCAAAA |
| | | CAACAGACGTGCAAACTTTTCTCAGTATGGTACAGGAATTG |
| | | ACATCGTAGCACCAGGGGTTAATGTACAAAGTACGTATCCT |
| | | GGAACCCGCTATGCAAGTTTAAATGGTACATCTATGGCTAC |
| | | TCCACACGTCGCCGGCGCCGCCGC<u>ACTAGT</u> |
| SEQ ID NO:10 | 3B3 | <u>GTCGAC</u>TCAAGATGGGAACGGGCACGGGACGCACGTTGCTG |
| | | CAACGATTGCGGCTCTTGATAATTCAATCGGTGTGATTGGT |
| | | GTGGCACCAAGTGCTGATCTATACGCTGTAAAAGTACTTGG |
| | | AGCAAATGGTAGAQGAAGCGTTAGTGGAATTGCTCAAGGTC |
| | | TAGAGTGGGCTGCAGCGAATAACATGCATATTGCTAACATG |
| | | AGTCTCGGTAGTGATGCACCTACTACTACACTTGAGCGTGC |
| | | AGTCAACTACGCGACAAGCCAAGGTGTACTAGTTATTGCAG |
| | | CGACTGGTAACAACGGTTCTGGTTCAGTTGGCTATCCTGCT |
| | | CGTTATGCAAACGCAATGGCTGTAGGAGCGACTGACCAAAA |
| | | CAACAGACGTGCAAACTTTTCTCAGTATGGTACAGGAATTG |
| | | ACATCGTAGCACCAGGGGTTAATGTACAAAGTACGTATCCT |
| | | GTTGCACCGAGCGCTGAACTGTATGCAGTTAAAGTTCTGGG |
| | | CGCAAGCGGCAGAGGCTCAGTTTCAGGCATTGCACAGGGCC |
| | | TGGAATGGGCAGGAACAAATGGCATGCATGTTGCAAATATG |
| | | TCACTGGGCACACCTGCACCGTCAGCAACACTGGAACAGGC |

-continued

| SEQ ID | Clone ID | Sequence |
|---|---|---|
| | | AGTTAATGCAGCAACATCACAGGGCGTTCTGGTTATTGCAG |
| | | CATCAGGCAATAGCGGCTCAGGCACAGTTAGCTATCCGGCA |
| | | AGATATGCAAATGCAATGGCAGTTGGCGCAACAGATCAAAA |
| | | TAATAATAGAGCAAGCTTTTCACAATATGGCGCAGGCCTTG |
| | | ATACTGTTGCACCGGGCGTTGGCGTTCAATCAACATATCCG |
| | | GGCAGCACATATGCTTCAATGAGCGGCACATCAATGGCATC |
| | | ACCGCATGTTGCAGGCGTTGCAGC<u>ACTAGT</u> |
| | | <u>GTCGAC</u>ACAAGATGGCAATGGACATGGCACACATGTTGCAG |
| SEQ ID NO:1235c | | GCACAGTTGCAGCACTGAATAATAACATTGGCGTTCTTGGC |
| | | GTTGCACCGAGCGTTGAACTGTATGGAGTTAAAGTTCTGGG |
| | | CGCAAGCGGCAGCGGCTCAGTTTCAAGCATTGCACAGGGCC |
| | | TGGAATGGGCAGCAGATAATGGCATGCATGTTGCAAATATG |
| | | TCACTGGGCTCACCTTTTCCGTCATCAACACTGGAACAGGC |
| | | AGTTAATTCAGCAACATCACGGGCGTTCTGGTTGTTGCAG |
| | | CATCAGGCAATAGCGGCTCAGGCACAGTTGGCTATCCGGCA |
| | | AGATATGCAAATGCAATGGCAGTTGGCGCAACAGATCAAAA |
| | | TAATAATAGAGCAAGCTTTTCACAATATGGCGCAGGCCTTG |
| | | ATATTGTTGCACCGGGCGTTGGCGTTCAATCAACATATCCG |
| | | GGCAGCAGATATGCTTCACTGAGCGGCACATCAATGGCAAC |
| | | ACCGCATGTTGCAGGCGTTGCAGC<u>ACTAGT</u> |
| | | GTCGACACAAGATGGCAATGGACATGGCACACATGTTGCAG |
| SEQ ID NO:1246c | | GCACAATTGCAGCACTGAATAATAGCATTGGCGTTATTGGC |
| | | GTTGCACCGAGCGTTGATCTGTATGGAGTTAAAGTTCTGGG |
| | | CGCAAGCGGCAGCGGCTCAGTTTCAAGCATTGCACGGGGCC |
| | | TGGAATGGGCAGGAGATAATGGCATGCATGTTGCAAATCTG |
| | | TCACTGGGCTCACCTTCACCGTCAGCAACACTGGAACAGGC |
| | | AGTTAATTCAGCAACATCACGGGCGTTCTGGTTATTGCAG |
| | | CAACAGGCAATACCGGCGCAGGCACACTTAGCTATCCGGCA |
| | | AGATATGCAAATGCAATGGCAGTTGGCGCAACAGATCAAAA |
| | | TAATAATAGAGCAAGCTTTTCACAATATGGCACCGGCCTTG |
| | | ATATTGTTGCACCGGGCGTTGGCGTTCAATCAACATATCCG |
| | | GGCAGCACATATGTTTCACTGAACGGCACATCAATGGCAAC |
| | | ACCGCATGTTGCAAGCGCTGCAGC<u>ACTAGT</u> |
| | | GTCGACACAAGATGGCAATGGACATGGCACACATGTTGCAG |
| SEQ ID NO:1257c | | GCACAATTGCAGCACTGAATAATAGCGTTGGCGTTCTTGGC |
| | | GTTGCACCGAACGTTGAACTGTATGCAGTTAAAGTTCTGGG |
| | | CGCAAGCGGCAGAGGCACAATTTCAGGCATTGCACAGGGCC |
| | | TGGAATGGGCAGCAGATAATGGCACGCATATTGCAAATCTG |

-continued

| SEQ ID | Clone ID | Sequence |
|---|---|---|
| | | TCACTGGGCACATCTTTTCCGTCAGCAACACTGGAACGGGC |
| | | AGTTAATTCAGCAACATCACGGGGCGTTCTGGTTGTTGCAG |
| | | CAACAGGCAATACCGGCGCAGGCTCAATTAGCTATCCGGCA |
| | | AGATTTGCAAATGCAATGGCAGTTGGCGCAACAGATCAAAA |
| | | TAATAGAAGAGCAAGCTTTTCACAATATGGCGCAGGCCTTG |
| | | ATATTGTTGGACCGGGCGTTGGCGTTCAATCAACATATCCG |
| | | GGCAGCACATATGCTTCACTGAGCGGCACATCAATGGCAAC |
| | | ACCGCATGTTGCAGGCGCTGCAGC<u>ACTAGT</u> |
| | | <u>GTCGAC</u>ACAAGATGGCAATGGACATGGCAC |
| | | ACATGTTGCAG |
| SEQ ID NO:1268c | | GCACAGTTCCAGCACTGAATAATAGCGATGGCGTTATTGGC |
| | | GTTGCACCGAGCGCTGATCTGTATCCAGTTAAAGTTCTGGG |
| | | CGCAAACGGCAGCGGCTCAGTTTCAAGCATTGCACAGGGCC |
| | | TGGAATGGGCAGCAGATAATGGCATGCATATTGCAAATATG |
| | | TCACTGGGCACATCTTCACCGTCAGTAACACTGGAACGGGC |
| | | AGTTAATGCAGCAACATCACAGGGCGTTCTGGTTGTTCCAG |
| | | CATCAGGCAATACCGGCGCAGGCTCAATTGGCTATCCGGCA |
| | | AGATATGCAAATGCAATGGCAGTTGGCGCAACAGATCAAAA |
| | | TAATAGAAGAGCAAGCTTTTCACAATATGGCGCAGGCCTTG |
| | | ATATTGTTGCACCGGGCGTTAATGTTCAATCAACATATCCG |
| | | GGCAGCAGATATGCTTCACTGAGCGGCACATCAATGGCATC |
| | | ACCGCATGTTGCAGGCGCTGCAGC<u>ACTAGT</u> |
| | | <u>GTCGAC</u>ACAAGATGGCAATGGACATGGCACACATGTTGCAG |
| SEQ ID NO:1297c | | GCACAGTTGCAGCACTGAATAATAGCATTGGCGTTATTGGC |
| | | GTTGCACCGAGCGCTGAACTGTATGGAGTTAAAGTTCTGGG |
| | | CGCAAACGGCAGCGGCTCGGTTTCAAGCATTGCACGGGGCC |
| | | TGGAATGGGCAGGAAATAATGGCATGCATATTGCAAATCTG |
| | | TCACTGGGCTCAGATTTTCCGTCAGCAACACTGGAACAGGC |
| | | AGTTAATGCAGCAACATCACGGGGCGTTCTGGTTGTTGCAG |
| | | CATCAGGCAATAACGGCTCAGGCTCAGTTGGCTATCCGGCA |
| | | AGATATGCAAATGCAATGGGAGTTGGCGCAACAGATCAAAA |
| | | TAATAGAAGAGCAAACTTTTCACAATATGGCGCAGGCCTTG |
| | | ATATTGTTGCACCGGGCGTTGGCGTTCAATCAACATATCCG |
| | | GGCAACACATATGTTTCACTGAACGGCACATCAATGGCAAC |
| | | ACCACATGTTGCGGGCGTTGCAGC<u>ACTAGT</u> |
| | | <u>GTCGAC</u>ACAAGATGGCAATGGACATGGCACACATGTTGCAG |
| SEQ ID NO:1289c | | GCACAGTTGCAGCACTGAATAATAGCGATGGCGTTATTGGC |
| | | GTTGCACCGAACGTTGAACTGTATGGAGTTAAAGTTCTGGG |

-continued

| SEQ ID | Clone ID | Sequence |
|---|---|---|
| | | CGCAAACGGCAGAGGCACAGTTTCAGGCATTGCACAGGGCC |
| | | TGGAATGGGCAGCAGCAAATGGCATGCATGTTGCAAATCTG |
| | | TCACTGGGCTCACCTGCACCGTCAGCAACACTGGAACAGGC |
| | | AGTTAATGCAGCAACATCACGGGCGTTCTGGTTATTGCAG |
| | | CATCAGGCAATAGCGGCGCAGGCACAGTTGGCTATCCGGCA |
| | | AGATATGCAAATGCAATGGCAGTTGGCGCAACAGATCAAAA |
| | | TAATAATAGAGCAAACTTTTCACAGTATGGCGCAGGCCTTG |
| | | ATATTGTTGCACCGGGCGTTGGCGTTCAATCAACATATCCG |
| | | GGCAACACATATACTTCACTGAGCGGCACATCAATGGCATC |
| | | ACCGCATGTTGCAGGCGTTGCAGC<u>ACTAGT</u> |
| SEQ ID NO:129 | 99c | <u>GTCGAC</u>ACAAGATGGCAATGGACATGGCACACATGTTGCAG |
| | | GCACAATTGCAGCACTGAATAATAACGTTGGCGTTCTTGGC |
| | | GTTGCACCGAGCGTTGATCTGTATGGAGTTAAAGTTCTGGA |
| | | CGCAAGCGGCAGAGGCACAATTTCAGGCATTGCACGGGGCC |
| | | TGGAATGGGCAGCAGCAAATGGCATGCATATTGCAAATATG |
| | | TCACTGGGCTCAGATCAACCGTCAACAACACTGGAACGGGC |
| | | AGTTAATGCAGCAACATCACGGGCGTTCTGGTTGTTGCAG |
| | | CATCAGGCAATACCGGCTCAGGCACAGTTAGCTATCCGGCA |
| | | AGATATGCAAATGCAATGGCAGTTGGCGCAACAGATCAAAA |
| | | TAATAATAGAGCAAACTCTTCACAATATGGCGCAGGCCTTG |
| | | ATATTGTTGCACCGGGCGTTGGCGTTCAATCAACATATCCG |
| | | GGCAGCACATATGCTTCACTGAGCGGCACATCAATGGCATC |
| | | ACCGCATGTTGCAGGCGTTGCAGC<u>ACTAGT</u> |
| SEQ ID NO:130 | 9C | <u>GTCGAC</u>ACAAGATGGCAATGGACATGGCACACATGTTGCAG |
| | | GCACAATTGCAGCACTGAATAATAGCGTTGGCGTTATTGGC |
| | | GTTGCACCGAGCGCTGAACTGTATGGAGTTAAAGTTCTGGG |
| | | CGCAAACGGCAGCGGCACAGTTTCAGGCATTGCACGGGGCC |
| | | TGGAATGGGCAGCAGATAATGGCATGCATGTTGCAAATATG |
| | | TCACTGGGCTCATCTGCACCGTCAGCAACACTGGAACGGGC |
| | | AGTTAATTCAGCAACATCACGGGCGTTCTGGTTGTTGCAG |
| | | CAACAGGCAATACCCGCGCAGGCTCAATTAGCTATCCGGCA |
| | | AGATATGCAAATGCAATGGCAGTTGGCGCAACAGATCAAAA |
| | | TAATAATAGAGCAAGCTTTTCACAATATGGCACAGGCCTTG |
| | | ATATTGTTGCACCGGGCGTTAATGTTCAATCAACATATCCG |
| | | GGCAGCAGATATGCTTCAATGAGCGGCACATCAATGGCATC |
| | | ACCGCATGTTGCAGGCGCTGCAGC<u>ACTAGT</u> |
| SEQ ID NO:131 | 1C10 | STQDGNGHGTHVAGTIAALDNDEGVVGVAPNADLYAVKVLS |
| | | ASGSGSISSTAQGLEWSGENGMDIANLSLGSSAPSATLEQA |

-continued

| SEQ ID | Clone ID | Sequence |
|---|---|---|
| | | VNAATSRGVLVIAASGNSGAGSVGYPARYANAMAVGATDQN |
| | | NRRASSSQYGAGLDIVAPGVGVQSTYPGNRYASLNGTSMAT |
| | | PHVAGVAAAL |
| SEQ ID NO:132 | 1C4 | STQDGNGHGTHVAGTVAALNNSIGVIGVAPSADLYAVKVLG |
| | | ANGRGSVSGIAQGLEWAAANNMHIANMSLGSDFPSSTLERA |
| | | VNYATSQGVLVIAATGNNGSGSVGYPARYANAMAVGATDQN |
| | | NRRATSQYGTGTDIVAPGVJNVQSTYPGNRYASLNGTSMAT |
| | | PHVAGAAAL |
| SEQ ID NO:133 | 1F6 | STQDGNGHGTHVAGTIAALNNSIGVLGVAPNAELYAVKVLG |
| | | ANGRGSVSGIAQGLEWAAANNMHIANMSLGSDAPSTTLERA |
| | | VNYATSQGVLVIAATGNNGSGSVGYPARYANAMAVGATDQN |
| | | NRRANFSQYGTGIDIVAPGVNVQSTYPGNRYVSMNGTSMAT |
| | | PHVAGVAAL |
| SEQ ID NO:134 | 2B4 | STQDGNGHGTHVAGTVAALNNSIGVIGVAPSADLYAVKVLG |
| | | ANGRGSVSGIAQGLEWAAANNMHIANMSLGSDAPSTTLGRA |
| | | VNYATSQGVLVIAATGNNGSGSVGYPARYANAMAVGATDQN |
| | | NRRANFSQYGTGIDIVAPGVNVQSTYPGNRYASLNGTSMAT |
| | | PHVAGVAAL |
| SEQ ID NO:135 | 2B8 | STQDGNGHGTHVAGTVAALNNSIGVIGVAPSADLYAVKVLG |
| | | ANGRGSVSGIARGLEWAAANNHIANMSLGSDAPSTTLERA |
| | | VNYATSQGVLVIAATGNNGSGSVGYPARYANAMAVGATDQ |
| | | NNPRANFSQYGTGIDIVAPGVNVQSTYPGNRYASLNGTSM |
| | | APHVAGVAAL |
| SEQ ID NO:136 | 2G6 | STQDGNGHGTHVAGTIAALNNNVGVLGVAPNVELYGVKVLG |
| | | ASGSGSISGIAQGLQWAGNNGMHANMSLGTSAPSATLEQA |
| | | VNAATSRGVLVTAASGNSGAGSVGYPARYANAMAVGATDQ |
| | | NNRRANFSQYGTGIDIVAPGVNVQSTYPGNRYVSMNGTSM |
| | | ATPHVAGVAAL |
| SEQ ID NO:137 | 3A3 | STQDGNGHGTHVAGTVAALNNSIGVIGVAPSADLYAVKVLG |
| | | ANGRGSVSGIAQGLEWAAANNMHIANMSLGSDAPSTTLERA |
| | | VNYATSQGVLVIAATGNNGSGSVGYPARYANAMAVGATDQN |
| | | NRRANFSQYGTGIDIVAPGVNVQSTYPGNRYVSMSGTSMAT |
| | | PHVAGAAAL |
| SEQ ID NO:138 | 3A7 | STQDGNGHGTHVAGTVAALXNSIGVIGVAPSADLYAVKVLG |
| | | ANGRGSVSGIAQGLEWAANNMHIANMSLGSDAPSTTLERA |
| | | VNYATSQGVLVIAATGNNGSGSVGYPARYANAMAVGATDQ |
| | | NNRRANFSQYGTGIDIVAPGVNVQSTYPGNRYVSMNGTSM |
| | | ATPHVAGAAAL |

-continued

| SEQ ID | Clone ID | Sequence |
| --- | --- | --- |
| SEQ ID NO:139 | 3B2 | STQDGNGHGTHVAGTIAALNNSVGVLGVAPNAELYAVKVLG ANGRGSVSGIAQGLEWAAANNMHIANMSLGSDAPSTTLERA VNYATSQGVLVIAATGNNGSGSVGYPARYANAMAVGATDQN NRRANFSQYGTGIDIVAPGVNVQSTYPGTRYASLNGTSMAT PHVAGAAAL |
| SEQ ID NO:140 | 3B3 | STQDGNGHGTHVAGTIAALDNSIGVIGVAPSADLYAVKVLG ANGRGSVSGIAQGLEWAAANNMHIANMSLGSDAPSTTLERA VNYATSQGVLVIAATGNNGSGSVGYPARYANAMAVGATDQN NRRANFSQYGTGIDIVAPGVNVQSTYPGNRYASLNGTSMAT PHVAGAAAL |
| SEQ ID NO:141 | 3D11 | STQDGNGHGTHVAGTVAALNNSIGVIGVAPSADLYAVKVLG ANGSGSVSGIARGLEWAATNNMHIANMSLGSDFPSSTLERA VNYATSRDVLVIAATGNNGSGSVGYPARYANAMAVGATDQN NRRANFSQYGTGIDIVAPGVNVQSTYPGNRYASLNGTSMAT PHVAGAAAL |
| SEQ ID NO:142 | 3E2 | STQDGNGHGTHVAGTVAALNNSIGVIGVAPSADLYAVKVLG ANGRGSVSGIAQGLEWAAANNMHIANMSLGSDAPSTTLERA VNYATSQGVLVTAATGNNGSGSVGYPARYANAMAVGATDQN NRRANFSQYGTGIDIVAPGVNVQSTYPGNRYASLSGTSMAT PHVAGVAAL |
| SEQ ID NO:143 | 3G9 | STQDGNGHGTHVAGTVAALNNSIGVIGVAPSADLYAVKVLG ANGRGSVSGIAQGLEWAAANNMHIANMSLGSDFPSSTLERA VNYATSRDVLVIAATGNNGSGSVGYPARYANAMAVGATDQN NRRANFSQYGTGTDTVAPGVNVQSTYPGNRYASLNGTSMAT PHVAGVAAL |
| SEQ ID NO:144 | 4C2 | STQDGNGHGTHVAGTVAALNNSIGVIGVAPSADLYAVKVLG ANGRGSVSGIAQGLEWAAANNMHIANMSLGSDAPSTTLERA VNYATSRDVLVIAATGNNGSGSVGYPARYANAMAVGATDQN NRRANFSQYGTGIDIVAPGVNVQSTYPGNRYASLSGTSMAT PHVAGVAAL |
| SEQ ID NO:145 | 4C6 | STQDGNGHGTHVAGTVAALNNSIGVIGVAPSADLYAVKVLG ANGRGSVSGIAQGLEWAAANNMHIANMSLGSDAPSTTLERA VNYATSQGVLVIAATGNNGSGSVGYPARYANAMAVGATDQN NRRANFSQYGTGIDIVAPGNVQSTYPGNRYASLSGTSMATP HVAGAAAL |
| SEQ ID NO:146 | 4D10 | STQDGNGHGTHVAGTVAALNNSIGVIGVAPSADLYAVKVLG ANGRGSVSGIAQGLEWAAANNMHIANMSLGSDAPSTTLERA VNYATSQGVLVIAATGNNGSGSVGYPARYAMAMAVCATDQN |

-continued

| SEQ ID | Clone ID | Sequence |
|---|---|---|
| | | NRRANFSQYGTGTIDIVAPGVNVQSTYPGNRYVSMNGTSMA |
| | | TPHVAGVAAL |
| SEQ ID NO:147 | 4D7 | STQDGNGHGTHVAGTVAALDNSVGVLGVAPEADLYAVKVLS |
| | | ASGAGSISSIAQGLEWSAANNMHIANMSLGSDAPSTTLERA |
| | | VNYATSQGVLVIAATGNNGSGSVGYPARYANAMAVGATDQN |
| | | NRRANFSQYGTGIDIVAPGVNVQSTYPGNRYASLNGTSMAT |
| | | PHVAGVAAL |
| SEQ ID NO:148 | 5B11 | STQDGNGHGTHVAGTIAALNKSIGVIGVAPSADLYAVKVLG |
| | | ANGRGSVSGIAQGLEWAAANNMHIANMSLGSDAPSTTLERA |
| | | VNYATSQGVLVIAATGNNGSGSVGYPARYANAMAVGATDQN |
| | | NRRNFSQYGTGIDIVAPGVNVQSTYPGNRYVSMNGTSMATP |
| | | HVAGAAAL |
| SEQ ID NO:149 | 5E1 | STQDGNGHGTHVAGTIAALDNDEGVVGVAPNADLYAVKVLS |
| | | ASGSGSISSIAQGLEWSGENGMDIANLSLGSSAPSATLEQA |
| | | VNAATSRGVLVIAASGNSGAGSVGYPARYANAMAVGATDQN |
| | | NNRASFSQYGAGLDIVAPGVGVQSTYPGNRYASLNGTSMAT |
| | | PHVAGAAAL |
| SEQ ID NO:150 | 5F4 | STQDGNGHGTHVAGTIAALNNSTGVLGVAPNADLYAVKVLG |
| | | ANGSGSVSGIARGLEWAATNNMHIANMSLGSDAPSTTLERA |
| | | VNYATSQGVLVIAATGNNGSGSVGYPARYANAMAVGATDQN |
| | | NRRANFSQYGTGIDIVAPGVNVQSTYPGNRYARLNGTSMAT |
| | | PHVAGVAAL |
| SEQ ID NO:151 | 5H9 | STQDGNGHGTHVAGTIAALDNSIGVIGVAPSADLYAVKVLG |
| | | ANGSGSVSGIARGLEWAATNNMHIANMSLGSDAPSTTLERA |
| | | VNYATSQGVLVIAATGNNGSGSVGYPARYANANAVGATDQN |
| | | NRRANFSQYGTGIDIVAPGVNVQSTYPGNRYASLNGTSMAT |
| | | PHVAGAAAL |
| SEQ ID NO:152 | 6A4 | STQDGNGHGTHVAGTIAALDNDEGVVGVAPNADLYAVKVLS |
| | | ASGAGSISSIAQGLEWSGENGMDIANLSLGSSAPSATLEQA |
| | | VNAATSRGVLVIAASGNSGAGSVGYPARYANAMAVGATDQN |
| | | NNRASFSQYGAGLDIVAPGVGVQSTYPGSTYASLNGTSMAT |
| | | PHVAGVAAL |
| SEQ ID NO:153 | 6B11 | STQDGNGHGTHVAGTIAALNNSIGVLGVAPNAELYAVKVLG |
| | | ASGSGSISGIAQGLEWAAANNMHIANMSLGSDAPSTTLERA |
| | | VNYATSQGVLVIAATGNNGSGSVGYPARYANAMAVGATDQN |
| | | NRRANFSQYGTGTDIVAPGVNVQSTYPGNRYASLNGTSMAT |
| | | PHVAGVAAL |
| SEQ ID NO:154 | 6B6 | STQDGNGHGTHVAGTIAALNNSTGVLGVAPNAELYAVKVLG |

-continued

| SEQ ID | Clone ID | Sequence |
|---|---|---|
| | | ANGRGSVSGTAQGLEWAAANNMHIANMSLGSDAPSTTLERA |
| | | VKYATSQGVLVIAATGNNGSGSVGYPARYANAMAVGATDQN |
| | | NNRASFSQYGAGLDIVAPGVNVQSTYPGSTYDSLSGTSMAT |
| | | PHVAGVAAL |
| SEQ ID NO:155 | 6G6 | STQDGNGHGTHVAGTVAALNNSIGVIGVAPSADLYAVKVLG |
| | | ANGRGSVSGIAQGLEWAAANNMHIANMSLGSDAPSTTLERA |
| | | VNYATSQGVLVIAATGNNGSGSVGYPARYANAMAVGATDQN |
| | | NRRANFSQYGTGIDIVAPGVNVQSTYPGGQYAELSGTSMAS |
| | | PHVAGAAAL |
| SEQ ID NO:156 | 7A2 | STQDGNGHGTHVAGTVAALNNSIGVLGVAPNAELYAVKVLG |
| | | ASGSGSISGIAQGLEWAAANNMHIANMSLGSDAPSTTLERA |
| | | VNYATSQGVLVIAATGNNGSGSVGYPARYANAMAVGATDQN |
| | | NRRANFSQYGTGTDTVAPGVEIESTYPGSSYDSLRGTSMAT |
| | | PHVAGAAAL |
| SEQ ID NO:157 | 7C6 | STQDGNGHGTHVAGTTAALDNDEGVVGVAPNADLYAVKVLG |
| | | ANGRGSVSGIAQGLEWAAANNMHIANMSLGSDAPSTTLERA |
| | | VNYATSQGVLVIAATGNNGSGSVGYPARYANAMAVGATDQN |
| | | NRRANFSQYGTGIDIVAPGVEIESTYPGNRYASLNGTSMAT |
| | | PHVAGVAAL |
| SEQ ID NO:158 | 7F11 | STQDGNGHGTHVAGTIAALNNSVGVLGVAPNADLYAVKVLG |
| | | ANGRGSVSGTAQGLEWAAANNMHIANMSLGSDAPSTTLERA |
| | | VNYATSQGVLVTAATGNNGSGSVGYPARYANAXAVGATDQN |
| | | NRRANFSQYGTGIDIVAPGVGVQSTYPGNRYASLSGTSMAT |
| | | PHVAGVAAL |
| SEQ ID NO:159 | 8C2 | STQDGNGHGTHVAGTIAALNNSIGVLGVAPNAELYAVKVLG |
| | | ANGRGSVSGTAQGLEWAAANNMHIAANSLGSDAPSTTLKRA |
| | | VNYATSQGVLVTAATGNNGSGSVGYPARYANAMAVGATDQN |
| | | NRRANFSQYGTGIDIVAPGVNVQSTYPGNRYASLNGTSMAS |
| | | PHVAGAAAL |
| SEQ ID NO:160 | 8H2 | STQDGNGHGTHVAGTIAALNNSIGVIGVAPNAELYAVKVLG |
| | | ANGSGSVSGIAQGLEWATNNTMHIANMSLGSDFPSSTLERA |
| | | VNYATSQGVLVIAATGNNGSGSVGYPARYANAMAVGATDQN |
| | | NRRANFSQYGTGIDIVAPGVNVQSTYPGNRYASLNGTSMAT |
| | | PHVAGVAAL |
| SEQ ID NO:161 | 9A1 | STQDGNGHGTHVAGTVAALNNSEGVTGVAPSADLYAVKVLG |
| | | ANGRGSVSGTAQGLEWAAANNMHIANMSLGSDAPSTTLERA |
| | | VNYATSQGVLVIATGNNGSGSVGYPARYANAMAVGATDQN |
| | | NRRANFSQYGTGIDIVAPGVNVQSTYPGNRYASLNGTSMAT |

-continued

| SEQ ID | Clone ID | Sequence |
|---|---|---|
| | | PHVAGVAAL |
| SEQ ID NO:162 | 9B4 | STQDGNGHGTHVAGTIAALDNDEGVVGVAPNADLYAVKVLS ASGAGSISSIAQGLEWSGENGMDIANLSLGSSAPSATLEQA VNAATSRGVLVIAASGNSGAGSVGYPARYANAMAVGATDQN NNRASFSQYGAGLDIVAPGVGVQSTYPGSTYASLNGTSMAT PHVAGVAAL |
| SEQ ID NO:163 | 9E3 | STQDGNGHGTHVAGTIAALNNNVGVLGVAPNVBLYGVKVLG ASGSGSISGIAQGLQWAGNNGMHIANMSLGTSAPSATLEQA VNAATSRGVLVIAASGNSGAGSVGYPARYANAMAVGATDQN NRRANFSQYGTGIDIVAPGVNVQSTYPGNRYVSMNGTSMAT PHVAGVAAL |
| SEQ ID NO:164 | 9F1 | STQDGNGHGTHVAGTVAALNNSIGVTGVAPSADLYAVKVLG ANGRGSVSGIAQGLEWAAANNMHIANMSLGSDAPSTTLERA VNYATSQGVLVIATGNNGSGSVGYPARYANAMAVGATDQN NRRAMFSQYGTGIDIVAPGVNVQSTYPGNRYASLNGTSMAT PHVAGVAAL |
| SEQ ID NO:165 | 9H5 | STQDGNGHGTHVAGTVAALNNSIGVIGVAPSADLYAVKVLG ANGRGSVSGIAQGLEWAAANNMHIANMSLGSDAPSTTLEPA VNYATSQGVLVIAATGNNGSGSVGYPARYANAMAVGATDQN NRRANFSQYGTGIDIVAPGVNVQSTYPGNRYASLNGTSMAT PHVAGVAAL |
| SEQ ID NO:166 | 100c | STQDGNGHGTHVAGTVAALNNNDGVLGVAPNVDLYAVKVLG ANGRGSISGIARGLQWAADNGTHVANLSLGTDQPSTTLERA VNYATSRGVLVVAATGNTGSGTVSYPARYANAMAVGATDQN NNRANFSQYGAGIDIVAPGVNVQSTYPGNTYVSLNGTSMAT PHVAGAAAL |
| SEQ ID NO:167 | 101c | STQDGNGHGTHVAGTVAALNNSVGVLGVAPSVELYAVKVLG ANGRGSISGIAQGLEWAGANGMHIANMSLGTSAPSSTLERA VNSAASRGVLVVAASGNNGAGSVSYPARYANAMAVGATDQN NRRANFSQYGAGLDIVAPGVGVQSTYPGSTYASLSGTSMAT PHVAGAAAL |
| SEQ ID NO:168 | 102c | STQDGNGHGTHVAGTVAALNNSDGVIGVAPSADLYAVKVLG ANGRGSISGIARGLEWAANNGMHVANMSLGTDQPSATLERA VNQATSQGVLVIAATGNNGSGSVSYPARYANAMAVGATDQN NNRASFSQYGAGLDIVAPGVGVQSTYPGSRYASLNGTSMAT PHVAGAAAL |
| SEQ ID NO:169 | 103c | STQDGNGHGTHVAGTTAALNNNIGVLGVAPSVELYGVKVLG ASGRGSISGIARGLEWAGDNGMHVANLSLGTDQPSATLERA |

-continued

| SEQ ID | Clone ID | Sequence |
|---|---|---|
| SEQ ID NO:170 | 104c | STQDGNGHGTHVAGTVAALNNNIGVLGVAPSVELYGVKVLG ASGRGSVSGTARGLQWTADNGMHTANLSLGSSSPSATLERA VNYATSRGVLVLAATGNTGAGTISYPARYANAMAVGATDQN NNRASFSQYGTGLDTVAPGVGVQSTYPGSTYASLNGTSMAT PHVAGAAAL |
| | | VNAATSQGVLVIAATGNSGSGSVSYPARYATAMAVGATDQN NNRASSSQYGTGLDIVAPGVGVQSTYPGSTYVSLNGTSNAT PHVAGAAAL |
| SEQ ID NO:171 | 105c | STQDGNGHGTHVAGTIAALNNSIGVLGVAPSADLYGVKVLG ASGRGSISSIARGLQWAADNGMHVANLSLGSDFPSATLERA VNSATSRGVLVVAASGNSGAGSISYPARYANAMAVGATDQN NNRASFSHYGAGLDIVAPGVGVQSTYPONTYASLNGTSMAT PHVAGVAAL |
| SEQ ID NO:172 | 106c | STQDGNGHGTHVAGTVAALNNMVGVLGVAPSVDLYAVKVLG ASGRGSVSSIAQGLEWAATNNMHVANLSLGSSQPSSTLEQA VNAATSRGVLVTAASGNNGSGTVSYPARYANAMAVGATDQN NNRANFSHYGTGLDIVAPGVGVQSTYPGSRYASLNGTSMAS PHVAGVAAL |
| SEQ ID NO:173 | 107c | STQDGNGHGTHVAGTIAALNNSVGVLGVAPSAELYAVKVLG ASGRGTVSGIARGLQWAADNGMHVANLSLGTPQPSATLERA VNQATSRGVLVIAASGNTGSGTVSYPARYANAMAVGATDQN NRRANFSQYGAGLDIVAPGVGVQSTYRGSTYASLSGTSMAS PHVAGVAAL |
| SEQ ID NO:174 | 109c | STQDGNGHGTHVAGTIAALNNSVGVLGVAPNADLYGVKVLG ASGRGTISSIARGLEWAGANGMHVANLSLGTSSPSSTLEQA VNQATSRGVLVVAASGNTGSGTVSYPATYANAMAVGATDQN NNRANFSQYGTGLDIVAPGVGVQSTYPGSRYASLNGTSMAS PHVAGAAAL |
| SEQ ID NO:175 | 10c | STQDGNGHGTHVAGTIAALNNNVGVLGVAPSAELYGVKVLG ASGSGSISGIARGLEWAAAKGMHVANMSLGTPFPSATLEQA VKAATSRGVLVVAASGNSGAGSISYPARYANAMAVGATDQN NNRASFSQYGTGIDIVAPGVGVKSTYPGSTYVSLSGTSMAS PHVAGVAAL |
| SEQ ID NO:176 | 110c | STQDGNGHGTHVAGTVAALNNNVGVLGVAPSAELYAVKVLG ANGSGTVSSIAQGLEWAGNNGMHVANLSLGTDQPSATLERA VNAATSRGVLVVAASGNTGSQSVGYPARYANAMAVGATDQN NNRANFSQYGAGLDTVAPGVGVQSTYPGNRYASMNGTSMAT PHVAGAAAL |

-continued

| SEQ ID | Clone ID | Sequence |
|---|---|---|
| SEQ ID NO:177 | 112c | STQDGNGHGTHVAGTIAALNNNIGVLGVAPSAELYAVKVLG ASGRGSVSSIAQGLEWAGDNGMHVANLSLGSPFPSSTLERA VNAATSRGVLVTAASGNSGSGSISYPARYANAMAVGATDQN NNRANSSQYGAGLEIVAPGVGVQSTYPGSTYVSMSGTSMAS PHVAGAAAL |
| SEQ ID NO:178 | 113c | STQDGNGHGTHVAGTIAALNKNVGVIGVAPNVELYGVKVLG ANGRGTTSSIARGLEWAANNGTHIANLSLGTDQPSATLERA VNQATSQGVLVIAASGNSGSGSVSYPARYANAMAVGATDQN NNRASFSHYGTGLDIVAPGVGVQSTYPGSRYASLNGTSMAS PHVAGVAAL |
| SEQ ID NO:179 | 114c | STQDGNGHGTHVAGTVAALNUSVGVLGVAPSADLYAVKVLG ASGRGTVSSIARGLEWAADNNMHIANLSLGTDQPSATLEQA VNAATSQGVLVVAASGNNGSGSIGYPARYANAMAVGATDQN NNRASFSQYGTGLDIVAPGVGVQSTYPGNTYVSLSGTSMAT PHVAGAAAL |
| SEQ ID NO:180 | 115c | STQDGNGHGTHVAGTVAALNNNVGVIGVAPSADLYAVKVLG ASGRGTISGIAQGLEWAGDNGMHVANLSLGSDQPSATLEQA VNAATSQGVLVVAASGNSGSGSVGYPARYANAMAVGATDQN NNRASFSQYGQGLDIVAPGVGVQSTYPGSRYASMSGTSMAS PHVAGVAAL |
| SEQ ID NO:181 | 116c | STQDGNGHGTHVAGTVAALNNSIGVLGVAPSVDLYAVKVLG ANGRGTVSGIAQGLEWAADKGNHVANLSLGSSSPSTTLEQA VNAATSQGVLVTAATGNSGAGSISYPARYANAMAVGATDQN NNRASFSQYGQGLDTVAPGVGVQSTYPGSTYVSLSGTSMAT PHVAGAAAL |
| SEQ ID NO:182 | 117c | STQDGNGHGTHVAGTIAALNNNDGVLGVAPSVELYGVKVLG ASGRGTVSSIARGLEWAANUGMHVANMSLGTPAPSTTLERA VNQATSRGVLVIAASGNNGSGSISYPARYANAMAVGATDQN NRRASFSQYGAGLDTVAPGVGVQSTYPGSRYASLSGTSMAS PHVAGVAAL |
| SEQ ID NO:183 | 118c | STQDGNGHGTHVAGTVAALNNSVGVFGVAPSVDLYAVKVLG ASGSGTVSSVAQGLQWAGDNGMHVANLSLGSDAPSATLEQA VNSATSRGVLVVAASGNTGAGTVGYPARYANAMAVGATDQN NRRANFSQYGAGLDIVAPGVGVQSTYPGSTYASLNGTSMAT PHVAGVAAL |
| SEQ ID NO:184 | 119c | STQDGNGHGTHVAGTVAALNUSVGVLGVAPSVELYAVKVLG ASGSGSISGIARGLEWAADNUTHVANLSLGSDFPSATLERA VNYATSRGVLVVAASGNTGSGTIGYPARYANAMAVGATDQN |

-continued

| SEQ ID | Clone ID | Sequence |
|---|---|---|
| | | NRRASFSQYGTGLDIVAPGVGVQSTYPGSRYASLNGTSMAS |
| | | PHVAGVAAL |
| SEQ ID NO:185 | 11c | STQDGNGHGTHVAGTVAALNNSDGVIGVAPSAELYAVKVLG |
| | | ANGSGSVSGIARGLEWAGANGMHVANLSLGTDQPSATLEQA |
| | | VNQATSRGVLVVAASGNSGSGTVGYPARYANAMAVGATDQN |
| | | NNRASFSQYGAGIDIVAPGVGVQSTYPGSRYTSLSGTSMAT |
| | | PHVAGAAAL |
| SEQ ID NO:186 | 121c | STQDGNGHGTHVAGTVAALNNNIGVIGVAPNVELYAVKVLG |
| | | ASGSGSVSSIARGLQWAANNGMHIANLSLGSSAPSATLERA |
| | | VNAATSRGVLVVAASGNSGAGSIGYPARYANAMAVGATDQN |
| | | NNRASFSQYGAGLDILAPGVGVQSTYPGSTYASMSGTSMAT |
| | | PHVAGAAAL |
| SEQ ID NO:187 | 122c | STQDGNGHGTHVAGTVAALNNSVGVLGVAPSADLYAVKVLG |
| | | ASGRGSVSGIAQGLEWADNGMEHVANMSLGTDFPSATLEQA |
| | | VNAATSRDVLVVAATGNTGSGTVGYPARYANAMAVGATDQN |
| | | NNRANFSQYGTGLDIVAPGVGVQSTYPGSRYVSMSGTSMAS |
| | | PHVAGAAAL |
| SEQ ID NO:188 | 123c | STQDGNGHGTHVAGTIAALNNSVGVLGVAPSADLYAVKVLG |
| | | ASGRGSVSSTARGLEWAANNGMHVANLSLGSPFPSSTLERA |
| | | VNYATSRDVLVIAATGNSGAGTVGYPARYANAMAVGATDQN |
| | | NNRASSSQYGAGLDIVAPGVGVQSTYPGSTYASLNGTSMAS |
| | | PHVAGAAAL |
| SEQ ID NO:189 | 124c | STQDGNGHGTHVAGTVAALNNSIGVLGVAPSADLYGVKVLG |
| | | ASGRGSISSIARGLEWAGNNGNHIANMSLGSDQPSATLERA |
| | | VNSATSRGVLVVAASGNSGAGSVTYPARYANAMAVGATDQN |
| | | NRRASFSHYGAGLDIVAPGVGVQSTYPGSRYASLSGTSMAS |
| | | PHVAGVAAL |
| SEQ ID NO:190 | 125c | STQDGNGKGTHVAGTVAALNNNVGVTGVAPSAELYAVKVLG |
| | | ASGSGTTSGIAQGLQWAADNGTHVANLSLGSDFPSSTLEQA |
| | | VNSATSRGVLVVAASGNNGSGSVSYPAGYANAMAVGATDQN |
| | | NRRASSSQYGAGLDIVAPGVGVQSTYPGSRYASLSGTSMAT |
| | | PHVAGAAAL |
| SEQ ID NO:191 | 126c | STQDGNGHGTMVAGTVAALNNNDGVLGVAPSADLYGVKVLG |
| | | ANGRGSVSGIARGLEWAADNGMHVANMSLGTSAPSATLEQA |
| | | VNQATSRGVLVVAASGNSGAGTIGYPARYANAMAVGATDQN |
| | | NNRASFSQYGAGLDIVAPGVGVQSTYPGSTYVSLNGTSMAT |
| | | PHVAGVAAL |
| SEQ ID NO:192 | 127c | STQDGNGHGTHVAGTVAALNNSTGVLGVAPSADLYAVKVLG |

-continued

| SEQ ID | Clone ID | Sequence |
|---|---|---|
| | | ASGRGTVSSIAQGLEWAANNGTHVANLSLGTPSPSTTLERA |
| | | VNYATSRGVLVVAASGNSGAGSVSYPARYANAMAVGATDQN |
| | | NRRASFSQYGAGLDIVAPAVNVQSTYPGSTYASMSGTSMAS |
| | | PHVAGAAAL |
| SEQ ID NO:193 | 128c | STQDGNGHGTHVAGTIAALNNSDGVIGVAPNADLYAVKVLG |
| | | ASGRGTVSGIAQGLEWAAANGMHVANMSLGTPQPSATLERA |
| | | VNAATSQGVLVVAASGNNGSGSISYPARYANAMAVCATDQN |
| | | NRRASSSQYGTGLDIVAPGVGVQSTYPGSRYASLNGTSMAS |
| | | PHVACVAAL |
| SEQ ID NO:194 | 129c | STQDGNGHGTHVAGTIAALNNSIGVLGVAPNAELYGVKVLG |
| | | ASGSGTVSGIARGLEWAANNGMHIANMSLGTDAPSSTLEQA |
| | | VNSATSQGVLVIAATGNSGAGTTSYPARYANAMAVGATDQN |
| | | NRRASFSQYGTGTDTVAPGVGVQSTYPGSTYASLNGTSMAS |
| | | PHVAGAAAL |
| SEQ ID NO:195 | 12c | STQDGNGHGTHVAGTVAALNNSTGVLGVAPNAELYGVKVLG |
| | | ANGSGSISGIARGLEWAGNNGMHIANLSLGTDSPSATLEQA |
| | | VNYATSRGVLVIAASGNSGSGTVGYPARYANAMAVGATDQN |
| | | NNRASFSQYGTGLDIVAPGVGVQSTYPGSTYASLNGTSMAS |
| | | PHVAGAAAL |
| SEQ ID NO:196 | 130c | STQDGNGHGTHVAGTVAALNNSVGVIGVAPNADLYAVKVLG |
| | | ANGRGTISSIARGLEWAGDNGMHVANLSLGSPAPSATLEQA |
| | | VNQATSRGVLVTAASGNNGSGSVSYPARYANAMAVGATDQN |
| | | NNRASSSQYGAGLDIVAPGVGVQSTYPGSTYASLSGTSMAT |
| | | PHVAGAAAL |
| SEQ ID NO:197 | 131c | STQDGNGHGTHVAGTVAALNNSVGVLGVAPSAELYAVKVLG |
| | | ASGRGTISGIAQGLEWAADNGMHVANLSLGTSAPSATLERA |
| | | VNAATSRGVLVVAASGNSGAGTVSYPARYANAMAVGATDQN |
| | | NRRASFSQYGTGLDIVAPGVGVQSTYPGNTYASMSGTSMAS |
| | | PHVAGAAAL |
| SEQ ID NO:198 | 132c | STQDGNGHGTHVAGTVAALNNNVGVLGVAPSAELYAVKVLG |
| | | ASGRGTVSSIARGLQWAGDNGMHVANMSLGTSFPSATLEQA |
| | | VNAATSQGVLVVAASGNTGSGSVGYPARYANAMAVGATDQN |
| | | NNRANFSQYGTGIDIVAPGVGVQSTYPGSTYASLNGTSMAT |
| | | PHVAGAAAL |
| SEQ ID NO:199 | 133c | STQDGNGHGTHVAGTIAALNNSVGVLGVAPSVDLYGVKVLG |
| | | ASGRGSVSGIAQGLEWAAANGMRVANMSLGSDAPSATLERA |
| | | VNQATSRGVLVTAATGNNGSGSISYPARYAIAMAVGATDQN |
| | | NRRASFSQYGAGLDIVAPGVNVQSTYPGSTYVSLSGTSMAS |

-continued

| SEQ ID | Clone ID | Sequence |
|---|---|---|
| | | PHVAGAAAL |
| SEQ ID NO:200 | 134c | STQDGNGHGTHVAGTVAALNNNDGVLGVAPNAELYAVKVLG ASGSGTVSGIAQGLEWAADNGTHIANLSLGTPQPSATLERA VKSATSRGVLVVAASGNSGAGSVSYPARThKAMAVGATDQN NNRASFSQYGAGIDIVAPGVGVQSTYPGSTYASMSGTSMAT PHVAGVAAL |
| SEQ ID NO:201 | 133c | STQDGNGHGTHVAGTVAALNNSDGVIGVAPSADLYGVKVLG ANGSGSISGIAQGLEWAAANGMHVANMSLGTSFPSSTLEQA VNAATSRGVLVVAASGNSGAGTVSYPARYANAMAVGATDQN NNRASFSQYGAGIDIVAPGVGVQSTYPGNRCVSLSGTSMAT PHVAGAAAL |
| SEQ ID NO:202 | 136c | STQDGNGHGTHVAGTVAALNNNVGVLGVAPSVDLYAVKVLG ANGSGTTSGTAQGLEWAANNGMHVANMSLGSPAPSATLERA VNQATSRGVLVVAATGNSGSGTVGYPARYANAMAVGATDQN NNRASFSQYGAGTDTVAPGVGVQSTYPGSRYVSLSGTSMAS PHVAGVAAL |
| SEQ ID NO:203 | 137c | STQDGNGHGTHVAGTVAALNNNDGVIGVAPSAELYAVKVLG ASGSGSISSIARGLEWAADNGTHTANMSLGTPQPSATLERA VNSATSRGVLVVAASGNSGSGSVSYPARYANAMAVGATDQN NNRASFSQYGAGLDILAPGVGVQSTYPGSTYASLNGTSMAS PHVAGVAAL |
| SEQ ID NO:204 | 13c | STQDGNGHGTHVAGTVAALNNSTGVLGVVPSADLYAVKVLG ASGRGTVSGIAQGLEWAGNNNMHVATLSLGSDFPSSTLERA VNAATSPDVLVVAASGNTGSGSISYPARYANAMAVGATDQN NNRANFSQYGQGIDIVAPGVGVQSTYPGSRYASLSGTSMAS PHVAGVAAL |
| SEQ ID NO:205 | 14c | STQDGNGHGTHVAGTVAALNNSDGVLGVAPSVDLYGVKVLG ASGSGSISGIAQGLQWAADNGMHVANLSLGSPQPSATLERA VNYATSRGVLVVAATGNTGAGSVGYPARYANAMAVGATDQN NRRASFSQYGAGLDIVAPGVGVQSTYPGNRYVSLSGTSMAT PHVAGAAAL |
| SEQ ID NO:206 | 15c | STQDGNGHGTHVAGTIAALNNNIGVLGVAPNVDLYGVKVLG ASGRGSVSGIARGLEWAGDNGMHVANLSLGSSQPSATLEQA VNSATSRGVLVIATGNTGAGTVSYPARYHANAMAVGATDQN NNRANFSQYGTGLDIVAPGVGVQSTYPGSTYASMNGTSMAT PHVAGAAAL |
| SEQ ID NO:207 | 16c | STQDGNGHGTHVAGTVAALNNNIGVLGVAPSAELYGVKVLG ASGRGTVSGIAQGLEWAGDNGMHVANLSLGTDQPSSTLERA |

-continued

| SEQ ID | Clone ID | Sequence |
|---|---|---|
| | | VNAATSRGVLVVAASGNTGAGSIGYPARYANAMAVGATDQN |
| | | NNRANFSQYGAGLDIVAPGVGVQSTYPGSRYASLNGTSMAT |
| | | PHVAGVAAL |
| SEQ ID NO:208 | 17c | STQDGNGHGTHVAGTVAALNNNVGVLGVAPSAELYAVKVLG |
| | | ASGSGTISSTAQGLEWAGTNGTHIANLSLGTDQPSATLERA |
| | | VNAATSRGVLVVAASGNNGSGSVSYPARYANAMAVGATDQN |
| | | NRRANFSQYGAGLDIVAPGVGVQSTCPGNRYVSLSGTSMAS |
| | | PHVAGVAAL |
| SEQ ID NO:209 | 18c | STQDGNGHGTHVAGTTAALNNSVGVLGVAPSAELYGVKVLG |
| | | ASGRGSVSSIAQGLEWAADNGMHVANMSLGTSFPSSTLERA |
| | | VNAATSRGVLVLAASGNSGSGTIGYPGRYANAMAVGATDQN |
| | | NNRASFSQYGTGIDTVAPGVGVQSTYPGSTYASLSGTSMAT |
| | | PHVAGAAAL |
| SEQ ID NO:210 | 190c | STQDGNGHGTHVAGTIAALNNNVLGVAPSVELYAVKVLG |
| | | ANGSGTISGIAQGLEWAANNGTHVANLSLGTDAPSATLERA |
| | | VNQATSRGVLVVAASGNSGSGTIGYPARYANAMAVGATDQN |
| | | NNRASFSQYGAGIDIVAPGVGVQSTYPGSTYALLSGTSMAT |
| | | PHVAGVAAL |
| SEQ ID NO:211 | 191c | STQDGNGHGTHVAGTVAALNNSIGVLGVAPSAELYAVKVLG |
| | | ASGRGSVSSIAQGLEWAGANGMHIANLSLGSPAPSSTLERA |
| | | VNSATSRGVLVIAATGNTGSGSISYPARYANAMAVGATDQN |
| | | NRRASFSQYGAGTDIVAPGVGVQSTYPGNTYVSMSGTSMAT |
| | | PHVAGAAAL |
| SEQ ID NO:212 | 192c | STQDGNGHGTHVAGTVAALNNNIGVLGVAPNVGLYAVKVLG |
| | | ASGRGTVSGIARGLEWAATNGMHVANLSLGSDAPSATLEQA |
| | | VNQATSRGVLVVAATGNTGSGTISYPARYANAMAVGATDQN |
| | | NRRANFSQYGQGLDIVAPGVGVQSTYPGNTYVSMSGTSMAS |
| | | PHVAGVAAL |
| SEQ ID NO:213 | 193c | STQDGNGHGTHVAGTVAALNNSDGVLGVAPSADLYAVKVLG |
| | | ASGRGSVSSIARGLEWAAANGMHVANLSLGSDQPSSTLERA |
| | | VNEATSQGVLVVAASGNNGAGTVGYPARYANAMAVGATDQN |
| | | NRRASFSQYGAGLDIVAPGVGVQSTYPGSTYASMNGTSMAT |
| | | PHVAGAAAL |
| SEQ ID NO:214 | 195c | STQDGNGHGTHVAGTVAALNNSVGVLGVAPSVELYGVKVLG |
| | | ANGSGSISSIARGLEWAADNGKHIANLSLGSSFPSATLEQA |
| | | VNQATSRGVLVIAATGNSGSGTVGYPARYANAMAVGATDQN |
| | | NNRANFSQYGAGLDTVAPGVGVQSTYTGSTYASMNGTSMAS |
| | | PHVAGAAAL |

-continued

| SEQ ID | Clone ID | Sequence |
|---|---|---|
| SEQ ID NO:215 | 196c | STQDGNGHGTHVAGTIAALNNSDGVLGVAPNVDLYGVKVLG ANGSGTVSGIARGLQWAGDNGMHVANLSLGTDAPSATLERA VNQATSRGVLVVAASGNTGAGSISYPARYANAMAVGATDQN NRRANFSQYGAGLDIVAPGVGVQSTYTGNRYVSMNGTSMAS PHVAGAAAL |
| SEQ ID NO:216 | 197c | STQDGNGHGTHVAGTIAALNNNAGVLGVAPNVDLYAVKVLG ANGSGSTSGIARGLEWAGDNGMHVANLSLGSPQPSATLERA VNAATSRGVLVVAASGNNGVGSVSYPARYANAMAVGATDQN NNRANFSQYGTGLDTVAPGVGVQSTYPGSRFASLNGTSMAS PHVAGVAAL |
| SEQ ID NO:217 | 199c | STQDGNGHGTHVAGTVAALNNNVGVLGVAPNAELYAVKVLG ANGSGSVSGIAQGLEWAGANGMHVANMSLGSPSPSATLERA VNAATSRGVLVVAATGNSGAGSVSYPARYANAMAVGATDQN NNRASFSQYGAGLDIVAPGVGVQSTYPCNTYVSLNGTSMAT PHVAGVAAL |
| SEQ ID NO:218 | 19c | STQDGNGHGTHVAGTVAALNNNIGVLGVAPSADLYAVKVLG ASGSGTTSSTAQGLEWAGANGMHVANLSLGTSFPSTTLERA VNSATSRGVLVIAASGNSGSGTVGYPARYANAMAVGATDQN NRRASSSQYGAGLDTVAPGVGVQSTYTGSTYVSLSGTSMAT PHVAGVAAL |
| SEQ ID NO:219 | 1c | STQDGNGHGTHVAGTVAALNMSVGVIGVAPSAELYAVKVLG ASGRGTISSIARGLEWAANNGTHVANLSLGSPAPSATLERA VNSATSRGVLVVAATGNNGSGTTSYPARYANAMAVGATDQN NNRANSSQYGTGLDTVAPGVGVQSTYPGSTYASLSGTSMAT PHVAGAAAL |
| SEQ ID NO:220 | 200c | STQDGNGHGTHVAGTVAALNNSDGVLGVAPSVDLYAVKVLG ASGSGTISSTARGLEWAGNNGMHVANMSLGSPSPSATLERA VNQATSRGVLVVAATGNTGAGTVGYPARYANAMAVGATDQN NNRANFSQYGAGLDIVAPGVNVQSTYPGSRYASLNGTSMAS PHVAGVAAL |
| SEQ ID NO:221 | 201c | STQDGNGHGTHIAGTIAALNNSVGVLGVAPSVDLYGVKVLG ASGRGSVSSTAQGLEWAGDNGMHVANLSLGTDQPSATLERA VNSATSQGVLVVAASGNSGAGSVSYPARYANAMAVGATDQN NRRASFSQYGAGLDTVAPGVGVQSTYPGSRYASMNGTSMAS PHVAGAAAL |
| SEQ ID NO:222 | 20c | STQDGNGHGTHVAGTVAALNNNIGVLGVAPNAELYAVKVLG ASGRGTVSCIARGLEWAGDNGMHVANLSLGTSSPSSTLEQA VNYATSQGVLVVAATGNSGSGTISYPARYANAMAVGATDQN |

-continued

| SEQ ID | Clone ID | Sequence |
|---|---|---|
| | | NNRASFSQYGTGLDIVAPGVRVQSTYPGNRYASLSGTSMAS |
| | | PHVAGVAAL |
| SEQ ID NO:223 | 21c | STQDGNGHGTHVAGTVAALNNSVGVLGVAPNAELYGVKVLG |
| | | ANGRGTISSTARGLEWAGANGMHVANLSLGTPAPSATLEQA |
| | | VNQATSQGVLVVAASGNSGAGSISYPARYANAMAVGATDQN |
| | | NRRASFSQYGTGLDTVAPGVGVQSTYPGSTYASLNGTSMAS |
| | | PHVAGAAAL |
| SEQ ID NO:224 | 22c | STQDGNGHGTHVAGTIAALNNSVGVLGVAPNAELYAVKVLG |
| | | ASGSGSVSGIARGLEWAGDNGMHVANLSLGSPFPSATLEQA |
| | | VNAATSRGVLVVAASGNSGSGTVGYPARYANAMAVGATDQN |
| | | NNRASFSEYGAGLDTVAPGVGVQSTYPGSRYASLSGTSMAS |
| | | PHVAGAAAL |
| SEQ ID NO:225 | 23c | STQDGNGHGTHVAGTVAALNNNVGVIGVAPSAELYGVKVLG |
| | | ASGSGSISSIARGLEWAGMMGMHVANMSLGTDAPSATLERA |
| | | VNQATSRGVLVVAATGNSGAGSVAYPARYANAMAVGATDQN |
| | | NNRANFSQYGAGLDIVAPGVGVQSTYPGSTYASLNGTSMAT |
| | | PHVAGVAAL |
| SEQ ID NO:226 | 24c | STQDGNGHCTHVAGTVAALNNWGVLGVAPSADLYAVKVLG |
| | | ASGRGTVSSIARGLQWAANNGMHVANLSLGSDQPSTTLERA |
| | | VNYATSQGVLVIAASGNTGSGSIGYPARYANAMAVGATDQN |
| | | NNRANFSQYGAGLDIVAPGVGVQSTYPGSTYASMNGTSMAS |
| | | PHVAGAAAL |
| SEQ ID NO:227 | 25c | STQDGNGHGTHVAGTVAALNIVGVTJGVAPNAELYAVKVLG |
| | | ASGRGSVSSVAQGLEWAADNGTHVANLSLGSDFPSATLERA |
| | | VNSATSRGVLVVAATGNNGSGTVSYPARYANAMAVGATDQN |
| | | NNRASFSQYGAGLDIVAPGVGVQSTYPGSTYASLNGTSMAT |
| | | PHVAGAAAL |
| SEQ ID NO:228 | 26c | STQDGNGHGTHAGTIAALNTSVGVLGVAPNADLYGVKVLG |
| | | ASGRGSISGTAQGLEWAATNCMHVAMLSLGTDQPSATLEPA |
| | | VNYATSRGVLVWASGNTGSGTIGYPARYANAMAVGATDQN |
| | | NNRASFSQYGAGIDIVAPGVGVQSTYTGSRYALMSGTSMAT |
| | | PHVAGVAAL |
| SEQ ID NO:229 | 27c | STQDGNGHGTHVAGTVAALMMNVGVLGVAPSVDLYGVKVLG |
| | | ASGRGTVSGTVRGLEWAADNGMHVLSLGTPFPSATLERA |
| | | VNAATSQGVLVIAASGNSGSGSISYPARYANAMAVGATDQN |
| | | NNRASFSQYGAGIDIVAPGVGVQSTYPGNRYASLSGTSMAT |
| | | PHVAGAAAL |
| SEQ ID NO:230 | 28c | STQDGNGHGTHVAGTVAALNNSDGVIGVAPSVELYAVKVLG |

-continued

| SEQ ID | Clone ID | Sequence |
|---|---|---|
| | | AMGRGSVSGTARGLEWAATHVAKLSLGTSSPSSTLERA |
| | | VKAATSQGVLVVAASGNNGAGTICYPARYANAMAVGATDQN |
| | | NNRASFSQYGAGLDIVAPGVGVQSTYPGNTYASLNGTSMAT |
| | | PHVAGVAAL |
| SEQ ID NO:231 | 29c | STQDGNGHGTHVAGTVAALNNNVGVLGVAPSADLYGVKVLG |
| | | ANGSGSVSSIARGLEWAAANNMHVANLSLGSPQPSATLERA |
| | | VNAATSQGVLVVAASGNTGSGIVSYPARYANAMAVGATDQN |
| | | NNRASFSQYGTGLDTVAPGVGVQSTYPGSRYASLSGTSMAT |
| | | PHVAGAAAL |
| SEQ ID NO:232 | 2c | STQDGNGHGTHVAGTVAALISIGVLGVAPSVELYGVKVLG |
| | | ANGRGSISGTARGLEWAAAKGMHIANLSLGTSFPSTTLEPA |
| | | VNQATSRGVLVVAASGNNGSGTVGYPATYANAMAVGATDQN |
| | | NRRANFSQYGAGIDIVAPGVGVQSTYTGNRYASLSGTSMAS |
| | | PHVAGAAAL |
| SEQ ID NO:233 | 30c | STQDGNGHGTHVAGTVAALNMWGVIGVAPSVELYAVKVLG |
| | | ANGSGTISGIARGLEWAGANGMHIANMSLGTDFPSSTLERA |
| | | VNYATSQGVLVIAASGNSGAGSVGYPARYANAMAVGATDQN |
| | | NRRANSSQYGTGLDIVAPGVGVQSTYPGSRYVSLSGTSMAT |
| | | PHVAGVAAL |
| SEQ ID NO:234 | 31c | STQDGNGHGTHVAGTIAALNNSVGVLGVAPSVELYAVKVLG |
| | | ASGRGSISGIARGLEWAGNNGMHVANMSLGSPFPSATLERA |
| | | VNQATSRGVLVIAASGNSGAGSVSYPARYANAMAVGATDQN |
| | | NNRASFSQYGAGLDTVAPGVGVQSTYPGSTYASLSGTSMAS |
| | | PHVAGAAAL |
| SEQ ID NO:235 | 32c | STQDGNGHGTHVAGTTAALNNVGVIGVAPNADLYAVKVLG |
| | | ASGRGTISGIARGLEWAGANGMHIAMJSLGTPSPSTTLERA |
| | | VNAATSRDVLVVAASGNGGSGSTGYPARYANAMAVGATDQN |
| | | NNRASFSQYGAGLDIVAPGVGVQSTYPGSTYASLNGTSMAS |
| | | PHVAGVAAL |
| SEQ ID NO:236 | 33c | STQDGNGHGTHVAGTVAALNNSVGVLGVAPSAELYAVKVLG |
| | | ASGSGTVSSIARGLEWAADNNTAHTAMSLGTPSPSATLERA |
| | | VNQATSRGVLVVAATGNSGSGSIGYPARYATAMAVGATDQN |
| | | NRRANFSQYGTGLDIVAPGVGVQSTYPGSRYVSLSGTSMAT |
| | | PHVAGVAAL |
| SEQ ID NO:237 | 34c | STQDGNGHGTHVAGTVAALNNSVGVLGVAPSVELYAVKVLG |
| | | ASGRGTVSGIAQGLQWAAANGMHVANLSLGTDFPSATLEQA |
| | | VNAATSRGVLVVAASGNSGSGSISYPARYANAIAVGATDQN |
| | | NNRANFSQYGGGLDIVAPGVGVQSTYPGSTYVSLSGTSMAV |

-continued

| SEQ ID | Clone ID | Sequence |
|---|---|---|
| | | PHVAGAAAL |
| SEQ ID NO:238 | 35c | STQDGNGHGTHVAGTIAALNNSVGVIGVAPNVDLYGVKVLG ASGSGTTSSTAQGLEWAADNGNTVANLSLGTPAPSSTLERA VNAATSRGVLVVAASGNSGAGSISYPARYANAMAVGATDQN NNRASFSQYGTGTDIVAPGVGVQSTYPGNTYASLNGTSMAS PHVAGAAAL |
| SEQ ID NO:239 | 36c | STQDGNGHGTHVAGTVAALNISVGVLGVAPSVELYAVKVLG ASGRGTVSSIARGLEWAAINGTHVAISLGTSQPSATLEQA NAATSRGVLVVAASGNSGSGTVGYPARYANAMAVGATDQN NNRASFSQYGTGLIVAPGVGVQSTYPGSRYASLSGTSMAS PHVAGVAAL |
| SEQ ID NO:240 | 37c | STQDGNGHGTHVAGTIAALJKSDGVIGVAPSADLYAVKVLG ANGSGTVSSIARGLQWAANAMAGHVNLSLGSDQPSATLERA VNAATSRGVLVVAASGNSGAGTVGYPARYANAMAVGATDQN NNRASFSQYGTGLDIVAPGVGVQSTYPGNTYVSMSGTSMAS PHVAGVAAL |
| SEQ ID NO:241 | 38c | STQDGNGHGTHVAGTVAALMNNVGVIGVAPSVDLYAVKVLG ASGRGSVSGIARGLQWAAANGMHIANLSLGSSQPSATLERA VNYATSRGVLVVAASGNSGSGTVSYPARYANAMAVGATDQN NNRANSSQYGTGLDIVAPGVGVQSTYPGNTYASLSGTSMAT PHVAGAAAL |
| SEQ ID NO:242 | 39c | STQDGNGHGTHVAGTVAALNNNVGVLGVAPSAELYAVKVLG ANGRGTISGIAQGLEWAANNGMHVANLSLGSPSPSATLEQA VNAATSRGVLVVAASGNSGAGTIGYPATYANAMAVGATDQN NNRASFSQYGTGTDTVAPGVGVQSTYPGNRYASMSGTSMAT PHVAGAAAL |
| SEQ ID NO:243 | 40c | STQDGNGHGTHVAGTVAALNNNIGVLGVAPSADLYAVKVLG TSGSGTVSSIARGLEWAASNGMHVANMSLGTSQPSATLERA NAATSRGVLVAATGNSGSGTIGYPARYAMANAVGATDQN NRRASFSQYGTGLDTVAPGVGVKSTYPGSTYASLNGTSMAS PHVAGVAAL |
| SEQ ID NO:244 | 41c | STQDGNGHGTHVAGTIAALNSIGVLGVAPSVELYGVKVLG ANGSGTISSIARGLEWAGNNGMHVAIMSLGSDFPSSTLEQA VNAATSRGVLVVAASGNSGSGSVGYPARYANAMAVGATDQN NRRANFSQYGAGLDIVAPGVGVQSTYPGSRYVSLSGTSMAS PHVAGAAAL |
| SEQ ID NO:245 | 42c | STQDGNGHGTHVTGTTAALNNSIGVIGVAPSVELYGVKVLG ASGRGSISGIARGLEWAADNGMHVANMSLGSPQPSATLEQA |

-continued

| SEQ ID | Clone ID | Sequence |
|---|---|---|
| | | VNSATSRGVLVIAATGNSGSGTIAYPARYPNAMAVGATDQN |
| | | NKRASFSQYGQGLDIVAPGVGVQSTYPGSRYASLNGTSMAS |
| | | PHVAGAAAL |
| SEQ ID NO:246 | 43c | STQDGNGHGTHVAGTTAALNNNDGVLGVAPSVDLYGVKVLG |
| | | ASGRGTVSSIAQGLLWATMGTHVAISLGSSAPSTTLERA |
| | | VNYATSRGVLVVAASGNSGSGTISYPARYANAMAVGATDQN |
| | | NNRASFSQYGAGIDIVAPGVNVQSTYPGSTYVSLSGTSMAS |
| | | PHVAGVAAL |
| SEQ ID NO:247 | 44c | STQDGNGHGTHVAGTIAALNNSVGVIGVAPSADLYAVKVLG |
| | | ASGRGSVSGIARGLEWAAMNGMHVANLSLGSPAPSATLERA |
| | | VNYATSRGVLVTAASGNSGAGSVGYPARYAMANVGATDQN |
| | | NNRASFSQHGTGLDIVAPGVGVQSTYPGSRYASLSGTSMAS |
| | | PHVAGAAAL |
| SEQ ID NO:248 | 45c | STQDGNGHGTHVAGTVAALNNSVGVLGVAPSADLYAVKVLG |
| | | ASGSGTISGIAQGLEWAANNGTHVANLSLGTSQPSATLERA |
| | | VNAATSQGVLVVAATGNTGAGTIGYPARYANMAVGATDQN |
| | | NNRASFSQYGTGLDIVAPGVGVQSTYPGSRYASLSGTSMAT |
| | | PHVAGAAAL |
| SEQ ID NO:249 | 46c | STQDGNGHGTHVAGTVAALNNSIGVLGVAPSVELYAVKVLG |
| | | ASGRGSISSTARGLEWAGDNGMHIANMSLGTDQPSATLEQA |
| | | VNAATSRGVLVIAATGNTGAGSISYPARYANAMAVGATDQN |
| | | NNRAIFSQYGAGLDIVAPGVGVQSTYPGSRYASMNGTSMAT |
| | | PHVAGVAAL |
| SEQ ID NO:250 | 47c | STQDGNGHGTHVAGTVAALNTIDGVLGVAPNVDLYAVKVLG |
| | | ASGRGSVSGIARGLEWAGAIWMHTANMSLGTSFPSATLEQA |
| | | VNAATSRGVLVVAATGNNGAGTVGYPARYANAMAVGATDQN |
| | | NNRASSSQYGAGLDTVAPGVGVQSTYPGSRYASLSGTSMAT |
| | | PHVAGAAAL |
| SEQ ID NO:251 | 48c | STQDGNGHGTHVAGTVAALNNSDGVIGVAPSVDLYGVKVLG |
| | | ASGRGSVSSIARGLEWAADNGMHVANLSLGSDQLSTTLERA |
| | | VNQATSRGVLWAASGNGSGTVSYPARYANAMAVGATDQN |
| | | NNRASSSQYGTGLDTVAPGVGVQSTYPGSRYASLSGTSMAS |
| | | PHVAGVAAL |
| SEQ ID NO:252 | 4c | STQDGNGHGTHVAGTVAALNKSIGVLGVAPSAELYAVKVLG |
| | | ASGRGSVSGTAQGLEWAGTNGIHVAISLGTPAPSATLEQA |
| | | VNAATSQGVLVIAASGNSGSGTVSYPARYANAMAVGATDQN |
| | | NNFASFSQYGAGLDTVAPGVGVQSTYPGSTYASMSGTSMAS |
| | | PHVAGVAAL |

-continued

| SEQ ID | Clone ID | Sequence |
|---|---|---|
| SEQ ID NO:2535 | c | STQDGNGHGTHVAGTVAALNTNIGVLGVAPSVELYGVKVLG |
| | | ASGSGSVSSIAQGLEWAADNGMHVANMSLGSPFPSSTLEQA |
| | | VNSATSRGVLVVAASGNSGSGTVGYPARYANAMAVGATDQN |
| | | NNRASFSQYGAGLDIVAPGVGVQSTYPGSRYASLSGTSMAT |
| | | PHVAGVAAL |
| SEQ ID NO:2546 | c | STQDGNGHGTHVAGTTAALNUSIGVTGVAPSVDLYGVKVLG |
| | | ASGSGSVSSIARGLEWAGDNGMHVANLSLGSPSPSATLEQA |
| | | VNSATSRGVLVTAATGNTGAGTLSYPARYANAMVGATDQN |
| | | NNRASFSQYGTGLDIVAPGVGVQSTYPGSTYVSLNGTSMAT |
| | | PHVASAAAL |
| SEQ ID NO:2557 | c | STQDGNGHGTHVAGTIAALNJNTSVGV-LGVAPNVELYAVKVLG |
| | | ASGRGTISGTAQGLEWAADNGTHTANLSLGTSFPSATLERA |
| | | VNSATSRGVLVVAATGNTGAGSISYPARFANAMAVGATDQN |
| | | NRRASFSQYGAGLDTVGPGVGVQSTYPGSTYASLSGTSMAT |
| | | PHVAGAAAL |
| SEQ ID NO:2568 | c | STQDGNGHGTHVAGTVAALNNSDGVIGVAPSADLYAVKVLG |
| | | ANGSGSVSSTAQGLEWAADNGMHINMSLGTSSPSVTLEPA |
| | | XTNAATSQGVLVVAASGNTGAGSIGY-PARYAJNIAMAVGATDQN |
| | | NRRASFSQYGAGLDIVAPGVNVQSTYPGSRYASLSGTSMAS |
| | | PHVAGAAAL |
| SEQ ID NO:2579 | 7c | STQDGNGHGTHVAGTVAALNNSIGVIGVAPSAELYGVKVLG |
| | | ANGSGSVSSIARGLEWAGNNGMHIANLSLGSDFPSATLEQA |
| | | VNAATSRGVLVVAASGNNGSGSVGYPARYANAMGVGATDQN |
| | | NRRANFSQYGAGLDIVAPGVGVQSTYPGNTYVSLNCTSMAT |
| | | PHVAGVAAL |
| SEQ ID NO:2589 | 8c | STQDGNGHGTHVAGTVAALNNSDGVTGVAPNVELYGVKVLG |
| | | ANGRGTVSGIAQGLEWAAANGMHVANLSLGSPAPSATLEQA |
| | | VNAATSRGVLVIAASGNSGAGTVGYPARYANAMAVGATDQN |
| | | NNRANFSQYGAGLDIVAPGVGVQSTYPGNTYTSLSGTSMAS |
| | | PHVAGVAAL |
| SEQ ID NO:2599 | 9c | STQDGNGHGTHVAGTIAALNNNVGVLGVAPSVDLYGVKVLD |
| | | ASGRGTISGIARGLEWAAANGMHIANMSLGSDQPSTTLERA |
| | | VNAATSRGVLVVAASGNTGSGTVSYPARYANAMAVGATDQN |
| | | NNRANSSQYGAGLDIVAPGVGVQSTYPGSTYASLSGTSMAS |
| | | PHVAGVAAL |
| SEQ ID NO:2609 | c | STQDGNGHGTHVAGTTAALNNSVGVTGVAPSAELYGVKVLG |
| | | ANGSGTVSGTARGLEWAADNGMHVANMSLGSSAPSATLERA |

| SEQ ID | Clone ID | Sequence |
|---|---|---|
| | | VNSATSRGVLVVAATGNSGAGSISYPARYANAMAVGATDQN |
| | | NNRASFSQYGTGLDTVAPGVNVQSTYPGSRYASMSGTSMAS |
| | | PHVAGAAAL |
| Q ID NO:261 | Savinase | mkkplgkivastallisvafsssiasaaeeakekyligfne |
| | | qeavsefveqveandevailseeeeveiellhefetipvls |
| | | velspedvdaleldpaisyieedaevttmAQSVPWGlSRVQ |
| | | APAAHNRGLTGSGVKVAVLDTGISTHPDLNTRGGASFVPGE |
| | | PSTQDGNGHGTHVAGTIAALNNSIGVLGVAPSAELYAVKVL |
| | | GASGSGSVSSIAQGLEWAGNNGTHVANLSLGSPSPSATLEQ |
| | | AVNSATSRGVLVVAASGNSGAGSISYPARYANAMAVGATDQ |
| | | NNNRASFSQYGAGLDIVAPGVNVQSTYPGSTYASLNGTSMA |
| | | TPHVAGVAALVKQKNPSWSNVQIRNHLKNTATSLGSTNLYG |
| | | SGLVNAEAATR |

What is claimed is:

1. An isolated or recombinant polypeptide having endoprotease activity, which has an amino sequence that is at least 96% identical to SEQ ID NO:137 over a comparison window of SEQ ID NO:137, wherein the percent amino acid sequence identity is determined using the BLASTP program using the following parameters: wordlength of 3 and expectation of 10, and the BLOSUM62 scoring matrix.

2. The polypeptide of claim 1, which has an amino acid sequence that is at least 97% identical to SEQ ID NO: 137 over a comparison window of SEQ ID NO: 137.

3. The polypeptide of claim 2, which has an amino acid sequence that is at least 98% identical to SEQ ID NO: 137 over a comparison window of SEQ ID NO: 137.

4. The polypeptide of claim 3, which has an amino acid sequence that is at least 99% identical to SEQ ID NO: 137 over a comparison window of SEQ ID NO: 137.

5. The polypeptide of claim 4, which has an amino acid sequence that comprises SEQ ID NO: 137.

6. The polypeptide of claim 1, which is about 269 amino acids in length.

7. The polypeptide of claim 6, which is 269 amino acids in length.

8. A detergent composition comprising a polypeptide of claim 1 and a surfactant.

9. An isolated DNA sequence encoding a polypeptide of claim 1.

10. An expression vector comprising a DNA sequence of claim 9.

11. A microbial host cell transformed with an expression vector of claim 10.

12. A method of producing a polypeptide, comprising:
   (a) culturing a host cell of claim 11 under conditions conducive to the production of the polypeptide.
   (b) recovering the polypeptide.

13. The polypeptide of claim 1, which has an amino acid sequence that comprises SEQ ID NO: 132.

14. The polypeptide of claim 1, which has an amino acid sequence that comprises SEQ ID NO: 133.

15. The polypeptide of claim 1, which has an amino acid sequence that comprises SEQ ID NO: 134.

16. The polypeptide of claim 1, which has an amino acid sequence that comprises SEQ ID NO: 135.

17. The polypeptide of claim 1, which has an amino acid sequence that comprises SEQ ID NO: 138.

18. The polypeptide of claim 1, which has an amino acid sequence that comprises SEQ ID NO: 140.

19. The polypeptide of claim 1, which has an amino acid sequence that comprises SEQ ID NO: 142.

20. The polypeptide of claim 1, which has an amino acid sequence that comprises SEQ ID NO: 144.

21. The polypeptide of claim 1, which has an amino acid sequence that comprises SEQ ID NO: 145.

22. The polypeptide of claim 1, which has an amino acid sequence that comprises SEQ ID NO: 146.

23. The polypeptide of claim 1, which has an amino acid sequence that comprises SEQ ID NO: 148.

24. The polypeptide of claim 1, which has an amino acid sequence that comprises SEQ ID NO: 155.

25. The polypeptide of claim 1, which has an amino acid sequence that comprises SEQ ID NO: 161.

26. The polypeptide of claim 1, which has an amino acid sequence that comprises SEQ ID NO: 164.

27. The polypeptide of claim 1, which has an amino acid sequence that comprises SEQ ID NO: 165.

\* \* \* \* \*